United States Patent
Zhong et al.

(10) Patent No.: US 11,299,512 B2
(45) Date of Patent: Apr. 12, 2022

(54) CYCLIC DI-NUCLEOTIDE COMPOUNDS AND METHODS OF USE

(71) Applicants: ImmuneSensor Therapeutics, Inc., Dallas, TX (US); The Board of Regents of the University of Texas System, Austin, TX (US)

(72) Inventors: Boyu Zhong, Irving, TX (US); Heping Shi, Dallas, TX (US); Yuanwei Dai, Dallas, TX (US); Qi Wei, Dallas, TX (US); Chuo Chen, Dallas, TX (US); Zhijian Chen, Dallas, TX (US); Lijun Sun, Dallas, TX (US)

(73) Assignees: IMMUNESENSOR THERAPEUTICS, INC., Dallas, TX (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 469 days.

(21) Appl. No.: 16/438,153

(22) Filed: Jun. 11, 2019

(65) Prior Publication Data
US 2020/0010501 A1  Jan. 9, 2020

Related U.S. Application Data

(63) Continuation of application No. 15/953,492, filed on Apr. 15, 2018, now Pat. No. 10,519,188, which is a continuation of application No. PCT/US2017/023093, filed on Mar. 17, 2017.

(60) Provisional application No. 62/396,140, filed on Sep. 17, 2016, provisional application No. 62/355,382, filed on Jun. 28, 2016, provisional application No. 62/310,364, filed on Mar. 18, 2016.

(51) Int. Cl.
| | |
|---|---|
| C07H 21/02 | (2006.01) |
| C07H 21/04 | (2006.01) |
| C07H 21/00 | (2006.01) |
| A61K 31/7084 | (2006.01) |
| A61K 45/06 | (2006.01) |

(52) U.S. Cl.
CPC ......... *C07H 21/02* (2013.01); *A61K 31/7084* (2013.01); *A61K 45/06* (2013.01); *C07H 21/00* (2013.01); *C07H 21/04* (2013.01)

(58) Field of Classification Search
CPC ........ C07H 21/02; C07H 21/04; C07H 21/00; C07H 45/06; A61K 31/7084; A61K 45/06
USPC ....... 514/265.1, 263.4, 263.37; 544/277, 276
See application file for complete search history.

(56) References Cited

U.S. PATENT DOCUMENTS

| | | | |
|---|---|---|---|
| 8,367,716 B2 | 2/2013 | Karaolis | |
| 9,549,944 B2 | 1/2017 | Dubensky, Jr. et al. | |
| 9,597,391 B2 | 3/2017 | Ebensen et al. | |
| 9,642,830 B2 | 5/2017 | Chang et al. | |
| 9,695,212 B2 | 7/2017 | Dubensky, Jr. et al. | |
| 9,718,848 B2 | 8/2017 | Adams et al. | |
| 9,724,408 B2 | 8/2017 | Dubensky, Jr. et al. | |
| 9,770,467 B2 | 9/2017 | Dubensky, Jr. et al. | |
| 9,840,533 B2 | 12/2017 | Patel et al. | |
| 9,944,992 B2 | 4/2018 | Zheng et al. | |
| 9,994,607 B2 | 6/2018 | Adams et al. | |
| 10,011,630 B2 | 7/2018 | Vernejoul et al. | |
| 10,047,115 B2 | 8/2018 | Biggadike et al. | |
| 10,092,592 B2 | 10/2018 | Tan et al. | |
| 10,106,574 B2 | 10/2018 | Altman et al. | |
| 10,131,686 B2 | 11/2018 | Patel et al. | |
| 10,364,266 B2 | 7/2019 | Adams et al. | |
| 10,519,188 B2 | 12/2019 | Zhong et al. | |
| 10,738,074 B2 | 8/2020 | Altman et al. | |
| 10,759,825 B2 | 9/2020 | Altman et al. | |
| 10,766,919 B2 | 9/2020 | Altman et al. | |
| 2006/0040887 A1 | 2/2006 | Karaolis | |
| 2008/0286296 A1 | 11/2008 | Ebensen et al. | |
| 2011/0262485 A1 | 10/2011 | Barber | |
| 2012/0164107 A1 | 6/2012 | Portnoy et al. | |
| 2013/0266612 A1 | 10/2013 | Fukasaka et al. | |
| 2014/0205653 A1 | 7/2014 | Dubensky, Jr. et al. | |
| 2014/0329889 A1 | 11/2014 | Vance et al. | |
| 2014/0341976 A1 | 11/2014 | Dubensky, Jr. et al. | |
| 2015/0010613 A1 | 1/2015 | Dubensky, Jr. et al. | |
| 2015/0056224 A1 | 2/2015 | Dubensky, Jr. et al. | |
| 2015/0343056 A1 | 12/2015 | Chen et al. | |
| 2016/0068560 A1 | 3/2016 | Patel et al. | |
| 2016/0210400 A1 | 7/2016 | Patel et al. | |
| 2016/0287623 A1 | 10/2016 | Gajewski et al. | |
| 2016/0362441 A1 | 12/2016 | Vernejoul et al. | |
| 2017/0037400 A1 | 2/2017 | Barber | |
| 2017/0044206 A1 | 2/2017 | Altman et al. | |
| 2017/0146519 A1 | 5/2017 | DeFilippis et al. | |

(Continued)

FOREIGN PATENT DOCUMENTS

| | | |
|---|---|---|
| CN | 106318997 A | 1/2017 |
| CN | 1063108997 A | 1/2017 |

(Continued)

OTHER PUBLICATIONS

European Search Report corresponding to European Application No. 19218894.4 dated Jun. 25, 2020.
Ablasser et al. 2013 "cGAS produces a 2'-5'-linked cyclic dinucleotide second messenger that activates STING," Nature 498(7454):380-384.

(Continued)

*Primary Examiner* — Joseph R Kosack
*Assistant Examiner* — Sagar Patel
(74) *Attorney, Agent, or Firm* — Hugo Garrido; Carl Morales; Fenwick & West LLP

(57) ABSTRACT

Disclosed are cyclic-di-nucleotide cGAMP analogs, methods of synthesizing the compounds, pharmaceutical compositions comprising the compounds thereof, and use of compounds and compositions in medical therapy.

34 Claims, No Drawings

(56) References Cited

U.S. PATENT DOCUMENTS

| | | |
|---|---|---|
| 2017/0158724 A1 | 6/2017 | Adams et al. |
| 2017/0158772 A1 | 6/2017 | Thompson et al. |
| 2017/0196902 A1 | 7/2017 | Tan et al. |
| 2017/0233430 A1 | 8/2017 | Adams et al. |
| 2017/0239283 A1 | 8/2017 | Gough et al. |
| 2017/0298139 A1 | 10/2017 | Thompson et al. |
| 2017/0319680 A1 | 11/2017 | Ishii et al. |
| 2017/0333552 A1 | 11/2017 | Dubensky, Jr. et al. |
| 2017/0340658 A1 | 11/2017 | Vernejoul et al. |
| 2018/0064745 A1 | 3/2018 | Katibah et al. |
| 2018/0086713 A1 | 3/2018 | Elkon et al. |
| 2018/0092937 A1 | 4/2018 | Oost et al. |
| 2018/0093964 A1 | 4/2018 | Altman et al. |
| 2018/0105514 A1 | 4/2018 | Mehlmann et al. |
| 2018/0118777 A1 | 5/2018 | Patel et al. |
| 2018/0127454 A1 | 5/2018 | Patel et al. |
| 2018/0162899 A1 | 6/2018 | Bignan et al. |
| 2018/0169159 A1 | 6/2018 | Barber |
| 2018/0186828 A1 | 7/2018 | Biggadike et al. |
| 2018/0230177 A1 | 8/2018 | Zhong et al. |
| 2018/0230178 A1 | 8/2018 | Altman et al. |
| 2018/0237469 A1 | 8/2018 | Altman et al. |
| 2018/0243387 A1 | 8/2018 | Saito et al. |
| 2018/0244712 A1 | 8/2018 | Altman et al. |
| 2018/0258132 A1 | 9/2018 | Adams et al. |
| 2018/0273578 A1 | 9/2018 | Oost et al. |
| 2018/0344758 A1 | 12/2018 | Li et al. |
| 2018/0354983 A1 | 12/2018 | Vernejoul et al. |
| 2018/0369268 A1 | 12/2018 | Katibah et al. |
| 2019/0328762 A1 | 10/2019 | Cemerski et al. |
| 2020/0002370 A1 | 1/2020 | Adams et al. |
| 2020/0040028 A1 | 2/2020 | Genieser et al. |
| 2020/0113924 A1 | 4/2020 | Cemerski et al. |

FOREIGN PATENT DOCUMENTS

| | | |
|---|---|---|
| CN | 106552265 A | 4/2017 |
| CN | 106554416 | 4/2017 |
| CN | 106554416 A | 4/2017 |
| CN | 107335049 A | 11/2017 |
| CN | 107412260 A | 12/2017 |
| CN | 108498529 A | 9/2018 |
| EP | 2996473 B1 | 3/2016 |
| EP | 3322713 A1 | 5/2018 |
| EP | 3366691 A1 | 8/2018 |
| EP | 3386536 A2 | 10/2018 |
| EP | 3431484 A1 | 1/2019 |
| EP | 3523314 A1 | 8/2019 |
| EP | 3544989 A1 | 10/2019 |
| WO | 2005/030186 A2 | 4/2005 |
| WO | 2005/087238 A2 | 9/2005 |
| WO | 2007/054279 A2 | 5/2007 |
| WO | 2010/017248 A2 | 2/2010 |
| WO | 2011/003025 A1 | 1/2011 |
| WO | 2013/166000 A1 | 11/2013 |
| WO | 2013/185052 A1 | 12/2013 |
| WO | 2014/093936 A1 | 6/2014 |
| WO | 2014/099824 A1 | 6/2014 |
| WO | 2014/109256 A1 | 7/2014 |
| WO | 2014/144666 A2 | 9/2014 |
| WO | 2014/179335 A1 | 11/2014 |
| WO | 2014/179760 A1 | 11/2014 |
| WO | 2014/189805 A1 | 11/2014 |
| WO | 2014/189806 A1 | 11/2014 |
| WO | 2015/017652 A1 | 2/2015 |
| WO | 2015/061294 A2 | 4/2015 |
| WO | 2015/077354 A1 | 5/2015 |
| WO | 2015/161762 A1 | 10/2015 |
| WO | 2015/185565 A1 | 12/2015 |
| WO | 2016/079899 A1 | 5/2016 |
| WO | 2016/096174 A1 | 6/2016 |
| WO | 2016/096577 A1 | 6/2016 |
| WO | 2016/100261 A2 | 6/2016 |
| WO | 2016/120305 A1 | 8/2016 |
| WO | 2016/145102 A1 | 9/2016 |
| WO | 2016/176222 A1 | 11/2016 |
| WO | 2016/201450 A2 | 12/2016 |
| WO | 2017/011444 A1 | 1/2017 |
| WO | 2017/011622 A1 | 1/2017 |
| WO | 2017/027645 A1 | 2/2017 |
| WO | 2017/027646 A1 | 2/2017 |
| WO | 2017/075477 A1 | 5/2017 |
| WO | 2017/093933 A1 | 6/2017 |
| WO | 2017/096963 A1 | 6/2017 |
| WO | 2017/100305 A2 | 6/2017 |
| WO | 2017/106740 A1 | 6/2017 |
| WO | 2017/123657 A1 | 7/2017 |
| WO | 2017/123669 A1 | 7/2017 |
| WO | 2017/151922 A1 | 9/2017 |
| WO | 2017/156391 A1 | 9/2017 |
| WO | 2017/157437 A1 | 9/2017 |
| WO | 2017/161349 A1 | 9/2017 |
| WO | 2017/162055 A1 | 9/2017 |
| WO | 2017/175147 A1 | 10/2017 |
| WO | 2017/175156 A1 | 10/2017 |
| WO | 2017/186711 A1 | 11/2017 |
| WO | 2017/218358 A1 | 12/2017 |
| WO | 2017/223422 A1 | 12/2017 |
| WO | 2018/009466 A1 | 1/2018 |
| WO | 2018/009648 A1 | 1/2018 |
| WO | 2018/009652 A1 | 1/2018 |
| WO | 2018/013887 A1 | 1/2018 |
| WO | 2018/029256 A1 | 2/2018 |
| WO | 2018/045058 A1 | 3/2018 |
| WO | 2018/045204 A1 | 3/2018 |
| WO | 2018/053508 A1 | 3/2018 |
| WO | 2018/060323 A1 | 4/2018 |
| WO | 2018/065360 A1 | 4/2018 |
| WO | 2018/067423 A1 | 4/2018 |
| WO | 2018/068132 A1 | 4/2018 |
| WO | 2018/098203 A1 | 5/2018 |
| WO | 2018/100558 A2 | 6/2018 |
| WO | 2018/118664 A1 | 6/2018 |
| WO | 2018/118665 A1 | 6/2018 |
| WO | 2018/119117 A1 | 6/2018 |
| WO | 2018/119325 A1 | 6/2018 |
| WO | 2018/119328 A1 | 6/2018 |
| WO | 2018/138684 A1 | 8/2018 |
| WO | 2018/138685 A2 | 8/2018 |
| WO | 2018/140831 A2 | 8/2018 |
| WO | 2018/144082 A1 | 8/2018 |
| WO | 2018/156625 A1 | 8/2018 |
| WO | 2018/172206 A1 | 9/2018 |
| WO | 2018/198084 A1 | 11/2018 |
| WO | 2018/208667 A1 | 11/2018 |
| WO | 2019033710 A1 | 2/2019 |
| WO | 2019/043634 A2 | 3/2019 |
| WO | 2019/046511 A1 | 3/2019 |
| WO | 2019/180683 A1 | 9/2019 |

OTHER PUBLICATIONS

Burdette et al. 2011 "STING is a direct innate immune sensor of cyclic di-GMP," Nature 478(7370): 515-518.

Chen et al. 2010 "The potential of 3',5'-cyclic diguanylic acid (c-di-GMP) as an effective vaccine adjuvant," Vaccine 28:3080-3085.

Chiu et al. 2009 "RNA polymerise III detects cytosolic DNA and induces type I interferons through the RIG-I pathway," Cell 138(3):576-591.

Clivio et al. 2013 "(3?-5?)-Cyclic Dinucleotides: Synthetic Strategies and Biological Potential," Chem. Rev. 113, 7354-7401.

Davies et al. 2012 "Coordinated regulation of accessory genetic elements produces cyclic di-nucleotides for V. cholera virulence," Cell, 149(2):358-370.

Davies et al. 2012 Supplement to "Coordinated Regulation of Accessory Genetic Elements Produces Cyclic Di-Nucleotides for V. cholerae Virulence," Cell 149:358-370.

Desmet and Ishii 2012 "Nucleic acid sensing at the interface between innate and adaptive immunity in vaccination," Nat Rev Immunol., 12(7):479-491.

Diner et al. 2013 "The Innate Immune DNA Sensor cGAS Produces a Noncanonical Cyclic Dinucleotide that Activates Human STING," Cell Rep 3(5):1355-1361.

(56) References Cited

OTHER PUBLICATIONS

Gao et al. 2013 "Cyclic [G(21,51)pA(31,51)p] Is the Metazoan Second Messenger Produced by DNA-Activated Cyclic GMP-AMP Synthase," Cell, 153:1094-1107.
Gao et al. 2013 "Cyclic GMP-AMP synthase is an innate immune sensor of HIV and other retroviruses," Science, 341:903-906, and Supplementary Materials, 18 pages.
Huang et al. 2012 "The structural basis for the sensing and binding of cyclic di-GMP by STING," Nature Structural & Molecular Biology, 19:728-730.
International Preliminary Report on Patentability for International Application No. PCT/US2017/023093 dated Sep. 18, 2018.
International Search Report for International Application No. PCT/US2017/023093 dated Aug. 7, 2017.
Kalia et al. 2013 "Nucleotide, c-di-GMP, c-di-AMP, cGMP, cAMP, (p)ppGpp signaling in bacteria and implications in pathogenesis," Chem. Soc. Rev. 42, 305-341.
Kranzusch et al. 2013 "Structure of Human cGAS Reveals a Conserved Family of Second-Messenger Enzymes in Innate Immunity" Cell Reports 3(5):1362-1368.
Li et al. 2013 "Pivotal roles of cGAS-cGAMP signaling in antiviral defense and immune adjuvant effects," Science, 341:1390-1394.
Ouyang et al. 2012 "Structural analysis of the STING adaptor protein reveals a hydrophobic dimer interface and mode of cyclic di-GMP binding," Immunity, 36:1073-1086.
Pedersen et al. 2011 "Evaluation of the sublingual route for administration of influenza H5N1 virosomes in combination with the bacterial second messenger c-di-GMP," PLoS ONE, 6(11):e26973.
Schoggins et al. 2011 “A diverse range of gene products are effectors of the type I interferon antiviral response” Nature 472:481.
Shu et al. 2012 “Structure of STING bound to cyclic di-GMP reveals the mechanism of cyclic dinucleotide recognition by the immune system” Nature Structural & Molecular Biology 19:722-724.
Shanahan et al. 2013 “Identification of c-di-GMP derivatives resistant to an EAL domain phosphodiesterase,” Biochemistry 52(2): 365-377.
Sun et al. 2013 “Cyclic GMP-AMP Synthase Is a Cytosolic DNA Sensor That Activates the Type I Interferon Pathway,” Science 339, 786-791.
Takaku et al. 1984 “DI(2,2,2-Trifluoroethyl) Phosphonate, a New Phosphorylating Agent, Its Application in the Synthesis of Oligodeoxyribonucleotides By the Phosphotriester Approach,” Chem. Lett., 1267-1270.
Third Party Observations for International Application No. PCT/US2017/023093 submitted Jul. 12, 2018.
Woodward et al. 2010 “c-di-AMP secreted by intracellular Listeria monocytogenes activates a host type I interferon response,” Science, 328:1703-1705.
Wu et al. 2013 “Cyclic GMP-AMP Is an Endogenous Second Messenger in Innate Immune Signaling by Cytosolic DNA” Science 339, 826-830.
Yang, Q. and Njardarson, J.T. 2013 “Base mediated deprotection strategies for trifluoroethyl (TFE) ethers, a new alcohol protecting group,” Tet. Lett., 54(51).
Yin et al. 2012 “Cyclic di-GMP sensing via the innate immune signaling protein STING,” Molecular Cell, 46:735-745.
Zhang, Xu et al. 2013 “Cyclic GMP-AMP Containing Mixed Phosphodiester Linkages is an Endogenous High-Affinity Ligand for STING,” Mol Cell 51, 226-235.
MedicineNet.com (2004) Web <http://www.medterms.com>.
Auto-immune Diseases: MedlinePlus. (2014). Web: <https://www.nlm.nih.gov/medlineplus/autoimmunediseases.html>.
Infections: MedlinePlus. (2016) Web:< https://www.nlm.nih.gov/medlineplus/infections.html>.
Guo, Fang. Anitmicrobial Agents and Chemotherapy. 59:2 (2015) 1273-1281.
Corrales, et al., “Direct Activation of STING in the Tumor Microenvironment Leads to Potent and Systemic Tumor Regression and Immunity,” Cell Reports (2015) 11, 1018-1030.
Fu, et al., “STING agonist formulated cancer vaccines can cure established tumors resistant to PD-1 blockade,” Sci. Transl. Med. 283, 283ra52 (2015).
Gao, et al., “Structure-Function Analysis of STING Activation by c[G(2',5')pA(3',5')p] and Targeting by Antiviral DMXAA ,”Mol Cell 154, 748-762 (2013).
Yan, et al., “Synthesis and immunostimulatory properties of the phosphorothioate analogues of cdiGMP,” Bioorganic & Medicinal Chemistry Letters, vol. 18, No. 20, 5631-5634 (2008).

CYCLIC DI-NUCLEOTIDE COMPOUNDS AND METHODS OF USE

CROSS-REFERENCE TO RELATED APPLICATIONS

This application is a continuation of U.S. application Ser. No. 15/953,492, filed Apr. 15, 2018, which is a continuation of International Application No. PCT/US17/023093, filed on Mar. 17, 2017, which claims the benefit of U.S. Provisional Application No. 62/310,364, filed Mar. 18, 2016, U.S. Provisional Application No. 62/355,382, filed Jun. 28, 2016, and U.S. Provisional Application No. 62/396,140, filed Sep. 17, 2016, the entire contents of each of which is hereby incorporated by reference herein.

TECHNICAL FIELD

The present invention provides novel cyclic di-nucleotide cGAMP analogs, pharmaceutical compositions thereof, their synthetic methods and their use in medical therapy. In particular, the compounds of the invention enhance the body's immune responses by activating STING (Stimulator of Interferon Genes) and are useful for the immunotherapy of cancer, infectious diseases and immune disorders. The compounds are also useful as adjuvants for developing vaccines against cancer and infectious diseases.

BACKGROUND

Cytosolic DNA induces type-I interferons and other cytokines that are important for immune defense against microbial infections and malignant cells but can also result in autoimmunity. This DNA signaling pathway requires the adaptor protein STING (Stimulator of Interferon Genes) and the transcription factor IRF3, but the mechanism of DNA sensing was unclear until recently. WO 2014099824 to The University of Texas disclosed that mammalian cytosolic extracts synthesized cyclic-GMP-AMP (cGAMP) in vitro from ATP and GTP in the presence of DNA but not RNA. DNA transfection or DNA virus infection of mammalian cells also triggered cGAMP production. cGAMP bound to STING, lead to the activation of IRF3 and induction of type-I interferons including interferon-β (IFN-β). Thus, cGAMP represents the first cyclic di-nucleotide in metazoa and it functions as an endogenous second messenger that triggers interferon production in response to cytosolic DNA.

Through biochemical fractionation and quantitative mass spectrometry, the inventors on WO 2014099824 also identified a cGAMP synthase (cGAS), which belongs to the nucleotidyltransferase family. Overexpression of cGAS activated the transcription factor IRF3 and induced IFN in a STING-dependent manner. Knockdown of cGAS inhibited IRF3 activation and IFN induction by DNA transfection or DNA virus infection. cGAS bound to DNA in the cytoplasm and catalyzed cGAMP synthesis. These results indicate that cGAS is a cytosolic DNA sensor that induces interferons by producing the second messenger cGAMP. The inventors on WO 2014099824 also determined that the second messenger cGAMP they isolated and synthesized contains two phosphodiester linkages, one between the 2'-OH of GMP and 5'-phosphate of AMP, and the othe between the 3'-OH of AMP and 5'-phosphate of GMP; this molecule is referred to as 2'3'-cGAMP.

Several additional patents applications in this field have henceforth published:

US20140205653 and US 20140341976 to Aduro Biotech disclose cyclic-di-nucleotide (CDN) compounds that activate and inhibit STING, respectively. In particular, the CDNs of the invention are provided in the form of a composition comprising one or more cyclic purine dinucleotides which activate or inhibit STING-dependent TBK1 activation and the resulting production of type I interferon.

WO 2015077354 A1 to The University of Chicago discloses Methods and compositions for treating cancer by intratumorally administering a stimulator of interferon genes (STING) agonist. In some embodiments, there are provided compositions and methods concerning methods for treating cancer in a subject comprising administering to the subject an effective amount of a stimulator of interferon genes (STING) agonist, wherein the STING agonist is administered intratumorally.

WO 2015161762 to Fudan University discloses the use of cyclic dinucleotide cGAMP for preparing antitumor drugs, wherein the tumor is gastric cancer, lung cancer, colon cancer, liver cancer, prostate cancer or pancreatic cancer. cGAMP was shown to inhibit the growth of human tumor cell lines in immune compromised mice.

WO 2015185565 to GlaxoSmithKline discloses a class of cyclic dinucleotide compounds, or a pharmaceutically acceptable salt and tautomers thereof, compositions, combinations and medicaments containing said compounds and processes for their preparation. The invention also relates to the use of said compounds, combinations, compositions and medicaments, in the treatment of diseases and conditions in which modulation of STING is beneficial, for example inflammation, allergic and autoimmune diseases, infectious diseases, cancer and as vaccine adjuvants.

WO 2014179335 to Memorial Sloan Kettering Cancer Center discloses compositions, methods, kits, and assays related to the use and/or exploitation of isomers of cGAMP as well as the structure of the enzyme cGAS.

There is still a need for the discovery and development of new cyclic di-nucleotide cGAMP analogs for use in medical therapy. Specifically, cGAMP analogues with better potency, stability and specificity than endogenous cGAMP are still needed cGAMP analogues with superior safety and efficacy in animal models of human diseases, including cancer and infectious diseases, have yet to be developed.

SUMMARY OF THE INVENTION

Formula I encompasses Formula Ia-Ii.

In one aspect, the present invention provides a compound of Formula Ia

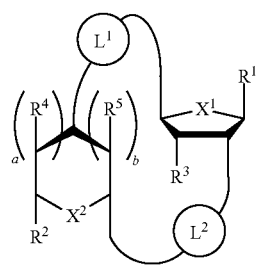

Formula Ia wherein:

a and b are independently 0 or 1 and a+b=1, when a is 1, b is 0 and $R^5$ is not present; and when a is 0, b is 1 and $R^4$ is not present;

$X^1$ and $X^2$ are independently O, S or Se in a five-membered ring;

$L^1$, starting from the carbon alpha to $X^1$, and $L^2$, starting from the carbon alpha to $X^2$, are independently —CH$_2$O—P(O)R$^6$—O—, —CH$_2$O—P(S)R$^6$—O—, —C(Y$^1$)(Y$^2$)O—P(O)R$^6$—C(Y$^3$)(Y$^4$)—, —CH$_2$NHSO$_2$NH—, —CH$_2$NHC(O)NH—, —CH$_2$NHC(S)NH—, —CH$_2$NHC(NH)NH—, —CH$_2$NHC(O)CH$_2$—, —CH$_2$NHSO$_2$CH$_2$—, —CH$_2$CH$_2$C(O)NH—, —CH$_2$CH$_2$SO$_2$NH—, —CH$_2$NH(3,4-dioxocyclobuten-1,2-diyl)NH—,

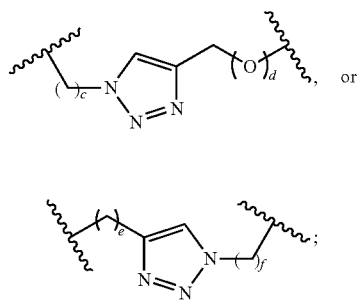

c is 0, 1, or 2;

d, e, and f are independently 0 or 1;

$Y^1$, $Y^2$, $Y^3$, and $Y^4$ are independently H or F;

$R^6$ is hydroxyl, thiol, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), borano (—BH$_3^-$), or —NR$^7$R$^8$;

$R^7$ and $R^8$ are independently hydrogen, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, cyclic —($C_{1-6}$alkyl)-, cyclic —($C_{1-6}$alkyl)- selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, or di($C_{1-6}$alkyl)amino groups, cyclic —($C_{1-6}$oxaalkyl)-, or cyclic —($C_{1-6}$oxaalkyl)- selectively functionalized with one or more halogen, thiol, hydroxyl, carbonyl, carboxyl, carbonyloxyl, $C_{1-6}$hydroxyalkoxy, amino, $C_{1-6}$alkylamino, or di($C_{1-6}$alkyl)amino groups;

$R^1$ and $R^2$ are independently aromatic rings or heteroaromatic rings with the following general structure including its tautomeric forms:

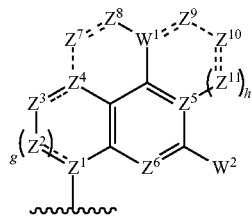

g and h are independently 0 or 1;

$W^1$ and $W^2$ are independently hydrogen, halogen, hydroxyl, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR$^7$R$^8$;

$Z^1$, $Z^2$, $Z^3$, $Z^4$, $Z^5$, and $Z^6$ are independently CH or N;

if present, $Z^7$, $Z^8$, $Z^9$, $Z^{10}$, and $Z^{11}$ are independently CH or N, and then $W^1$ is CH or N; and $R^3$, $R^4$, and $R^5$ are independently hydrogen, halogen, hydroxyl, amino, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR$^7$R$^8$;

or a pharmaceutically acceptable salt thereof.

In one embodiment, the present invention provides a compound of Formula Ib

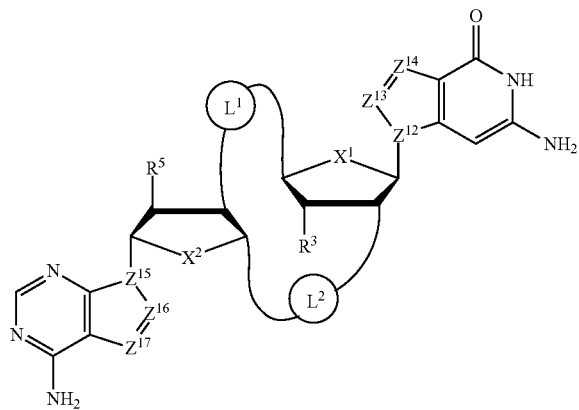

Formula Ib wherein:

$X^1$ and $X^2$ are independently O, S or Se;

$Z^{12}$, $Z^{13}$, $Z^{14}$, $Z^{15}$, $Z^{16}$, and $Z^{17}$ are independently CH or N;

$L^1$, starting from the carbon alpha to $X^1$, and $L^2$, starting from the carbon alpha to $X^2$, are independently —CH$_2$O—

P(O)R⁶—O—, —CH₂O—P(S)R⁶—O—, —C(Y¹)(Y²)O—P(O)R⁶—C(Y³)(Y⁴)—, —CH₂NHSO₂NH—, —CH₂NHC(O)NH—, —CH₂NHC(S)NH—, —CH₂NHC(NH)NH—, —CH₂NHC(O)CH₂—, —CH₂NHSO₂CH₂—, —CH₂CH₂C(O)NH—, —CH₂CH₂SO₂NH—, —CH₂NH(3,4-dioxocyclobuten-1,2-diyl)NH—,

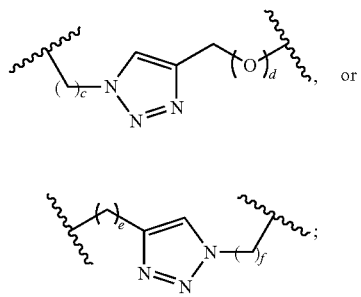, or c is 0, 1, or 2;

d, e, and f are independently 0 or 1;

$Y^1$, $Y^2$, $Y^3$, and $Y^4$ are independently H or F;

$R^6$ is hydroxyl, thiol, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), borano (—BH₃⁻), or —NR⁷R⁸;

$R^7$ and $R^8$ are independently hydrogen, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, cyclic —($C_{1-6}$alkyl)-, cyclic —($C_{1-6}$alkyl)- selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, or di($C_{1-6}$alkyl)amino groups, cyclic —($C_{1-6}$oxaalkyl)-, or cyclic —($C_{1-6}$oxaalkyl)- selectively functionalized with one or more halogen, thiol, hydroxyl, carbonyl, carboxyl, carbonyloxyl, $C_{1-6}$hydroxyalkoxy, amino, $C_{1-6}$alkylamino, or di($C_{1-6}$alkyl)amino groups; and $R^3$ and $R^4$ are independently hydrogen, halogen, hydroxyl, amino, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR⁷R⁸;

or a pharmaceutically acceptable salt thereof.

In another embodiment, the present invention provides a compound of Formula Ic

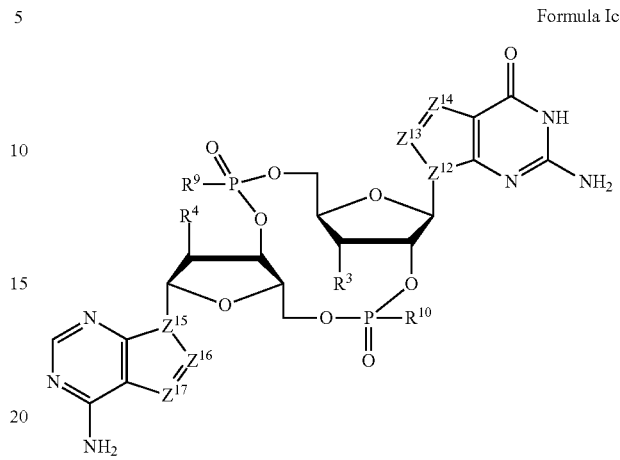

Formula Ic wherein:

$Z^{12}$, $Z^{13}$, $Z^{14}$, $Z^{15}$, $Z^{16}$, and $Z^{17}$ are independently CH or N;

$R^3$ and $R^4$ are independently hydrogen, halogen, hydroxyl, amino, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR⁷R⁸;

$R^7$ and $R^8$ are independently hydrogen, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, cyclic —($C_{1-6}$alkyl)-, cyclic —($C_{1-6}$alkyl)- selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, or di($C_{1-6}$alkyl)amino groups, cyclic —($C_{1-6}$oxaalkyl)-, or cyclic —($C_{1-6}$oxaalkyl)- selectively functionalized with one or more halogen, thiol, hydroxyl, carbonyl, carboxyl, carbonyloxyl, $C_{1-6}$hydroxyalkoxy, amino, $C_{1-6}$alkylamino, or di($C_{1-6}$alkyl)amino groups; and $R^9$ and $R^{10}$ are independently hydroxyl, thiol, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), borano (—BH₃⁻), or —NR⁷R⁸;

or a pharmaceutically acceptable salt thereof.

In another embodiment, the oxygen atom in one or both of the tetrahydrofuranyl rings of Formula Ic is replaced by a sulfur or a selenium atom.

In another embodiment, the present invention provides a compound of Formula Id

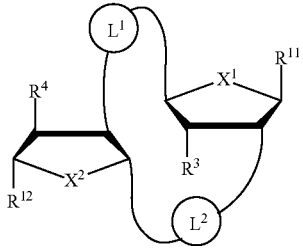

Formula Id wherein:

$X^1$ and $X^2$ are independently O, S or Se;

$L^1$, starting from the carbon alpha to $X^1$, and $L^2$, starting from the carbon alpha to $X^2$, are independently —CH$_2$O—P(O)R$^6$—O—, —CH$_2$O—P(S)R$^6$—O—, —C(Y$^1$)(Y$^2$)O—P(O)R$^6$—C(Y$^3$)(Y$^4$)—, —CH$_2$NHSO$_2$NH—, —CH$_2$NHC(O)NH—, —CH$_2$NHC(S)NH—, —CH$_2$NHC(NH)NH—, —CH$_2$NHC(O)CH$_2$—, —CH$_2$NHSO$_2$CH$_2$—, —CH$_2$CH$_2$C(O)NH—, —CH$_2$CH$_2$SO$_2$NH—, —CH$_2$NH(3,4-dioxocyclobuten-1,2-diyl)NH—,

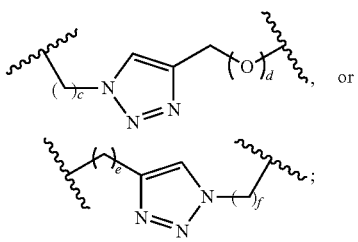

, or c is 0, 1, or 2;

d, e, and f are independently 0 or 1;

$Y^1$, $Y^2$, $Y^3$, and $Y^4$ are independently H or F;

$R^6$ is hydroxyl, thiol, C$_{1-6}$alkyl, C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, C$_{1-6}$alkoxy, C$_{1-6}$alkoxy selectively functionalized with one or more halogen, thiol, hydroxyl, carbonyl, carboxyl, carbonyloxyl, C$_{1-6}$hydroxyalkoxy, amino, C$_{1-6}$alkylamino, di(C$_{1-6}$alkyl)amino, or azido groups, C$_{3-5}$alkenyl-O—, C$_{3-5}$alkynyl-O—, oligo(ethylene glycol), poly(ethylene glycol), borano (—BH$_3^-$), or —NR$^7$R$^8$;

$R^7$ and $R^8$ are independently hydrogen, C$_{1-6}$alkyl, C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, cyclic —(C$_{1-6}$alkyl)-, cyclic —(C$_{1-6}$alkyl)- selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, or di(C$_{1-6}$alkyl)amino groups, cyclic —(C$_{1-6}$oxaalkyl)-, or cyclic —(C$_{1-6}$oxaalkyl)- selectively functionalized with one or more halogen, thiol, hydroxyl, carbonyl, carboxyl, carbonyloxyl, C$_{1-6}$hydroxyalkoxy, amino, C$_{1-6}$alkylamino, or di(C$_{1-6}$alkyl)amino groups;

$R^3$ and $R^4$ are independently hydrogen, halogen, hydroxyl, amino, C$_{1-6}$alkyl, C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, C$_{1-6}$alkoxy, C$_{1-6}$alkoxy selectively functionalized with one or more halogen, thiol, hydroxyl, carbonyl, carboxyl, carbonyloxyl, C$_{1-6}$hydroxyalkoxy, amino, C$_{1-6}$alkylamino, di(C$_{1-6}$alkyl)amino, or azido groups, C$_{3-5}$alkenyl-O—, C$_{3-5}$alkynyl-O—, oligo(ethylene glycol), poly(ethylene glycol), azido, or —NR$^7$R$^8$;

$R^{11}$ and $R^{12}$ are independently selected from the group consisting of:

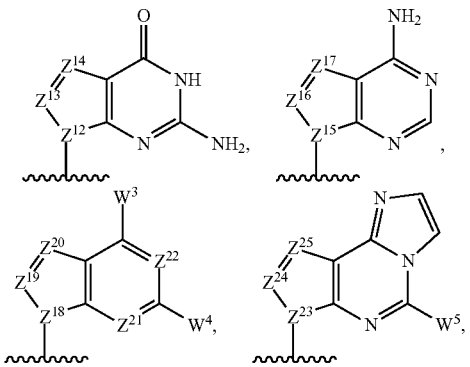

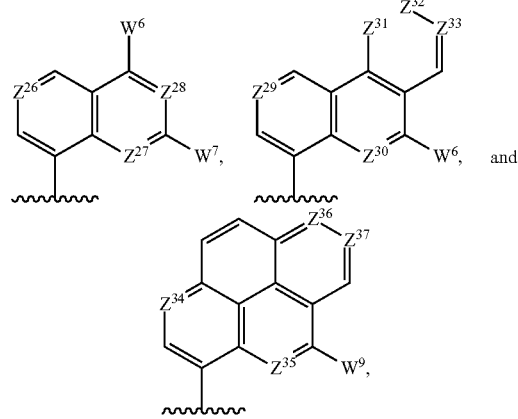

with at least one of $R^{11}$ and $R^{12}$ being

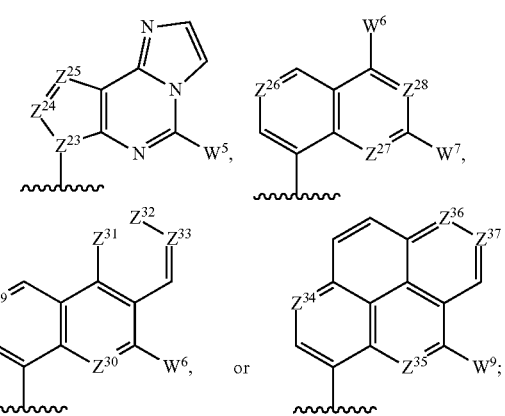

$Z^{12}$, $Z^{13}$, $Z^{14}$, $Z^{15}$, $Z^{16}$, $Z^{17}$, $Z^{18}$, $Z^{19}$, $Z^{20}$, $Z^{21}$, $Z^{22}$, $Z^{23}$, $Z^{24}$, $Z^{25}$, $Z^{26}$, $Z^{27}$, $Z^{28}$, $Z^{29}$, $Z^{30}$, $Z^{31}$, $Z^{32}$, $Z^{33}$, $Z^{34}$, $Z^{35}$, $Z^{36}$, and $Z^{37}$ are each independently CH or N; and $W^3$, $W^4$, $W^5$, $W^6$, $W^7$, $W^8$, and $W^9$ are independently hydrogen, halogen, hydroxyl, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR$^7$R$^8$;

or a pharmaceutically acceptable salt thereof.

In another embodiment, the present invention provides a compound of Formula Ie

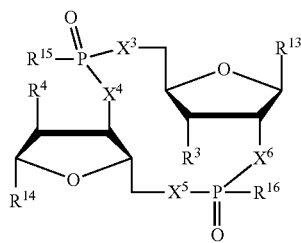

Formula Ie wherein:

$X^3$, $X^4$, $X^5$, and $X^6$ are independently O, NH, CH$_2$, CHF, or CF$_2$;

$R^{13}$ and $R^{14}$ are independently selected from the group consisting of:

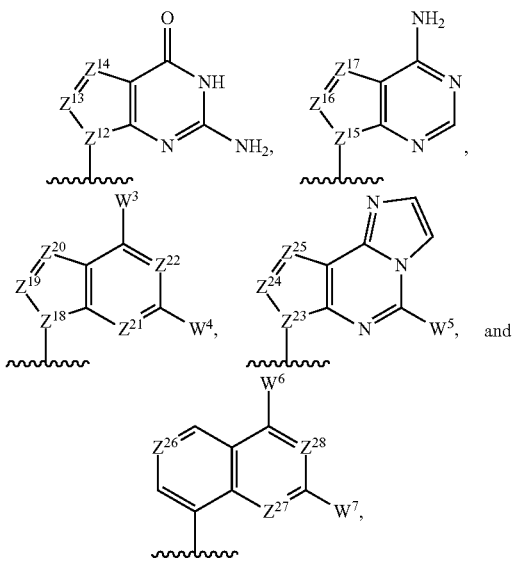

$Z^{12}$, $Z^{13}$, $Z^{14}$, $Z^{15}$, $Z^{16}$, $Z^{17}$, $Z^{18}$, $Z^{19}$, $Z^{20}$, $Z^{21}$, $Z^{22}$, $Z^{23}$, $Z^{24}$, $Z^{25}$, $Z^{26}$, $Z^{27}$, and $Z^{28}$ are each independently CH or N; and $W^3$, $W^4$, $W^5$, $W^6$, and $W^7$ are independently hydrogen, halogen, hydroxyl, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR$^7$R$^8$;

$R^7$ and $R^8$ are independently hydrogen, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, cyclic —($C_{1-6}$alkyl)-, cyclic —($C_{1-6}$alkyl)- selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, or di($C_{1-6}$alkyl)amino groups, cyclic —($C_{1-6}$oxaalkyl)-, or cyclic —($C_{1-6}$oxaalkyl)- selectively functionalized with one or more halogen, thiol, hydroxyl, carbonyl, carboxyl, carbonyloxyl, $C_{1-6}$hydroxyalkoxy, amino, $C_{1-6}$alkylamino, or di($C_{1-6}$alkyl)amino groups;

$R^3$ and $R^4$ are independently hydrogen, halogen, hydroxyl, amino, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR$^7$R$^8$; and $R^{15}$ and $R^{16}$ are independently hydroxyl, thiol, methoxy, ethoxy, amino, N-methylamino, N,N-dimethylamino, N-ethylamino, N,N-diethylamino, N-morpholino, or borano (—BH$_3^-$);

or a pharmaceutically acceptable salt thereof.

In another embodiment, the oxygen atom in one or both of the tetrahydrofuranyl rings of Formula Ie is replaced by a sulfur or a selenium atom.

In another embodiment, the compound is:

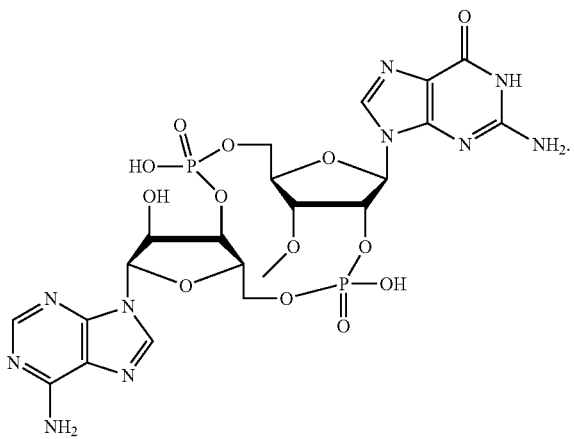

In another embodiment, the compound is:
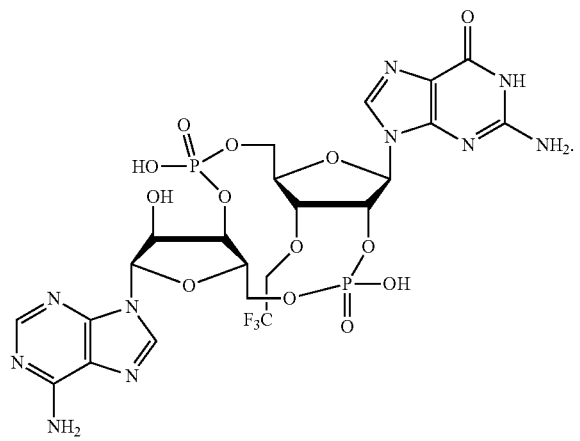
In another embodiment, the compound is:
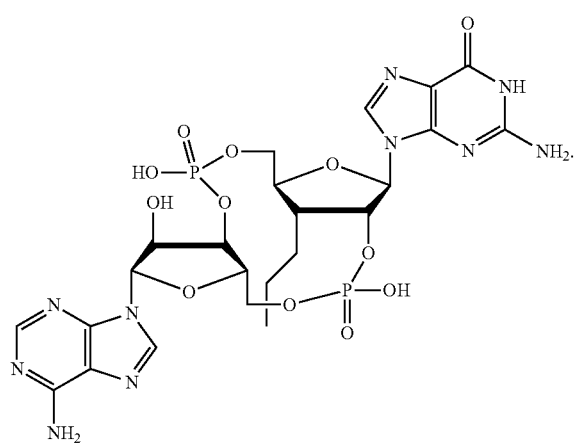
In another embodiment, the compound is:
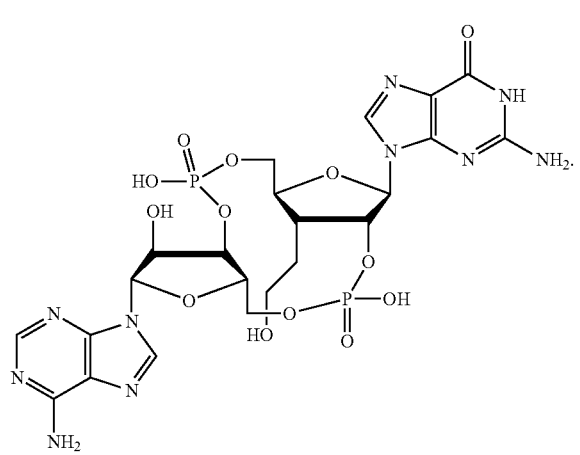
In another embodiment, the compound is:
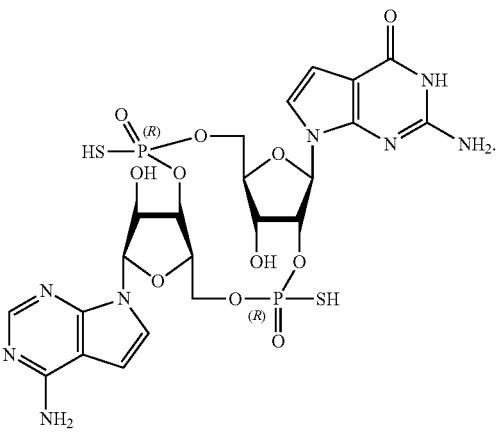
In another embodiment, the compound is:
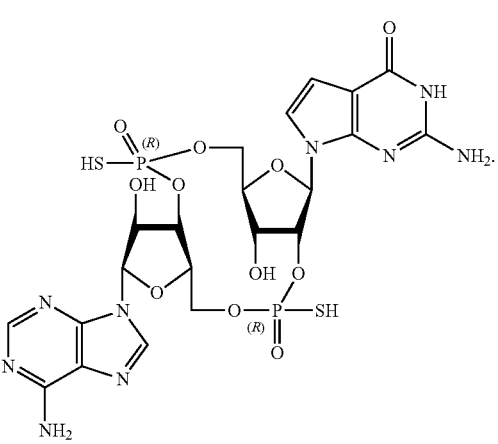
In another embodiment, the compound is:
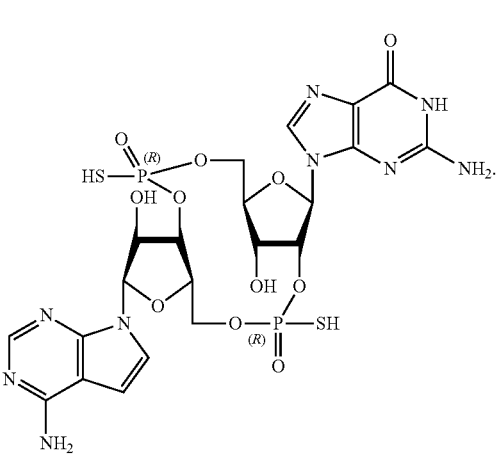

[In another embodiment, the compound is:
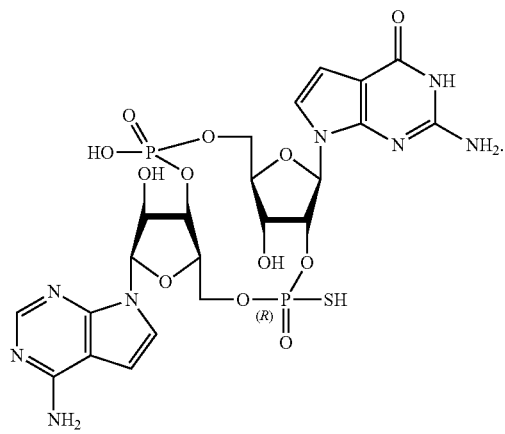
In another embodiment, the compound is:
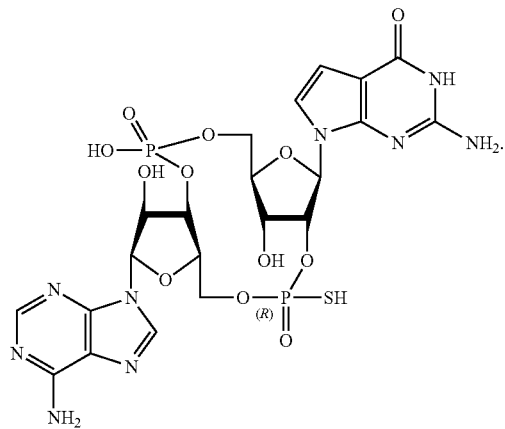
In another embodiment, the compound is:
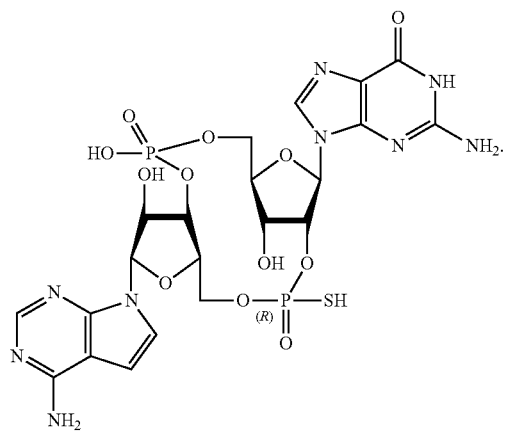
In another embodiment, the compound is:
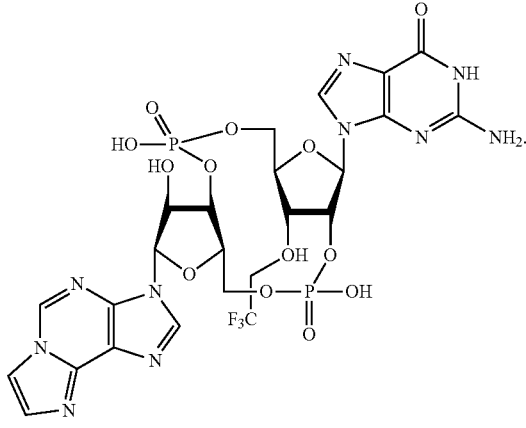
In another embodiment, the compound is:
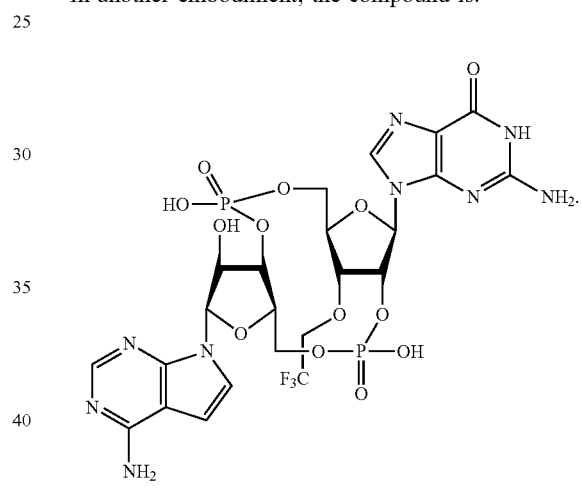
In another embodiment, the compound is:
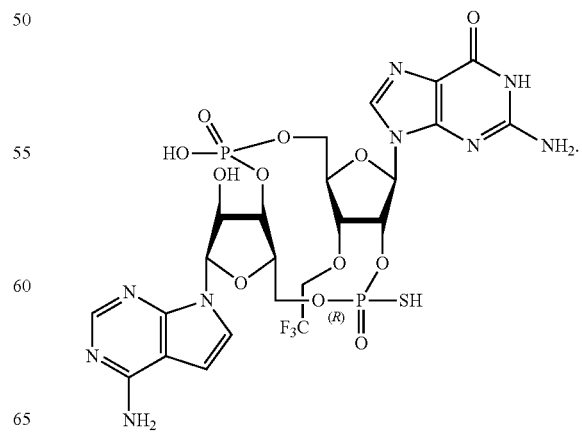

In another embodiment, the compound is:
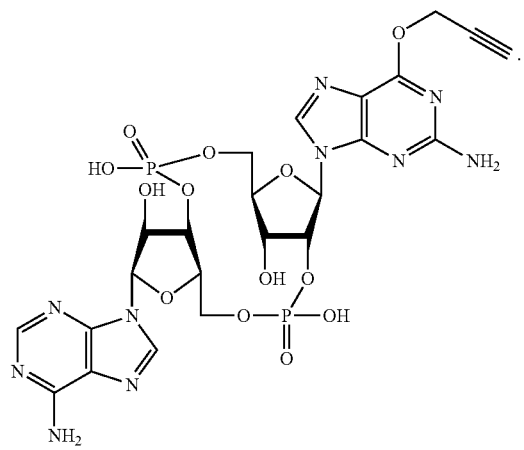
In another embodiment, the compound is:
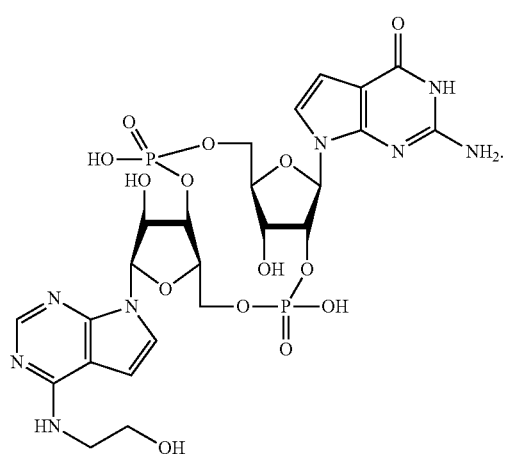
In another embodiment, the compound is:
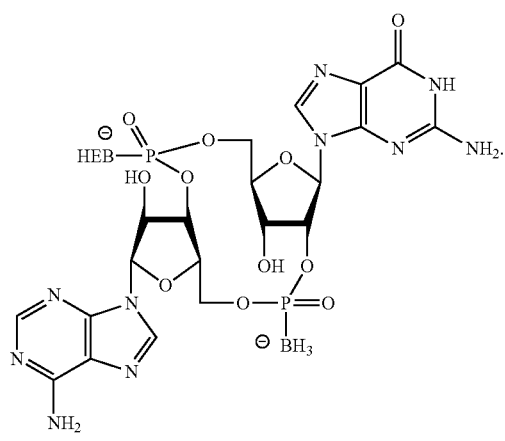
In another embodiment, the compound is:
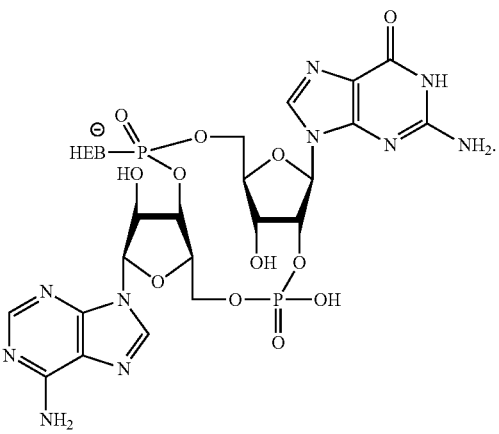
In another embodiment, the compound is:
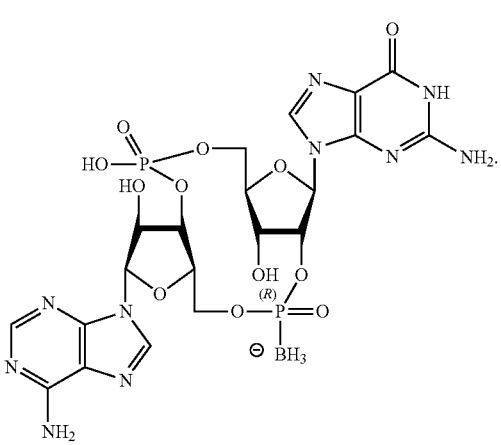
In another embodiment, the compound is:
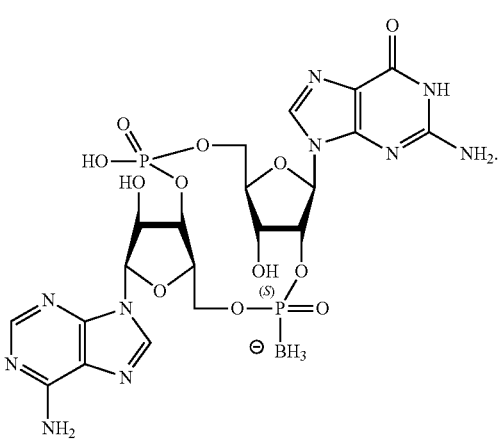

In another embodiment, the compound is:

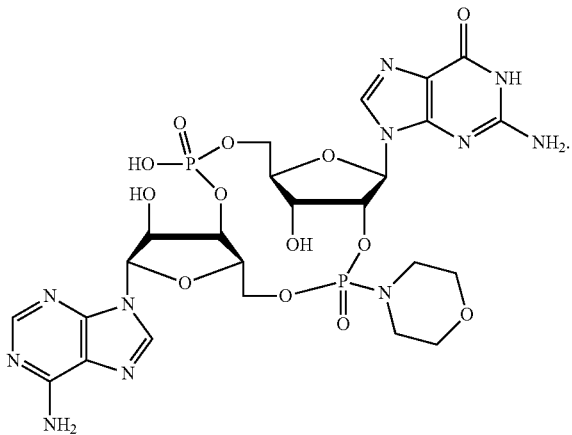

In another embodiment, the compound is:

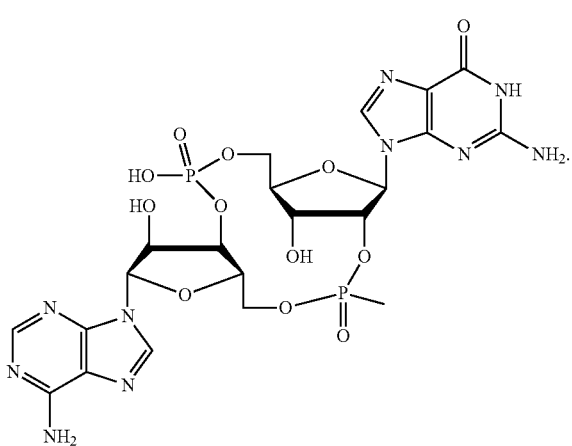

In one embodiment, the present invention provides a compound of Formula If

Formula If

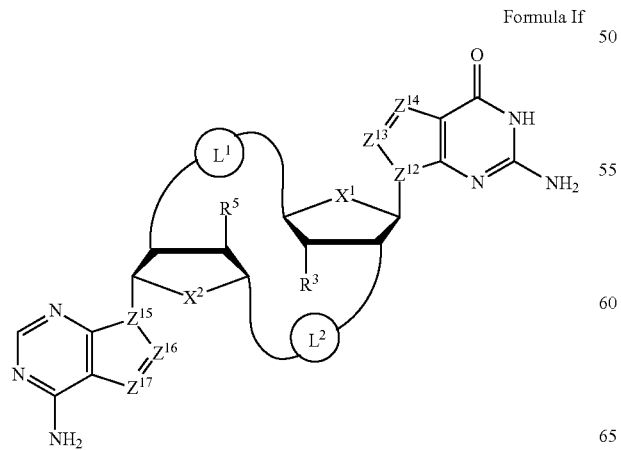

wherein:
$X^1$ and $X^2$ are independently O, S or Se;
$Z^{12}$, $Z^{13}$, $Z^{14}$, $Z^{15}$, $Z^{16}$, and $Z^{17}$ are independently CH or N;
$L^1$, starting from the carbon alpha to $X^1$, and $L^2$, starting from the carbon alpha to $X^2$, are independently —CH$_2$O—P(O)R$^6$—O—, —CH$_2$O—P(S)R$^6$—O—, —C(Y$^1$)(Y$^2$)O—P(O)R$^6$—C(Y$^3$)(Y$^4$)—, —CH$_2$NHSO$_2$NH—, —CH$_2$NHC(O)NH—, —CH$_2$NHC(S)NH—, —CH$_2$NHC(NH)NH—, —CH$_2$NHC(O)CH$_2$—, —CH$_2$NHSO$_2$CH$_2$—, —CH$_2$CH$_2$C(O)NH—, —CH$_2$CH$_2$SO$_2$NH—, —CH$_2$NH(3,4-dioxocyclobuten-1,2-diyl)NH—,

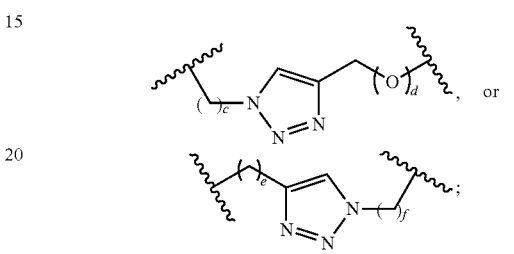

c is 0, 1, or 2;
d, e, and f are independently 0 or 1;
$Y^1$, $Y^2$, $Y^3$, and $Y^4$ are independently H or F;
$R^6$ is hydroxyl, thiol, C$_{1-6}$alkyl, C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, C$_{1-6}$alkoxy, C$_{1-6}$alkoxy selectively functionalized with one or more halogen, thiol, hydroxyl, carbonyl, carboxyl, carbonyloxyl, C$_{1-6}$hydroxyalkoxy, amino, C$_{1-6}$alkylamino, di(C$_{1-6}$alkyl)amino, or azido groups, C$_{3-5}$alkenyl-O—, C$_{3-5}$alkynyl-O—, oligo(ethylene glycol), poly(ethylene glycol), borano (—BH$_3^-$), or —NR$^7$R$^8$;
$R^7$ and $R^8$ are independently hydrogen, C$_{1-6}$alkyl, C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, cyclic —(C$_{1-6}$alkyl)-, cyclic —(C$_{1-6}$alkyl)- selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, or di(C$_{1-6}$alkyl)amino groups, cyclic —(C$_{1-6}$oxaalkyl)-, or cyclic —(C$_{1-6}$oxaalkyl)- selectively functionalized with one or more halogen, thiol, hydroxyl, carbonyl, carboxyl, carbonyloxyl, C$_{1-6}$hydroxyalkoxy, amino, C$_{1-6}$alkylamino, or di(C$_{1-6}$alkyl)amino groups; and
$R^3$ and $R^5$ are independently hydrogen, halogen, hydroxyl, amino, C$_{1-6}$alkyl, C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, C$_{1-6}$alkoxy, C$_{1-6}$alkoxy selectively functionalized with one or more halogen, thiol, hydroxyl, carbonyl, carboxyl, carbonyloxyl, C$_{1-6}$hydroxyalkoxy, amino, C$_{1-6}$alkylamino, di(C$_{1-6}$alkyl)amino, or azido groups, C$_{3-5}$alkenyl-O—, C$_{3-5}$alkynyl-O—, oligo(ethylene glycol), poly(ethylene glycol), azido, or —NR$^7$R$^8$;
or a pharmaceutically acceptable salt thereof.

In one embodiment, the present invention provides a compound of Formula Ig

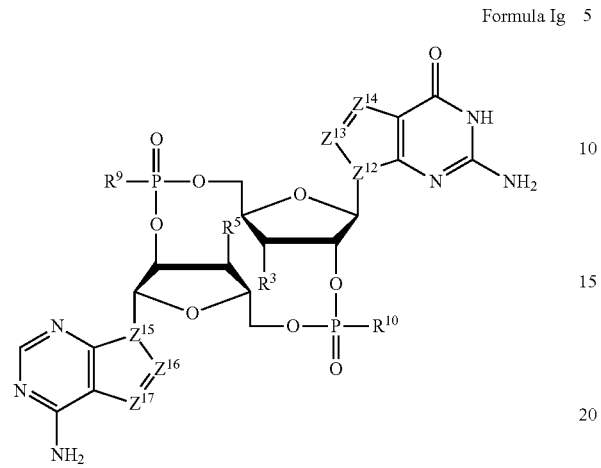

Formula Ig wherein:
$Z^{12}$, $Z^{13}$, $Z^{14}$, $Z^{15}$, $Z^{16}$, and $Z^{17}$ are independently CH or N;

$R^3$ and $R^5$ are independently hydrogen, halogen, hydroxyl, amino, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR$^7$R$^8$;

$R^7$ and $R^8$ are independently hydrogen, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, cyclic —($C_{1-6}$alkyl)-, cyclic —($C_{1-6}$alkyl)- selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, or di($C_{1-6}$alkyl)amino groups, cyclic —($C_{1-6}$oxaalkyl)-, or cyclic —($C_{1-6}$oxaalkyl)- selectively functionalized with one or more halogen, thiol, hydroxyl, carbonyl, carboxyl, carbonyloxyl, $C_{1-6}$hydroxyalkoxy, amino, $C_{1-6}$alkylamino, or di($C_{1-6}$alkyl)amino groups; and $R^9$ and $R^{10}$ are independently hydroxyl, thiol, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), borano (—BH$_3^-$), or —NR$^7$R$^8$;

or a pharmaceutically acceptable salt thereof.

In another embodiment, the oxygen atom in one or both of the tetrahydrofuranyl rings of Formula Ig is replaced by a sulfur or a selenium atom.

In another embodiment, the present invention provides a compound of Formula Ih

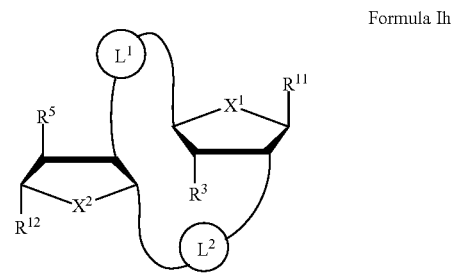

Formula Ih wherein:
$X^1$ and $X^2$ are independently O, S or Se;

$L^1$, starting from the carbon alpha to $X^1$, and $L^2$, starting from the carbon alpha to $X^2$, are independently —CH$_2$O—P(O)R$^6$—O—, —CH$_2$O—P(S)R$^6$—O—, —C(Y$^1$)(Y$^2$)O—P(O)R$^6$—C(Y$^3$)(Y$^4$)—, —CH$_2$NHSO$_2$NH—, —CH$_2$NHC(O)NH—, —CH$_2$NHC(S)NH—, —CH$_2$NHC(NH)NH—, —CH$_2$NHC(O)CH$_2$—, —CH$_2$NHSO$_2$CH$_2$—, —CH$_2$CH$_2$C(O)NH—, —CH$_2$CH$_2$SO$_2$NH—, —CH$_2$NH(3,4-dioxocyclobuten-1,2-diyl)NH—,

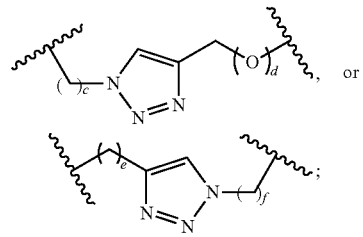

c is 0, 1, or 2;
d, e, and f are independently 0 or 1;
$Y^1$, $Y^2$, $Y^3$, and $Y^4$ are independently H or F;
$R^6$ is hydroxyl, thiol, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), borano (—BH$_3^-$), or —NR$^7$R$^8$;

$R^7$ and $R^8$ are independently hydrogen, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, cyclic —($C_{1-6}$alkyl)-, cyclic —($C_{1-6}$alkyl)- selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, or di($C_{1-6}$alkyl)amino groups, cyclic —($C_{1-6}$oxaalkyl)-, or cyclic —($C_{1-6}$oxaalkyl)- selectively functionalized with one or more halogen, thiol, hydroxyl, carbonyl, carboxyl, carbonyloxyl, $C_{1-6}$hydroxyalkoxy, amino, $C_{1-6}$alkylamino, or di($C_{1-6}$alkyl)amino groups;

$R^3$ and $R^5$ are independently hydrogen, halogen, hydroxyl, amino, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —$NR^7R^8$;

$R^1$ and $R^{12}$ are independently selected from the group consisting of:

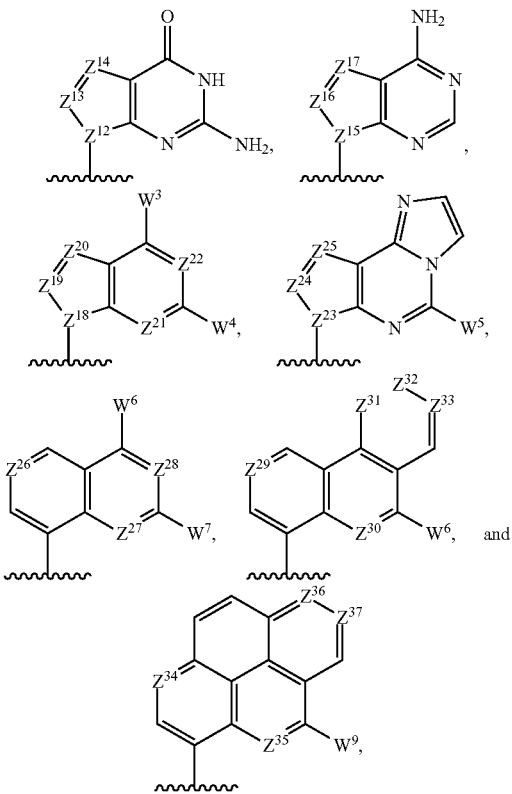

with at least one of $R^{11}$ and $R^{12}$ being

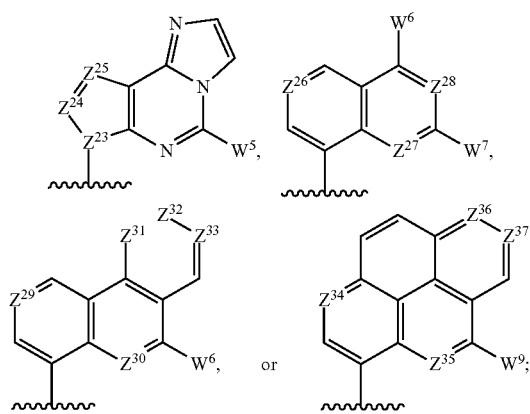

$Z^{12}, Z^{13}, Z^{14}, Z^{15}, Z^{16}, Z^{17}, Z^{18}, Z^{19}, Z^{20}, Z^{21}, Z^{22}, Z^{23}, Z^{24}, Z^{25}, Z^{26}, Z^{27}, Z^{28}, Z^{29}, Z^{30}, Z^{31}, Z^{32}, Z^{33}, Z^{34}, Z^{35}, Z^{36}$, and $Z^{37}$ are each independently CH or N; and $W^3, W^4, W^5, W^6, W^7, W^8$, and $W^9$ are independently hydrogen, halogen, hydroxyl, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —$NR^7R^8$;

or a pharmaceutically acceptable salt thereof.

In another embodiment, the present invention provides a compound of Formula Ii

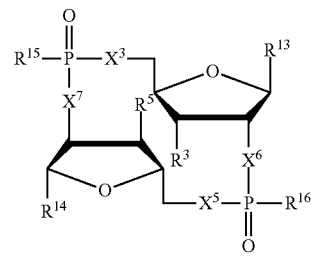

Formula Ii wherein:

$X^3, X^5, X^6$, and $X^7$ are independently O, NH, $CH_2$, CHF, or $CF_2$;

$R^{13}$ and $R^{14}$ are independently selected from the group consisting of:

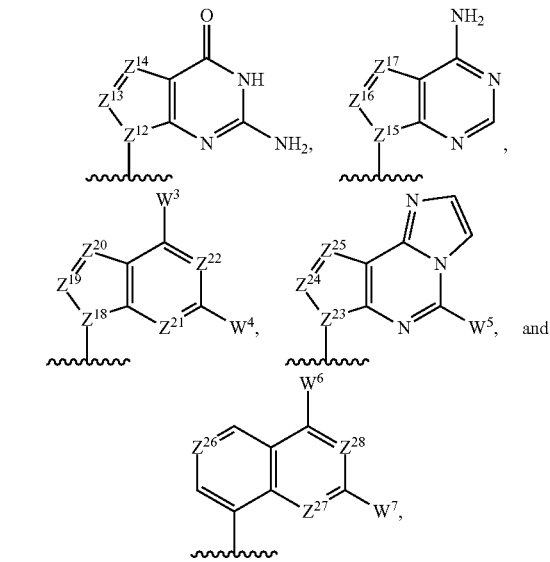

$Z^{12}, Z^{13}, Z^{14}, Z^{15}, Z^{16}, Z^{17}, Z^{18}, Z^{19}, Z^{20}, Z^{21}, Z^{22}, Z^{23}, Z^{24}, Z^{25}, Z^{26}, Z^{27}$, and $Z^{28}$ are each independently CH or N; and $W^3, W^4, W^5, W^6$, and $W^7$ are independently hydrogen, halogen, hydroxyl, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR$^7$R$^8$;

R$^7$ and R$^8$ are independently hydrogen, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, cyclic —($C_{1-6}$alkyl)-, cyclic —($C_{1-6}$alkyl)- selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, or di($C_{1-6}$alkyl)amino groups, cyclic —($C_{1-6}$oxaalkyl)-, or cyclic —($C_{1-6}$oxaalkyl)- selectively functionalized with one or more halogen, thiol, hydroxyl, carbonyl, carboxyl, carbonyloxyl, $C_{1-6}$hydroxyalkoxy, amino, $C_{1-6}$alkylamino, or di($C_{1-6}$alkyl)amino groups;

R$^3$ and R$^5$ are independently hydrogen, halogen, hydroxyl, amino, $C_{1-6}$alkyl, $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, $C_{1-6}$alkoxy, $C_{1-6}$alkoxy selectively functionalized with one or more halogen, thiol, hydroxyl, carbonyl, carboxyl, carbonyloxyl, $C_{1-6}$hydroxyalkoxy, amino, $C_{1-6}$alkylamino, di($C_{1-6}$alkyl)amino, or azido groups, $C_{3-5}$alkenyl-O—, $C_{3-5}$alkynyl-O—, oligo(ethylene glycol), poly(ethylene glycol), azido, or —NR$^7$R$^8$; and R$^{15}$ and R$^{16}$ are independently hydroxyl, thiol, methoxy, ethoxy, amino, N-methylamino, N,N-dimethylamino, N-ethylamino, N,N-diethylamino, N-morpholino, or borano (—BH$_3^-$);

or a pharmaceutically acceptable salt thereof.

In another embodiment, the oxygen atom in one or both of the tetrahydrofuranyl rings of Formula Ii is replaced by a sulfur or a selenium atom.

In another embodiment, the compound is:

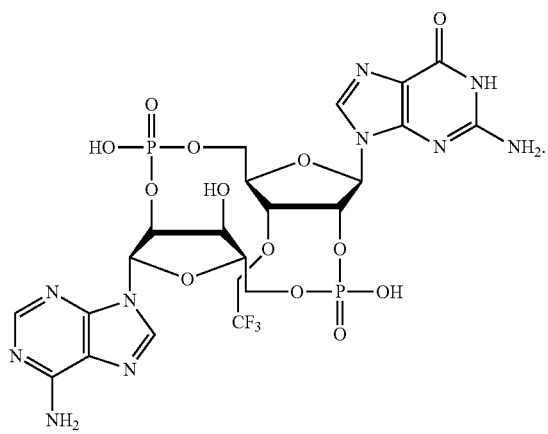 [SMILES: Nc1nc2c(ncn2[C@@H]2O[C@@H]3COP(=O)(O)OC4[C@@H](O)[C@@H](COP(=O)(O)OC2[C@H]3OCC(F)(F)F)O[C@H]4n2cnc3c(N)ncnc32)c(=O)[nH]1]

In another embodiment, the compound is:

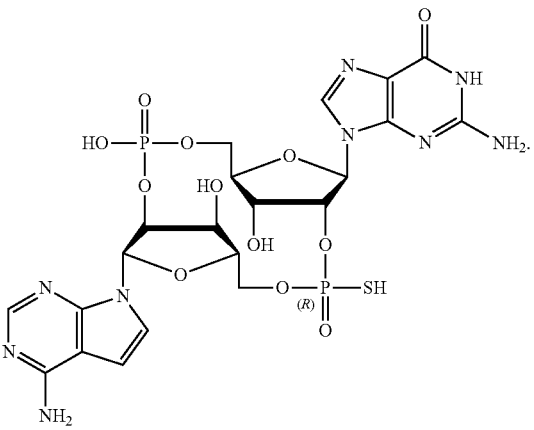

In another aspect, the present invention provides a pharmaceutical composition comprising a compound of Formula I or a pharmaceutically acceptable salt thereof, and one or more pharmaceutically acceptable excipients.

In another aspect, the present invention provides a method of treating a disease or condition in which modulation of STING is beneficial comprising: administering to a patient in need thereof a compound of Formula I or a pharmaceutically acceptable salt thereof.

In another aspect, the present invention provides a compound of Formula I or a pharmaceutically acceptable salt thereof, for use in the treatment of a disease or condition in which modulation of STING is beneficial.

In another aspect, the present invention provides a compound of Formula I or a pharmaceutically acceptable salt thereof, for use in therapy.

In another aspect, the present invention provides a compound of Formula I or a pharmaceutically acceptable salt thereof, for use in the treatment of cancer.

In another aspect, the present invention provides a compound of Formula I or a pharmaceutically acceptable salt thereof, or a pharmaceutically composition thereof, such as a nanoparticle or a delivery vehicles that enhances the cellular uptake, stability and efficacy of a compound of Formula I for use in the treatment of cancer.

In another aspect, the present invention provides a method of treating cancer comprising: administering a therapeutically effective amount of a compound of Formula I, or a pharmaceutically acceptable salt thereof, to a patient in need thereof.

In another aspect, the present invention provides the use of a compound of Formula I, or a pharmaceutically acceptable salt thereof, in the manufacture of a medication for the treatment of cancer.

In another aspect, the present invention provides pharmaceutical composition comprising: a compound of Formula I, or a pharmaceutically acceptable salt thereof, and at least one further therapeutic agent.

In another aspect, the present invention provides a pharmaceutical composition comprising: a compound of Formula I, or a pharmaceutically acceptable salt thereof, at least one further therapeutic agent, and one or more of pharmaceutically acceptable excipients.

In another aspect, the present invention provides a pharmaceutical composition comprising: a compound of Formula I, or a pharmaceutically acceptable salt thereof, and at least one further therapeutic agent for use in therapy.

In another aspect, the present invention provides a pharmaceutical composition comprising: a compound of Formula I, or a pharmaceutically acceptable salt thereof, and at least one further therapeutic agent for use in the treatment of a disease or condition for which modulation of STING is beneficial.

In another aspect, the present invention provides a pharmaceutical composition comprising: a compound of Formula I, or a pharmaceutically acceptable salt thereof, and at least one further therapeutic agent for use in the treatment of cancer.

In another aspect, the present invention provides a method for treating a disease or condition for which modulation of STING is beneficial comprising: administering to a patient in need thereof a therapeutically effective amount of a combination comprising a compound of Formula I, or a pharmaceutically acceptable salt thereof, and at least one further therapeutic agent.

In another aspect, the present invention provides a method of treating cancer comprising: administering to a patient in need thereof a therapeutically effective amount of a pharmaceutical composition comprising: a compound of Formula I, or a pharmaceutically acceptable salt thereof, and at least one further therapeutic agent.

In another aspect, the present invention provides a pharmaceutical composition comprising: a compound of Formula I, or a pharmaceutically acceptable salt thereof, and at least one further therapeutic agent for use in the treatment of cancer. The therapeutic agent includes but is not limited to immune checkpoint inhibitors, such as humanized antibodies against PD1, PD-L1, CTLA4 and other molecules that block effective anti-tumor immune responses.

In another aspect, the present invention provides a method of treating cancer comprising: administering to a patient in need thereof a therapeutically effective amount of a pharmaceutical composition comprising: a compound of Formula I, or a pharmaceutically acceptable salt thereof, and at least one further therapeutic agent. The therapeutic agent includes but is not limited to immune checkpoint inhibitors, such as humanized antibodies against PD1, PD-L1, CTLA4 and other molecules that block effective anti-tumor immune responses.

In another aspect, the present invention provides a pharmaceutical composition comprising: a compound of Formula I, or a pharmaceutically acceptable salt thereof, and at least one further therapeutic agent for use in the treatment of cancer. The therapeutic agent includes radiation, such as high-dose radiation, which directly kills tumor cells, enhances presentation of tumor antigens and activates the STING pathway.

In another aspect, the present invention provides a method of treating cancer comprising: administering to a patient in need thereof a therapeutically effective amount of a pharmaceutical composition comprising: a compound of Formula I, or a pharmaceutically acceptable salt thereof, and at least one further therapeutic agent. The therapeutic agent includes radiation, such as high-dose radiation, which directly kills tumor cells, enhances presentation of tumor antigens and activates the STING pathway.

In another aspect, the present invention provides a pharmaceutical composition comprising: a compound of Formula I, or a pharmaceutically acceptable salt thereof, and at least one further therapeutic agent for use in the treatment of cancer. The therapeutic agent includes another chemotherapeutic agent that selectively kills tumor cells and enhances presentation of tumor antigens.

In another aspect, the present invention provides a method of treating cancer comprising: administering to a patient in need thereof a therapeutically effective amount of a pharmaceutical composition comprising: a compound of Formula I, or a pharmaceutically acceptable salt thereof, and at least one further therapeutic agent. The therapeutic agent includes another chemotherapeutic agent that selectively kills tumor cells and enhances presentation of tumor antigens.

In another aspect, the present invention provides a pharmaceutical composition comprising: a compound of Formula I, or a pharmaceutically acceptable salt thereof, a pharmaceutical formulation including a nanoparticle, and at least one further therapeutic agent for use in the treatment of cancer. The therapeutic agent includes radiation and/or another chemotherapeutic agent.

In another aspect, the present invention provides a method of treating cancer comprising: administering to a patient in need thereof a therapeutically effective amount of a pharmaceutical composition comprising: a compound of Formula I, or a pharmaceutically acceptable salt thereof, a pharmaceutical formulation including a nanoparticle, and at least one further therapeutic agent for use in the treatment of cancer. The therapeutic agent includes radiation and/or another chemotherapeutic agent.

In another aspect, the present invention provides a method of treating cancer comprising: administering to a patient in need thereof a therapeutically effective amount of a pharmaceutical composition comprising: a compound of Formula I, or a pharmaceutically acceptable salt thereof, a pharmaceutical formulation including a nanoparticle, and at least one further therapeutic agent for use in the treatment of cancer. The compound of Formula I, may be injected directly to tumors, or systemically, including injection into muscles (intramuscular), skins (subcutaneous and intradermal), peritoneal (intraperitoneal), lymph nodes (intralymphatic) or veins (intravenous).

In another aspect, the present invention provides a compound of Formula I, or a pharmaceutically acceptable salt thereof, for use as a vaccine adjuvant.

In another aspect, the present invention provides a compound of Formula I, or a pharmaceutically acceptable salt thereof, or a pharmaceutical composition thereof, such as a nanoparticle or a delivery vehicles that enhances the cellular uptake, stability and efficacy of a compound of Formula I, for use as a vaccine adjuvant.

In one embodiment, the pharmaceutical composition is a vaccine.

In another embodiment, the present invention provides a method of inducing or promoting an immune response comprising: administering to a patient in need thereof a therapeutically effective amount of a pharmaceutical composition comprising a compound of Formula I, or a pharmaceutically acceptable salt thereof, as an adjuvant and a tumor antigen.

In another embodiment, the present invention provides a method of inducing or promoting an immune response comprising: administering to a patient in need thereof a therapeutically effective amount of a pharmaceutical composition comprising a compound of Formula I, or a pharmaceutical composition thereof, as an adjuvant, a tumor antigen, or a pharmaceutical composition thereof, such as a nanoparticle or a delivery vehicles that enhances the cellular uptake of the adjuvant and tumor antigen.

In another aspect, the present invention provides a pharmaceutical composition comprising: a compound of Formula I, or a pharmaceutically acceptable salt thereof, as an adjuvant and an immunogen for a target pathogen.

In another aspect, the present invention provides a compound of Formula I, or a pharmaceutically acceptable salt thereof, for use as a vaccine adjuvant.

In another embodiment, the present invention provides a method of inducing or promoting an immune response comprising: administering to a patient in need thereof a therapeutically effective amount of a pharmaceutical composition comprising a compound of Formula I, or a pharmaceutically acceptable salt thereof, as an adjuvant and an immunogen for a target pathogen.

In another aspect, the present invention provides a vaccine adjuvant comprising: a compound of Formula I, or a pharmaceutically acceptable salt thereof.

In another aspect, the present invention provides an immunogenic composition comprising: an antigen or antigen composition and a compound of Formula I, or a pharmaceutically acceptable salt thereof.

In another aspect, the present invention provides an immunogenic composition comprising: an antigen or antigen composition and a compound of Formula I, or a pharmaceutically acceptable salt thereof, for use in the treatment or prevention of a disease, including cancer and infectious diseases.

In another aspect, the present invention provides the use of a compound of Formula I, or a pharmaceutically acceptable salt thereof, for the manufacture of an immunogenic composition comprising an antigen or antigen composition, for the treatment or prevention of a disease, including cancer and infectious diseases.

In another aspect, the present invention provides a method of treating or preventing a disease comprising: administering to a patient suffering from or susceptible to the disease, an immunogenic composition comprising an antigen or antigen composition and a compound of Formula I, or a pharmaceutically acceptable salt thereof.

In another aspect, the present invention provides a vaccine composition comprising: an antigen or antigen composition and a compound of Formula I, or a pharmaceutically acceptable salt thereof, for use in the treatment or prevention of a disease, including cancer and infectious diseases.

In another aspect, the present invention provides the use of a compound of Formula I, or a pharmaceutically acceptable salt thereof, for the manufacture of a vaccine composition comprising an antigen or antigen composition for the treatment or prevention of a disease, including cancer and infectious diseases.

In another aspect, the present invention provides a method of treating or preventing disease comprising the administration to a patient suffering from or susceptible to the disease, a vaccine composition comprising an antigen or antigen composition and a compound of Formula I, or a pharmaceutically acceptable salt thereof.

In another aspect, the present invention provides a compound of Formula I, or a pharmaceutically acceptable salt thereof, for use in the treatment of immune disorders, including autoimmune and autoinflammatory diseases.

In another aspect, the present invention provides a compound of Formula I, or a pharmaceutically acceptable salt thereof, or a pharmaceutical composition thereof, such as a nanoparticle or a delivery vehicles that enhances the cellular uptake, stability and efficacy of a compound of Formula I, for use in the treatment of immune disorders, including autoimmune and autoinflammatory diseases.

In another aspect, the present invention provides a method of treating immune disorders comprising: administering a therapeutically effective amount of a compound of Formula I, or a pharmaceutically acceptable salt thereof, to a patient in need thereof.

In another aspect, the present invention provides the use of a compound of Formula I, or a pharmaceutically acceptable salt thereof, in the manufacture of a medication for the treatment of immune disorders, including autoimmune and autoinflammatory diseases.

It will be appreciated that all combinations of the above aspects/embodiments, and other aspects/embodiments disclosed elsewhere herein, are contemplated and are further embodiments of the invention.

DETAILED DESCRIPTION

The present invention provides novel cGAMP analogs, pharmaceutical compositions thereof, and uses thereof in therapy. 2'3'-cGAMP is an endogenous second messenger produced by mammalian cells. It is a high affinity ligand for STING, inducing conformational changes therein, and a potent inducer of type-I interferons. cGAS and the cGAS-cGAMP pathway is important for triggering inflammatory responses to self and foreign DNA. As such, cGAS is important for immune defense against microbial pathogens that contain DNA and require DNA in their life cycles. These pathogens include DNA viruses, retroviruses including HIV, bacteria including *Mycobacterium tuberculosis*, fungi and parasites. cGAS can also detect tumor DNA and is important for the body's intrinsic immunity against malignant cells. Activation of the cGAS-cGAMP-STING pathway is important for cancer immunotherapy.

As a potent inducer of type-I interferons, cGAMP (and hence the cGAMP analogs of the present invention) provides a rational immune adjuvant. As such, a compound of Formula I or a pharmaceutically acceptable salt thereof may be used as a vaccine adjuvant, particularly with mucosal vaccines, and may be formulated with immunogens and delivered as have been cyclic-di-GMP and c-di-AMP as vaccine adjuvants (see, e.g. Pedersen, et al. PLoS ONE, November 2011, 6, 11, e26973; Ebensen et al., Vaccine 29, 2011, 5210-5220; Chen et al., Vaccine 28, 2010, 3080-3085). In fact, such adjuvants are often more effective because cGAMP (and the cGAMP analogs of the present invention) is more potent than c-di-GMP in inducing interferons.

In one aspect, the invention provides a pharmaceutical composition comprising a compound of Formula I or a pharmaceutically acceptable salt thereof, for use in the treatment of cancer. In one embodiment, the pharmaceutical composition is a compound of Formula I. In another embodiment, the pharmaceutical composition is a compound of Formula I in a pharmaceutical formulation including a nanoparticle or another delivery vehicle. In another embodiment, the pharmaceutical composition is a compound of Formula I in combination with at least one further therapeutic agent, which includes but is not limited to immune checkpoint inhibitors such as antibodies against PD-1, PD-L1 or CTLA-4. The therapeutic agent used in combination with a compound of Formula I also includes radiation of tumors or a chemotherapeutic agent that targets tumor cells.

In another aspect, the invention provides a pharmaceutical composition comprising a compound of Formula I or a pharmaceutically acceptable salt thereof, as an adjuvant and an immunogen for a target pathogen. In one embodiment, the pharmaceutical composition is a vaccine. In another embodiment, the present invention provides a method of inducing or promoting an immune response comprising: administering to a patient in need thereof an effective amount a pharmaceutical composition comprising a compound of Formula I or a pharmaceutically acceptable salt thereof as an adjuvant and an immunogen for a target pathogen.

As used herein:

The terms "halo" and "halogen", alone or in combination with other groups, refers to fluoro-, chloro-, bromo- and iodo-.

The term "$C_{1-6}$ alkyl", alone or in combination with other groups, refers to monovalent, linear chain or branched chain alkyl groups containing from 1 to 6 carbon atoms. Exemplary $C_{1-6}$ alkyl groups include but not limited to methyl, ethyl, n-propyl, iso-propyl, n-butyl, sec-butyl and tert-butyl groups. More preferred are $C_{1-4}$ alkyls.

The term "$C_{1-6}$ alkoxy" refers to, alone or in combination with other groups, R'—O—, where R' is $C_{1-6}$ alkyl.

The term "halo$C_{1-6}$alkyl", alone or in combination with other groups, refers to a $C_{1-6}$ alkyl group substituted with one or more halo substitutents, for example $CF_3$ and $CH_2CF_3$.

The term "a compound of the invention" or "a compound of Formula I" includes all solvates, complexes, poly morphs, radiolabeled derivatives, tautomers, stereoisomers, and optical isomers of the compounds of Formula I and salts thereof unless otherwise specified.

The term "effective amount" means that amount of a drug or pharmaceutical agent that will elicit the biological or medical response of a tissue, system, animal or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "prophylaxis" includes prevention and refers to a measure or procedure which is to prevent rather than cure or treat a disease. Preventing refers to a reduction in risk of acquiring or developing a disease causing at least one clinical symptom of the disease not to developing a subject that may be exposed to a disease-causing agent or a subject predisposed to the disease in advance of disease outset.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The term "pharmaceutically acceptable excipients" includes all diluents, carriers, binders, glidants, and other components of pharmaceutical formulations with which the compound of the invention is administered.

The compounds of the invention may exist in solid or liquid form. In solid form, compound of the invention may exist in a continuum of solid states ranging from fully amorphous to fully crystalline.

The term 'amorphous' refers to a state in which the material lacks long range order at the molecular level and, depending upon the temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ('glass transition').

The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compound of Formula I may exist in solvated and unsolvated forms. As used herein, the term "solvate" refers to a complex of variable stoichiometry formed by a solute (in this invention, a compound of Formula I or a salt) and a solvent. Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water. The present invention includes all such solvates.

It is also noted that some compounds may form tautomers. 'Tautomers' refer to compounds that are interchangeable forms of a particular compound structure, and that vary in the displacement of hydrogen atoms and electrons. Thus, two structures may be in equilibrium through the movement of re electrons and an atom (usually H). For example, enols and ketones are tautomers because they are rapidly interconverted by treatment with either acid or base. It is understood that all tautomers and mixtures of tautomers of the compounds of the present invention are included within the scope of the compounds of the present invention.

The compounds of Formula I may be in the form of a salt. Typically, the salts of the present invention are pharmaceutically acceptable salts. Salts encompassed within the term "pharmaceutically acceptable salts" refer to non-toxic salts of the compounds of this invention. For a review on suitable salts, see e.g., Berge et al, J. Pharm. Sci, 1977, 66, 1-19. Suitable pharmaceutically acceptable salts can include acid addition salts. A pharmaceutically acceptable acid addition salt can be formed by reaction of a compound of Formula I with a suitable inorganic or organic acid (such as hydrobromic, hydrochloric, sulfuric, nitric, phosphoric, p-toluenesulfonic, benzenesulfonic, methanesulfonic, ethanesulfonic, naphthalenesulfonic such as 2-naphthalenesulfonic), optionally in a suitable solvent such as an organic solvent, to give the salt which is usually isolated for example by crystallization and filtration. A pharmaceutically acceptable acid addition salt of a compound of Formula I can be, for example, a hydrobromide, hydrochloride, sulfate, nitrate, phosphate, p-toluenesulfonate, benzenesulfonate, methanesulfonate, ethanesulfonate, or naphthalenesulfonate (e.g. 2-naphthalenesulfonate) salt. Other non-pharmaceutically acceptable salts, e.g. trifluoroacetates, may be used, for example in the isolation of compounds of the invention, and are included within the scope of this invention.

The invention includes within its scope all possible stoichiometric and non-stoichiometric forms of the compounds of Formula I.

While it is possible that, for use in therapy, the compound of the invention may be administered as the raw chemical, it is possible to present the compound of the invention as the active ingredient in a pharmaceutical composition. Such compositions can be prepared in a manner well known in the pharmaceutical art and comprise at least one active compound. Accordingly, the invention further provides pharmaceutical compositions comprising a compound of the invention and one or more pharmaceutically acceptable excipients. The excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable excipients. The pharmaceutical composition can be for use in the treatment and/or prophylaxis of any of the conditions described herein.

Generally, the compound of the invention is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like. Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert excipient such as ethanol, glycerol, water and the like. Powders are prepared by reducing the compound to a suitable fine size and mixing with a similarly prepared pharmaceutical excipient such as an edible carbohydrate, as, for example, starch or mannitol. Flavoring, preservative, dispersing and coloring agent can also be present.

Capsules are made by preparing a powder mixture, as described above, and filling formed gelatin sheaths. Excipients including glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, excipients including suitable binders, glidants, lubricants, sweetening agents, flavors, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, suspensions, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspension drops, gels or dry powders.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulization. Intranasal compositions may permit the compound(s) of Formula I or (a) pharmaceutically acceptable salt(s) thereof to be delivered to all areas of the nasal cavities (the target tissue) and further, may permit the compound(s) of Formula I or (a) pharmaceutically acceptable salt(s) thereof to remain in contact with the target tissue for longer periods of time. A suitable dosing regime for intranasal compositions would be for the patient to inhale slowly through the nose subsequent to the nasal cavity being cleared. During inhalation, the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicef (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an an amount of from 0.001 to 1% (w/w), such as from 0.015% to 0.5% (w/w) based on the total weight of the composition. Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of Formula I or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

Pharmaceutical compositions adapted for parental administration include aqueous and nonaqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example, those suitable for oral administration may include flavoring agents.

The compounds of Formula I and pharmaceutically acceptable salts thereof may also be formulated with other adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminium salts, oil and water emulsions, heat shock proteins, lipid A preparations and derivatives, glycolipids, other TLR agonists such as CpG DNA or similar agents, cytokines such as GM-CSF or IL-12 or similar agents.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

Suitably, the amount of the compound of the invention administered according to the present invention will be an amount selected from about 0.01 mg to about 1 g per day (calculated as the free or unsalted compound).

The compounds of Formula I and pharmaceutically acceptable salts thereof may be employed alone or in combination with other therapeutic agents. The compounds of Formula I and pharmaceutically acceptable salts thereof and the other pharmaceutically active agent(s) may be administered together or separately and, when administered separately, administration may occur simultaneously or sequentially, in any order, by any convenient route in separate or combined pharmaceutical compositions. The amounts of the compound(s) of Formula I or pharmaceutically acceptable salt(s) thereof and the other pharmaceutically active agent(s) and the relative timings of administration will be selected in order to achieve the desired combined therapeutic effect. The compound(s) of Formula I or pharmaceutically acceptable salt(s) thereof and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and vice versa. Such sequential administration may be close in time (e.g. simultaneously) or remote in time. Furthermore, it does not matter if the compounds are administered in the same dosage form, e.g. one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages. The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like. It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of Formula I is used in combination with a second therapeutic agent active against the same disease, condition or disorder, the dose of each compound may differ from that when the compound is used alone. Appropriate doses will be readily appreciated by those skilled in the art.

In one embodiment, the patient in the methods and uses of the present invention is a mammal. In another embodiment, the patient is a human. The compounds of the invention are useful in the treatment of diseases and conditions in which modulation of STING is beneficial, including cancer. As modulators of the immune response, the compounds of Formula I and pharmaceutically acceptable salts thereof may also be useful, as stand-alone, in combination or as adjuvants, in the treatment of diseases and conditions in which modulation of STING is beneficial.

In one aspect, the disease or condition to be treated is cancer. Examples of cancer diseases and conditions in which a compound of Formula I or pharmaceutically acceptable salt thereof, may have potentially beneficial anti-tumor effects include cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemangioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease; or a combination of one or more of the foregoing cancers.

In a further aspect, the present invention provides a compound of Formula I or a pharmaceutically acceptable salt thereof, for use in the treatment of cancer.

In a further aspect, the present invention provides a method of treating cancer comprising administering to a patient in need thereof a therapeutically effective amount of a compound of Formula I or a pharmaceutically acceptable salt thereof.

In a further aspect, the present invention provides the use of a compound of Formula I or a pharmaceutically acceptable salt thereof, in the manufacture of a medicament for the treatment of cancer.

A compound of the invention may be employed with other therapeutic methods of cancer treatment, e.g., in anti-neoplastic therapy, combination therapy with immune checkpoint inhibitors, other chemotherapeutic, hormonal, antibody agents as well as surgical and/or radiation treatments.

Immune checkpoint inhibitors, such as humanized antibodies against PD-1, PD-L1 and CTLA4, have recently been shown to be highly successful in treating several types of metastatic cancer, including melanoma, non-small cell lung cancers, renal cell carcinoma and bladder cancer (Sharma and Allison, 2015, Science 348, 56). However, still only a small percentage of cancer patients benefit from the checkpoint inhibitor therapies, in part because insufficient number of anti-tumor immune cells, such as CD8 T cells, are generated and/or infiltrated into the tumors. Activation of the cGAS-STING pathway activates anti-tumor immunity, including the production and infiltration of tumor-specific CD8 T cells. Therefore, cGAMP analogues are expected to function synergistically with immune checkpoint inhibitors and the combination therapies are likely to bring therapeutic benefits to a larger percentage of cancer patients.

In a further aspect, the present invention provides a pharmaceutical composition comprising a compound of Formula I or a pharmaceutically acceptable salt thereof, and at least one immune checkpoint inhibitor.

In a further aspect, the present invention provides a pharmaceutical composition comprising a compound of Formula I or a pharmaceutically acceptable salt thereof, and at least one immune checkpoint inhibitor for use in therapy.

In a further aspect, the present invention provides a pharmaceutical composition comprising a compound of Formula I or pharmaceutically acceptable salt thereof, and at least one immune checkpoint inhibitor for use in treating cancer.

In a further aspect, the present invention provides the use of a pharmaceutical composition comprising a compound of Formula I or a pharmaceutically acceptable salt thereof, and at least one immune checkpoint inhibitor in the manufacture of a medicament for the treatment of cancer.

In a further aspect, the present invention provides a method of treating cancer, comprising: administering to a patient in need thereof a therapeutically effective amount of a pharmaceutical composition comprising a compound of Formula I or a pharmaceutically acceptable salt thereof, and at least immune checkpoint inhibitor.

In a further aspect, the present invention provides a pharmaceutical composition comprising a compound of Formula I or a pharmaceutically acceptable salt thereof, at least one immune checkpoint inhibitor, and one or more of pharmaceutically acceptable carriers, diluents and excipients.

Radiation of tumors, especially high-dose radiation such as stereotatic body radiation therapy (SBRT), kills tumor cells with a high degree of precision. Dead tumor cells not only provide tumor antigens to generate tumor-specific cytotoxic T cells, but also release tumor DNA into antigen presenting cells to activate the cGAS-STING pathway (Deng et al., 2014, Immunity 41, 843). Therefore, cGAMP analogues are expected to function synergistically with radiation therapies to benefit a larger percentage of cancer patients.

In a further aspect, the present invention provides a pharmaceutical composition comprising a compound of Formula I or a pharmaceutically acceptable salt thereof, in combination with radiation therapy such as SBRT.

In a further aspect, the present invention provides a pharmaceutical composition comprising a compound of Formula I or pharmaceutically acceptable salt thereof, in combination with radiation therapy such as SBRT for use in treating cancer.

In a further aspect, the present invention provides the use of a pharmaceutical composition comprising a compound of Formula I or a pharmaceutically acceptable salt thereof, in combination with radiation therapy such as SBRT in the manufacture of a medicament for the treatment of cancer.

In a further aspect, the present invention provides a method of treating cancer, comprising: administering to a patient in need thereof a therapeutically effective amount of a pharmaceutical composition comprising a compound of Formula I or a pharmaceutically acceptable salt thereof, in combination with radiation therapy such as SBRT.

In a further aspect, the present invention provides a pharmaceutical composition comprising a compound of Formula I or a pharmaceutically acceptable salt thereof, and one or more of pharmaceutically acceptable carriers, diluents and excipients, in combination with radiation therapy such as SBRT for the treatment of cancer.

Anti-neoplastic agents include chemical compounds and antibodies that kill tumor cells by inhibiting cell cycle, signal transduction, DNA metabolism and angiogenesis and/or by promoting DNA damage, apoptosis and necrosis. These agents comprise that largest class of molecules currently used for cancer therapies. Anti-neoplastic agents selectively kill tumor cells, although many of them also kill normal cells, thereby generating severe side effects. Processing of dead tumor cell associated antigens by antigen presenting cells leads to the generation of tumor-specific cytotoxic T cells. This process can be enhanced by cGAMP analogues. Therefore, combination of cGAMP analogues with anti-neoplastic agents are likely to generate synergistic effects that benefit a larger percentage of patients.

In a further aspect, the present invention provides a pharmaceutical composition comprising a compound of Formula I or a pharmaceutically acceptable salt thereof, and at least one anti-neoplastic agent.

In a further aspect, the present invention provides a pharmaceutical composition comprising a compound of Formula I or a pharmaceutically acceptable salt thereof, and at least one anti-neoplastic agent for use in therapy.

In a further aspect, the present invention provides a pharmaceutical composition comprising a compound of Formula I or pharmaceutically acceptable salt thereof, and at least one anti-neoplastic agent for use in treating cancer.

In a further aspect, the present invention provides the use of a pharmaceutical composition comprising a compound of Formula I or a pharmaceutically acceptable salt thereof, and at least one anti-neoplastic agent in the manufacture of a medicament for the treatment of cancer.

In a further aspect, the present invention provides a method of treating cancer, comprising: administering to a patient in need thereof a therapeutically effective amount of a pharmaceutical composition comprising a compound of Formula I or a pharmaceutically acceptable salt thereof, and at least one anti-neoplastic agent.

In a further aspect, the present invention provides a pharmaceutical composition comprising a compound of Formula I or a pharmaceutically acceptable salt thereof, at least one anti-neoplastic agent, and one or more of pharmaceutically acceptable carriers, diluents and excipients.

Any anti-neoplastic agent that has activity versus a susceptible tumor being treated may be utilized in the combination. Typical anti-neoplastic agents useful include anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include paclitaxel and its analog docetaxel.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include vinblastine, vincristine, and vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include oxaliplatin, cisplatin and carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include nitrogen mustards such as cyclophosphamide, melphalan, and chlorambucil; alkyl sulfonates such as busulfan; nitrosoureas such as carmustine; and triazenes such as dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include actinomycins such as dactinomycin, anthrocyclins such as daunorubicin and doxorubicin; and bleomycins.

Topoisomerase II inhibitors include epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include etoposide and teniposide.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include fluorouracil, methotrexate, cytarabine, mercaptopurine, thioguanine, and gemcitabine.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Hormones and hormonal analogues are useful compounds for treating cancers in which there is a relationship between the hormone(s) and growth and/or lack of growth of the cancer. Examples of hormones and hormonal analogues useful in cancer treatment include adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometria 1 carcinoma; estrogens, and anti-estrogens such as fulvestrant, flutamide, nilutamide, bicalutamide, cyproterone acetate and 5a-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3 domain blockers, serine/threonine kinases, phosphatidyl inositol-3 kinases, myoinositol signaling, and Ras oncogenes.

Several protein tyrosine kinases catalyze the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, e.g., in Kath, John C, Exp. Opin. Ther. Patents (2000) 10(6):803-818; Shawver et al. DDT Vol 2, No. 2 Feb. 1997; and Lofts, F. J. et al in "Growth factor receptors as targets", New Molecular Targets for Cancer Chemotherapy, ed. Workman, Paul and Kerr, David, CRC press 1994, London.

Tyrosine kinases which are not growth factor receptor kinases are termed nonreceptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described, e.g., in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including PI3-K p85 subunit, Src family kinases, adaptor molecules (She, Crk, Nek, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases include MAP kinase cascade blockers which include blockers of Raf kinases (rafk), Mitogen or Extracellular Regulated Kinase (M EKs), and Extracellular Regulated Kinases (ERKs); and Protein kinase C family member blockers including blockers of PKCs (alpha, beta, gamma, epsilon, mu, lambda, iota, zeta). I kB kinase family (I KKa, I KKb), PKB family kinases, akt kinase family members, and TGF beta receptor kinases. Such Serine/Threonine kinases and inhibitors thereof are described, e.g., in Yamamoto, T. et al., (1999), Journal of Biochemistry. 126 (5) 799-803; Brodt, P et al. (2000), Biochemical Pharmacology, 60. 1101-1107; Massague, J., and Weis-Garcia, F. (1996) Cancer Surveys. 27:41-64; Philip, P. A.; and Harris, A. L. (1995), Cancer Treatment and Research. 78: 3-27; Lackey, K. et al Bioorganic and Medicinal Chemistry Letters, (10), 2000, 223-226; U.S. Pat. No. 6,268,391; and Martinez-lacaci, L, et al., Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed, e.g., in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al. Cancer Res., (2000) 60(6), 1541-1545.

Also useful in the present invention are Myo-inositol signaling inhibitors such as phospholipase C blockers and Myoinositol analogues. Such signal inhibitors are described, e.g., in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., et al. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

Antibody antagonists to receptor kinase ligand binding may also serve as signal transduction inhibitors. This group of signal transduction pathway inhibitors includes the use of humanized antibodies to the extracellular ligand binding domain of receptor tyrosine kinases. Examples include Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer: erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-angiogenic agents such as non-receptor MEK angiogenesis inhibitors may also be useful, as well as those which inhibit the effects of vascular endothelial growth factor (e.g., the anti-vascular endothelial cell growth factor antibody bevacizumab [Avastin™]), and compounds that work by other mechanisms (e.g., linomide, inhibitors of integrin αvβ3 function, endostatin and angiostatin).

In one aspect, the present invention provides a pharmaceutical composition comprising a compound of Formula I or a pharmaceutically acceptable salt thereof, and at least one anti-neoplastic agent which is an anti-microtubule agent, platinum coordination complex, alkylating agent, antibiotic agent, topoisomerase II inhibitor, antimetabolite, topoisomerase I inhibitor, hormones and hormonal analogue, signal transduction pathway inhibitor, non-receptor tyrosine MEK angiogenesis inhibitor, immunotherapeutic agent, proapoptotic agent, or cell cycle signaling inhibitor.

In another aspect, the present invention provides a pharmaceutical composition comprising a compound of Formula I or a pharmaceutically acceptable salt thereof, and at least one anti-neoplastic agent selected from diterpenoids and vinca alkaloids.

In another aspect, the present invention provides a pharmaceutical composition comprising a compound of Formula I or a pharmaceutically acceptable salt thereof, and at least one anti-neoplastic agent which is a platinum coordination complex. In one embodiment, at least one anti-neoplastic agent is paclitaxel, carboplatin, or vinorelbine.

In another aspect, the present invention provides a pharmaceutical composition comprising a compound of Formula I or a pharmaceutically acceptable salt thereof, and at least one anti-neoplastic agent which is a signal transduction pathway inhibitor. In one embodiment, the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms. In another embodiment, the signal transduction pathway inhibitor is an inhibitor of a serine/threonine kinase rafk, akt, or PKC-zeta. In another embodiment, the signal transduction pathway inhibitor is an inhibitor of a non-receptor tyrosine kinase selected from the src family of kinases. In another embodiment, the signal transduction pathway inhibitor is an inhibitor of c-src. In another embodiment, the signal transduction pathway inhibitor is an inhibitor of Ras oncogene selected from inhibitors of farnesyl transferase and geranylgeranyl transferase. In another embodiment, the signal transduction pathway inhibitor is an inhibitor of a serine/threonine kinase selected from the group consisting of PI3K. In another embodiment, the signal transduction pathway inhibitor is a dual EGFr/erbB2 inhibitor, for example N-{3-Chloro-4-[(3-fluorobenzyl) oxy]phenyl}-6-[5-({[2-(methanesulphonyl) ethyl]amino}methyl)-2-furyl]-4-quinazolinamine.

In another aspect, the present invention provides a pharmaceutical composition comprising a compound of Formula I or a pharmaceutically acceptable salt thereof, and at least one anti-neoplastic agent which is a cell cycle signaling inhibitor. In one embodiment, the cell cycle signaling inhibitor is an inhibitor of CDK2, CDK4 or CDK6.

Compounds of Formula I may be prepared by methods known in the art of organic synthesis as set forth in the schemes below and/or the specific Examples described below. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3$^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula I.

It is understood that the examples and embodiments described herein are for illustrative purposes only and that various modifications or changes in light thereof will be suggested to persons skilled in the art and are to be included within the spirit and purview of this application and scope of the appended claims.

The following list provides definitions of certain abbreviations as used herein. It will be appreciated that the list is not exhaustive, but the meaning of those abbreviations not herein below defined will be readily apparent to those skilled in the art: Ac is acetyl; AcOH is acetic acid; Ac$_2$O is acetic anhydride; AIBN is 2,2'-azobisisobutyronitrile; Bn is benzyl; BSA is N,O-bis(trimethylsilyl)acetamide; BSTFA is N,O-bis(trimethylsilyl)trifluoroacetamide; Bu is butyl; Bz is benzoyl; CAN is ceric ammonium nitrate; CE is 2-cyanoethyl; DCA is dichloroacetic acid; DCM is dichloromethane; DDTT is 1,2,4-dithiazole-5-thione; DEAD is diethyl azodicarboxylate; DIAD is diisopropyl azodicarboxylate; DIPEA is N,N-diisopropylethylamine; DMAP is 4-(dimethylamino) pyridine; DMF is N,N-dimethylformamide; DMOCP is 2-chloro-5,5-dimethyl-1,3,2-dioxaphosphorinane 2-oxide; DMSO is dimethylsulphoxide; DMTr is 4,4'-dimethoxytrityl; EOAc is ethyl acetate; EtOH is ethanol; HMPT is hexamethylphosphorous triamide; HPLC is high performance liquid chromatography; ibu is isobutyryl; IBX is 2-iodoxybenzoic acid; Imid is imidazole; $^i$Pr is isopropyl; KOH is potassium hydroxide; Me is methyl; MeCN is acetonitrile; MeOH is methanol; MTBE is methyl tert-butyl ether; Ms is methanesulfonyl; Pd/C is palladium on activated charcoal; NIS is N-iodosuccinimide; NPE is 2-(4-nitrophenyl)ethyl; PE is petroleum ether; Ph is phenyl; PMB is p-methoxybenzyl; PPh$_3$ is triphenylphosphine; Py is pyridine; TBAF is tetra-n-butylammonium fluoride; TBAI is tetrabutylammonium iodide; TBDPS is tert-butyldiphenylsilyl; TBHP is tert-Butyl hydroperoxide; TBS is tert-butyldimethylsilyl; TCDI is 1,1'-thiocarbonyldiimidazole; TDA-1 is tris[2-(2-methoxyethoxy)ethyl]amine; TEA is triethylamine; Tf is trifluoromethanesulfonyl; TFA is trifluoroacetic acid; TFE is 2,2,2-trifluoroethyl; THF is tetrahydrofuran; TIPS is triisopropylsilyl; TLC is thin-layer chromatography; TMS is trimethylsilyl; TMSOTf is trimethylsilyl trifluoromethanesulfonate; Tol is p-toluoyl; Tr is trityl.

Intermediate Preparations

Preparation of B1:

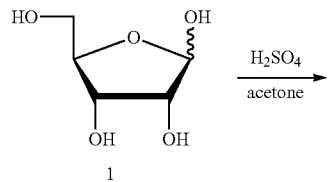

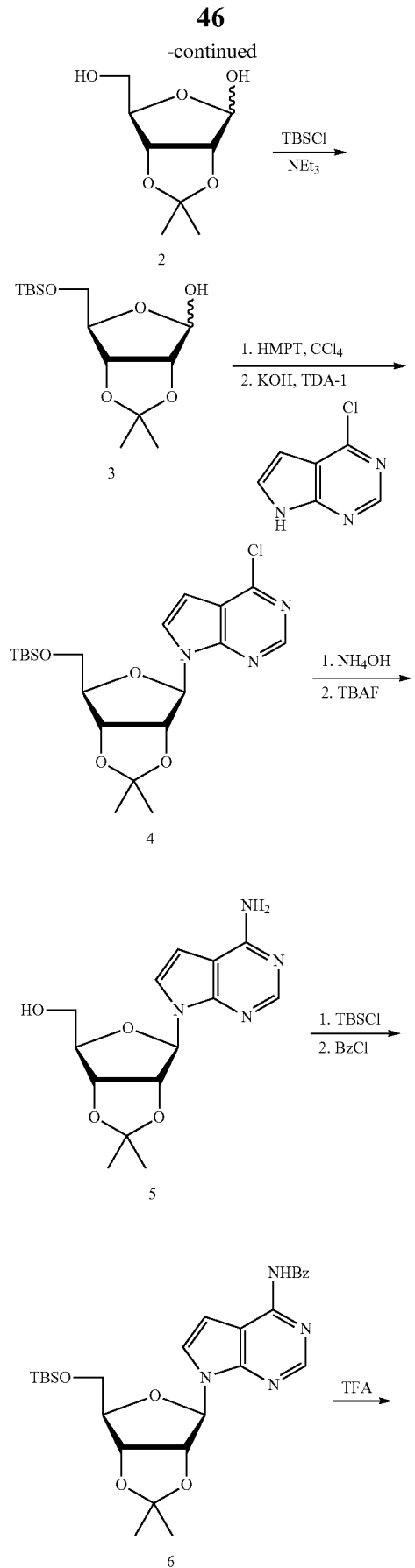

-continued

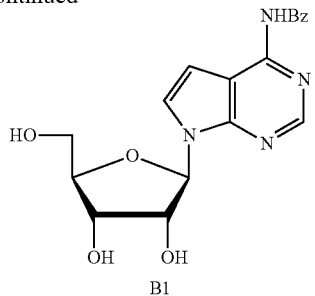

B1

Step 1: Acetonide 2

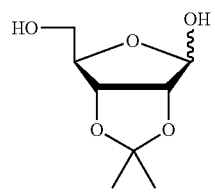

To a suspension of D-Ribose (1) (160 g, 1.07 mol) in acetone (2.0 L) is added concentrated sulfuric acid (10.7 g, 107 mmol, 5.8 mL) at 27° C. dropwise. After stirring for 12 hours, solid Sodium bicarbonate (100 g) is added. The mixture is then filtered and the filtrate is concentrated to give crude 2 (215.0 g).

Step 2: Silyl Ether 3

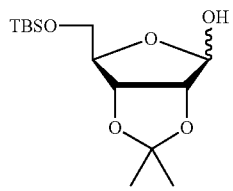

To a solution of crude 2 (215 g, 1.13 mol) in DCM (1.5 L) is added TBSCl (170 g, 1.13 mol) and TEA (172 g, 1.69 mol) at 0° C. After stirring at 27° C. for 12 hours, the mixture is filtered, concentrated, and purified by silica gel column chromatography (EA/PE=1/100 to 1/50) to give 3 as a colorless oil (285 g, 83% yield).

Step 3: Deazapurine 4

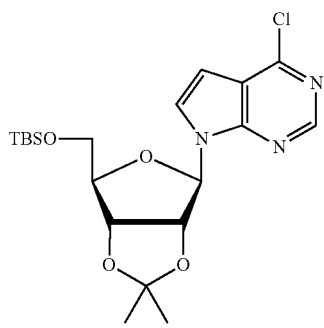

To a solution of 3 (60.0 g, 197.08 mmol) and carbon tetrachloride (67.3 g, 438 mmol, 42 mL) in THF (1.2 L) is added HMPT (63.0 g, 386 mmol, 70 mL) dropwise at −78° C. and stirred at 27° C. for 2 hours. To another solution of 6-chloro-7-deazapurine (24.2 g, 158 mmol) and KOH (16.6 g, 296 mmol) in MeCN (1.2 L) is added TDA-1 (6.37 g, 19.7 mmol) at 27° C. followed by the THF solution obtained above. After stirring at 27° C. for 12 hours, the reaction mixture is filtered, concentrated, and purified by silica gel column chromatography (EA/PE=1/50 to 1/10) to give 4 as a yellow oil (15.3 g, 18% yield).

Step 4: Adenine 5

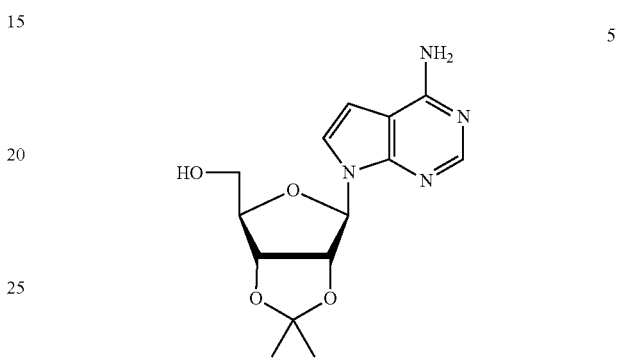

A solution of 4 (28.6 g, 64.9 mmol) in dioxane (150 mL) and ammonium hydroxide aqueous solution (500 mL) is stirred at 120° C. for 30 hours in a sealed autoclave. The volatiles are then removed and the aqueous solution is extracted with EA (300 mL×3). The combined organic layers are washed with brine (100 mL), dried over anhydrous sodium sulfate, filtered, concentrated, and partially purified by silica gel column chromatography (EA/DCM=1/1) to give a yellow foam (9.65 g). This residue is then dissolved in THF (50 mL) and treated with TBAF trihydrate (10.9 g, 34.4 mmol) at 27° C. After stirring for 2 hours, the mixture is concentrated and purified by silica gel column chromatography (EA/DCM=1/1 to 7/1) to give 5 (5.56 g, 79% yield) as yellow solid.

Step 5: Benzoate 6

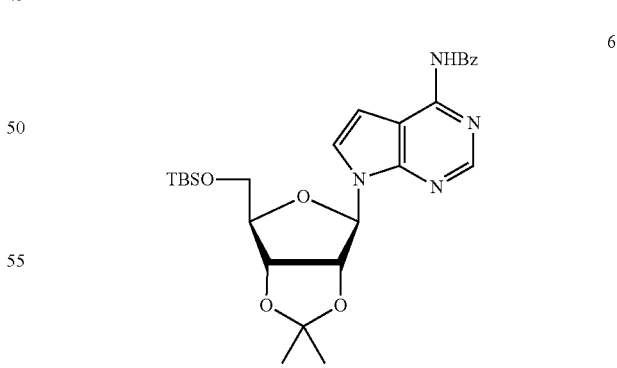

To a solution of 5 (7.26 g, 23.7 mmol) in DCM (60 mL) is added Imid (4.84 g, 71.1 mmol) and TBSCl (5.36 g, 35.6 mmol) at 27° C. After stirring at 27° C. for 1.5 hours, water (100 mL) is added and the mixture is extracted with DCM (200 mL). The organic layer is washed with brine (100 mL), dried over anhydrous sodium sulfate, filtered, concentrated to give crude TBS-5. To a solution of the crude TBS-5 obtained above in DCM (100 mL) is added benzoyl chloride (5.14 g, 36.6 mmol) at 27° C. After stirring for 12 hours, water (200 mL) is added the mixture is extracted with DCM (500 mL). The organic layer is dried over anhydrous sodium sulfate, filtered, concentrated, and purified by silica gel column chromatography (EA/PE=1/50 to 1/10) to give 6 as a yellow foam (8.12 g, 64% yield).

Step 6: B1

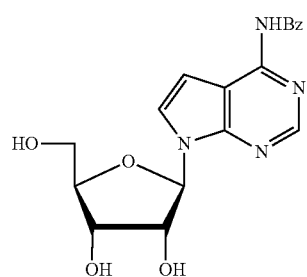

A solution of 6 (15.2 g, 28.9 mmol) in TFA (90 mL) and DCM (20 mL) is stirred at 27° C. for 12 hours. The volatiles are then removed and the residue is purified by silica gel column chromatography (MeOH/DCM=1/100 to 1/10) to B1 as a yellow solid (10.16 g, 95% yield).

Preparation of B2:

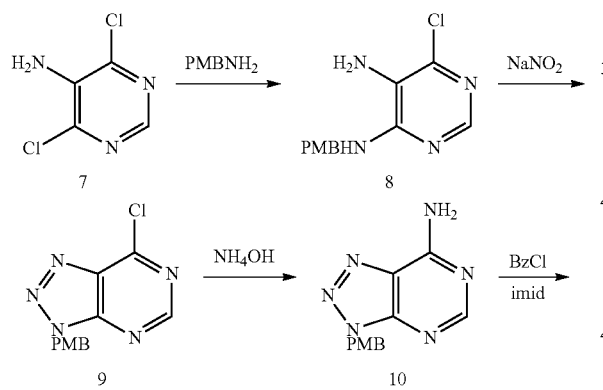

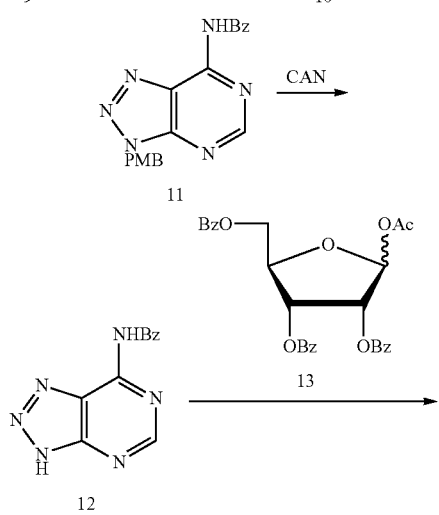

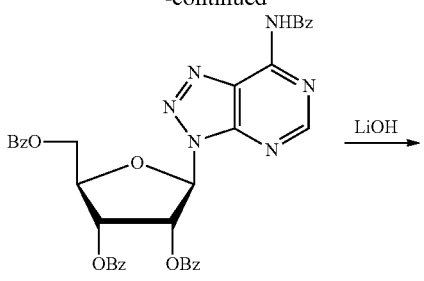

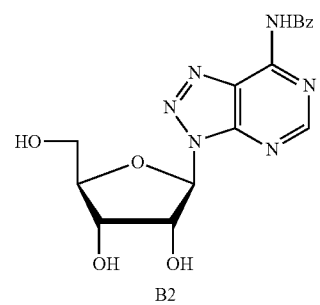

Step 1: Aniline 8

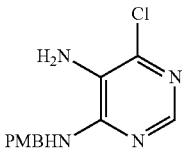

To a solution of 5-amino-4,6-dichloropyrimidine (63.0 g, 384 mmol) in n-BuOH (300.0 mL) is added p-methoxybenzylamine (58.0 g, 423 mmol, 55 mL) and DIPEA (99.3 g, 768 mmol, 134 mL). After stirring at 100-110° C. for 15 hours, the volatiles are removed before MTBE (100 mL) is added. The solid is collected by filtration and washed with EA to give 8 as an off-white solid (55.0 g, 54% yield). (MS: [M+H]$^+$ 265.0)

Step 2: Azapurine 9

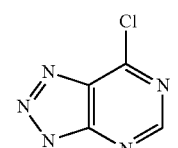

To a solution of 8 (10.0 g, 37.8 mmol) in a mixture of DCM (200 mL), AcOH (100 mL), and water (100 mL) is added sodium nitrite (2.87 g, 41.6 mmol, 2.3 mL) at 0° C. After stirring at 0-25° C. for 1 hour, DCM (30 mL) and saturated sodium bicarbonate aqueous solution (30 mL) are added. The layers are then separated and the aqueous phase is extracted with DCM (150 mL×3). The combined organic phases are dried over anhydrous sodium sulfate, filtered, concentrated, and purified by silica gel column chromatography (EA/PE=1/3) to give 9 as a light yellow solid (6.0 g, 88% yield). (MS: [M+H]$^+$ 276.0)

Step 3: Azaadenine 10

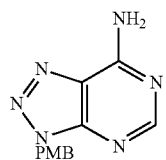

To a solution of 9 (6.0 g, 21.8 mmol) in 1,4-dioxane (30 mL) is added ammonium hydroxide aqueous solution (30 mL). After stirring at 30-40° C. for 5 hours, the solid is collected by filtration to give 10 as a white solid (4.0 g, 70% yield). (MS: [M+H]$^+$ 257.1)

Step 4: Azaadenine 11

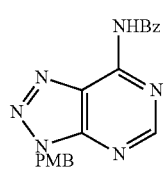

To a solution of 10 (17.0 g, 66.3 mmol) in Py (100 mL) is added DMAP (8.92 g, 73.0 mmol), Imid (13.6 g, 199 mmol) and benzoyl chloride (14.0 g, 99.5 mmol, 11.6 mL). After stirring at 110-120° C. for 18 hours, the volatiles are removed and DCM (300 mL) and water (300 mL) are added. The layers are separated and the organic phase is dried over anhydrous sodium sulfate, filtered, concentrated, and purified by silica gel column chromatography (EA/PE=1:1) to give 11 as an off-white solid (17.0 g, 68% yield). (MS: [M+H]$^+$ 361.2)

Step 5: Azaadenine 12

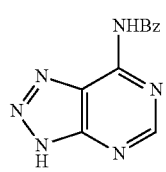

To a suspension of 11 (6.40 g, 17.8 mmol) in MeCN (60 mL) is added a solution of CAN (29.2 g, 53.3 mmol) and sodium bicarbonate (1.49 g, 17.76 mmol) in water (60 mL) at 0° C. After stirring at 0-25° C. for 12 hours, the mixture is neutralized with sodium bicarbonate to ~pH 7. The solid is collected by filtration to give 12 (2.6 g, 57% yield). (MS: [M+H]$^+$ 241.1)

Step 6: Azaadenosine 14

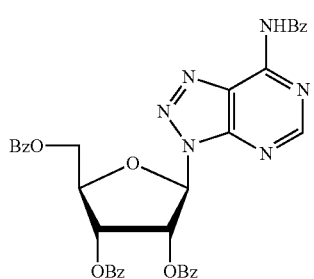

To a solution of 12 (9.30 g, 38.7 mmol) and 13 (20.5 g, 40.7 mmol) in MeCN (350 mL) is added tin(IV) chloride (30.3 g, 116 mmol, 13.6 mL) at 0° C. After stirring at 0-25° C. for 24 hours, the reaction mixture is poured into saturated sodium bicarbonate aqueous solution (300 mL). The solid is filtered off and washed with water (100 mL). The filtrate is extracted with DCM (150 mL×4) and the combined organic layers are dried over anhydrous sodium sulfate, filtered, concentrated, and purified by silica gel column chromatography (EA/DCM=1/10) to give 14 as an off-white gum (6.10 g, 21% yield). (MS: [M+H]$^+$ 684.9)

Step 7: B2

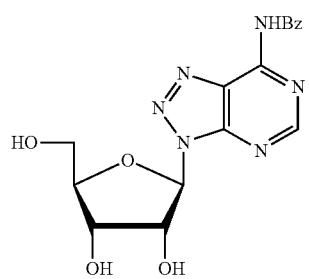

To a solution of 14 (6.1 g, 8.9 mmol) in a mixture of THF (35 mL) and MeOH (28 mL) is added lithium hydroxide aqueous solution (1M, 16.0 mL) at 0° C. After stirring at 0-25° C. for 3 hours, the mixture is neutralized with citric acid aqueous solution (1M) to ~pH 7 and then concentrated and purified by silica gel column chromatography (MeOH/DCM=1/20) to give B2 as an off-white solid (2.9 g, 87% yield). (MS: [M+H]$^+$ 373.1)

Preparation of DMTr-B3:

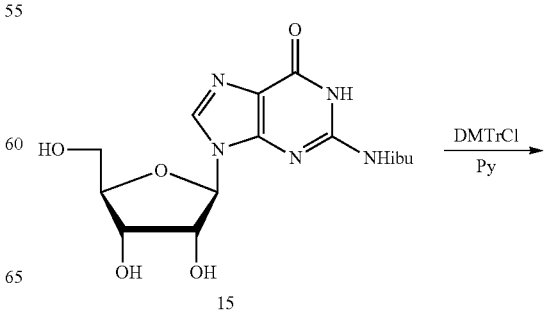

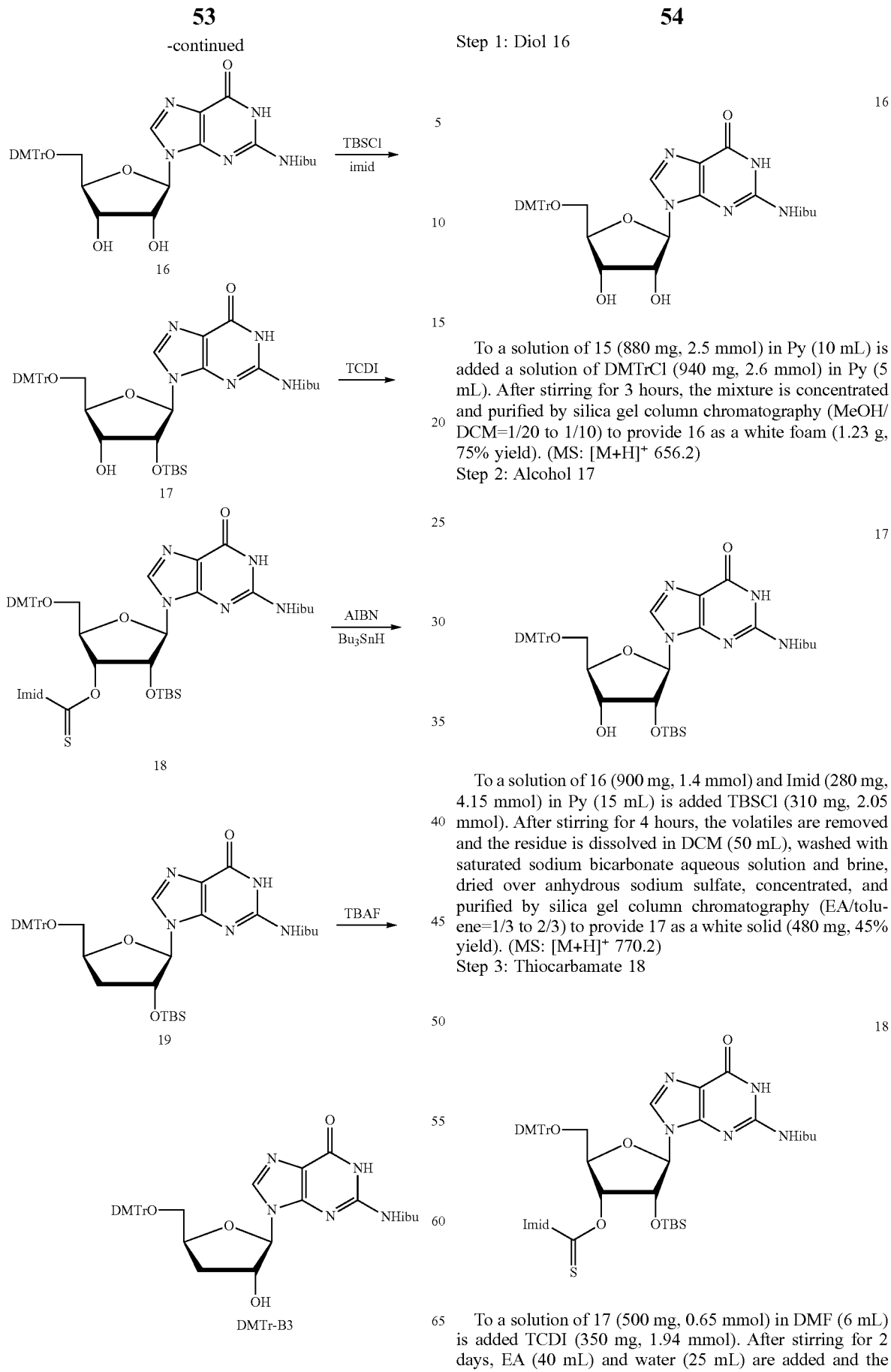

Step 1: Diol 16

To a solution of 15 (880 mg, 2.5 mmol) in Py (10 mL) is added a solution of DMTrCl (940 mg, 2.6 mmol) in Py (5 mL). After stirring for 3 hours, the mixture is concentrated and purified by silica gel column chromatography (MeOH/DCM=1/20 to 1/10) to provide 16 as a white foam (1.23 g, 75% yield). (MS: [M+H]$^+$ 656.2)

Step 2: Alcohol 17

To a solution of 16 (900 mg, 1.4 mmol) and Imid (280 mg, 4.15 mmol) in Py (15 mL) is added TBSCl (310 mg, 2.05 mmol). After stirring for 4 hours, the volatiles are removed and the residue is dissolved in DCM (50 mL), washed with saturated sodium bicarbonate aqueous solution and brine, dried over anhydrous sodium sulfate, concentrated, and purified by silica gel column chromatography (EA/toluene=1/3 to 2/3) to provide 17 as a white solid (480 mg, 45% yield). (MS: [M+H]$^+$ 770.2)

Step 3: Thiocarbamate 18

To a solution of 17 (500 mg, 0.65 mmol) in DMF (6 mL) is added TCDI (350 mg, 1.94 mmol). After stirring for 2 days, EA (40 mL) and water (25 mL) are added and the layers are separated. The aqueous layer is extracted with ethyl acetate (25 mL×3). The combined organic layers are washed with water (20 mL), brine (20 mL×2), dried over anhydrous sodium sulfate, and concentrated to give crude 18. (MS: [M+H]$^+$ 880.2)

Step 4: Silyl Ether 19

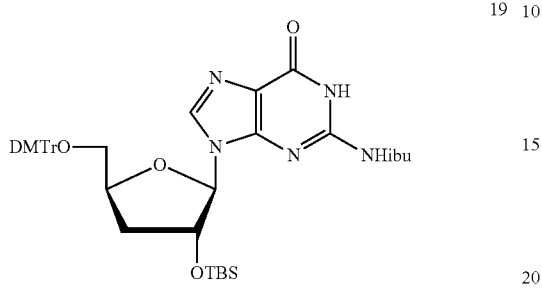

To a degassed solution of crude 18 in toluene (10 mL) at 110° C. is added a degassed solution of AIBN (57 mg, 0.34 mmol), tributyltin hydride (0.51 mL, 1.94 mmol) in toluene (3 mL) over 30 minutes. After stirring at 110° C. for 6 hours, the mixture is cooled to room temperature, concentrated, and purified by silica gel column chromatography (EA/hexanes=1/5 to 2/1) to give 19 as a yellow oil (195 mg, 40% yield over two steps). (MS: [M+H]$^+$ 754.2)

Step 5: DMTr-B3

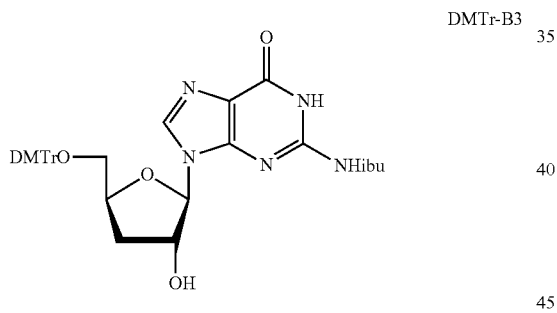

To a solution of 19 (190 mg, 0.252 mmol) in THF (5 mL) is added TBAF (1 M in THF, 0.50 mL). After stirring at room temperature for 2 hours, water (5 mL) is added and the mixture is extracted with EA (8 mL×3), dried over anhydrous sodium sulfate, concentrated, and purified by silica gel column chromatography (MeOH/DCM=1/20) to give DMTr-B3 as a white solid (132 mg, 82% yield). (MS: [M+H]$^+$ 640.2)

Preparation of B4:

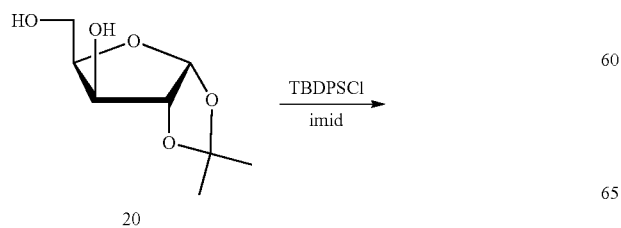

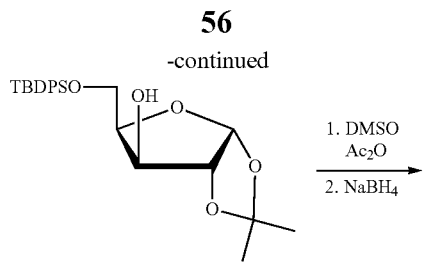

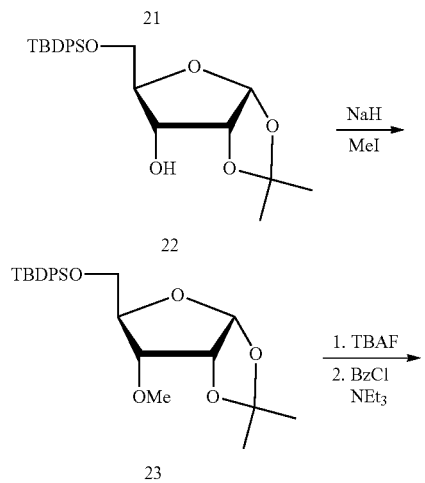

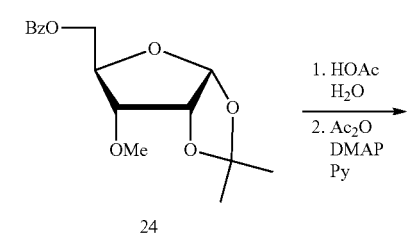

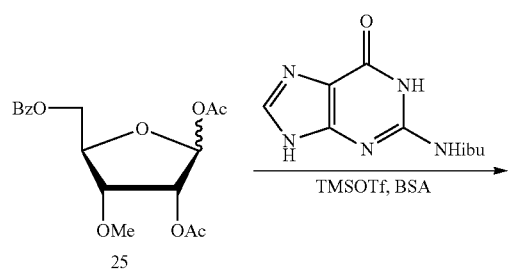

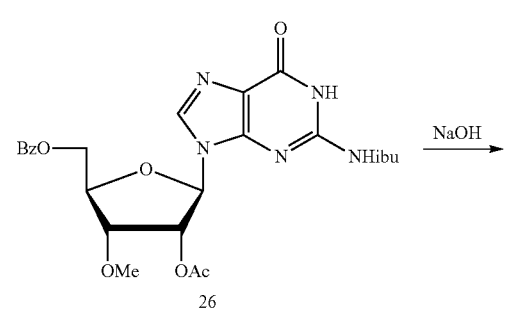

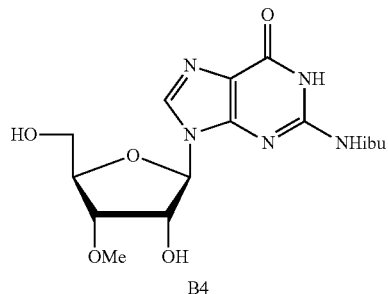

B4

Step 1: Alcohol 21

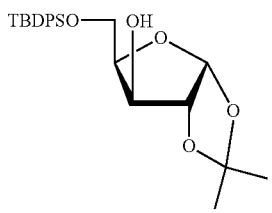

21

To a solution of 20 (12.8 g, 67.0 mmol) in Py (300 mL) is added TBDPSCl (21.0 mL, 80.4 mmol). After stirring for 3 h, MeOH (25 mL) is added and the mixture is concentrated. The residue is dissolved in diethyl ether (200 mL), washes with sodium bicarbonate aqueous solution (10%, 100 mL) and water (100 mL), dried over anhydrous sodium sulfate, filtered, concentrated, and purified by silica gel column chromatography (diethyl ether/PE=1/2) to give 21 as a white solid (27.2 g, 95% yield). (MS: [M+Na]$^+$ 451.2)

Step 2: Alcohol 22

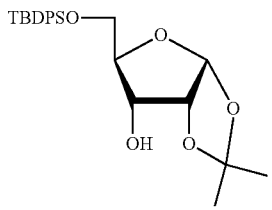

22

A solution of 21 (27.2 g, 63.7 mmol) in DMSO (200 mL) and Ac$_2$O (50 mL) is stirred for 16 hour before pouring into ice water (200 mL). The mixture is extracted with diethyl ether (100 mL×3) and the combined organic layers are washed with sodium bicarbonate aqueous solution (10%, 100 mL) and water (100 mL), and concentrated. The residue is then dissolved in MeOH (250 mL) and DCM (250 mL) at 0° C. followed by addition of sodium borohydride (12.0 g) in 10 portions. After stirring for 5 minutes, water (100 mL) is added and the layers are separated. The organic layer is then concentrated and purified by silica gel column chromatography (diethyl ether/PE=1/2) to give 22 as a white solid (20.4 g, 75% yield over two steps). (MS: [M+Na]$^+$ 451.2)

Step 3: Methyl Ether 23

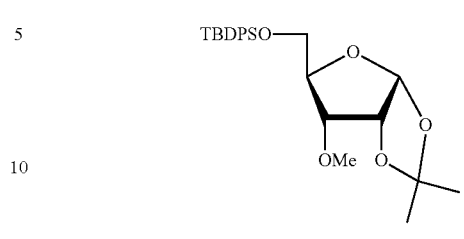

23

To a solution of 22 (4.0 g, 9.33 mmol) in DMF (45 mL) is added sodium hydride (484 mg, 12.1 mmol) at 0° C. and stirred for 30 minutes before methyl iodide (0.64 mL, 10.3 mmol) is added slowly. After stirring for 3 hours, water (3 mL) is added and the volatiles are removed and purified by silica gel column chromatography (EA/PE=1/10) to give 23 as a white solid (3.8 g, 92% yield). (MS: [M+Na]$^+$ 465.2)

Step 4: Benzoate 24

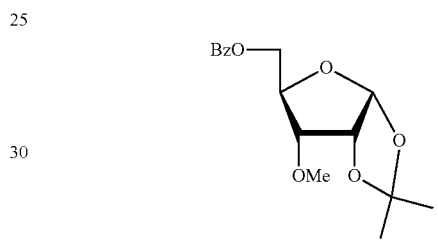

24

To a solution of 23 (3.1 g, 7.0 mmol) in THF (50 mL) is added TBAF (8.4 mL, 8.4 mmol) at 0° C. After stirring for 4 h at room temperature, water (5 mL) and EA are added. The layers are separated and the organic layer is washed with water and brine, concentrated, and the resulting residue is dissolved in DCM followed by addition of TEA (4.9 mL, 35 mmol) and benzoyl chloride (0.98 mL, 8.4 mmol). After stirring for 1 hour, water (3 mL) is added and the volatiles are removed. The residue is purified by silica gel column chromatography (EA/PE=1/5) to give 24 as a white solid (1.9 g, 88% yield). (MS: [M+Na]$^+$ 331.0)

Step 5: Acetate 25

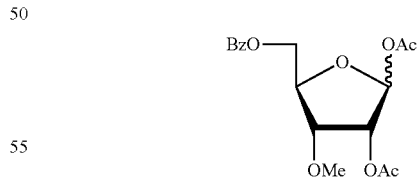

25

A solution of 24 (0.71 g, 2.3 mmol) in HOAc (14 mL) and water (6 mL) is heated under reflux for 30 minutes. After cooling to room temperature, the mixture is co-evaporated with toluene (10 mL×4) and the resulting residue is dissolved in Py/Ac$_2$O (10/1 v/v, 10 mL) followed by addition of DMAP (50 mg, 0.46 mmol). After stirring for 4 hours, the mixture is concentrated and purified by silica gel column chromatography (EA/PE=1/3) to give 25 as a white solid (0.75 g, 92% yield). (MS: [M+Na]$^+$ 375.0)

Step 6: Guanosine 27

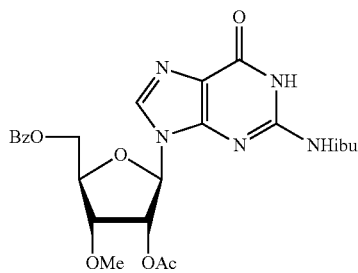

26

To a suspension of 25 (500 mg, 1.42 mmol) and N²-isobutyrylguanine (500 mg, 2.13 mmol) in DCM (20 mL) at 80° C. is added BSA (1.8 mL, 7.4 mmol) and stirred for 1 hour before addition of TMSOTf (0.77 mL, 4.26 mmol). After stirring at 80° C. for 3 hours, the mixture is cooled to room temperature before sodium bicarbonate aqueous solution (50 mL) is added. The mixture is then extracted with DCM (50 mL×3). The combined organic layers are dried over anhydrous sodium sulfate, concentrated, and purified by silica gel column chromatography (MeOH/DCM=1/20 to 1/10) to give 26 as a white powder (624 mg, 85% yield). (MS: [M+H]⁺ 514.2)

Step 7: B4

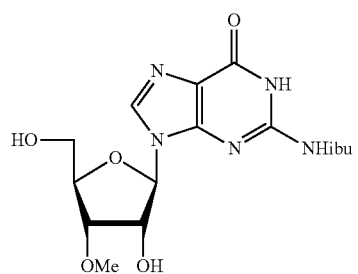

B4

To a solution of 27 (0.49 g, 0.96 mmol) in MeOH/THF/water (4/5/1 v/v/v, 20 mL) is added sodium hydroxide aqueous solution (10 M, 0.25 mL, 2.5 mmol) at 0° C. After stirring for 30 minutes, HOAc is added and the mixture is concentrated and purified by silica gel column chromatography (MeOH/DCM=1/10 to 1/5) to give B4 as an oil (322 mg, 92% yield). (MS: [M+H]⁺ 368.2)

Preparation of B5:

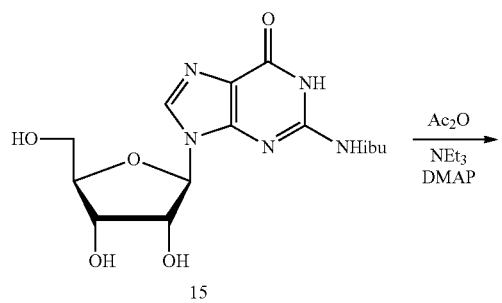

15

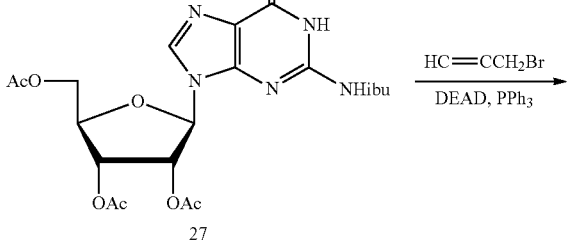

27

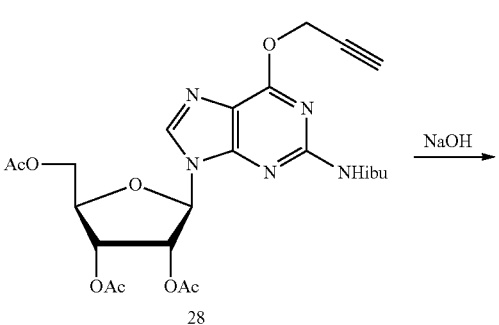

28

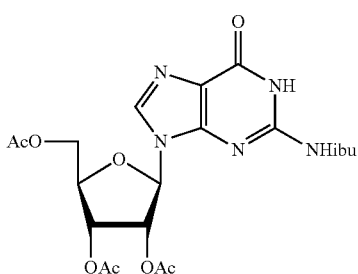

B5

Step 1: Acetate 28

27

To a solution of 15 (7.0 g, 20 mmol) in MeCN (100 mL) is added DMAP (1.2 g, 10 mmol) and Ac₂O (7.5 mL, 80 mmol) at 0° C. After stirring at room temperature overnight, the mixture is concentrated and purified by silica gel flash chromatography (MeOH/DCM=1/20 to 1/10) to give 27 as a white solid (8.77 g, 92% yield). (MS: [M+H]⁺ 480.0)

Step 2: Propargyl Ether 29

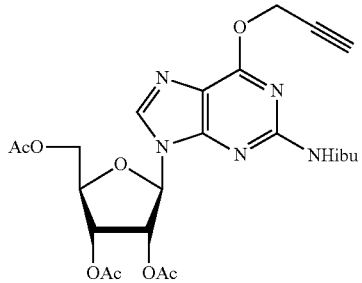

28

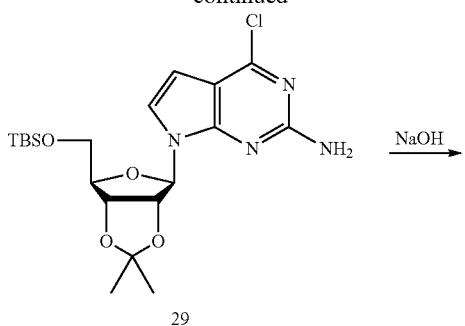

29

To a solution of 27 (480 mg, 1.0 mmol) in 1,4-dioxane (1 mL) is added PPh₃ (656 mg, 2.5 mmol), propargyl bromide (0.15 mL, 2 mmol) and a solution of DEAD (0.49 mL, 2.5 mmol) in dioxane (1 mL) at 0° C. After stirring for 2 hours, the mixture is concentrated and purified by silica gel column chromatography (MeOH/DCM=1/50 to 1/20) to give 28 as a white solid (440 mg, 47% yield). (MS: [M+H]$^+$ 518.2)

Step 3: B5

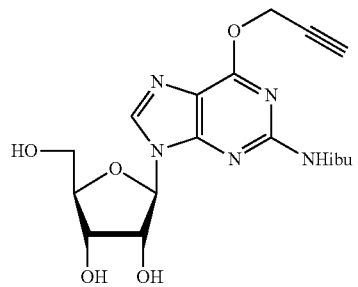

B5

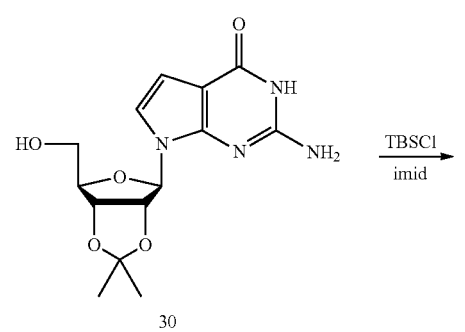

30

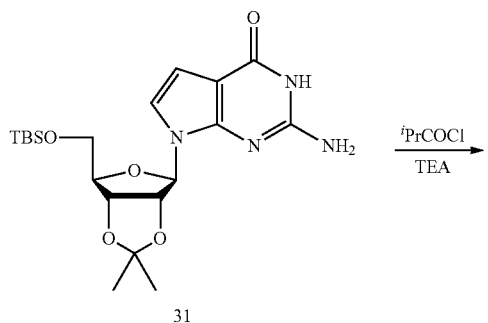

31

To a solution of 28 (150 mg, 0.17 mmol) in THF (4.5 mL) and MeOH (0.5 mL) is added sodium hydroxide aqueous solution (1 M, 0.5 mL) at 0° C. After stirring for 1 hour, HOAc (0.1 mL) is added and the mixture is concentrated and purified by silica gel column chromatography (MeOH/DCM=1/20 to 1/10) to give B5 as a white solid (40 mg, 64% yield). (MS: [M+H]$^+$ 392.0)

Preparation of B6:

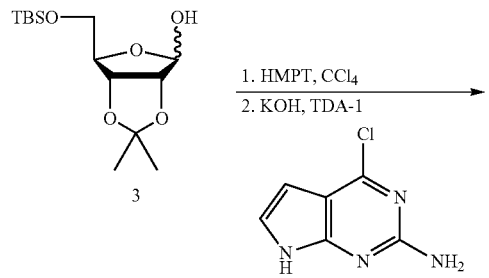

3

1. HMPT, CCl₄
2. KOH, TDA-1

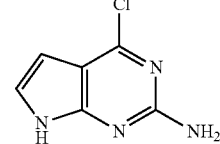

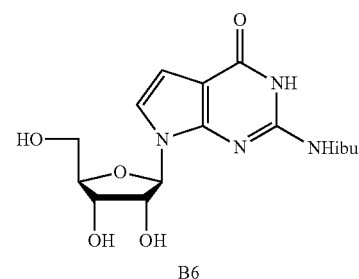

32

TFA

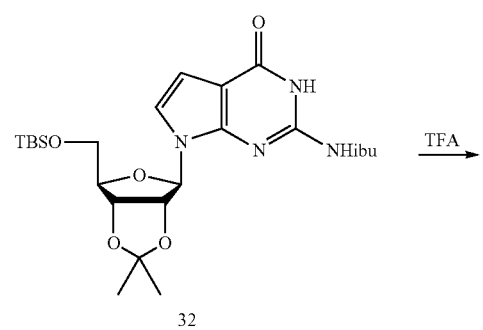

B6

Step 1: Deazapurine 29

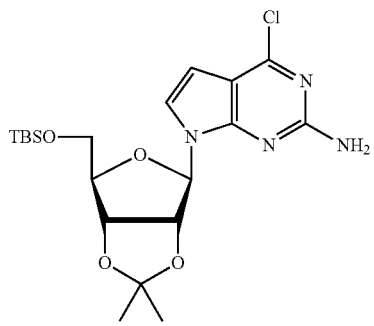

To a solution of 3 (40.0 g, 131 mmol) and carbon tetrachloride (33.6 g, 218 mmol, 21 mL) in THF (500 mL) at −78° C. is added HMPT (22.5 g, 138 mmol, 25 mL) over 15 min. After stirring for 2 hours with brief periods of slight warming to prevent gel formation, the mixture is concentrated to about 70 mL. To a suspension of KOH (25.8 g, 460 mmol) in MeCN (600 mL) is added TDA-1 (4.25 g, 13.14 mmol, 4.2 mL). After stirring at 25° C. for 10 minutes, 2-amino-6-chloro-7-deazapurine (22.2 g, 131 mmol) is added. The mixture is stirred for another 10 minutes before the THF solution obtained above is added. After stirring for 2 hours, the mixture is filtered, concentrated, and purified by silica gel column chromatography (EA/PE=3/17) to give 29 (9.20 g, 15% yield). (MS: [M+H]$^+$ 455.3)

Step 2: Alcohol 30

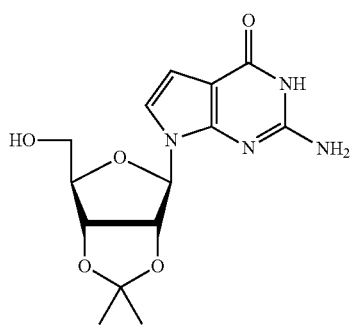

To a mixture of 29 (13.7 g, 30.1 mmol) in dioxane (10 mL) is added a solution of sodium hydroxide (11.7 g, 291 mmol) in water (100 mL) at 25° C. After stirring at 80° C. for 64 hours, the mixture is cooled to 0° C., neutralized with AcOH to ~pH 7, and extracted with EtOAc (100 mL×3). The combined organic layers are dried over anhydrous sodium sulfate, filtered, and concentrated to give crude 30. (MS: [M+1]$^+$ 323.1)

Step 3: Silyl Ether 31

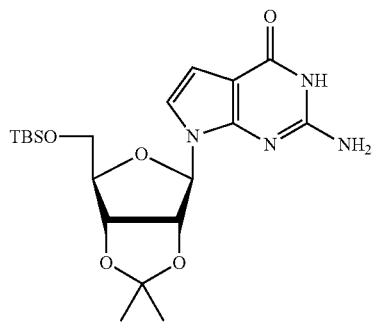

To a solution of crude 30 (9.7 g, 30.1 mmol) and Imid (4.1 g, 60.3 mmol) in DCM (10 mL) is added TBSCl (9.08 g, 60.3 mmol) at 25° C. After stirring for 16 hours, the mixture is diluted with DCM (100 mL), washed with brine (80 mL), dried over anhydrous sodium sulfate, filtered, concentrated, and purified by silica gel column chromatography (EA/PE=1/4 to 1/1 then MeOH/DCM=1/50) to give 31 (9.0 g, 68% yield) as a solid. (MS: [M+H]$^+$ 437.2)

Step 4: Isobutyrate 32

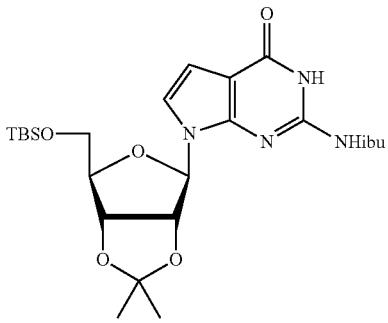

To a solution of 31 (9.0 g, 20.6 mmol) and TEA (4.2 g, 41.2 mmol) in DCM (80 mL) is added isobutyryl chloride (3.29 g, 30.9 mmol) at 0° C. After stirring at 25° C. for 16 hours, the mixture is diluted with DCM (100 mL), washed with saturated sodium bicarbonate aqueous solution (50 mL×2) and brine (50 mL), dried over anhydrous sodium sulfate, filtered, concentrated, and purified by silica gel column chromatography (EA/PE=1/5 to 1/2) to give 32 as a white solid (4.2 g, 40% yield). (MS: [M+H]$^+$ 507.2)

Step 5: B6

A solution of 32 (4.2 g, 8.29 mmol) in DCM (6 mL) and TFA (24 mL) is stirred at 25° C. for 1 hour before concentrated. The residue is then treated with hydrogen chloride (4M in MeOH, 10 mL) at 0° C. After stirring at 25° C. for 10 minutes, the mixture is concentrated to give crude B6 as a white solid (2.92 g, 99% yield). (MS: [M+H]+ 353.0)

Preparation of BA1:

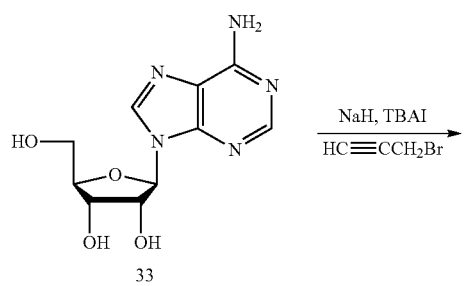

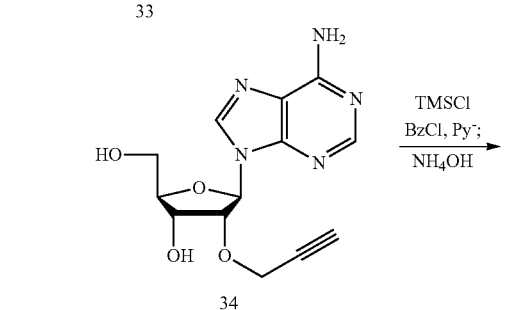

Step 2: BA1

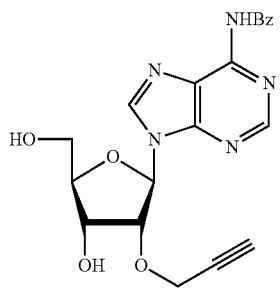

To a solution of 34 (1.4 g, 4.59 mmol, co-evaporated twice with Py) in Py (20 mL) is added TMSCl (2.4 mL, 18.9 mmol). After stirring for 30 minutes, benzoyl chloride (0.7 mL, 6.0 mmol) is added and the mixture is stirred for 3 hours before addition of water (10 mL) and ammonium hydroxide aqueous solution (15 mL) at 0° C. After stirring for 20 minutes at room temperature, the mixture is extracted with DCM (25 mL×3). The combined organic layers are dried over anhydrous sodium sulfate, concentrated, and purified by silica gel column chromatography (MeOH/DCM=5:95) to give BA1 as a white foam (1.73 g, 92%). (MS: [M+H]+ 410.2)

Preparation of BA2:

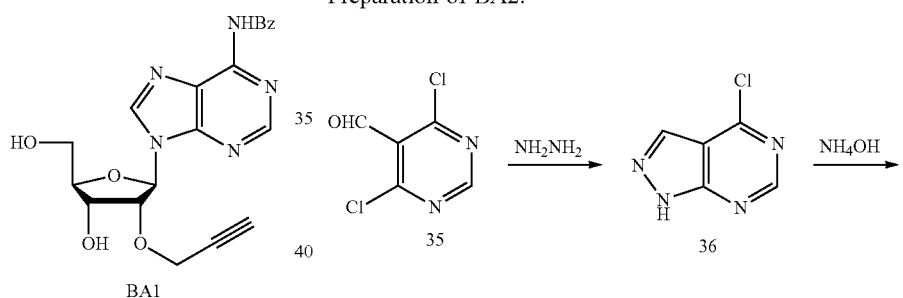

Step 1: Proparyl Ether 34

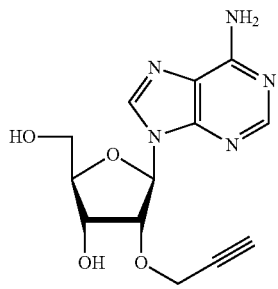

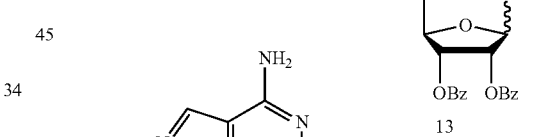

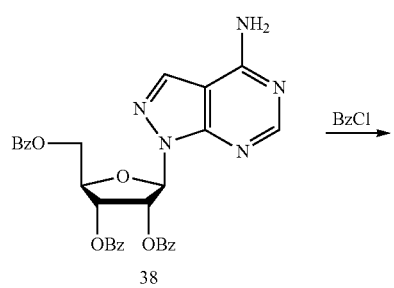

To a solution of adenosine (33) (5.0 g, 18.7 mmol) in DMF (200 mL) at 0° C. is added sodium hydride (60% dispersion in mineral oil, 1.0 g, 25 mmol) followed by the TBAI (1.5 g, 4.06 mmol) and propargyl bromide (2.12 mL, 20.9 mmol). After stirring at 55° C. for 2 days, the mixture is purified by silica gel column chromatography (MeOH/DCM=7/93) followed by re-crystallization from ethanol to give 34 as a pale yellow solid (2.56 g, 45%).

-continued

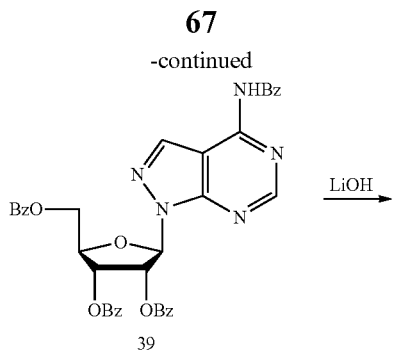

39

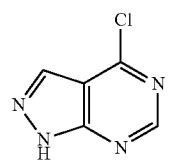

BA2

Step 1: Pyrazolopyrimidine 36

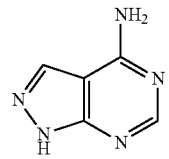

36

To a solution of 35 (10.0 g, 56.5 mmol) in THF (80 mL) is added DIPEA (7.3 g, 56.5 mmol, 9.9 mL). After stirring at 0° C. for 10 minutes, a solution of hydrazine (1.81 g, 56.5 mmol, 2.0 mL) in THF (20 mL) is added. The mixture is then stirred at 20° C. for 2 hours before concentrated. After addition of DCM (100 mL) and H$_2$O (100 mL) to the residue, the layers are separated and the aqueous layer is extracted with DCM (100 mL×3). The combined organic layers are washed with brine (100 mL), dried over anhydrous sodium sulfate, filtered, concentrated, and purified by silica gel column chromatography (EA/PE=1/15 to 1/8) to give 36 as a yellow solid (3.10 g, 35% yield). (MS: [M+H]$^+$ 155.1)

Step 2: Pyrazolopyrimidine 37

37

To a solution of 36 (200 mg, 1.29 mmol) in THF (2.0 mL) is added ammonium hydroxide (2.0 mL). After stirring at 20-30° C. for 2 hours, the mixture is concentrated, triturated with MeCN (0.5 mL), and collected by filtration to give 37 as a red solid (100 mg, 57% yield).

Step 3: Tribenzoate 38

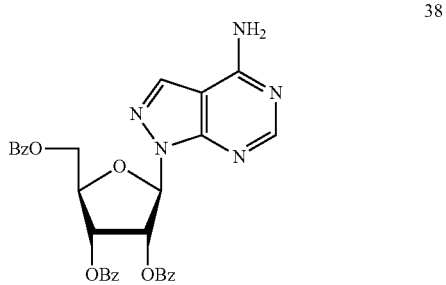

To a suspension of 37 (20.0 g, 148 mmol) and 13 (101 g, 200 mmol) in MeCN (1.2 L) is added boron trifluoride diethyl etherate (30.5 g, 215 mmol, 26.5 mL). After stirring at 75-85° C. for 2 hours, the mixture is concentrated and purified by silica gel column chromatography (EA/PE=1/5 to 2/1) to give 38 as a yellow solid (35.0 g, 40% yield). (MS: [M+H]$^+$ 580.3)

Step 4: Benzamide 39

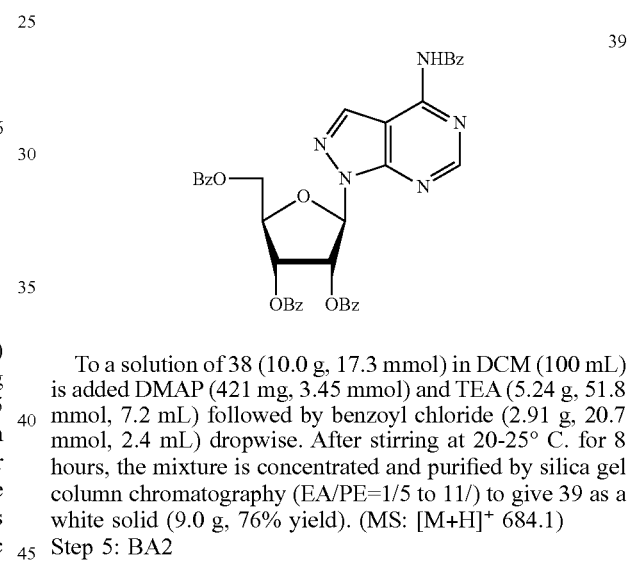

To a solution of 38 (10.0 g, 17.3 mmol) in DCM (100 mL) is added DMAP (421 mg, 3.45 mmol) and TEA (5.24 g, 51.8 mmol, 7.2 mL) followed by benzoyl chloride (2.91 g, 20.7 mmol, 2.4 mL) dropwise. After stirring at 20-25° C. for 8 hours, the mixture is concentrated and purified by silica gel column chromatography (EA/PE=1/5 to 1/1) to give 39 as a white solid (9.0 g, 76% yield). (MS: [M+H]$^+$ 684.1)

Step 5: BA2

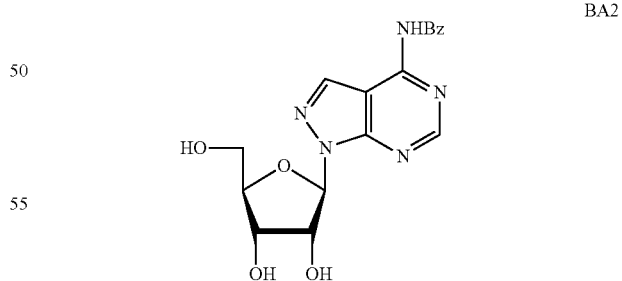

To a solution of 39 (1.0 g, 1.46 mmol) in THF (1.5 mL), MeOH (1.2 mL) and H$_2$O (0.3 mL) is added lithium hydroxide aqueous solution (5 M, 0.53 mL). After stirring at 0-25° C. for 2 hours, the mixture is neutralized with citric acid (1 M) to ~pH 7 before removal of the volatiles. The solid in the aqueous solution is then collected by filtration to give BA2 as an off-white solid (300 mg, 54% yield). (MS: [M+H]$^+$ 372.2)

Preparation of BA3:

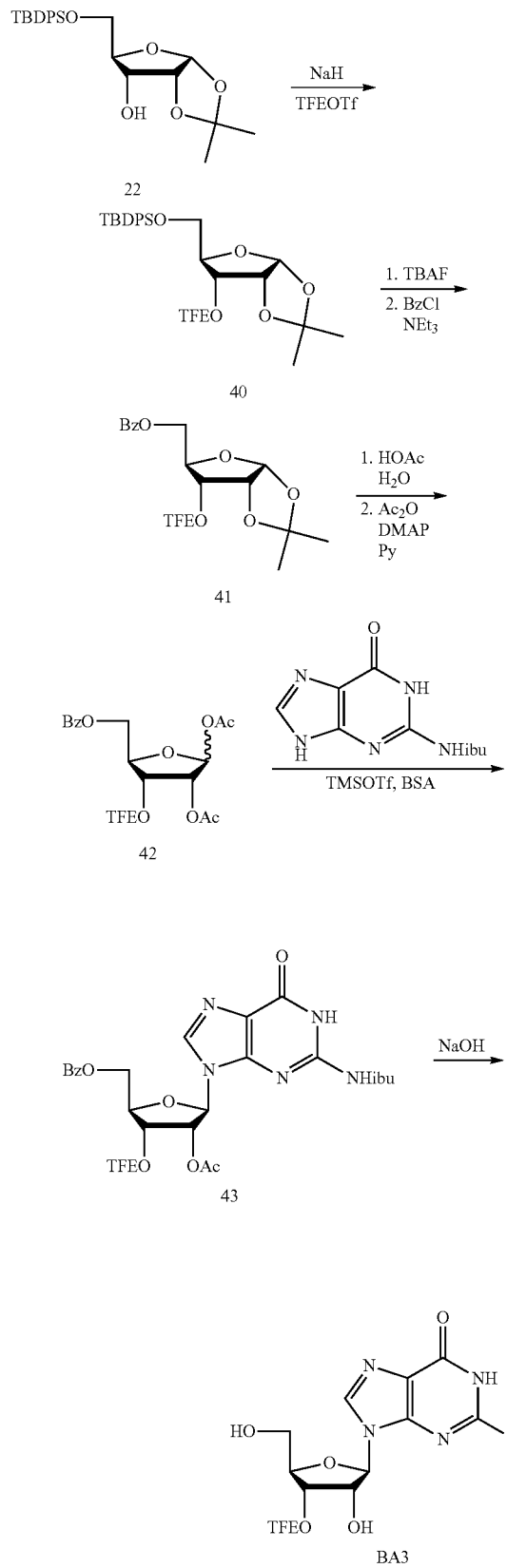

Step 1: Trifluoroethyl Ether 40

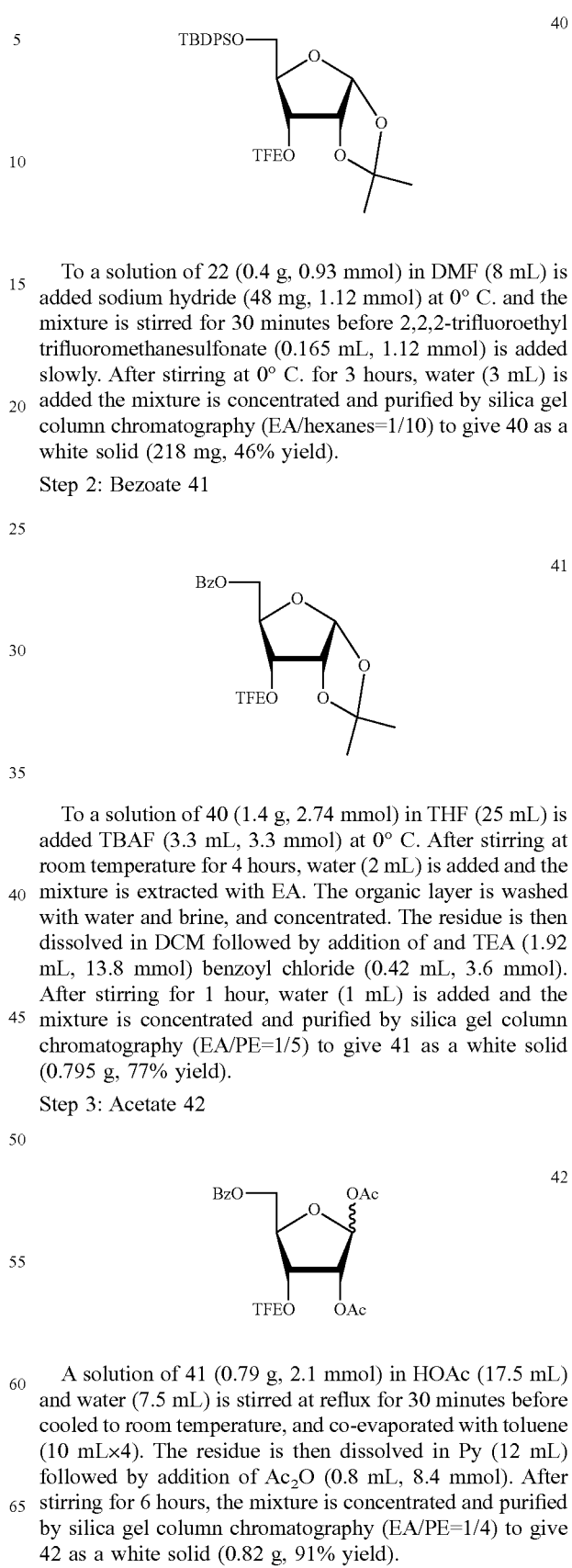

To a solution of 22 (0.4 g, 0.93 mmol) in DMF (8 mL) is added sodium hydride (48 mg, 1.12 mmol) at 0° C. and the mixture is stirred for 30 minutes before 2,2,2-trifluoroethyl trifluoromethanesulfonate (0.165 mL, 1.12 mmol) is added slowly. After stirring at 0° C. for 3 hours, water (3 mL) is added the mixture is concentrated and purified by silica gel column chromatography (EA/hexanes=1/10) to give 40 as a white solid (218 mg, 46% yield).

Step 2: Bezoate 41

To a solution of 40 (1.4 g, 2.74 mmol) in THF (25 mL) is added TBAF (3.3 mL, 3.3 mmol) at 0° C. After stirring at room temperature for 4 hours, water (2 mL) is added and the mixture is extracted with EA. The organic layer is washed with water and brine, and concentrated. The residue is then dissolved in DCM followed by addition of and TEA (1.92 mL, 13.8 mmol) benzoyl chloride (0.42 mL, 3.6 mmol). After stirring for 1 hour, water (1 mL) is added and the mixture is concentrated and purified by silica gel column chromatography (EA/PE=1/5) to give 41 as a white solid (0.795 g, 77% yield).

Step 3: Acetate 42

A solution of 41 (0.79 g, 2.1 mmol) in HOAc (17.5 mL) and water (7.5 mL) is stirred at reflux for 30 minutes before cooled to room temperature, and co-evaporated with toluene (10 mL×4). The residue is then dissolved in Py (12 mL) followed by addition of Ac$_2$O (0.8 mL, 8.4 mmol). After stirring for 6 hours, the mixture is concentrated and purified by silica gel column chromatography (EA/PE=1/4) to give 42 as a white solid (0.82 g, 91% yield).

Step 4: Guanosine 43

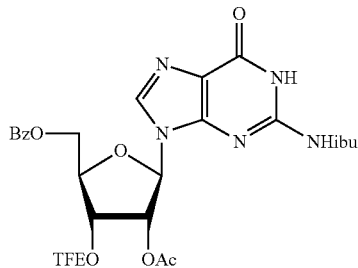

To a suspension of 42 (800 mg, 1.9 mmol) and N²-isobutyrylguanine (633 mg, 2.86 mmol) in dichloroethane (25 mL) at 80° C. is added BSA (2.74 mL, 10.1 mmol) and stirred for 1 hour before addition of TMSOTf (1.03 mL, 5.7 mmol). After stirring for 3 hours at 100° C., the mixture is poured into sodium bicarbonate aqueous solution (60 mL) and extracted with DCM (60 mL×3). The combined organic layers are dried over anhydrous sodium sulfate, concentrated, and purified by silica gel column chromatography (MeOH/DCM=1/20 to 1/10) to give 43 as a white solid (938 mg, 85% yield).

Step 5: BA3

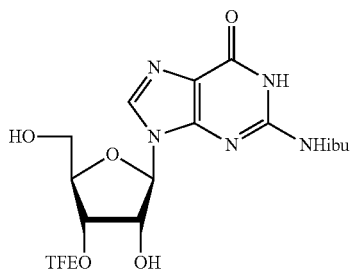

To a solution of 43 (0.5 g, 0.86 mmol) in MeOH (8 mL), THF (10 mL) and water (2 mL) is added sodium hydroxide aqueous solution (10 M, 0.34 mL) at 0° C. After stirring for 30 minutes, HOAc is added and the mixture is concentrated and purified by silica gel column chromatography (MeOH/DCM=1/10 to 1/5) to afford BA3 as an oil (348 mg, 93% yield).

Preparation of BB1

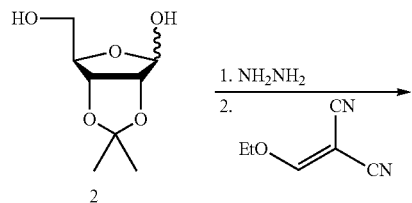

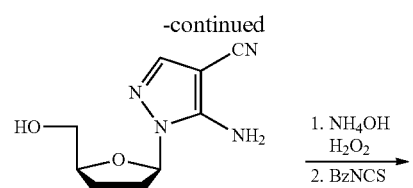

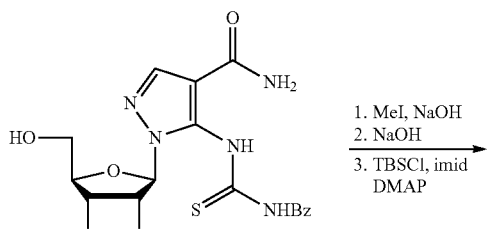

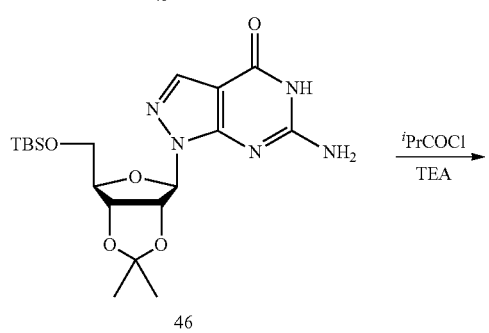

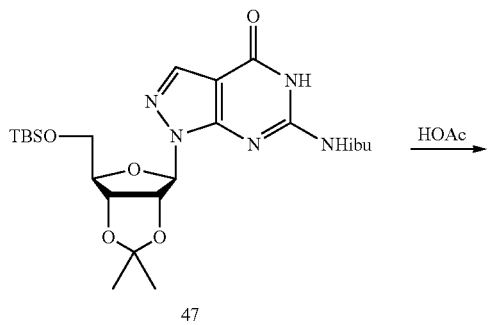

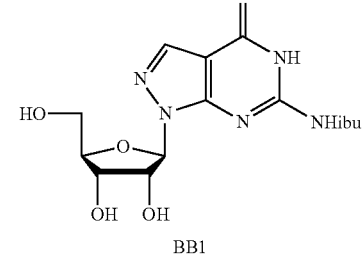

Step 1: Pyrazole 44

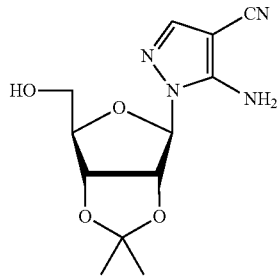

To a solution of 2 (75 g, 395 mmol) in MeOH (600 mL) is added hydrazine hydrate (120 mL) at 25° C. After stirring for 2 hours, the mixture is concentrated and the residue is dissolved in EtOH (600 mL) before addition of (ethoxymethylene)malononitrile (110 g, 901 mmol). After stirring at 78° C. for 30 minutes, the mixture is concentrated and purified by silica gel column chromatography (EA/PE=1/20 to 1/15) to give 44 as a pale yellow solid (42 g, 38% yield).

Step 2: Thiourea 45

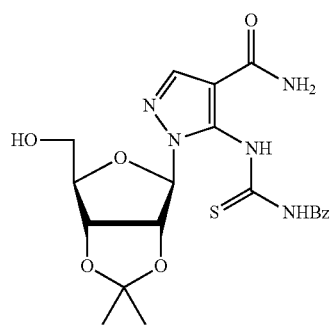

To a solution of 44 (16.0 g, 57 mmol) in MeOH (75 mL) and water (25 mL) is added ammonium hydroxide (280 mL) and hydrogen peroxide (150 mL). After stirring at 25° C. for 16 hours, the mixture is poured into sodium sulfite aqueous solution (2 L) and then extracted with EA (700 mL×3). The combined organic layers are dried over anhydrous sodium sulfate, filtered, and concentrated. The residue is then dissolved in acetone (90 mL) before benzoyl isothiocyanate (6.96 g, 42.7 mmol, 5.75 mL) is added at 25° C. After stirring at 60° C. for 4 hours, the mixture is concentrated to give crude 45 as a yellow solid.

Step 3: Pyrazolopyrimidinone 46

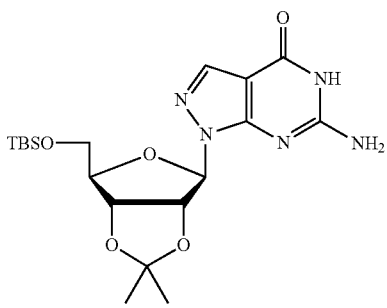

To a solution of the crude 45 obtained above in MeOH (150 mL) is added sodium hydroxide aqueous solution (0.7 M, 80 mL) followed by methyl iodide (6.8 g, 47.9 mmol, 3.0 mL). After stirring at 20° C. for 2 hours, the mixture is neutralized with HOAc to ~pH 6 followed by addition of water (80 mL), and extracted with EA (100 mL×3). The combined organic layers are dried over anhydrous sodium sulfate, filtered, and concentrated. The residue is then dissolved in MeOH (30 mL) and sodium hydroxide aqueous solution (1.4 M, 250 mL) is added. After stirring at 100° C. for 2 hours, the mixture is concentrated and the residue is co-evaporated with toluene (200 mL×3) and dissolved in DCM (500 mL). Imid (18.5 g, 271 mmol), DMAP (1.66 g, 13.6 mmol), and TBSCl (40.9 g, 271 mmol) are then added. After stirring at 25° C. for 18 hours, saturated sodium bicarbonate aqueous solution (1 L) is added and the mixture is extracted with EA (500 mL×3). The combined organic layers are dried over anhydrous sodium sulfate, filtered, concentrated, and purified by silica gel column chromatography (MeOH/DCM=1/60 to 1/30) to give 46 as a white solid (8.50 g, 34% yield over five steps).

Step 4: Isobutyrate 47

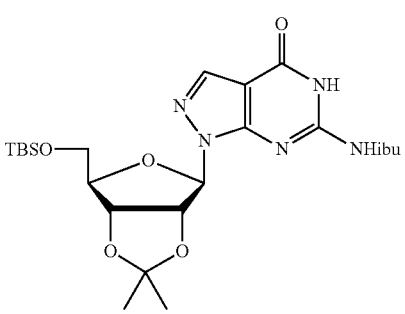

To a solution of 46 (23.4 g, 53.5 mmol) in Py (120 mL) is added isobutyryl chloride (11.4 g, 107 mmol, 11.2 mL) at 25° C. After stirring at 25° C. for 16 hours, ammonium hydroxide (0.5 mL) is added and the mixture is stirred for 30 minutes before concentrated. The residue is then dissolved in EtOAc (1.5 L), washed with saturated ammonium hydroxide aqueous solution (500 mL×3) and brine (500 mL), dried over anhydrous sodium sulfate, filtered, concentrated, and purified by silica gel column chromatography (EA/PE=1/10 to 1/3) to give 47 as a light yellow solid (24.0 g, 88% yield). (MS: $[M+Na]^+$ 530.1)

Step 5: BB1

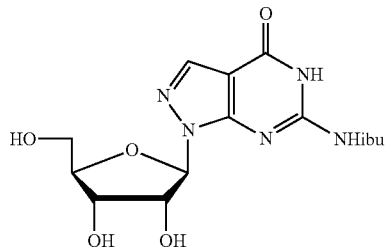

A solution of 47 (10.0 g, 19.7 mmol) in HOAc (6 mL) and water (3 mL) is stirred at 65° C. for 5 hours. The reaction mixture is then concentrated and triturated with DCM (15 mL). The solid is collected by filtration to give crude BB1 as a white solid (4.0 g). (MS: [M+H]⁺ 354.0)

Preparation of BC1:

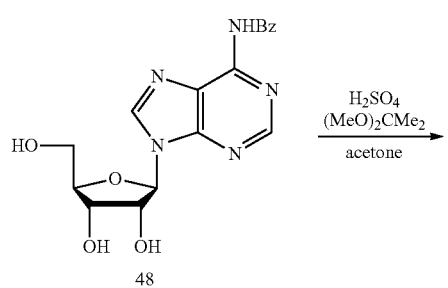

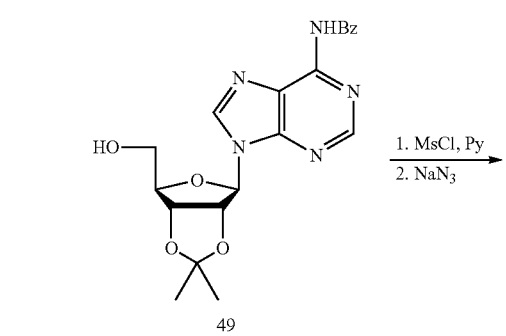

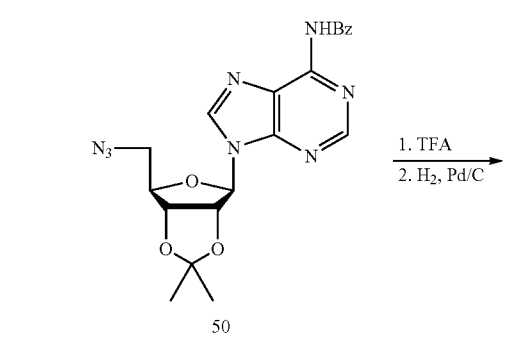

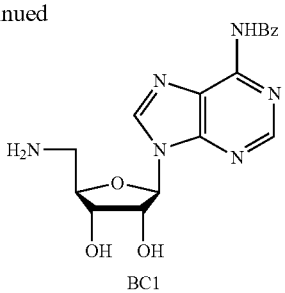

Step 1: Acetonide 49

To a solution of 48 (50 g, 135 mmol) in acetone (500 mL) is added 2,2-dimethoxypropane (85 g, 816 mmol, 100 mL) and concentrated sulfuric acid (1.32 g, 13.5 mmol, 0.72 mL). After stirring at 25° C. for 30 minute, saturated sodium bicarbonate aqueous solution (30 mL) is added. The solution is filtered, concentrated, and purified by silica gel column chromatography (MeOH/DCM=1/200 to 1/50) to give 49 as a white solid (35 g, 63% yield). (MS: [M+H]⁺ 412.1)

Step 2: Azide 50

To a solution of 49 (5.0 g, 12.2 mmol) in Py (50 mL) is added methanesulfonyl chloride (2.1 g, 18 mmol, 1.4 mL) at 0° C. After stirring at 25° C. for 1 hour, DCM (200 mL) is added, and the solution is washed with saturated sodium bicarbonate aqueous solution followed by brine, dried over anhydrous sodium sulfate, and concentrated. The residue is then dissolved in DMF (50 mL) followed by addition of sodium azide (3.4 g, 52.3 mmol). After stirring at 50° C. for 16 hours, DCM (400 mL) is added. The mixture is washed with water (300 mL), brine, dried over sodium sulfate, concentrate, and purified by silica gel column chromatography (EA/PE=1/1) to give 50 as a light yellow solid (4.0 g). (MS: [M+H]⁺ 437.1)

Step 3: BC1

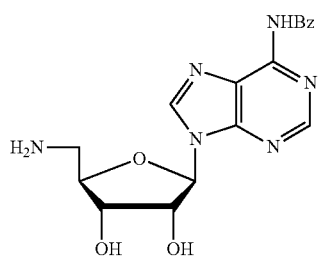

A solution of 50 (50 g, 115 mmol) in TFA (125 mL) and water (125 mL) is stirred at 25° C. for 5 hours before concentrated, co-evaporated twice with toluene, and dissolved in MeOH (50 mL). The mixture is then neutralized by sodium bicarbonate aqueous solution (1%) and triturated with MTBE. The solid is collected, washed with MTBE, dried, and dissolved in DMF (400 mL). Pd/C (10% w/w, 10 g) is then added and the mixture is stirred under an atmosphere of hydrogen (15 psi) at 25° C. for 6 hours before filtered and concentrated to give crude BC1 as a yellow oil (39 g). (MS: [M+H]$^+$ 371.1)

Preparation of BC2:

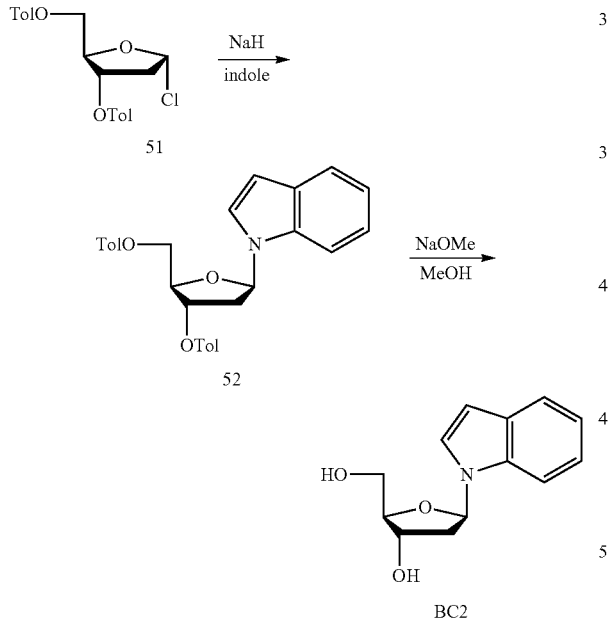

Step 1: Indole 52

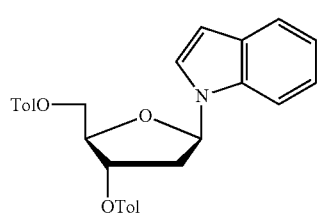

To a solution of indole (305 mg, 2.6 mmol) in MeCN (10 mL) is added sodium hydride (160 mg, 4.0 mmol) at 0° C. and stirred for 30 minutes before 51 (1.0 g, 2.6 mmol) is added. After stirring for 1 hour, saturated sodium bicarbonate aqueous solution (5 mL) is added and the mixture is extracted with EA (20 mL×3). The combined organic layers are washed with saturated sodium bicarbonate aqueous solution and brine, concentrated, and purified by silica gel column chromatography (EA/hexanes=1/4) to give 52 as a yellow oil (886 mg, 71% yield). (MS: [M+H]$^+$ 470.2)

Step 2: BC2

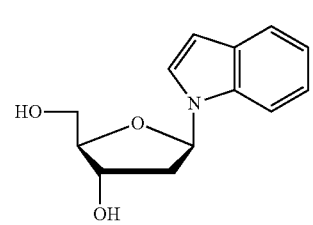

To a solution of 52 (610 mg, 1.3 mmol) in MeOH (9 mL) is added sodium methoxide (5.4 M in methanol, 0.54 mL). After stirring for 1 hour, hydrochloric acid (5 M, 0.5 mL) is added at 0° C. and the solution is stirred for 10 minutes before concentrated and purified by silica gel column chromatography (MeOH/DCM=1/9) to give the desired product as a white solid (197 mg, 92% yield). (MS: [M+H]$^+$ 234.1)

Preparation of BC3:

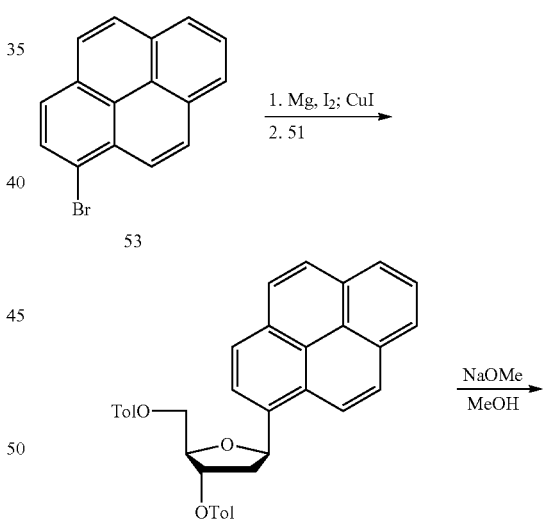

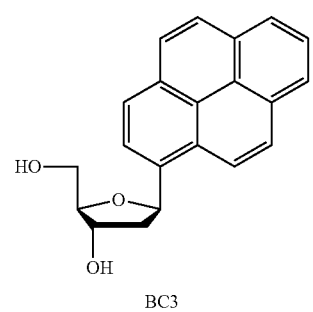

Step 1: Pyrene 54

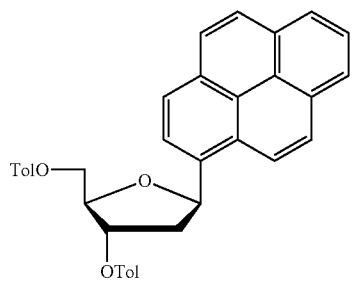

54

To a solution of 53 (560 mg, 2 mmol) in THF is added magnesium (54 mg, 2.3 mmol) followed by a small amount of iodine. After stirring at 55° C. for 3 hours, copper(I) iodide (213 mg, 1.1 mmol) is added at 0° C. The mixture is stirred at room temperature for 45 minutes before 51 (367 mg, 0.98 mmol) is added at 40° C. After stirring for 2 hours, saturated ammonium chloride aqueous solution (2 mL) and DCM (20 mL) are added. The layers are separated and the organic layer is washed by saturated sodium bicarbonate aqueous solution and brine, dried anhydride sodium sulfate, concentrated, and purified by silica gel column chromatography (EA/hexanes=1/10 to 1/5) to give 54 as a white solid (52 mg, 10%).

Step 2: BC3

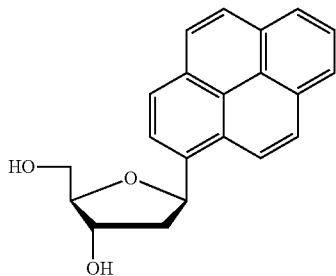

BC3

To a solution of 54 (230 mg, 0.4 mmol) in MeOH (5 mL) is added sodium methoxide (30% in MeOH, 0.23 mL, 1.2 mmol) at room temperature. After stirring for 1 hour, saturated ammonium chloride (5 mL) is added and the mixture is extracted by EA (10 mL×3). The organic layers are washed with brine, dried over anhydrous sodium sulfate, and concentrated to give crude BC3 as a white solid (150 mg).

Preparation of BC4:

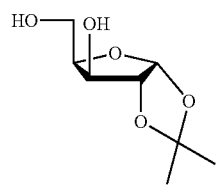 →TrCl, pyridine→

55

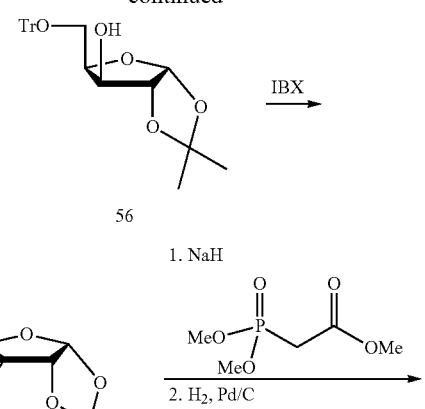 →IBX→

56

1. NaH, (MeO)$_2$P(O)CH$_2$CO$_2$Me
2. H$_2$, Pd/C

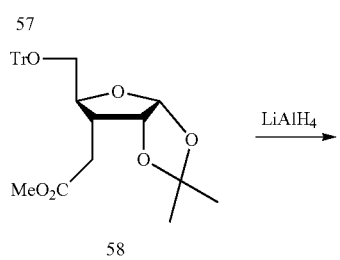 →LiAlH$_4$→

57

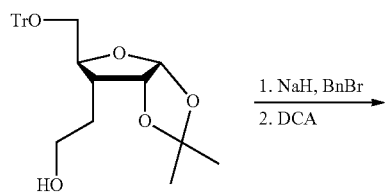

58

1. NaH, BnBr
2. DCA

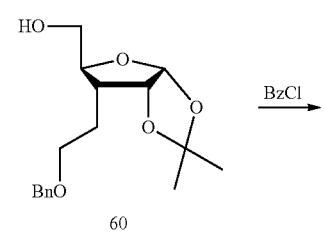

59

→BzCl→

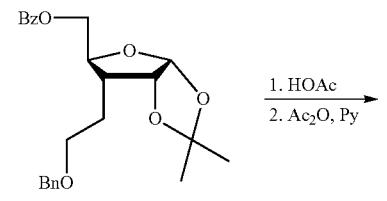

60

1. HOAc
2. Ac$_2$O, Py

61

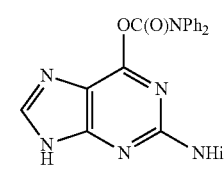

62

+ purine reagent (OC(O)NPh$_2$, NHibu), TMSOTf, BSA

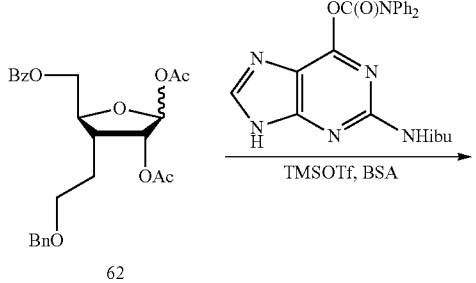

-continued

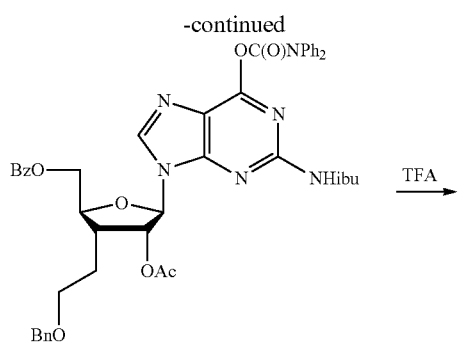
63

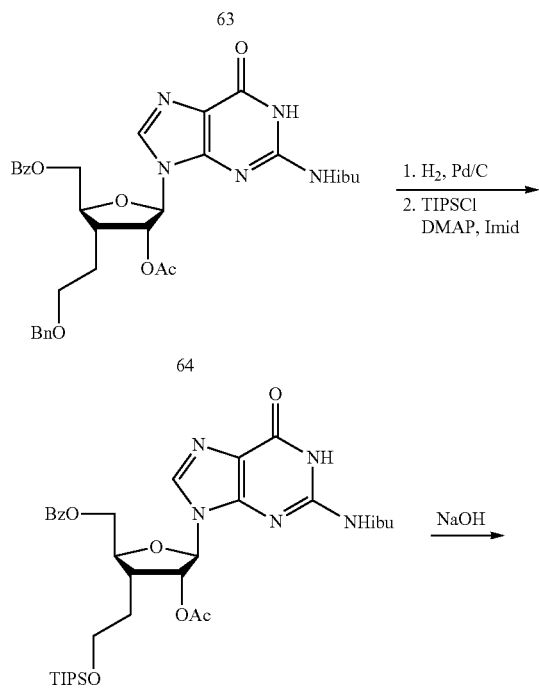

Step 1: Alcohol 56

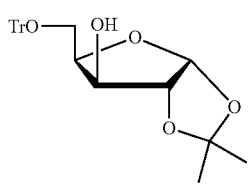
56

To a solution of 55 (91.4 g, 481 mmol) in Py (600 mL) is added trityl chloride (160.7 g, 577 mmol). After stirring at 60° C. for 16 hours, the mixture is concentrated and co-evaporated with toluene for three times. The residue is partitioned between DCM (400 mL) and saturated sodium bicarbonate aqueous solution (750 mL). The layers are separated and the aqueous phase is extracted with DCM (400 mL×2). The combined organic layers are dried over anhydrous sodium sulfate, filtered, concentrated, and purified by silica gel column chromatography (EA/PE=1/10 to 1/5) to afford 56 as a white solid (180.5 g, 87% yield). (MS: [M+Na]$^+$ 455.0)

Step 2: Ketone 57

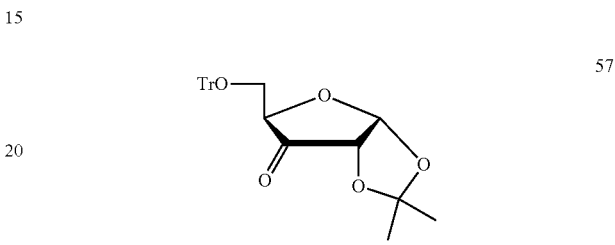

To a solution of 56 (176 g, 407 mmol) in MeCN (1.0 L) is added IBX (228 g, 814 mmol). After stirring at 90° C. for 6 hours, the mixture is filtered and concentrated to give crude 57 as a light yellow oil (175 g). (MS: [M+Na]$^+$ 453.0)

Step 3: Ester 58

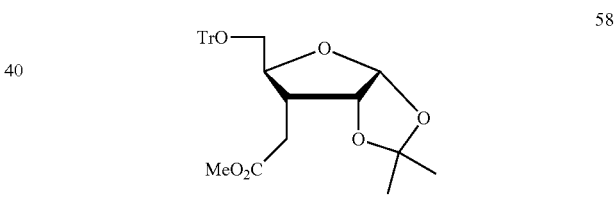

To a solution of sodium hydride (20.1 g, 502 mmol) in THF (1.0 L) is added methyl 2-dimethoxyphosphorylacetate (96.3 g, 529 mmol, 76.5 mL) at 0° C. dropwise over 15 minutes. After stirring for 60 minutes, crude 57 (175 g) obtained above in THF (500 mL) is added dropwise at 0° C. After stirring at 25° C. for 16 hours, water (50 mL) is added at 0° C. and the volatiles are removed and brine (500 mL) is added. The mixture is then extracted with DCM (500 mL×3). The combined organic layers are dried over anhydrous sodium sulfate, filtered, and concentrated. The residue (198 g of 216 g obtained above) is then dissolved in EA (500 mL) and Pd/C (10% w/w, 10 g) is added. After stirring under a hydrogen atmosphere (20 psi) at 25° C. for 16 hours, the mixture is filtered and the filtrate is concentrated and purified by silica gel column chromatography (EA/PE=1/15 to 1/10) to give 58 as a white solid (120 g, 66% yield) (MS: [M+Na]$^+$ 511.1)

Step 4: Alcohol 59

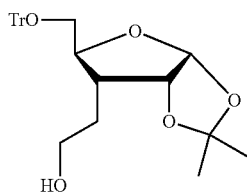

To a solution of lithium aluminum hydride (6.21 g, 164 mmol) in THF (200 mL) is added 58 (20.0 g, 40.9 mmol) in THF (50 mL) slowly at 0° C. After stirring at 25° C. for 16 hours, the reaction is quenched by sequential addition of water (6.2 mL), sodium hydroxide aqueous solution (15%, 6.2 mL), and water (18.6 mL). The mixture is then dried over anhydrous sodium sulfate, filtered, concentrated, and purified by silica gel column chromatography (EA/PE=1/10 to 1/4) to give 59 as a white solid. (MS: [M+Na]$^+$ 483.2)

Step 5: Alcohol 60

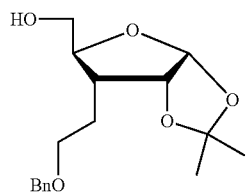

To a solution of sodium hydride (60% w/w, 6.95 g, 174 mmol) in THF (200 mL) is added 59 (20.0 g, 43.4 mmol) in THF (80 mL) at −20° C. dropwise over 5 minutes. After stirring at 25° C. for 2 hours, benzyl bromide (22.3 g, 130 mmol, 15.5 mL) is added dropwise and the mixture is stirred at 80° C. for 16 hours before water (2 mL) is added at 0° C. The mixture is diluted with water (200 mL) and extracted with DCM (200 mL×3). The combined organic layers are dried over anhydrous sodium sulfate, filtered and concentrated. The residue is then dissolved in DCM (200 mL) and DCA (5.48 g, 42.5 mmol, 12.0 mL) is added. After stirring at 25° C. for 3 hours, saturated sodium bicarbonate aqueous solution is added at 0° C. The mixture is then extracted with DCM (150 mL×3). The combined organic solvent are dried over anhydrous sodium sulfate, filtered, concentrated, and purified by silica gel column chromatography (EA/PE=1/5 to 1/2) to give 60 as a yellow oil (12.1 g, 90% yield).

Step 6: Benzoate 61

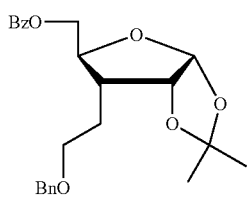

To a solution of 60 (24.0 g, 78 mmol) in DCM (500 mL) is added benzoyl chloride (16.4 g, 116.7 mmol, 13.6 mL) and TEA (23.6 g, 233.5 mmol, 32.4 mL). After stirring at 25° C. for 16 hours, the mixture is concentrated and purified by silica gel column chromatography (EA/PE=1/15 to 1/10) to give 61 as a light yellow oil (30.0 g, 93% yield). (MS: [M+Na]$^+$ 435.1)

Step 7: Acetate 62

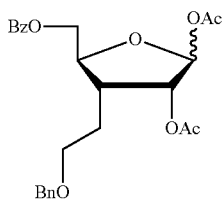

A mixture of 61 (29.0 g, 70.3 mmol) and water (3.0 mL) in HOAc (220 mL) is stirred at 70° C. for 16 hours before saturated sodium bicarbonate aqueous solution is added. The mixture is then extracted with DCM (400 mL×3). The combined organic layers are concentrated and the residue is dissolved in Py (30 mL) followed by addition of Ac$_2$O (28.5 g, 280 mmol, 26 mL). After stirring at 20° C. for 16 hours, saturated sodium bicarbonate aqueous solution is added and the mixture is then extracted with DCM (500 mL×3). The combined organic layers are concentrated and purified by silica gel column chromatography (EA/PE=1/10 to 1/5) to give 62 as a white solid (31.1 g, 97% yield). (MS: [M+Na]$^+$ 479.1)

Step 8: Purine 63

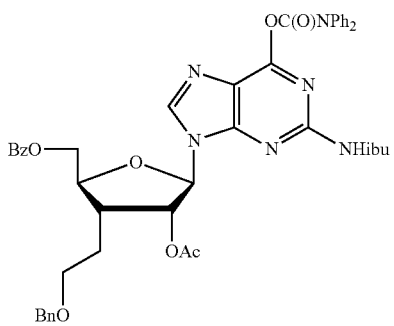

To a suspension of O$^6$-diphenylcarbamoyl-N$^2$-isobutyrylguanine (5.47 g, 13.1 mmol) in MeCN (150 mL) is added BSA (11.6 g, 57.0 mmol, 14.1 mL) at 20° C. After stirring at 63° C. for 30 minutes, the volatiles are removed and the residue is dissolved in MeCN (200 mL) before 62 (5.00 g, 11.0 mmol) in MeCN (50 mL) and TMSOTf (3.65 g, 16.4 mmol, 3.0 mL) are added at −15° C. After stirring at 63° C. for 50 minutes, the mixture is cooled to 0° C., poured into saturated sodium bicarbonate aqueous solution and extracted with EA (150 mL×3). The combined organic layers are dried over anhydrous sodium sulfate, and concentrated, and purified by silica gel flash chromatography (EA/PE=1/3 to 1/1) to give 63 as a white solid. (MS: [M+H]$^+$ 813.1)

Step 9: Guanosine 64

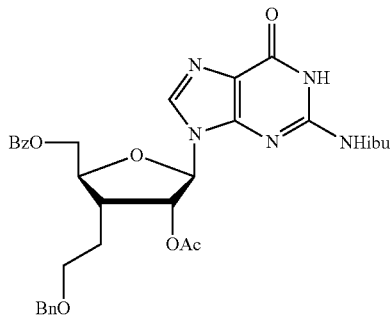

A solution of 63 (16.2 g, 19.9 mmol) in 90% TFA aqueous solution (60 mL) is stirred at 20° C. for 30 minutes before poured into saturated sodium bicarbonate aqueous solution at 0° C. and extracted with EA (100 mL×4). The combined organic layers are dried over anhydrous sodium sulfate, concentrated, and purified by silica gel flash chromatography (EA/PE=1/1 to 1/0) to give 64 as a white solid (11.4 g, 93% yield). (MS: [M+H]$^+$ 618.1)

Step 10: Silyl Ether 65

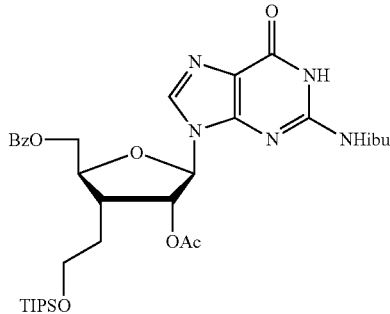

To a solution of 64 (15.0 g, 24.3 mmol) in EtOH (500 mL) is added Pd/C (10% w/w, 2.0 g) and concentrated hydrochloric acid (10 drops). After stirring at 50° C. under an atmosphere of hydrogen (45 psi) for 15 hours, the mixture is filtered and solid is washed with EtOH (100 mL×3). The filtrate is concentrated and one-third of the residue is dissolved in DMF (60 mL) followed by addition of Imid (1.57 g, 23.0 mmol), DMAP (46.9 mg, 0.38 mmol) and triisopropylsilyl chloride (2.22 g, 11.5 mmol, 2.5 mL). After stirring at 20° C. for 16 hours, saturated sodium bicarbonate aqueous solution (20 mL) and water (100 mL) are added. The mixture is then extracted with EA (100 mL×2). The combined organic layers are dried over anhydrous sodium sulfate, filtered, concentrated, and purified by silica gel column chromatography (EA/PE=1/5 to 2/1) to give 65 as a white solid (4.52 g, 86% yield). (MS: [M+H]$^+$ 684.4)

Step 11: BC4

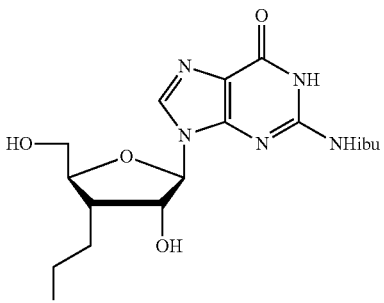

To a solution of 65 (3.0 g, 4.4 mmol) in EtOH (30 mL) is added sodium hydroxide aqueous solution (2 M, 31 mL) at 0° C. After stirring at 0° C. for 30 minute, the mixture is neutralized by addition of hydrochloric acid solution (1 N) and HOAc at 0° C. Toluene (30 mL) is then added and mixture is concentrated to give crude BC4 as a white solid (3.0 g). (MS: [M+H]$^+$ 538.2)

Preparation of BC5:

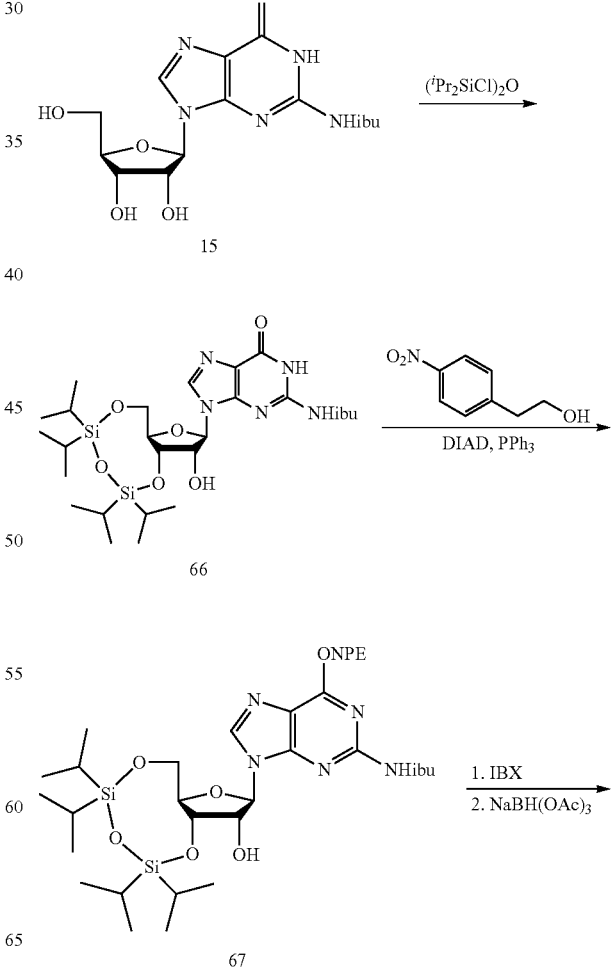

Step 2: Purine 67

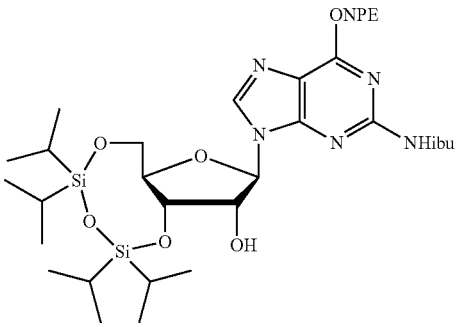

To a solution of 66 (8.0 g, 13.5 mmol) and 2-(4-nitrophenyl)ethanol (3.37 g, 20.2 mmol) in THF (100 mL) is added DIAD (6.81 g, 33.7 mmol, 6.6 mL) and PPh₃ (8.83 g, 33.7 mmol) at 25° C. slowly. After stirring at 25° C. for 12 hours, water (5 mL) is added and the mixture is concentrated and purified by silica gel column chromatography (MeOH/DCM=1/20) to give 67 as a pale yellow solid (4.5 g, 44% yield). (MS: [M+H]⁺ 745.3)

Step 3: Alcohol 68

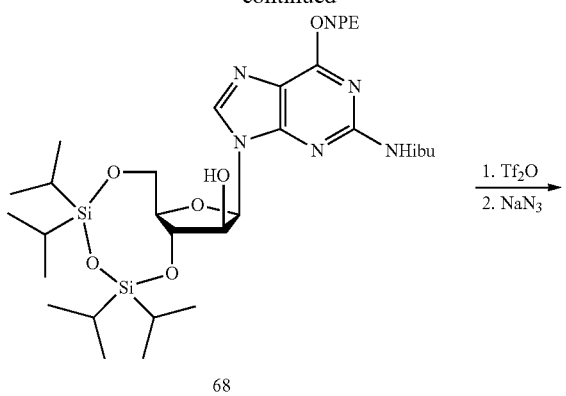

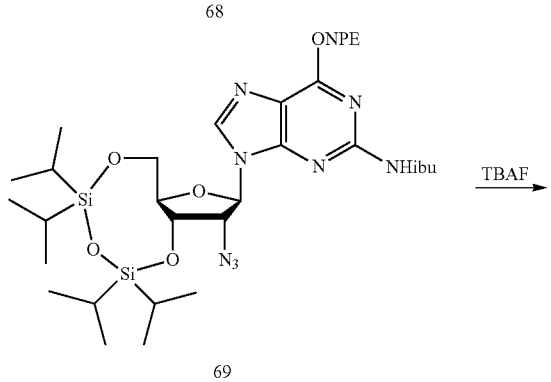

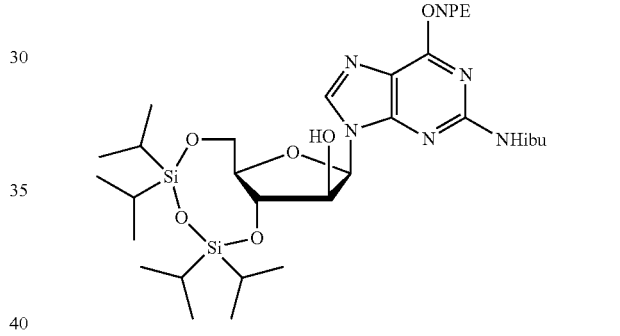

To a solution of 67 (4.20 g, 5.64 mmol) in MeCN (40 mL) at 25° C. is added IBX (3.16 g, 11.3 mmol). After stirring at 80° C. for 12 hours, the mixture is filtered and concentrated, and dissolved in THF (50 mL). Sodium triacetoxyborohydride (5.7 g, 27.0 mmol) is then added at 0° C. slowly. After stirring at 25° C. for 6 hours, water (5 mL) is added and the mixture is concentrated and purified by silica gel column chromatography (MeOH/DCM=1/20) to give 68 as a pale yellow oil (1.0 g, 33% yield). (MS: [M+H]⁺ 745.3)

Step 4: Azide 69

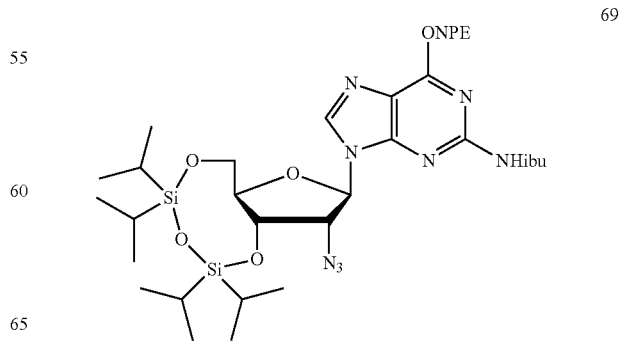

Step 1: Alcohol 66

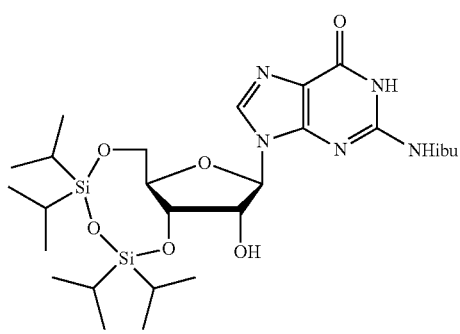

To a solution of 15 (2.0 g, 5.66 mmol) in Py (56 mL) at 0° C. is added 1,3-dichloro-1,1,3,3-tetraisopropyldisiloxane (1.79 g, 5.66 mmol, 1.8 mL) slowly. After stirring at 0° C. for 30 minutes and 25° C. for 12 hours, the solution is concentrated and purified by silica gel column chromatography (MeOH/DCM=1/20) to give 66 (1.6 g, 47% yield). (MS: [M+H]⁺ 596.3)

To a solution of 68 (2.2 g, 2.95 mmol) and DMAP (1.44 g, 11.8 mmol) in DCM (140 mL) and Py (10 mL) is added trifluoromethanesulfonic anhydride (1.33 g, 4.72 mmol, 0.78 mL) at 0° C. slowly. After stirring at 0° C. for 1.5 hours, the mixture is concentrated. The residue is then dissolved in DMF (10 mL) and sodium azide (0.49 g, 7.53 mmol) is added. After stirring at 60° C. for 6 hours, the solution is concentrated and purified by preparative HPLC (MeOH/water with 0.1% HCOOH: 40-100%) to give 69 as a pale yellow solid (1.50 g, 79% yield). (MS: [M+H]$^+$ 770.4)

Step 5: BC5

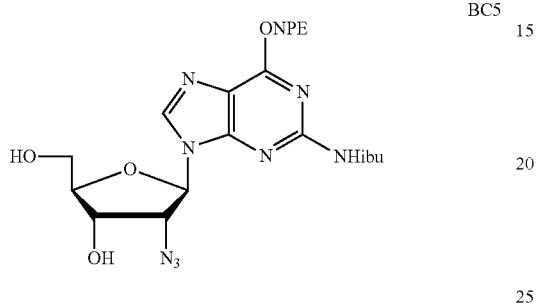

BC5

To a solution of 69 (2.50 g, 3.25 mmol) in THF (12 mL) is added TBAF (13.1 g, 50.1 mmol) and HOAc (1.50 g, 25.0 mmol, 1.43 mL) at 15° C. slowly. After stirring at 15° C. for 12 hours, the mixture is concentrated. The residue is then dissolved in DCM (20 mL), washed with water (5 mL×2), dried over anhydrous sodium sulfate, filtered, and purified by silica gel column chromatography (MeOH/DCM=1/20) to give BC5 as a pale yellow solid (900 mg, 53% yield). (MS: [M+H]$^+$ 528.2)

The following compounds are prepared essentially by the method for Intermediates BC3 and BC4 above.

TABLE 1

Intermediates BC6 and BC7

| Starting Material | Product | Reference of Preparation |
|---|---|---|
| 51 | BC6 | BC3 |
| 55 | BC7 | BC4 |

Preparation of A1 and A2:

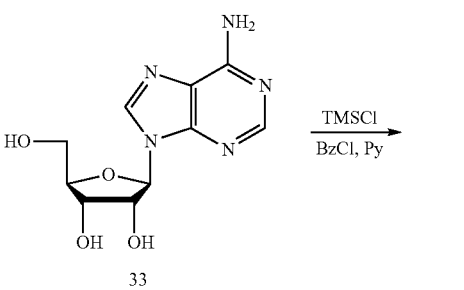

33

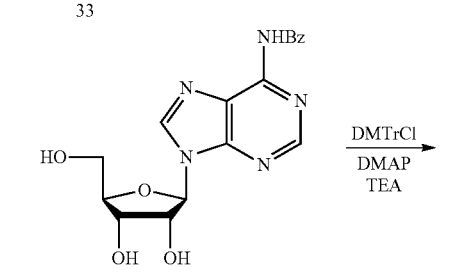

70

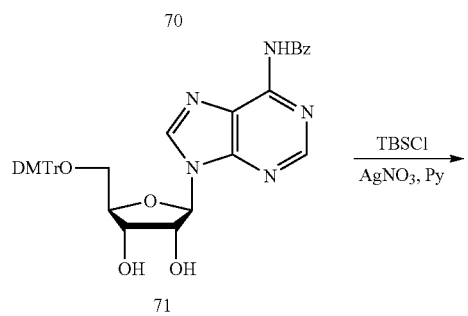

71

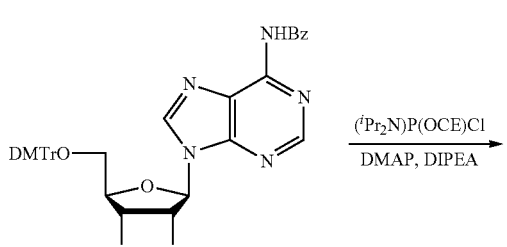

72

A2

91

-continued

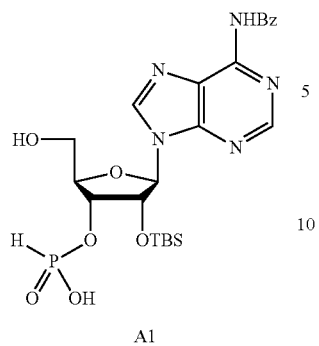

A1

Step 1: Benzoate 70

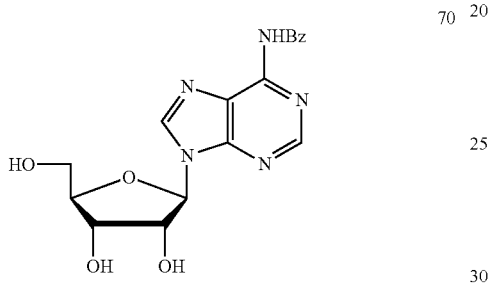

70

To a solution of 33 (120 g, 449 mmol) in Py (1.0 L) is added TMSCl (390 g, 3.59 mol, 454 mL). After stirring at 0° C. for 2 hours, benzoyl chloride (316 g, 2.25 mol, 261 mL) is added dropwise and the mixture is stirred at 25° C. for 14 hours before cooled to 0° C. Water (240 mL) is then added and the mixture is stirred at 25° C. for 30 minutes before ammonium hydroxide (460 mL) is added at 0° C. After stirring for 2 hours, the mixture is concentrated to give 70 as a white solid (150 g, 90% yield).

Step 2: Diol 71

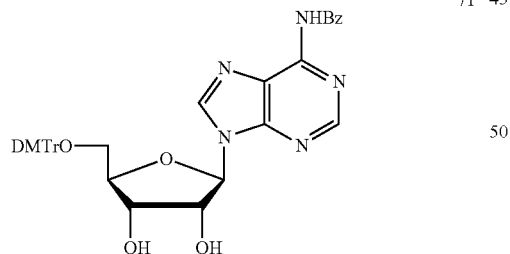

71

To a solution of 70 (150 g, 404 mmol) in Py (500 mL) is added DMTrCl (274 g, 808 mmol), TEA (81.8 g, 808 mmol, 112 mL) and DMAP (4.93 g, 40.4 mmol) at 0° C. After stirring at 25° C. for 16 hours, saturated sodium bicarbonate aqueous solution (1 L) is added and the mixture is extracted with EtOAc (600 mL×3). The combined organic layers are dried over anhydrous sodium sulfate, filtered, concentrated, and purified by silica gel column chromatography (EA/PE 1/4 to 1/2 then MeOH/DCM 1/100 to 1/20) to give 71 as a white solid (65.0 g, 24% yield).

92

Step 3: Silyl Ether 72

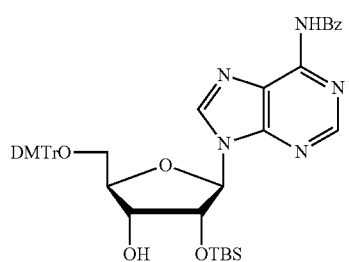

72

To a solution of 71 (65.0 g, 96.5 mmol) in Py (500 mL) is added silver nitrate (32.8 g, 193 mmol) and TBSCl (29.1 g, 193 mmol) at 25° C. After stirring at 25° C. for 1 hour, saturated sodium bicarbonate aqueous solution (1 L) is added and the mixture is extracted with EtOAc (600 mL×3). The combined organic layers are dried over anhydrous sodium sulfate, filtered, concentrated, and purified by silica gel column chromatography (EA/PE=1/4 to 1/1) to give 72 as a white solid (20.0 g, 26% yield).

Step 4: A2

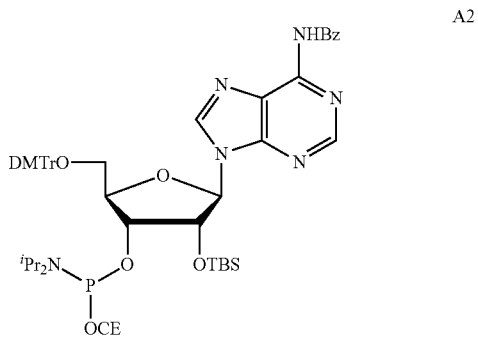

A2

To a solution of 72 (12.0 g, 15.2 mmol) in DIPEA (15 mL) and DCM (30 mL) is added DMAP (744 mg, 6.09 mmol) and 2-cyanoethyl N,N-diisopropylchlorophosphoramidite (5.41 g, 22.9 mmol) at 25° C. After stirring for 2 hours, the mixture is purified directly by basic silica gel column chromatography (EA/PE=1/4 to 1/1) to give A2 as a white solid (13.0 g, 86% yield).

Step 5: A1

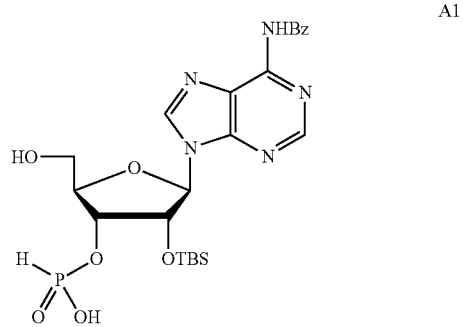

A1

To a solution of A2 (3.8 g, 3.9 mmol) in MeCN (20 mL) is added water (0.1 mL) and pyridinium trifluoroacetate (1.1 g, 5.8 mmol) at 25° C. and stirred for 5 minutes before tert-butylamine (14.0 g, 0.19 mmol) is added. After stirring for 15 minutes, the volatiles are removed and the residue is dissolved in DCM (20 mL). A solution of DCA (1.9 g, 14.6 mmol) in DCM (20 mL) is then added. After stirring for 30 minutes, TEA (3 mL) is added and the mixture is concentrated and purified by reverse-phase silica gel column chromatography (MeCN with 0.1% TEA/water=0% to 100%) to give A1•TEA salt as a white solid (1.5 g, 71% yield). (MS: [M+H]⁺ 549.2)

Preparation of AB1:

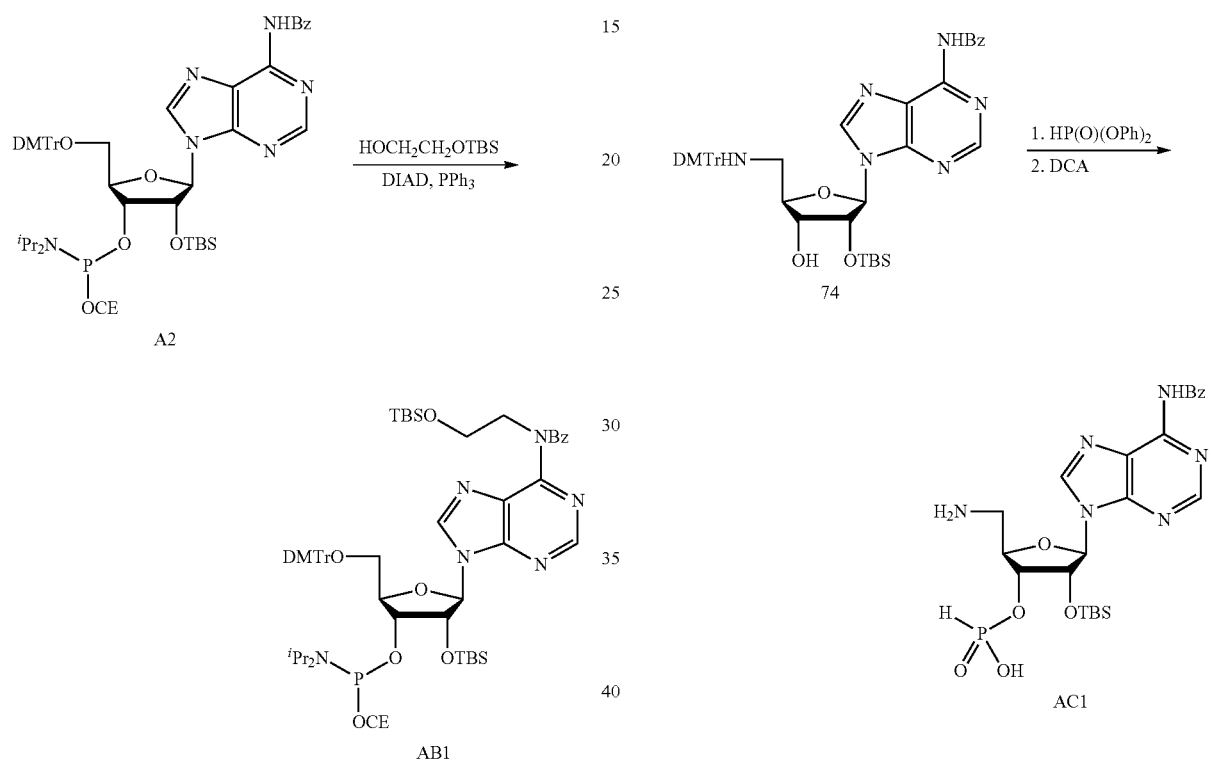

To a solution of A2 (494 mg, 0.5 mmol) and triphenylphosphine (197 mg, 0.75 mmol), and 2-(tert-butyldimethylsilyloxy)ethanol (132 mg, 0.75 mmol) in THF (5 mL) is added DIAD (0.15 mL, 0.75 mmol). After stirring at room temperature for 5 hours, the mixture is concentrated and purified by silica gel column chromatography (EA/hexanes=1/9 to 1/4) to give AB1 as a white solid (230 mg, 40% yield).

Preparation of AC1:

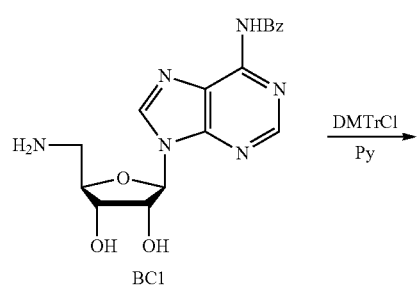

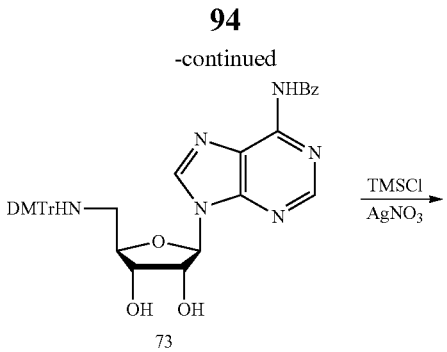

Step 1: Diol 73

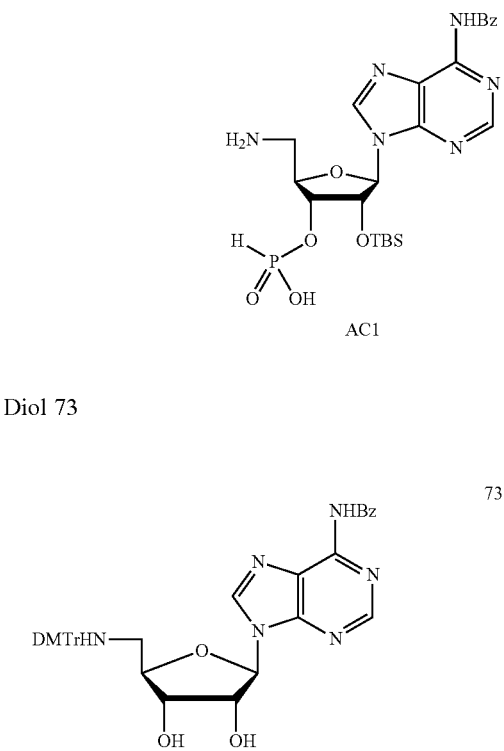

To a solution of crude BC1 (39 g) in Py (40 mL) is added DMTrCl (35.9 g, 106 mmol) at 0° C. After stirring at 25° C. for 16 hours, MeOH (50 mL) is added and the mixture is concentrated. The residue is then dissolved in DCM (600 mL), washed with saturated sodium bicarbonate aqueous solution and brine, concentrated, and purified by silica gel column chromatography (MeOH/DCM=1/100 to 1/50) to give 73 as a pale yellow solid (34.0 g, 48% yield over two steps). (MS: [M+H]⁺ 673.2)

Step 2: Silyl Ether 74

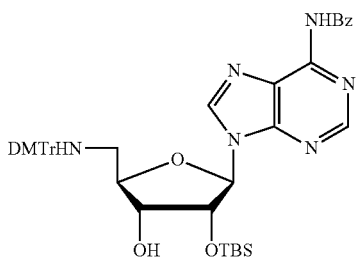
74

To a solution of 73 (1.0 g, 1.49 mmol) in Py (10 mL) is added silver nitrate (380 mg, 2.24 mmol, 0.38 mL) at 0° C. After stirring for 15 minutes, TBSCl (270 mg, 1.79 mmol) is added and the mixture is stirred at 25° C. for 2 hours before saturated sodium bicarbonate aqueous solution is added. The mixture is then extracted with EA (10 mL) and the organic layer is washed with brine, concentrated, and purified by silica gel column chromatography (EA/PE=1/5) to give 74 as a pale yellow solid (400 mg, 34% yield). (MS: [M+H]+ 787.3)

Step 3: AC1

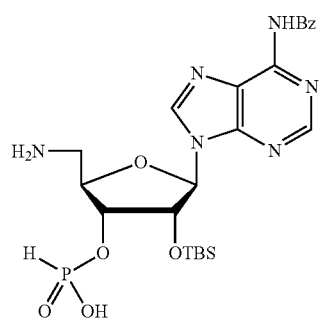
AC1

To a solution of 74 (1.0 g, 1.27 mmol) in Py (10 mL) is added diphenyl phosphite (80%, 744 mg, 2.54 mmol, 0.61 mL). After stirring at 20° C. for 1 hour, EA (2 mL) and saturated sodium bicarbonate aqueous solution (2 mL) are added and the mixture is stirred for 1 hour. The layers are separated and the organic layer is concentrated. The residue is then dissolved in DCM (1.0 mL) and DCA (164 mg, 1.27 mmol, 0.1 mL) is added. After stirring at 25° C. for 30 minutes, TEA (1 mL) is added and the solution is concentrated and purified by reverse-phase silica gel column chromatography (MeCN with 0.1% TEA/water=0% to 100%) to give AC1 as a white solid (500 mg, 72% yield). (MS: [M+H]+ 549.2)

Preparation of AC2

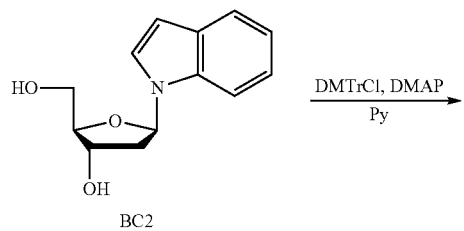
BC2

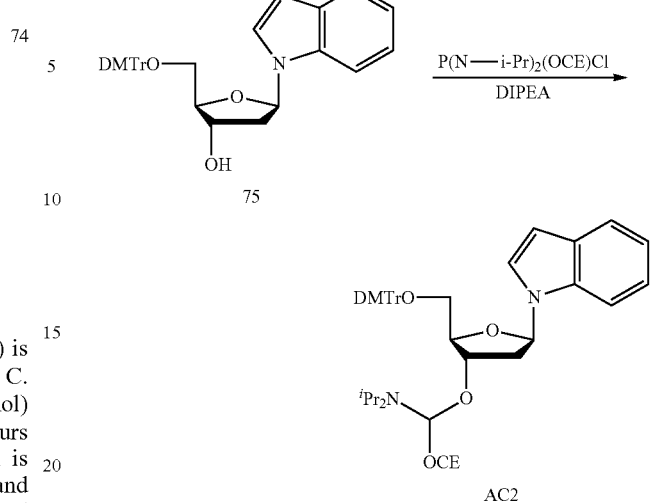

Step 1: Alcohol 75

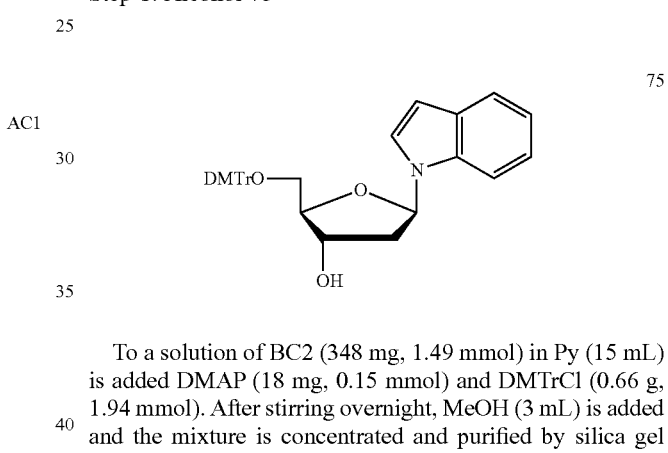
75

To a solution of BC2 (348 mg, 1.49 mmol) in Py (15 mL) is added DMAP (18 mg, 0.15 mmol) and DMTrCl (0.66 g, 1.94 mmol). After stirring overnight, MeOH (3 mL) is added and the mixture is concentrated and purified by silica gel column chromatography (EA/hexanes=1/4) to give 75 (662 mg, 83% yield). (MS: [M+H]+ 536.2)

Step 2: AC2

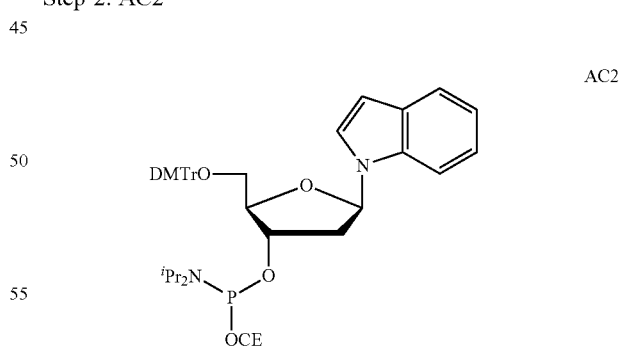
AC2

To a solution of 75 (0.2 g, 0.37 mmol) in DCM (4 mL) is added DIEPA (0.15 g, 1.2 mmol, 0.2 mL) and 2-cyanoethyl N,N-diisopropylchlorophosphoramidite (0.14 g, 0.56 mmol, 0.13 mL). After stirring for 4 hours, the mixture is concentrated and purified by silica gel column chromatography (EA/hexanes with 1% TEA=1/4) to give AC2 (232 mg, 85% yield). (MS: [M-N$^i$Pr$_2$+H$_2$O]+ 653.2)

Preparation of G1 and G2:

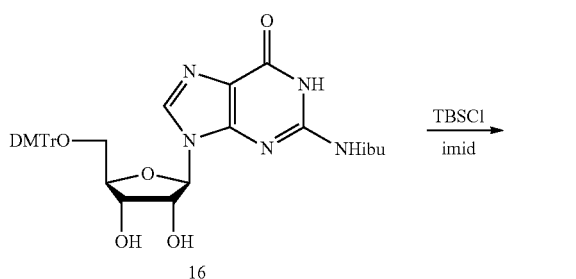

16

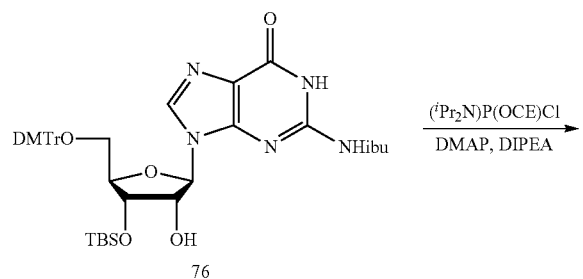

76

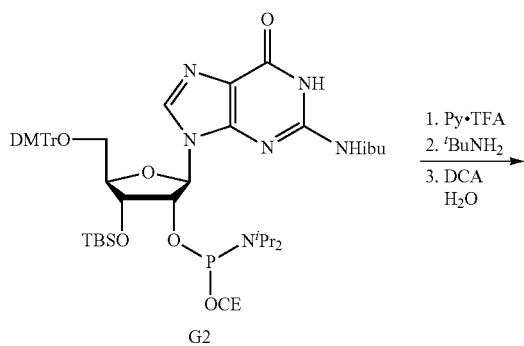

G2

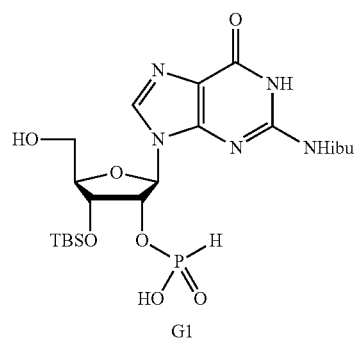

G1

Step 1: Silyl Ether 76

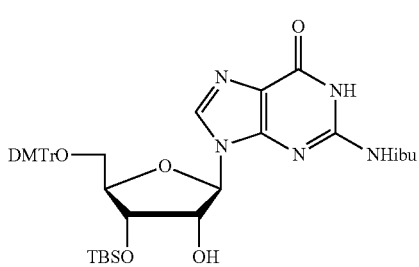

76

To a solution of 16 (11.0 g, 16.8 mmol) in DCM (80 mL) is added TBSCl (7.59 g, 50.3 mmol) and Imid (3.43 g, 50.3 mmol). After stirring at 25° C. for 16 hours, sodium bicarbonate aqueous solution (5%, 30 mL) is added and the mixture is extracted with DCM (60 mL×3). The combined organic layers are washed with brine (100 mL), dried over anhydrous sodium sulfate, filtered, concentrated, and purified by basic silica gel column chromatography (EA/PE=1/5 to 1/1) to 76 as a white solid (2.1 g, 16% yield).

Step 2: G2

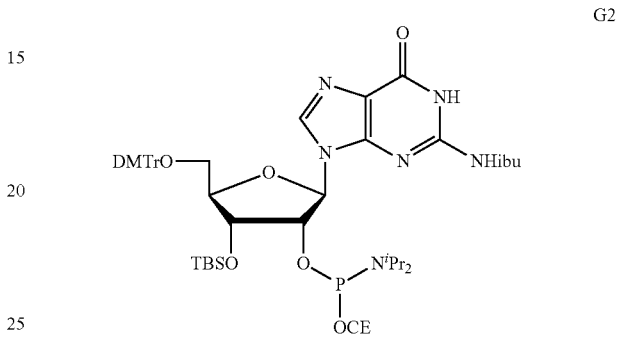

To a solution of 76 (900 mg, 1.17 mmol) in THF (4.0 mL) and DIEPA (4.0 mL) is added DMAP (14.3 mg, 0.12 mmol) followed by 2-cyanoethyl N,N-diisopropylchlorophosphoramidite (415 mg, 1.76 mmol) dropwise at 0° C. After stirring at 20-25° C. for 2 hours, sodium bicarbonate aqueous solution (5%, 15 mL) is added at 0° C. The mixture is then diluted with water (15 mL) and extracted with EA (15 mL×3). The combined organic layers are washed with brine (10 mL), dried over anhydrous sodium sulfate, filtered, concentrated, and purified by silica gel column chromatography (acetone/PE=1/10 to 1/3) to give G2 as a white solid (600 mg, 53% yield).

Step 3: G1

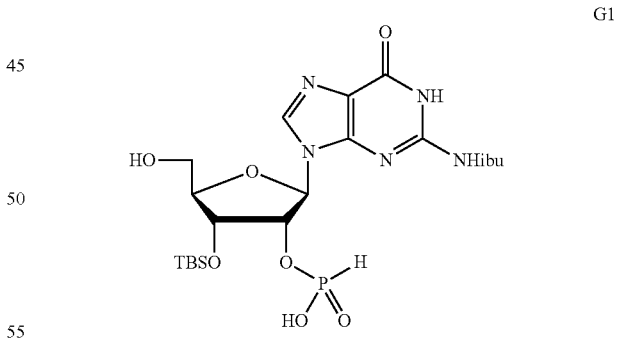

To a solution of G1 (7.0 g, 7.22 mmol) in MeCN (30 mL) is added water (0.11 mL) and pyridinium trifluoroacetate (4.18 g, 21.7 mmol) at 25° C. After stirring at 25° C. for 15 minutes, tert-butylamine (37 mL) is added and the mixture is stirred at 25° C. for 45 minutes before concentrated. The residue is then dissolved in DCM (30 mL) and a solution of DCA in DCM (6% v/v, 30 mL) is added dropwise. After stirring at 20-25° C. for 30 minutes, DCM (30 mL) and TEA (4 mL) are added. The mixture is then concentrated, dissolved in a mixture of MeCN (5 mL) and water (5 mL), and purified by C18 reverse-phase medium pressure liquid chromatography (MeCN with 0.1% TEA/water=0% to 60%) to give G1•TEA salt as a yellow solid (2.30 g, 56% yield). (MS: [M+H]⁺ 532.3)

Preparation of GB1 and GB2:

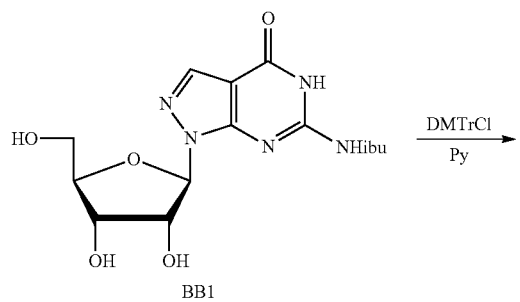

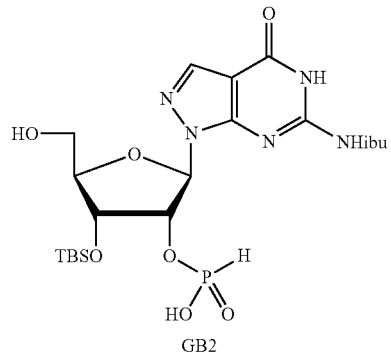

Step 1: Diol 77

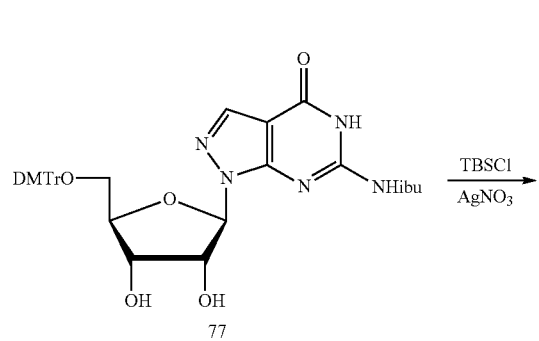

To a solution of two batches of the crude BB1 (8.0 g) obtained above in Py (50 mL) is added DMTrCl (9.2 g, 27.2 mmol). After stirring at 20-30° C. for 1 hour, MeOH (10 mL) is added and the mixture is concentrated and purified by silica gel column chromatography (EA/PE=1/5 to MeOH/DCM=1/20) to give 77 as a yellow solid (11.0 g, 30% yield over two steps). (MS: [M+Na]⁺ 678.2)

Step 2: Silyl Ether 78

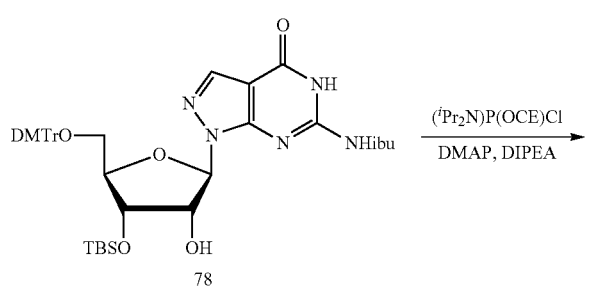

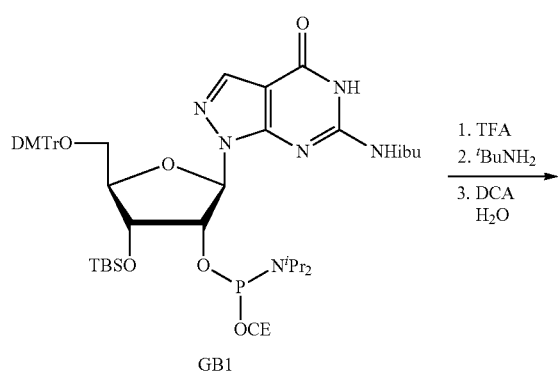

To a solution of 77 (9.0 g, 14.0 mmol) in Py (50 mL) is added TBSCl (2.48 g, 16.5 mmol) and silver nitrate (5.83 g, 34.3 mmol). After stirring at 25-30° C. for 30 minutes, saturated sodium bicarbonate aqueous solution is added. The mixture is then extracted with DCM (200 mL×2), and the combined organic layers are washed with water (50 mL), brine (50 mL), dried over anhydrous sodium sulfate, filtered, concentrated, and purified by silica gel column chromatography (EA/PE=1/10 to 1/5 to 1/3) to give 78 as a white foam (1.50 g, 14% yield). (MS: [M+Na]⁺ 792.2)

Step 3: GB1

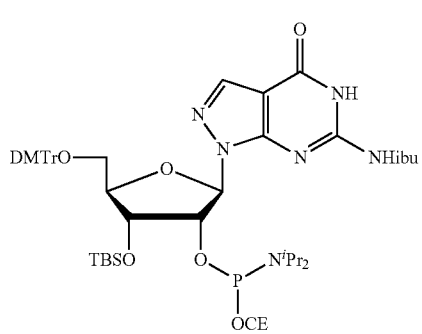
GB1

To a solution of 78 (2.50 g, 3.3 mmol) in DIEPA (5 mL) and DCM (5 mL) is added DMAP (200 mg, 1.62 mmol) and 2-cyanoethyl N,N-diisopropylchlorophosphoramidite (1.0 g, 4.22 mmol). After stirring at 20-25° C. for 2 hours, the mixture is concentrated and purified by silica gel column chromatography (EA/PE=1/10 to 1/4) to give GB1 as a white foam (2.30 g, 73% yield).

Step 4: GB2

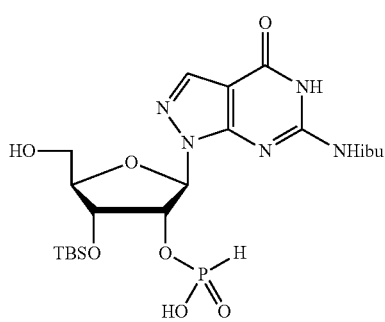
GB2

To a solution of GB1 (2.30 g, 2.4 mmol) in MeCN (2.0 mL) is added water (0.11 mL, 6.1 mmol) and pyridinium trifluoroacetate (687 mg, 3.56 mmol) at 25° C. After stirring at 25-30° C. for 30 minutes, the mixture is concentrated and the residue is dissolved in MeCN (20 mL) before tert-butylamine (10.5 g, 144 mmol, 15.0 mL) is added. After stirring at 25-30° C. for 30 minutes, the mixture is concentrated and DCM (20 mL) followed by addition of a solution of DCA in DCM (6% v/v, 18.2 mL). The mixture is stirred at 25-30° C. for 30 minutes before neutralized by TEA to ~pH 7, concentrated, and purified by C18 reverse-phase silica gel column chromatography (MeCN with 0.1% TEA/water=0% to 40%) to give GB2 as a white solid (800 mg, 63% yield). (MS: [M+H]+ 532.0)

Preparation of GC1

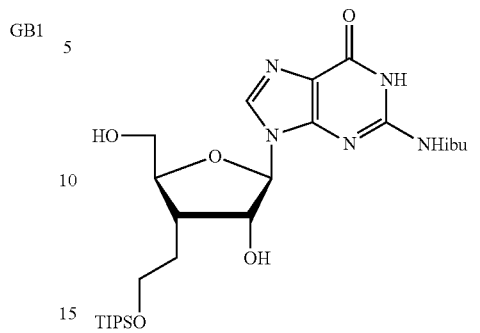

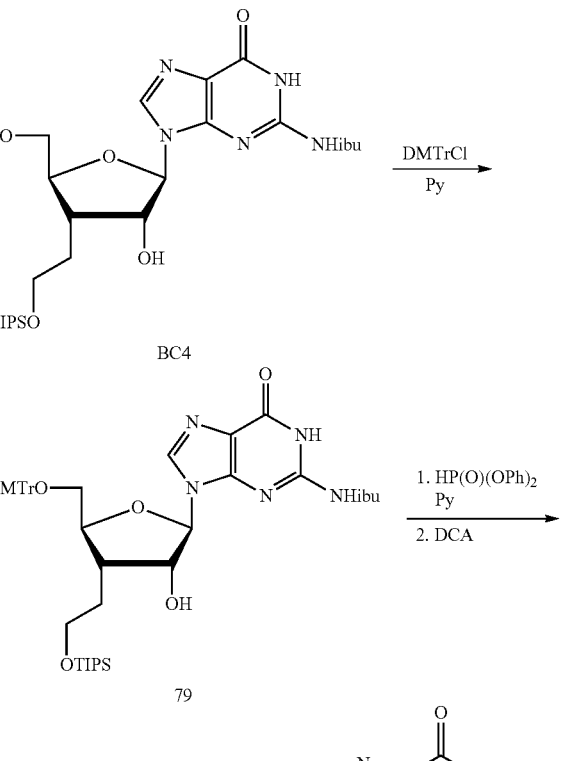
GC1

Step 1: Alcohol 79

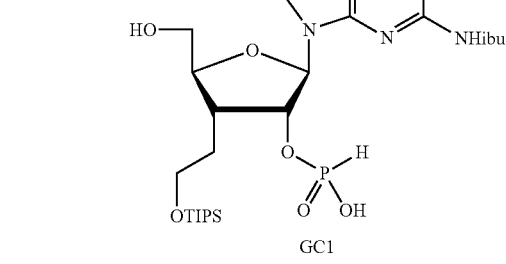
79

To a solution of BC4 (1.97 g, 2.4 mmol) in Py (20 mL) is added DMTrCl (984 mg, 2.90 mmol) at 25° C. After stirring for 3 hours, MeOH (30 mL) is added and the mixture is concentrated, and purified by basic silica gel flash chromatography (EA/PE=1/5 to 4/1) to give 79 as a light yellow powder (1.65 g, 82% yield). (MS: [M+H]+ 840.2)

Step 2: GC1

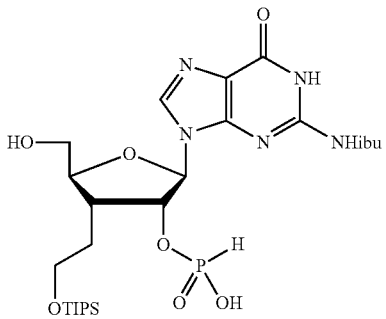

GC1

To a solution of 79 (2.0 g, 2.38 mmol) in Py (15 mL) is added diphenyl phosphite (1.7 g, 7.1 mmol, 1.4 mL). After stirring at 20° C. for 30 minutes, saturated sodium bicarbonate aqueous solution (30 mL) is added and the mixture is stirred for 1 hour. The mixture is then extracted with EA (30 mL×3). The combined organic layers are washed with saturated sodium bicarbonate aqueous solution (20 mL) and brine (20 mL), dried over anhydrous sodium sulfate, and concentrated. The residue is then dissolved in DCM (40 mL) followed by addition of water (0.4 mL) and DCA (6% v/v in DCM, 40 mL). After stirring at 20° C. for 15 minutes, the mixture is neutralized to ~pH 7 by TEA, concentrated, and purified by reverse-phase silica gel column chromatography (MeCN/water=25% to 90%) to give GC1 as a white solid (1.3 g, 90% yield). (MS: [M+H]$^+$ 602.1)

Preparation of GC2:

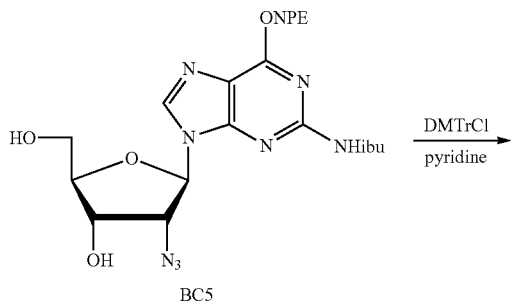

BC5

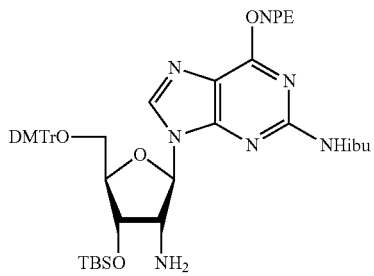

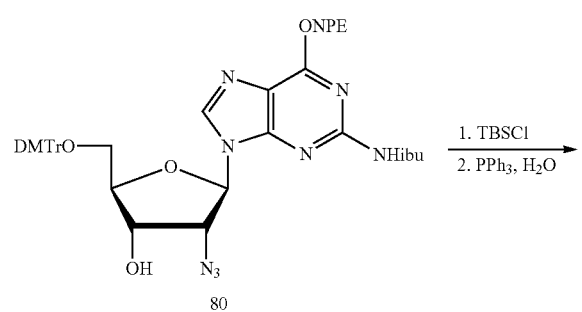

80

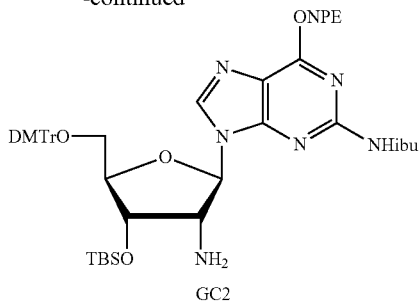

GC2

Step 1: Alcohol 80

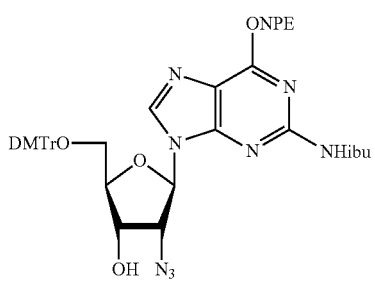

80

To a solution of BC5 (900 mg, 1.71 mmol) in Py (10 mL) is added DMTrCl (809 mg, 2.39 mmol) at 15° C. After stirring at 15° C. for 12 hours, MeOH (0.5 mL) is added and the mixture is concentrated and purified by silica gel column chromatography (MeOH/DCM=1/50) to give 80 as a yellow oil (1.0 g, 71% yield). (MS: [M+H]$^+$ 528.2)

Step 2: GC2

To a solution of 80 (2.05 g, 2.47 mmol) in DMF (5.0 mL) is added Imid (673 mg, 9.88 mmol) and TBSCl (745 mg, 4.94 mmol, 0.61 mL) at 15° C. After stirring at 15° C. for 12 hours, the mixture is concentrated and the residue is triturated with water (10 mL). The solid is then collected and washed with water (10 mL×2), PE (10 mL×2), dried, and dissolved in THF (18 mL) before PPh$_3$ (1.11 g, 4.24 mmol) is added at 15° C. After stirring at 15° C. for 2.5 hours, water (0.16 mL) is added and the mixture is stirred at 50° C. for 12 hours. The solution is then concentrated and purified by reverse-phase preparative-HPLC (MeOH with 0.1% TEA/water=20% to 80%), to give GC2 as a white solid (900 mg, 58% yield). (MS: [M+H]$^+$ 918.1)

The following compounds are prepared essentially by the method for Intermediates A1, A2, AC1, AC2, G1, G2, GC1, and GC2 above.

TABLE 2
Intermediates A1 to A5, AA1, AA2, AB1, AC1 to AC6, G1 to G7, GA1, GB1 to GB3, and GC1 to GC5
| Starting Material | Product | Reference of Preparation |
|---|---|---|
| 33 | 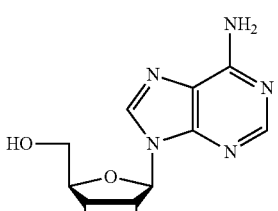 A1 | A1 |
| 33 | 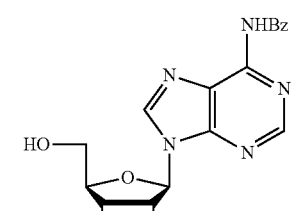 A2 | A2 |
| 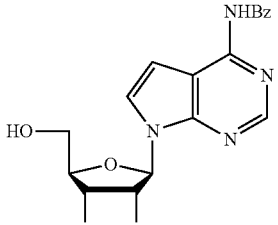 B1 | 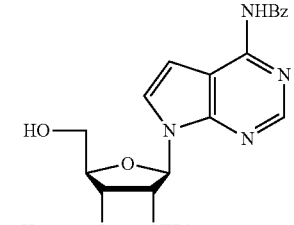 A3 | A1 |
| B1 | 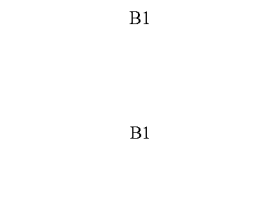 A4 | A2 |

TABLE 2-continued
Intermediates A1 to A5, AA1, AA2, AB1, AC1 to AC6, G1 to G7, GA1, GB1 to GB3, and GC1 to GC5
| Starting Material | Product | Reference of Preparation |
|---|---|---|
| B2 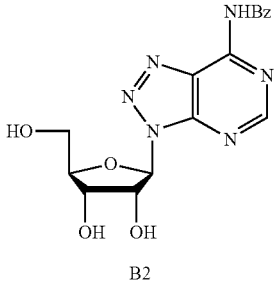 | A5 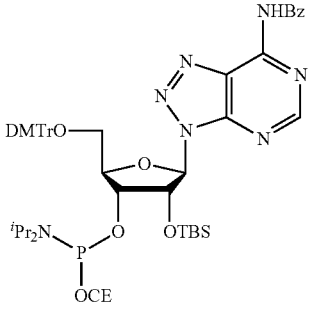 | A2 |
| BA1 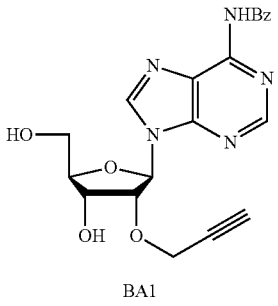 | AA1 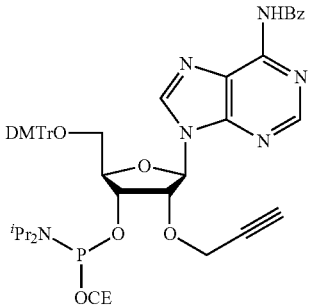 | A2 |
| BA2 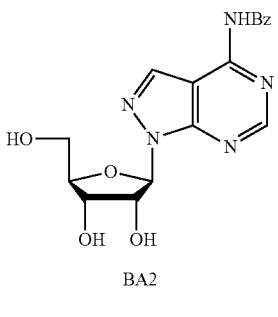 | AA2 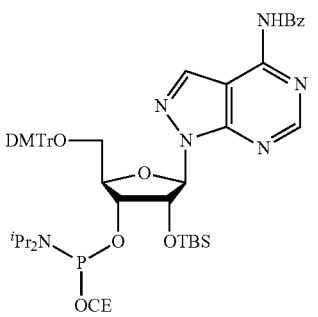 | A2 |
| A2 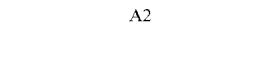 | AB1 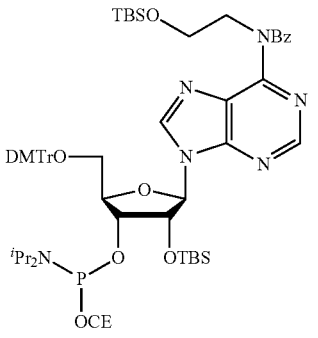 | AB1 |

TABLE 2-continued
Intermediates A1 to A5, AA1, AA2, AB1, AC1 to AC6, G1 to G7, GA1, GB1 to GB3, and GC1 to GC5
| Starting Material | Product | Reference of Preparation |
|---|---|---|
| BC1 | AC1 | AC1 |
| BC2 | AC2 | AC2 |
| B1 | AC3 | G1 |
| 33 | AC4 | G1 |
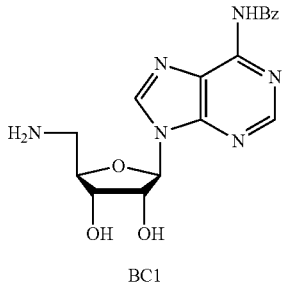

TABLE 2-continued

Intermediates A1 to A5, AA1, AA2, AB1, AC1 to AC6, G1 to G7, GA1, GB1 to GB3, and GC1 to GC5

| Starting Material | Product | Reference of Preparation |
|---|---|---|
| BC6 | AC5 | AC2 |
| BC3 | AC6 | AC2 |
| 37 | G1 | G1 |
| 37 | G2 | G2 |

TABLE 2-continued
Intermediates A1 to A5, AA1, AA2, AB1, AC1 to AC6, G1 to G7, GA1, GB1 to GB3, and GC1 to GC5
| Starting Material | Product | Reference of Preparation |
|---|---|---|
| DMTr-B3 | G3 | G1 |
| B4 | G4 | G1 |
| B5 | G5 | G2 |
| DMTr-B3 | G6 | G2 |
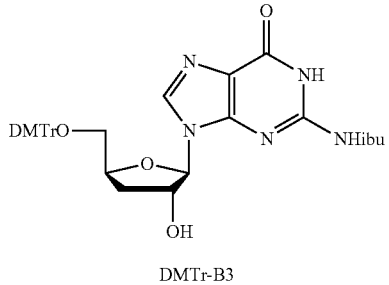

TABLE 2-continued

Intermediates A1 to A5, AA1, AA2, AB1, AC1 to AC6, G1 to G7, GA1, GB1 to GB3, and GC1 to GC5

| Starting Material | Product | Reference of Preparation |
|---|---|---|
| B6 | G7 | G2 |
| BA3 | GA1 | G2 |
| BB1 | GB1 | GB1 |
| GB1 | GB2 | GB2 |

TABLE 2-continued

Intermediates A1 to A5, AA1, AA2, AB1, AC1 to AC6, G1 to G7, GA1, GB1 to GB3, and GC1 to GC5

| Starting Material | Product | Reference of Preparation |
|---|---|---|
| G7 | GB3 | GB2 |
| BC4 | GC1 | GC1 |
| BC5 | GC2 | GC2 |
| GA1 | GC3 | G1 |

TABLE 2-continued
Intermediates A1 to A5, AA1, AA2, AB1, AC1 to AC6, G1 to G7, GA1, GB1 to GB3, and GC1 to GC5
| Starting Material | Product | Reference of Preparation |
|---|---|---|
| 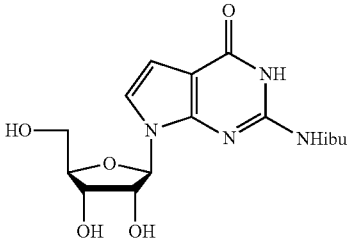<br>B6 | 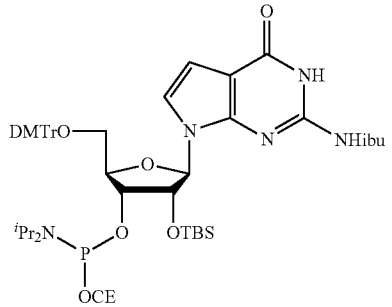<br>GC4 | A2 |
| 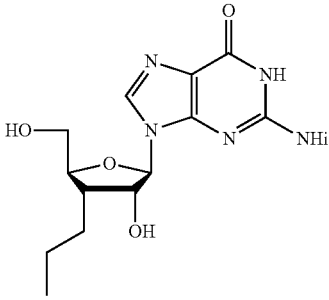<br>BC7 | 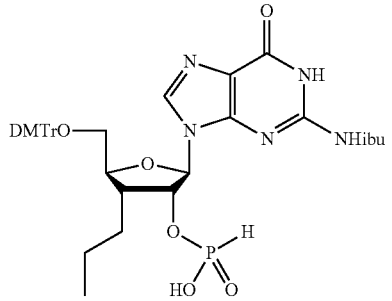<br>GC5 | GC1 |
Preparation of C1
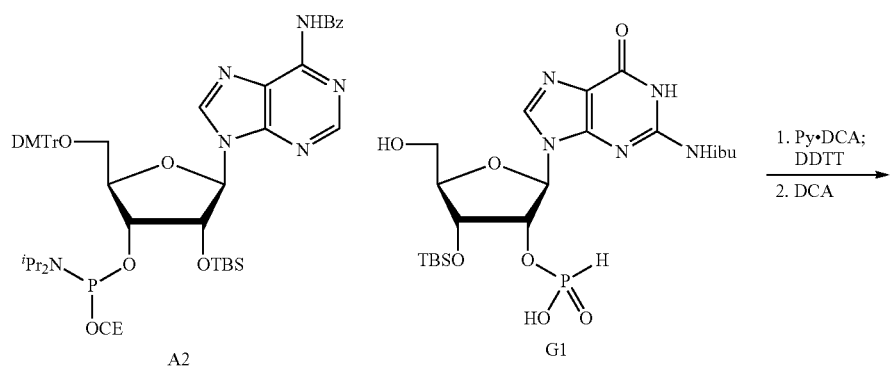

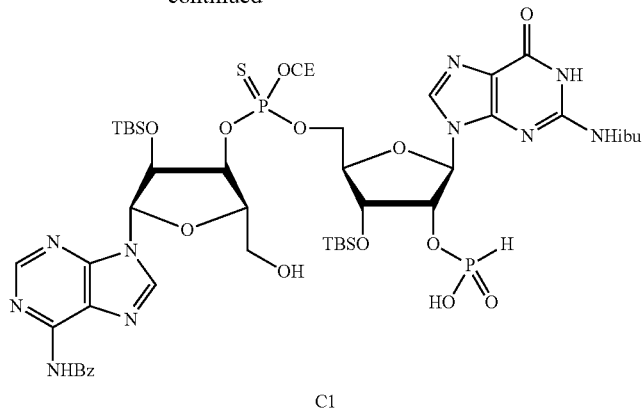

C1

To a solution of crude G1 (obtained from 187 mg of G2•TEA salt, 0.2 mmol, containing Py•DCA salt) in MeCN (0.5 mL) is added a solution of A2 (0.26 g, 0.26 mmol) in MeCN (0.2 mL). After stirring for 30 minutes, DDTT (46 mg, 0.22 mmol) is added and the mixture is stirred for 1 hour before concentrated. The residue is dissolved in DCM (4.8 mL) and water (0.036 mL) and DCA (6% in DCM, 4.8 mL) are added. After stirring for 10 minutes, Py (1 mL) is added and the mixture is concentrated and purified by silica gel column chromatography (MeOH/DCM=1/10 to 1/5) to give C1•Py salt as a white solid (86 mg, 35% yield). (MS: [M+H]$^+$ 1148.0)

Preparation of C2

To a mixture of A1 (1.0 g, 1.82 mmol, co-evaporated MeCN 20 mL×3) and G2 (2.3 g, 2.37 mmol, co-evaporated with MeCN 20 mL×3) is added tetrazole (0.45 M in MeCN, 10 mL) at 25° C. and stirred for 1 hour before elemental sulfur (1.75 g, 6.84 mmol) is added. After stirring for 1 hour, MeCN (20 mL) is added and the mixture is filtered and concentrated. The residue is dissolved in DCM (100 mL) and DCA (1.96 g, 15.2 mmol, 1.25 mL) is added. After stirring at 25° C. for 2 hours, saturated sodium bicarbonate aqueous solution (100 mL) is added. The layers are separated and the aqueous layer is extracted with EA (100 mL×3). The combined organic layers are dried over anhydrous sodium sulfate, filtered, concentrated, and purified by

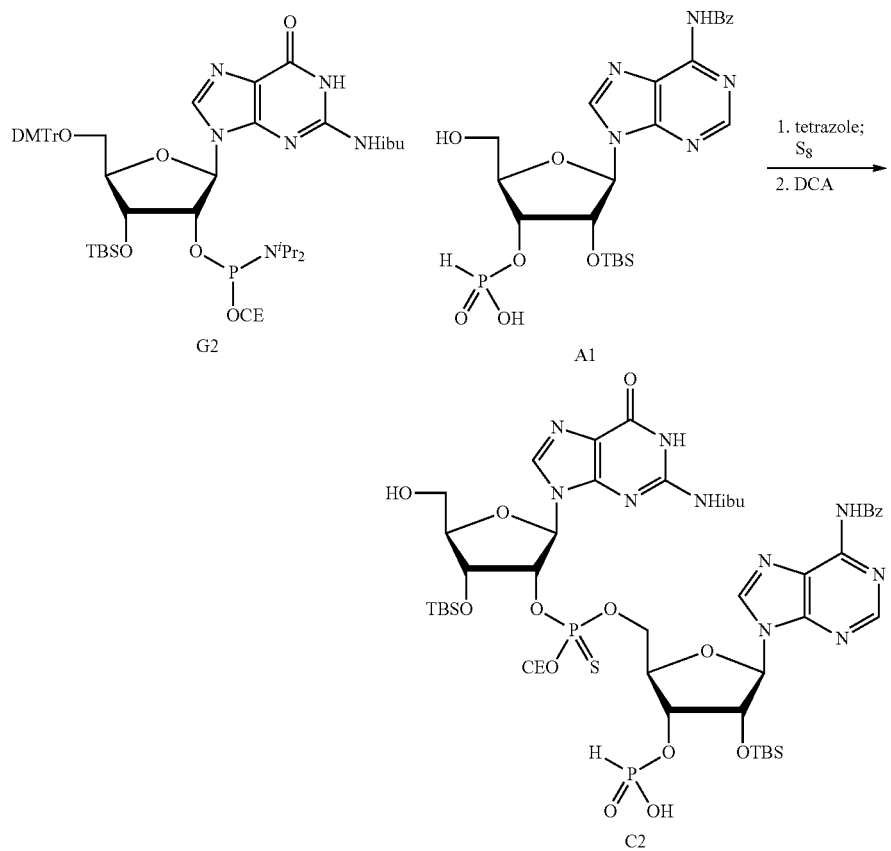

reverse-phase silica gel column chromatography (MeCN with 0.1% TEA/water=0% to 100%) to give C2•TEA salt as a white solid (100 mg, 5% yield). (MS: {[M+2H]$^{2+}$}/2 574.6)

Preparation of C3:

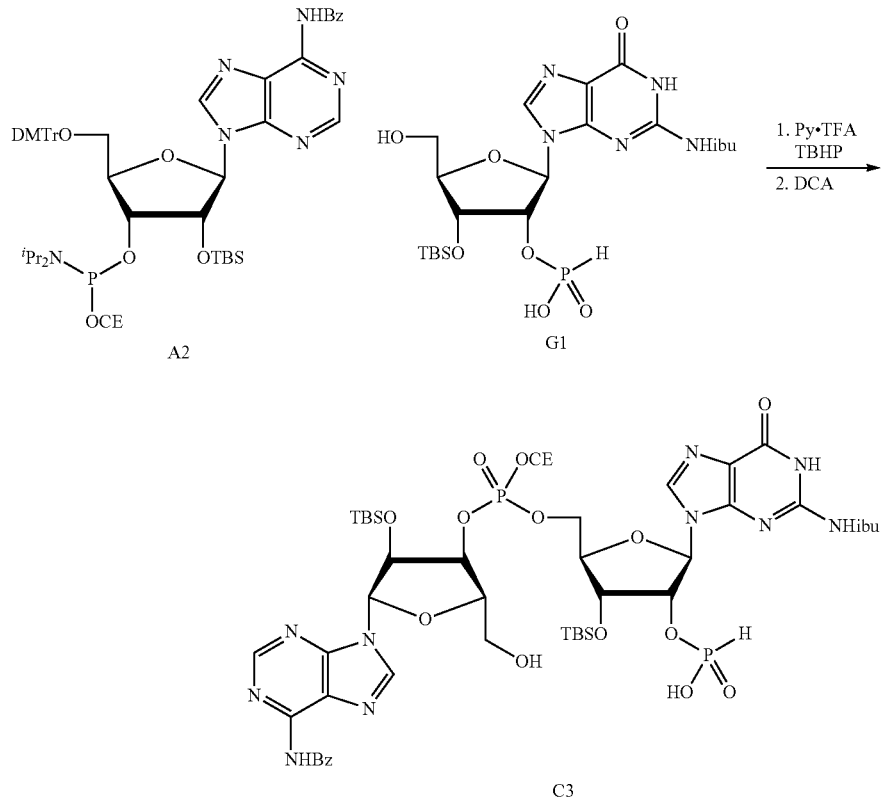

To a solution of A2 (510 mg, 0.52 mmol, co-evaporated with MeCN 5 mL×3) in MeCN (1 mL) treated with 3 Å MS (100 mg) for 30 minutes is added a mixture of G1 (250 mg, 0.47 mmol, co-evaporated with MeCN 5 mL×3) and pyridinium trifluoroacetate (109 mg, 0.56 mmol, co-evaporated with MeCN 5 mL×3) in MeCN (1.5 mL) treated with 3 Å MS (50 mg) for 30 minutes. After stirring for 4 hours, TBHP (5.5 M in decane, 0.26 mL) is added and the mixture is stirred for 30 minutes before sodium bisulfite aqueous solution (33%, 0.24 mL) is added at 0° C. The mixture is then stirred at room temperature for 10 minutes before filtered and concentrated. The residue is dissolved in DCM (6.2 mL) followed by addition of water (0.09 mL) and DCA (0.37 mL) in DCM (6.2 mL). After stirring at room temperature for 10 minutes, Py (0.73 mL, 9.05 mmol) and DCM (35 mL) are added. The mixture is washed with water (10 mL×2) and the combined aqueous layers are extracted by dichloromethane (10 mL×2). The combined organic layers are dried over anhydrous sodium sulfate, concentrated, and purified by silica gel column chromatography (MeOH/CH$_2$Cl$_2$/Py=10:89.5:0.5 to 25:74.5:0.5) to give C3 as a white solid (250 mg, 47%). (MS: [M+H]$^+$ 1132.2)

Preparation of CA1:

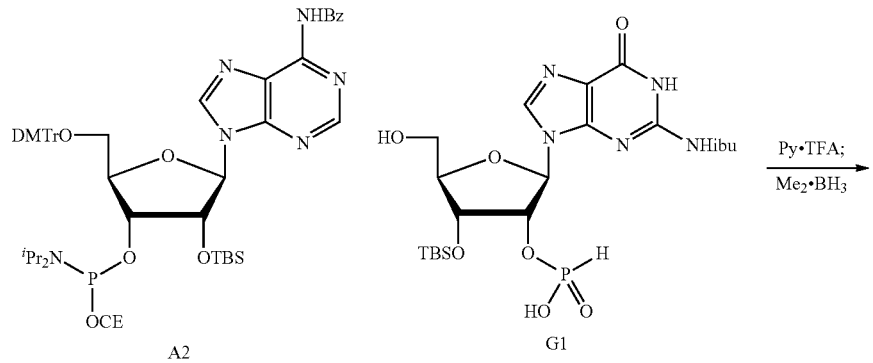

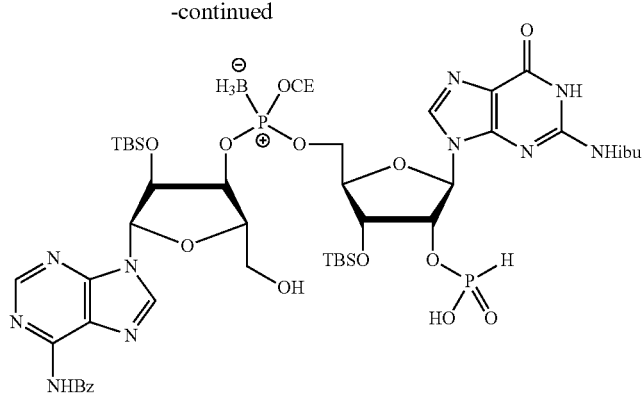

CA1

To a solution of G1 (500 mg, 0.94 mmol, co-evaporated with MeCN 10 mL×3) and pyridinium trifluoroacetate (218 mg, 1.13 mmol, co-evaporation with MeCN 10 mL×3) in MeCN (3 mL) treated with 3 Å MS (100 mg) for 30 minutes is added a solution of A2 (976 mg, 0.99 mmol, co-evaporated with MeCN 10 mL×3) in MeCN (2 mL) treated with 3 Å MS (200 mg) for 30 minutes. After stirring at room temperature for 2.5 hours, the mixture is concentrated and co-evaporated with MeCN (10 mL×2). The residue is then dissolved in DCM (20 mL) followed by addition of borane dimethyl sulfide complex (2 M in THF, 0.94 mL, 1.88 mmol) dropwise. After stirring at room temperature for 1 hour, MeOH (0.17 mL) is added at 0° C. and stirred for 20 minutes before concentrated to give crude CA1.

Preparation of CC1

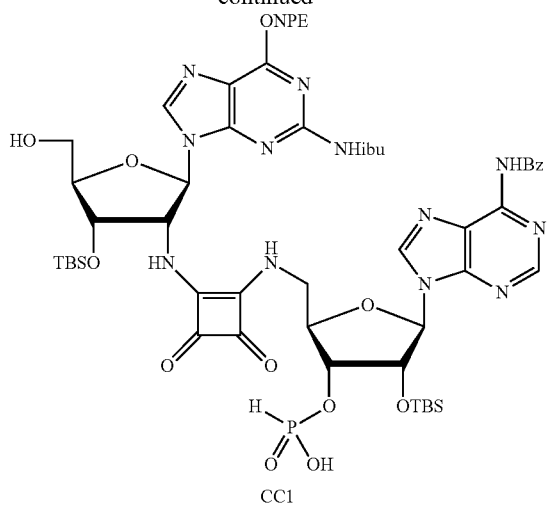

CC1

Step 1: Squaramide 81

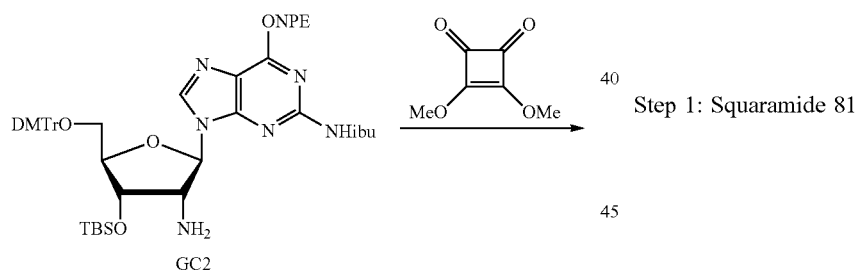

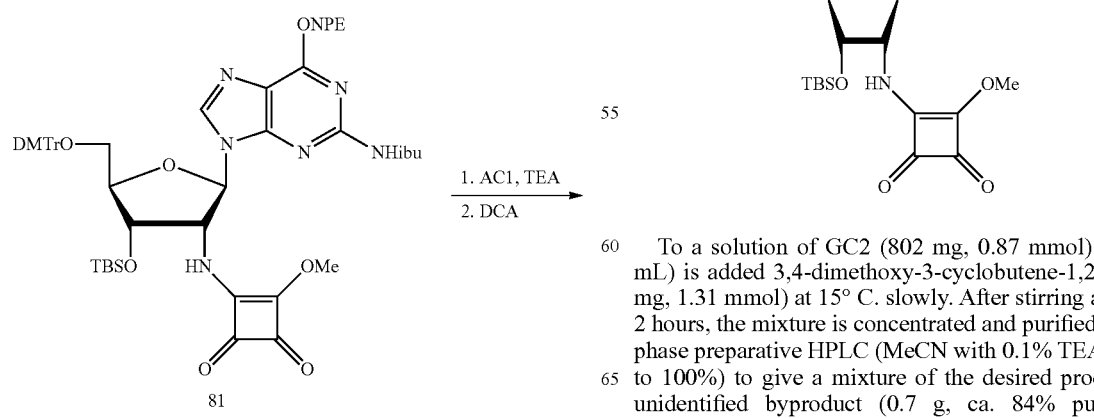

To a solution of GC2 (802 mg, 0.87 mmol) in DMF (5 mL) is added 3,4-dimethoxy-3-cyclobutene-1,2-dione (186 mg, 1.31 mmol) at 15° C. slowly. After stirring at 15° C. for 2 hours, the mixture is concentrated and purified by reverse-phase preparative HPLC (MeCN with 0.1% TEA/water=0% to 100%) to give a mixture of the desired product and an unidentified byproduct (0.7 g, ca. 84% purity). (MS: [M+H]$^+$ 1028.4)

Step 2: CC1

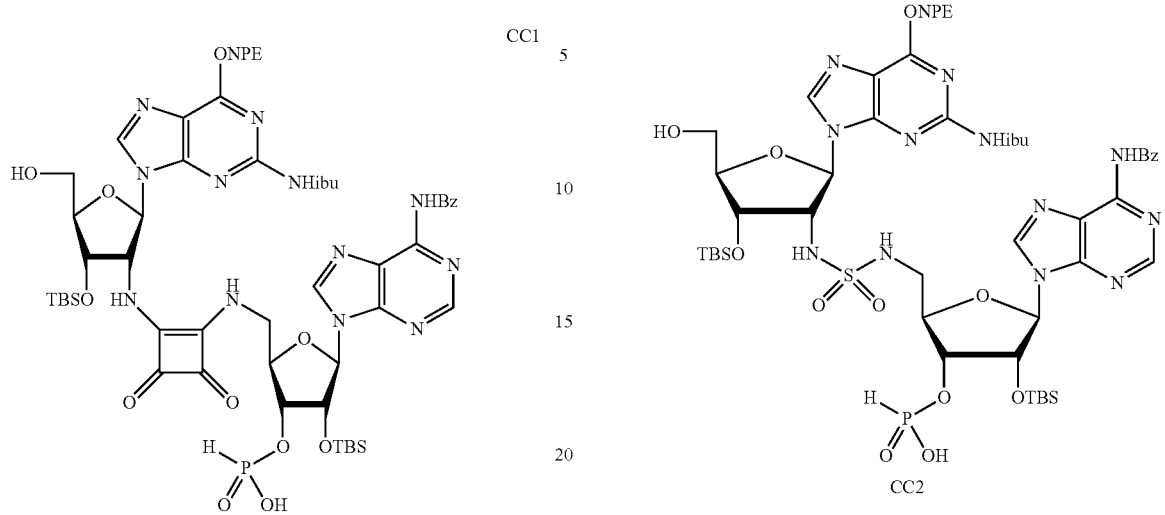

To a solution of 81 (ca. 84% pure, 0.6 g) obtained above and AC1 (0.64 g, 1.17 mmol) in DMF (5.0 mL) is added TEA (177 mg, 1.75 mmol, 0.24 mL) at 15° C. After stirring at 15° C. for 12 hours, the mixture is concentrated and the residue is dissolved in DCM (5.0 mL) before DCA (470 mg, 3.65 mmol, 0.3 mL) is added. The mixture is then stirred at 15° C. for 15 minutes before concentrated. The residue is purified by reverse-phase preparative HPLC (MeCN with 0.1% TEA/water=0% to 100%) to give CC1 as a while solid (0.54 g, 40% yield over two steps). (MS: [M+H]⁺ 1242.3)

Preparation of CC2

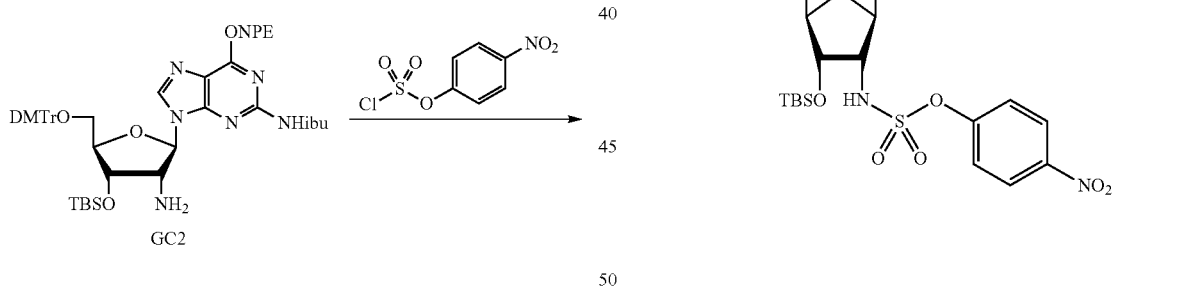

Step 1: Sulfamate 82

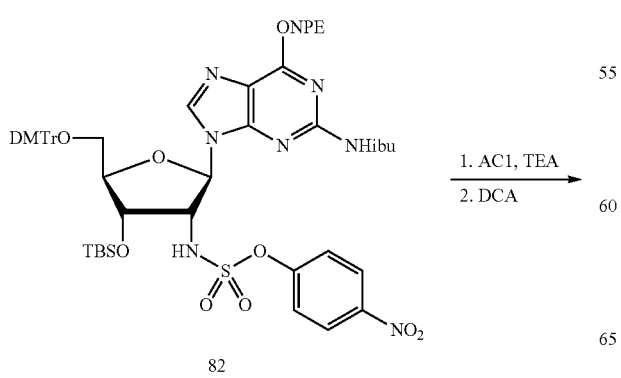

To a solution of 4-nitrophenyl chlorosulfate (0.31 g, 1.31 mmol) in DCM (1.0 mL) is added a solution of of GC2 (0.40 g, 0.44 mmol), 4-nitrophenol (0.61 g, 4.4 mmol) and TEA (0.73 mL, 5.23 mmol) in DCM (5 mL) at −78° C. After stirring for 30 minutes, the mixture is warmed to room temperature, diluted with DCM (20 mL), and washed with water (20 mL×3). The combined aqueous layers are extracted with DCM (20 mL×2) and the combined organic layers are dried over anhydrous magnesium sulfate, filtered, concentrated, and purified by silica gel column chromatography (EA/PE with 1% TEA=1/5 to 1/2) to give 82 (0.30 g, 59% yield) as a white solid. (MS: [M+H]⁺ 1118.9)

Step 2: CC2

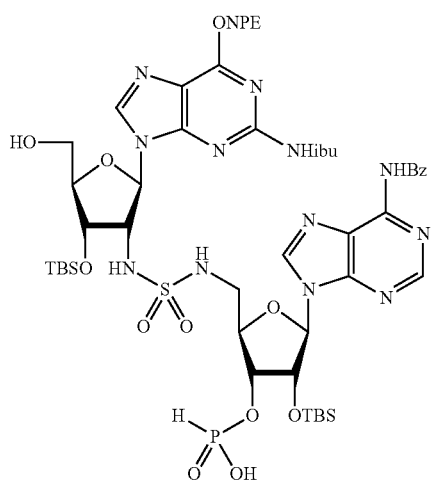

To a solution of 82 (0.2 g, 0.18 mmol) in THF (1.0 mL), 4 Å MS (0.05 g) and TEA (0.12 mL, 0.89 mmol) is added AC1 (0.12 g, 0.21 mmol). After stirring for 12 hours, the mixture is diluted with THF (2 mL), filtered, and concentrated. The residue is then dissolved in DCM (5.0 mL) before water (0.1 mL) and a solution of DCA (0.46 mL) in DCM (5.0 mL) are added. After stirring for 15 minutes, the mixture is neutralized with TEA to ~pH 7 before concentrated and purified by reversed-phase C18 silica gel column chromatography (MeCN with 0.5% TEA/water=0% to 40%) to give CC2 (0.11 g, 44% yield) as a white solid. (MS: $[M+H]^+$ 1226.0)

EXAMPLES

Example A: Synthesis of E5

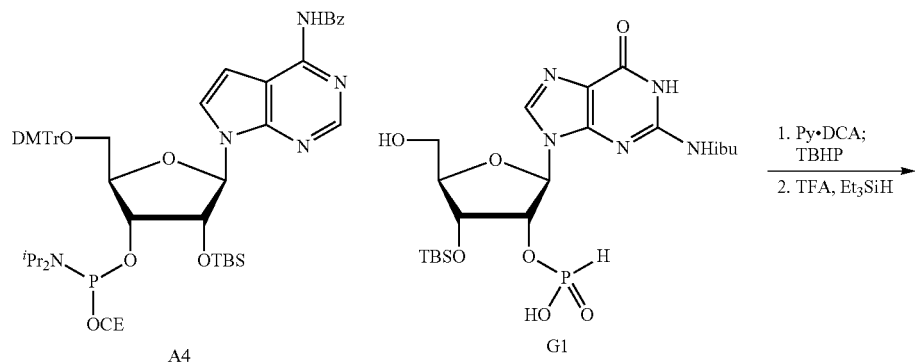

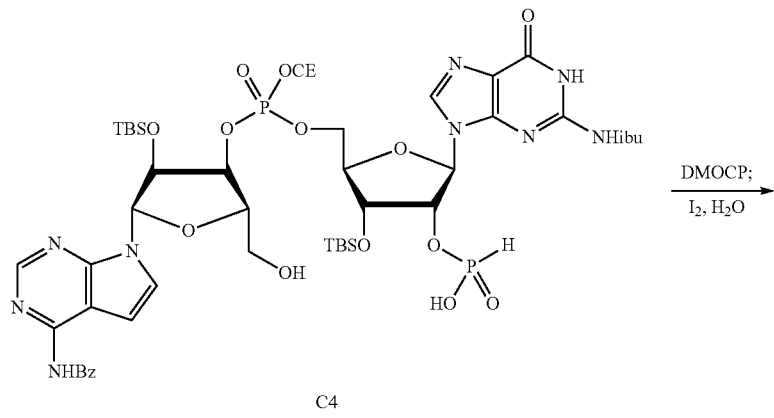

-continued
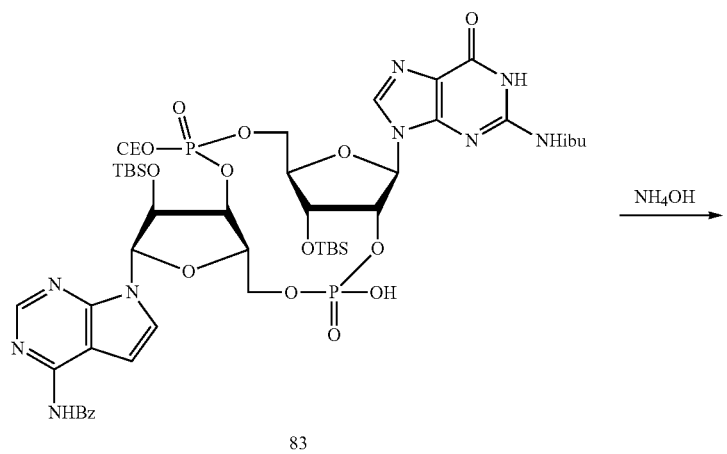
83
→ NH₄OH
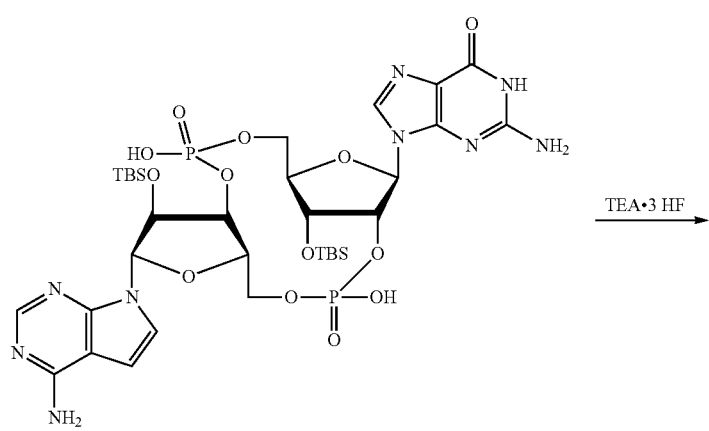
84
→ TEA·3 HF
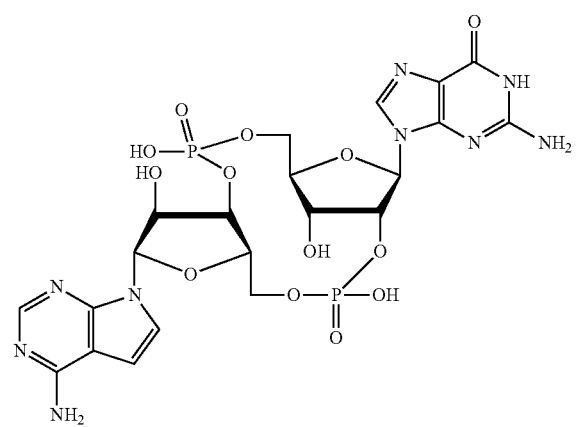
E5

Step 1: C4

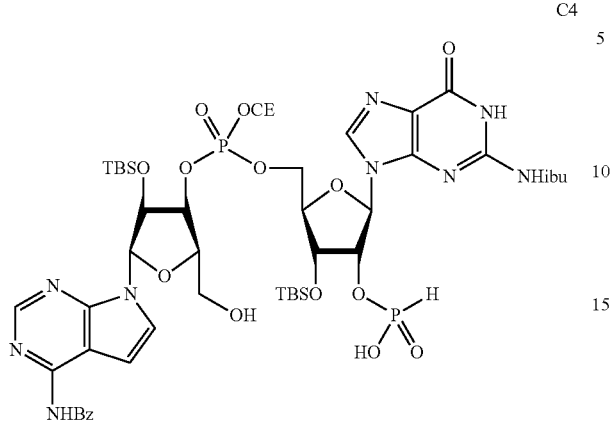

To a solution of A4 (1.0 g, 1.01 mmol) and G1 (1.07 g, 2.02 mmol) in MeCN (10 mL) is added Py•DCA (420 mg, 2.02 mmol). After stirring at 20° C. for 2 hours, TBHP (70% in water, 0.65 mL, 5.05 mmol) is added and the mixture is stirred for 1 hour before sodium bicarbonate aqueous solution (50 mL) is added. The mixture is extracted with ethyl acetate (100 mL) and the organic layer is washed with brine (30 mL), dried with anhydrous sodium sulfate, filtered, and concentrated. The residue is then dissolved in a mixture of DCM (20 mL), TFA (1.0 mL) and triethylsilane (5.0 mL). After stirring for 2 hours, the mixture is neutralized with solid sodium bicarbonate to ~pH 7. The mixture is then filtered and the solid is washed with EA (50 mL×3). The filtrate is concentrate and purified by preparative HPLC (MeCN with 0.1% TEA/water=0% to 30%) to give C4•TEA as a white solid (620 mg, 49% yield). (MS: [M+H]$^+$ 1131.1)

Step 2: Phosphodiester 83

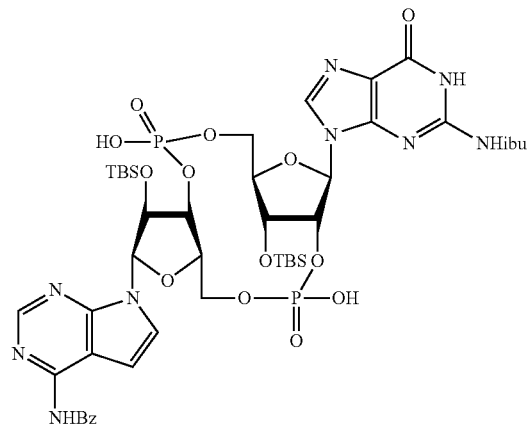

To a solution of C4 (583 mg, 0.515 mmol) in Py (10 mL) is added DMOCP (583 mg, 3.16 mmol) at 20° C. After stirring for 2 hours, iodine (654 mg, 2.58 mmol) is added and the mixture is stirred for 1 hour before saturated sodium sulfate aqueous solution (30 mL) and saturated sodium bicarbonate aqueous solution (30 mL) is added. The mixture is then extracted with EA (100 mL), washed with brine (60 mL), dried over anhydrous sodium sulfate, filtered, concentrated, and purified by reversed-phase silica gel column chromatography (MeCN with 0.1% TEA/water=20% to 40%) to give 83•TEA as a white solid (172.0 mg, 31% yield). (MS: [M+H]$^+$ 1076.1)

Step 3: Bisphosphodiester 84

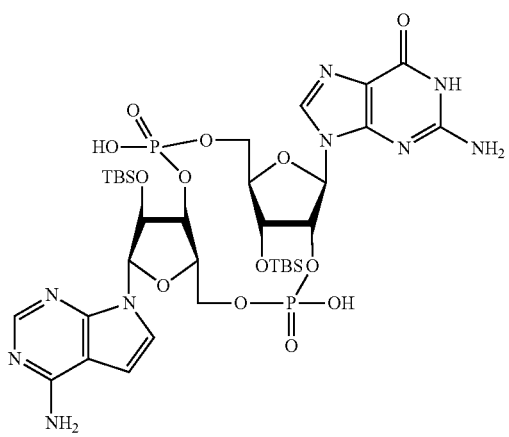

A solution of 83 (100 mg, 0.093 mmol) in MeOH (1.0 mL) and ammonium hydroxide (1.0 mL) is stirred at 50° C. for 12 hours. The mixture is then concentrated and purified by reverse-phase silica gel column chromatography (MeCN with 0.1% TEA/water=20% to 40%) to give 84 as a yellow solid (27.0 mg, 32% yield). (MS: [M+H]$^+$ 902.5)

Step 4: E5

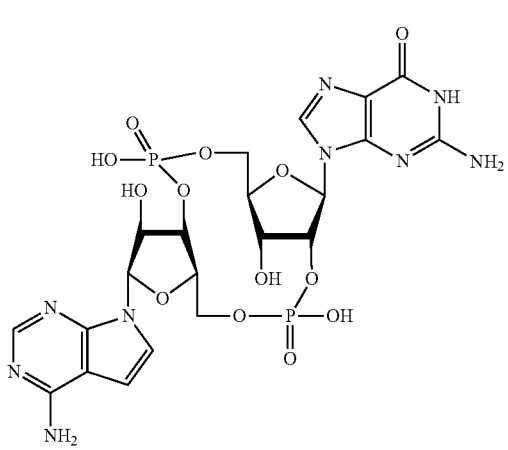

A solution of 84 (27 mg, 0.030 mmol) in TEA•3HF (10 mL) is stirred at 50° C. for 3 hours. The mixture is then neutralized with cold triethylammonium bicarbonate to ~pH 7, concentrated, and purified by a C18 reverse-phase silica gel column chromatography (MeCN with 0.1% TEA/water=0% to 20%) to give E5•TEA as a white solid (5.2 mg, 26% yield). (MS: [M+H]$^+$ 673.7)

Example B: Synthesis of E15-E18
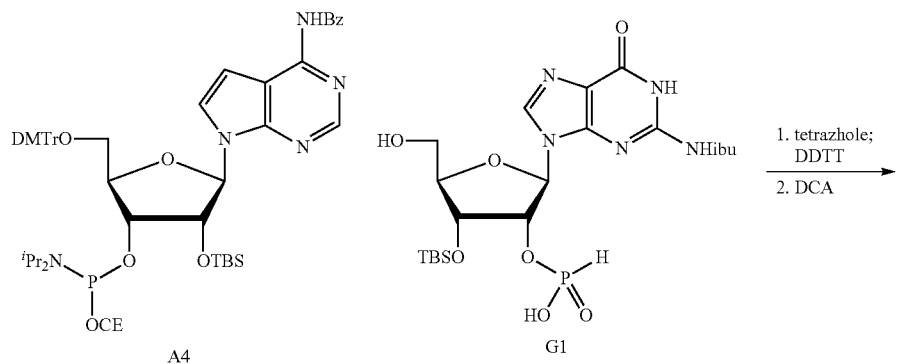
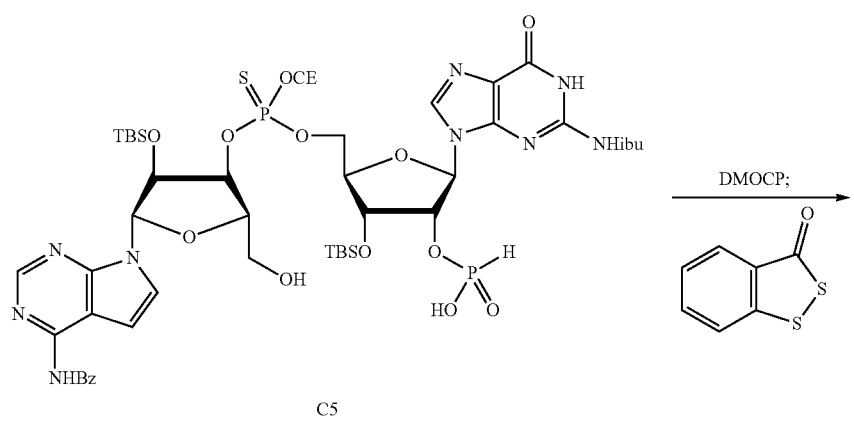
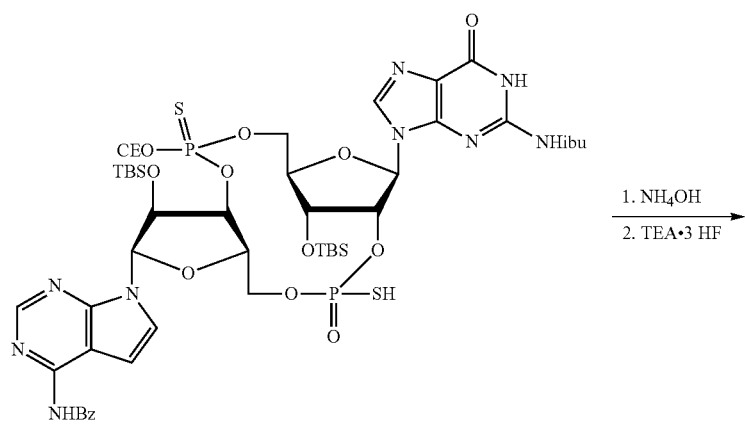

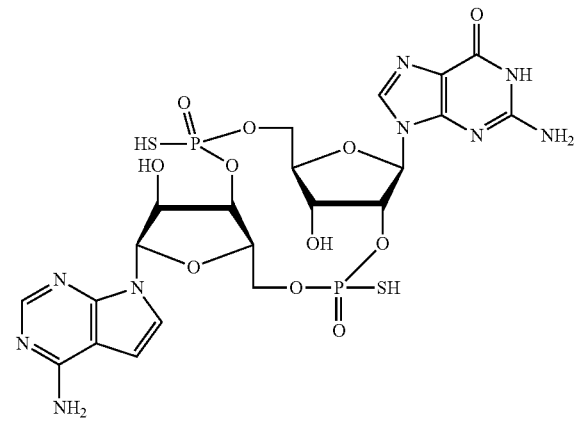

E15-18

Step 1: C5

Step 2: Phosphorothioate 85

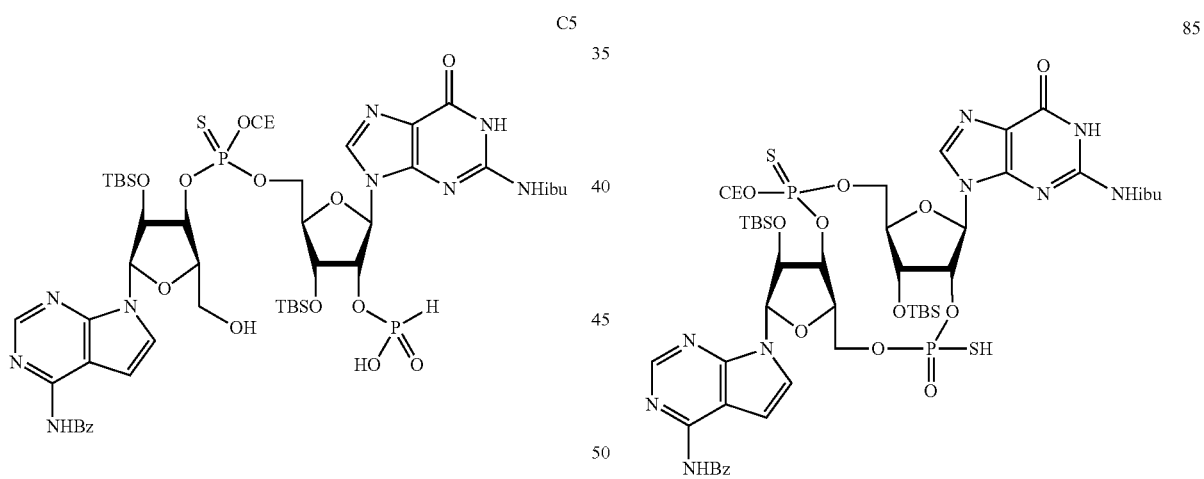

To a mixture of A4 (500 mg, 0.50 mmol, co-evaporated with MeCN 5 mL×1 and toluene 10 mL×2) and G1 (322 mg, 0.61 mmol, co-evaporated with MeCN 5 mL×1 and toluene 10 mL×2) is added tetrazole (0.45 M in MeCN, 4.0 mL). After stirring at 25° C. for 2 hours, DDTT (240 mg, 1.2 mmol) is added and the mixture is stirred for 16 hour before filtered and concentrated. The residue is then dissolved in DCM (10 mL) followed by addition of water (0.1 mL) and DCA (0.21 mL). After stirring for 10 minutes, TEA (1 mL) is added and the mixture is concentrate and purified by reverse-phase silica gel column chromatography (MeCN with 0.1% TEA/water=0% to 100%) to give C5•TEA as a white solid (250 mg, 35% yield). (MS: $\{[M+2H]^{2+}\}/2$ 574.6)

To a solution of C5 (600 mg, 0.423 mmol, co-evaporated with Py 3 mL×2) in Py (5.0 mL) is added DMOCP (313 mg, 1.69 mmol) at 25° C. After stirring for 2 hours, 3H-1,2-benzodithiol-3-one (142 mg, 0.85 mmol) is added and the mixture is stirred for 2 hours before sodium bicarbonate aqueous solution (5%, 10 mL) is added. The mixture is then extracted with EA (10 mL×3). The combined organic layers are dried with anhydrous sodium sulfate, filtered, concentrated, and purified by reverse-phase HPLC (MeCN with 0.1% TEA/water=0 to 100%) to give four diastereomers of 85•TEA as white solids. Isomer 1 (28 mg) (MS: $[M+H]^+$ 1160.9); Isomer 2 (25 mg) (MS: $[M+H]^+$ 1160.9); Isomer 3 (50 mg) (MS: $[M+H]^+$ 1160.9); Isomer 4 (52 mg) (MS: $[M+1]^+$ 1160.9)

Step 3: E15-E18

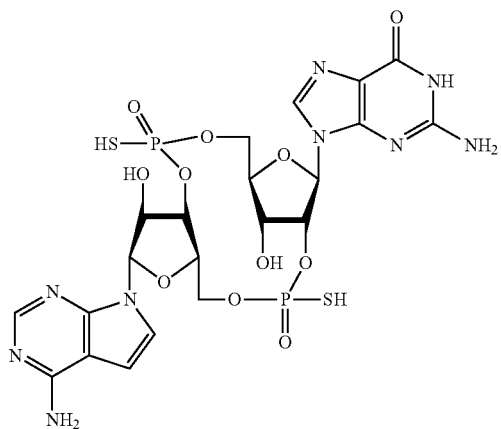

E15-18

Each of the isomers of 85•TEA (25 mg, 0.022 mmol) in ammonium hydroxide (5.6 mL) and MeOH (4.0 mL) is stirred at 50° C. for 16 hours. The mixture is then purged with nitrogen at room temperature for 5 minutes before concentrated. The residue is dissolved in TEA (0.5 mL) and Py (0.2 mL), and TEA•3HF (0.7 mL) is added. After stirring at 50° C. for 24 hours, triethylammonium bicarbonate aqueous solution (1M, 5 mL) is added and the mixture is purified by a reverse-phase silica gel column chromatography (MeCN with 0.1% TEA/water=0% to 30%) to give E15-E18 as white solids.

Example C: Synthesis of E24

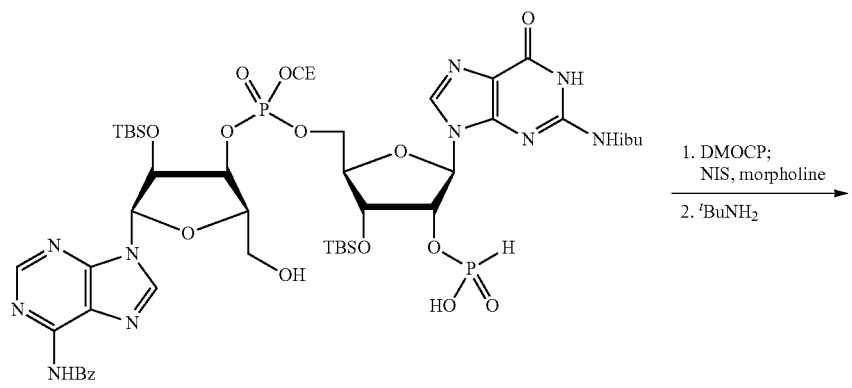

C3

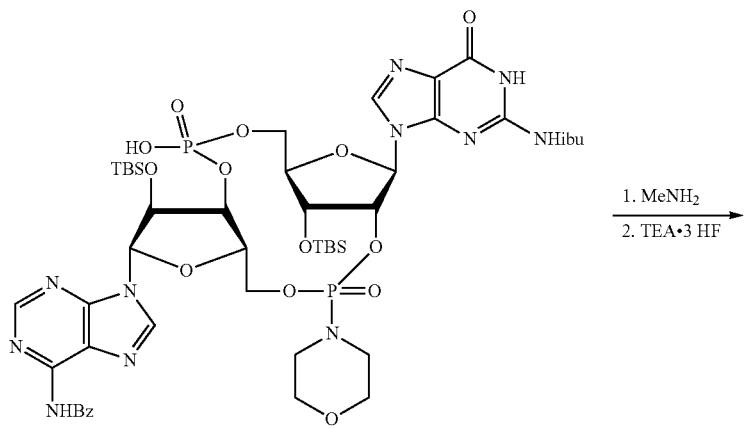

86

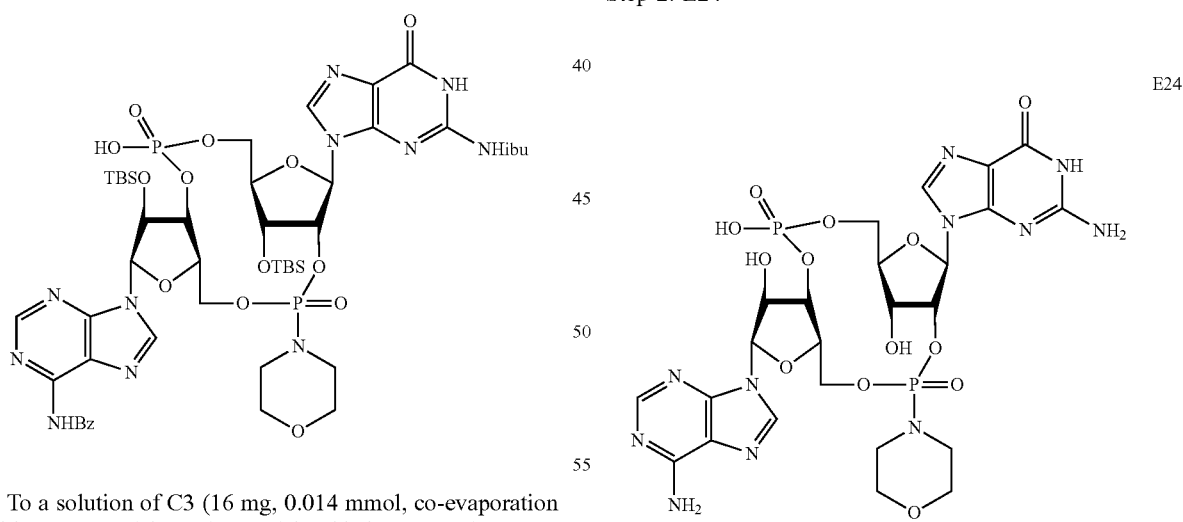

E24

Step 1: Phosphoramidate 44

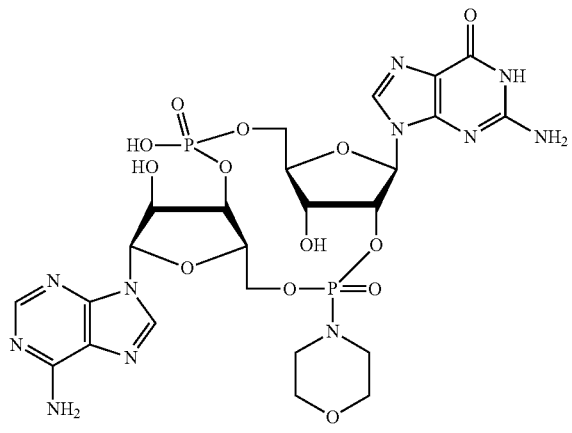

86

To a solution of C3 (16 mg, 0.014 mmol, co-evaporation with Py 1 mL×3) in Py (0.5 mL) is added DMOCP (10.4 mg, 0.056 mmol). After stirring for 15 minutes, NIS (4.1 mg, 0.0183 mmol) and morpholine (0.012 mL, 0.141 mmol) are added and the mixture is stirred for 1 hour before sodium bisulfite aqueous solution (0.14%, 1 mL) and sodium bicarbonate (80 mg) is added. The mixture is then extracted with DCM (5 mL×3), dried over anhydrous sodium sulfate, and concentrated. The residue is then stirred in MeCN (0.5 mL) and t-butylamine (0.5 mL) at room temperature for 15 minutes before concentrated. The resulting residue is then co-evaporated with MeCN (1 mL×3) and purified by HPLC to give 86 as a white solid (2.4 mg, 15%). (MS: [M+H]$^+$ 1146.2)

Step 2: E24

To 86 (2.4 mg, 0.0021 mmol) is added methylamine (33% in EtOH, 0.3 mL). After stirring at room temperature for 16 hours, the mixture is concentration and the residue is stirred in a mixture of TEA and TEA•3HF in THF (0.036 mL/0.018 mL/0.3 mL) at 35° C. for 18 hours. MeCN (1.0 mL) is then added and the solid is collected by centrifugation, washed with MeCN (1 mL×2) to give E24 as a white solid (0.6 mg, 38% yield). (MS: [M+H]$^+$ 744.0)

Example D: Synthesis of E25
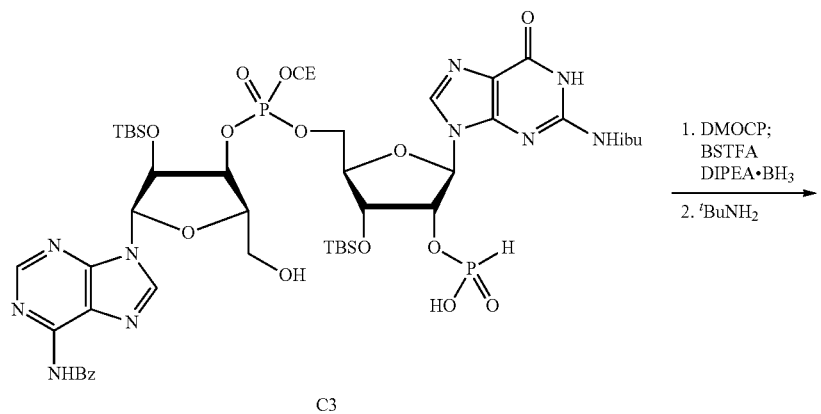
C3
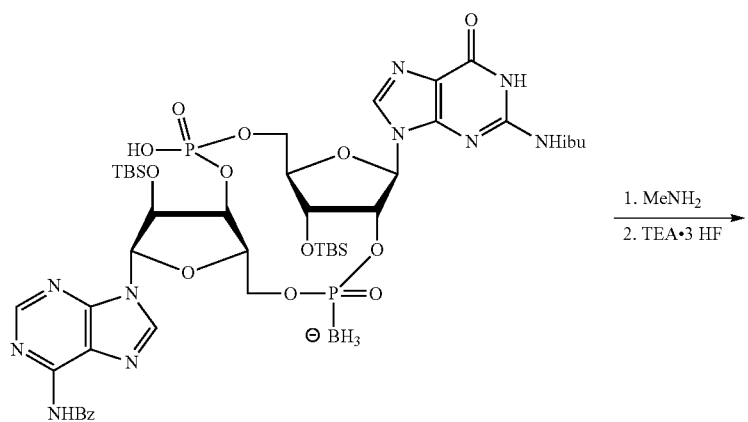
87
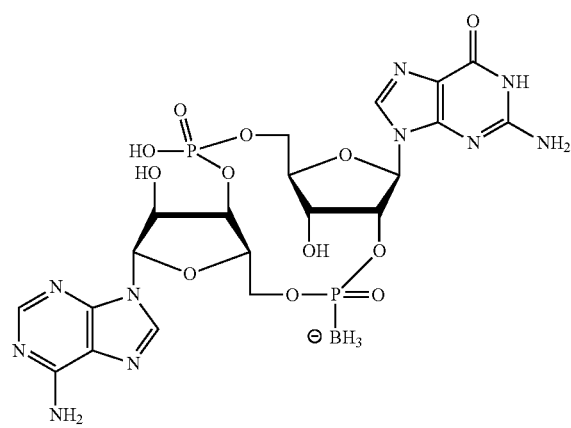
E25

Step 1: Boranophosphate 87

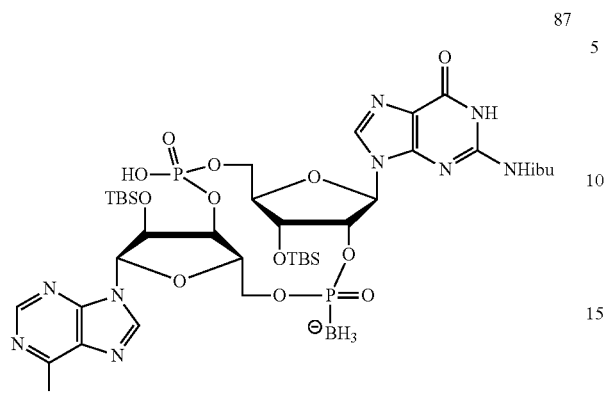

87

To a solution of C3 (100 mg, 0.088 mmol, co-evaporated with Py 4 mL×3) in Py (3 mL) is added DMOCP (57 mg, 0.337 mmol). After stirring for 15 minutes, BSTFA (0.10 mL, 0.371 mmol) is added dropwise and the mixture is stirred for 20 minutes before borane N,N-diisopropylethylamine complex (0.092 mL, 0.530 mmol) is added. The mixture is then stirred for 3 hours before concentrated and purified by silica gel column chromatography (MeOH/DCM=1/19 to 1/9) to give semi-pure CE-protected 87 as a yellow solid. The semi-pure CE-protected 87 obtained above is stirred in a mixture of MeCN (1 mL) and t-butylamine (0.5 mL) for 10 minutes before concentrated. The residue is then co-evaporated with MeCN (4 mL×3) and purified by reverse-phase HPLC (MeCN with 0.1% TEA/water=40% to 90%) to give 87 as a white solid (11 mg, 12% over two steps). (MS: [M]⁻ 1073.2)

Step 2: E25

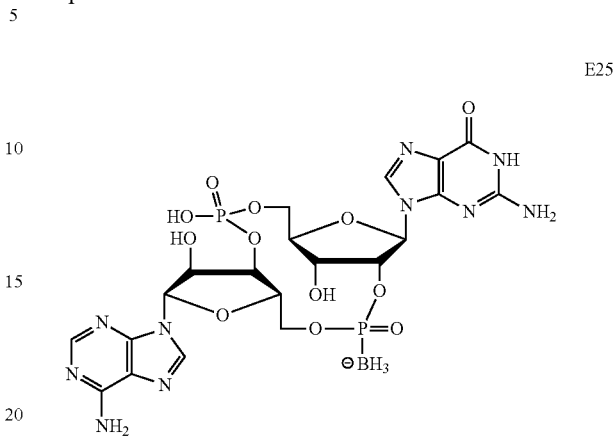

E25

To 87 (5.7 mg, 0.0053 mmol) is added methylamine (33% in EtOH, 1 mL). After stirring at room temperature for 18 hours, the mixture is concentration and the residue is stirred in a mixture of TEA (0.08 mL) and TEA•3HF (0.04 mL) in THF (0.5 mL) at 35° C. for 18 hours. MeCN (1.2 mL) is then added and the solid is collected by centrifugation, purified by reverse-phase HPLC (MeCN with 0.1% TFA/water=0% to 20%) to give E25 as a white solid (2.5 mg, 61% yield) (MS: [M]⁻ 671.2)

Example E: Synthesis of EB1 and EB2

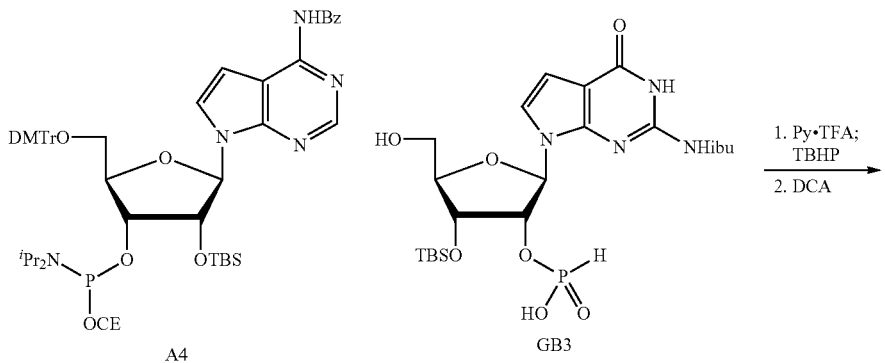

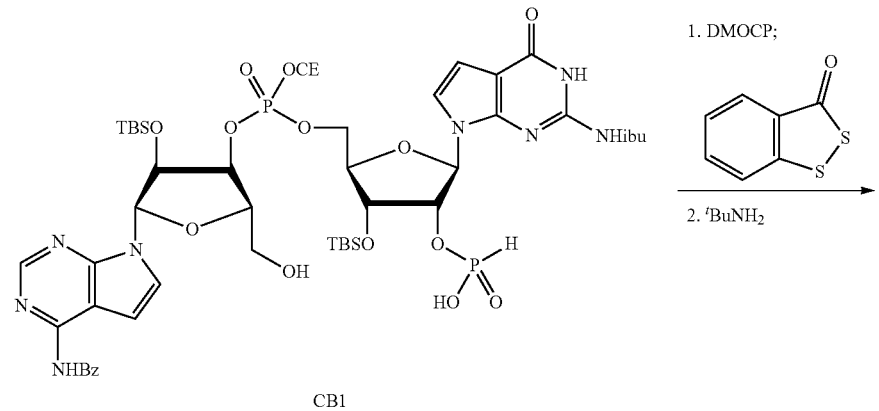

CB1

-continued

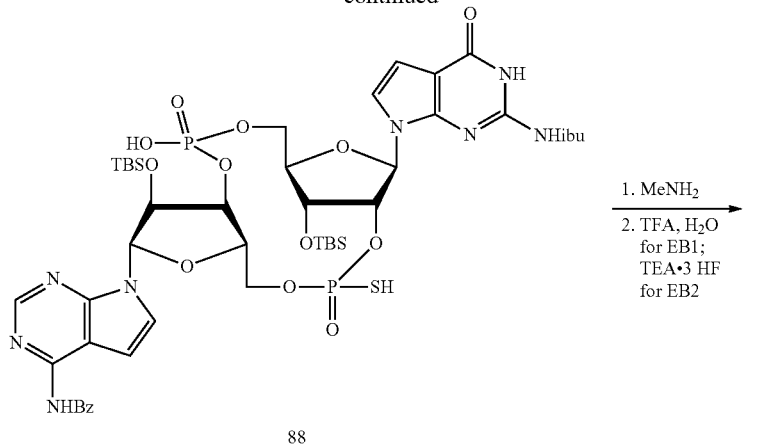

88

1. MeNH₂
2. TFA, H₂O
   for EB1;
   TEA·3 HF
   for EB2

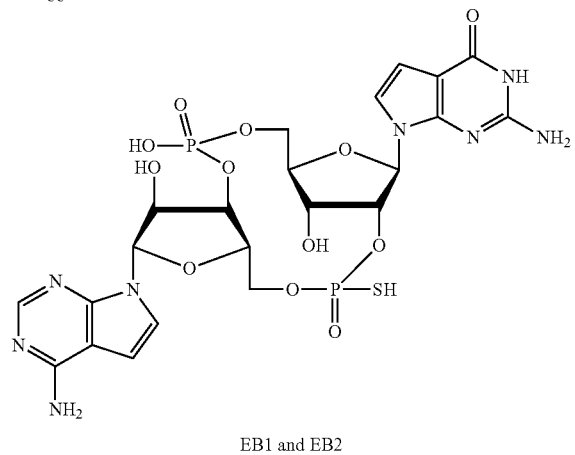

EB1 and EB2

Step 1: CB1

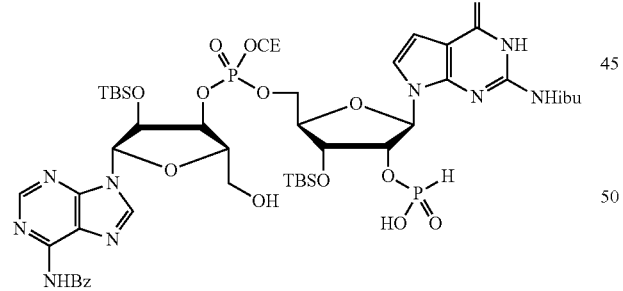

CB1

To a solution of GB3 (160 mg, 0.25 mmol, co-evaporated with MeCN 1 mL×3) and pyridinium trifluoroacetate (35 mg, 0.39 mmol, co-evaporation with MeCN 1 mL×3) in MeCN (1 mL) treated with 3 Å MS (500 mg) for 30 minutes is added a solution of A4 (355 mg, 0.36 mmol, co-evaporated with MeCN 1 mL×3) in MeCN (1 mL) treated with 3 Å MS (700 mg) for 30 minutes. After stirring at room temperature for 2 hours, TBHP (5.5 M in decane, 0.164 mL, 0.9 mmol) is added and the mixture is stirred for 30 minutes before sodium bisulfite aqueous solution (33%, 0.15 mL) is added at 0° C. The mixture is then concentrated and the residue is dissolved in DCM (4.8 mL) followed by addition of water (0.054 mL) and dichloroacetic acid (6% in methylene chloride, 4.8 mL). After stirring for 10 min, the Py (1.5 mL) is added and the mixture is concentrated and purified by silica gel column chromatography (MeOH/DCM=1/10 to 1/4 with 1% Py) to give CB1·Py as a white solid (213 mg, 66% yield).

Step 2: Phosphorothioate 88

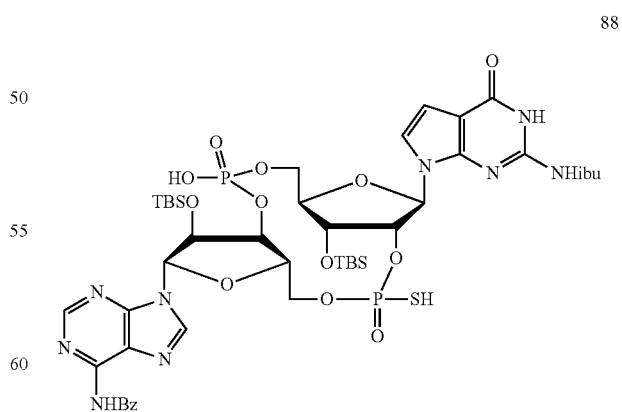

88

To a solution of CB1 (60 mg, 53 μmol) in Py (1 mL) is added DMOCP (30 mg, 162.5 μmol). After stirring for 10 minutes, water (0.027 mL) and 3H-1,2-benzodithiol-3-one (13 mg, 0.077 mmol) are added. The mixture is stirred for 5 minutes before pouring into a solution of sodium bicarbonate (210 mg) in water (7.5 mL). After stirring for 5 minutes, the mixture is extracted by EA/diethyl ether (1:1, 10 mL×3). The combined organic layers are concentrated to give a yellow solid (100 mg). To a solution of the yellow solid obtained above in MeCN (0.5 mL) is added tert-butylamine (0.5 mL). After stirring for 10 minutes, the mixture is concentrated and purified by HPLC (MeCN/water with 0.1% TFA: 50% to 100%) to give two diastereomers of 88. Isomer 1 (7 mg) ([M+H]$^+$ 977.0); Isomer 2 (16 mg) (MS: [M+H]$^+$ 977.0)

Step 3: EB1 and EB2

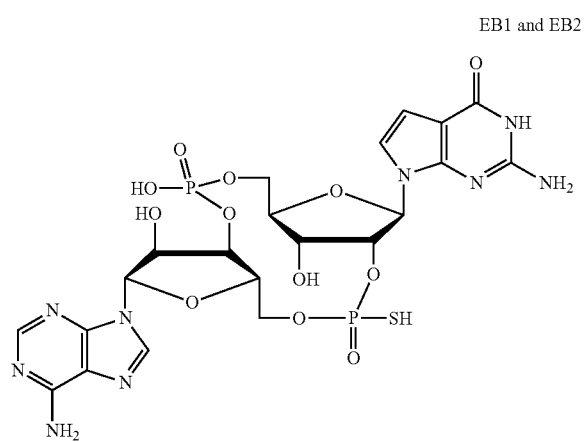

EB1 and EB2

To the Isomer 1 of 88 (7 mg) is added methylamine (33% in ethanol, 1 mL). After stirring at room temperature for 12 hours, the mixture is concentrated and the residue is dissolved in TFA aqueous solution (3% v/v, 1 mL). After stirring for 2 hours, the mixture is concentrated and purified by HPLC (MeCN/water with 0.1% TFA, 0% to 45%) to give EB1 as a white solid (2.5 mg, 57% yield). (MS: [M+H]$^+$ 689.0)

To the Isomer 2 of 63 (16 mg) is added methylamine (33% in ethanol, 2 mL) at 0° C. After stirring at room temperature for 12 hours, the mixture is concentrated and the residue is co-evaporated with a mixture of Py/TEA (5 mL/2 mL×3) before dissolved in Py (0.04 mL). TEA (0.25 mL) and TEA•3HF (0.15 mL are then added. After stirring at 55° C. for 3 hours, acetone (2 mL) is added. The solid is collected (10 mg) by filtration and purified by HPLC (MeCN/water with 0.1% TFA, 0% to 30%) to give EB2 as a white solid (5 mg, 45% yield). (MS: [M+H]$^+$ 689.0, [M−H]$^-$ 687.0)

Example F: Synthesis of EC25

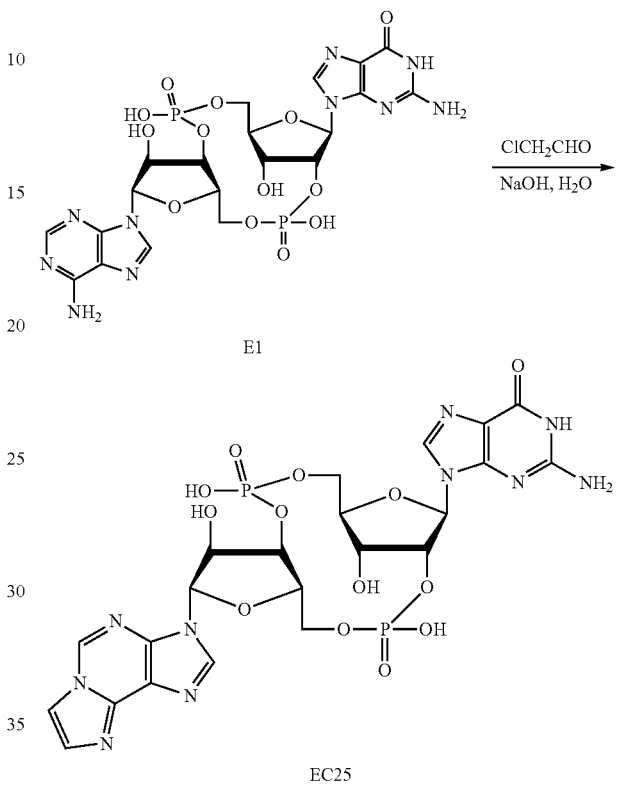

To a solution of E1•TEA salt (10 mg, 0.0114 mmol) in water (0.3 mL) is added 2-chloroacetaldehyde (0.015 mL, 0.118 mmol) and sodium hydroxide aqueous solution (1 M, 0.012 mL, 0.012 mmol). After stirring at 37° C. for 18 hours, the mixture is concentrated and purified by reverse-phase HPLC (MeCN/water with 0.1% TFA=0% to 30%) to give EC26 as a white solid. (MS: [M]$^-$ 697.1)

The following compounds are prepared essentially by the methods above.

TABLE 3
Examples E1 to E25, EA1 to EA11, EB1 to EB7, and EC1 to EC24
| Example | Intermediate 1 | Intermediate 2 | Structure | Reference of Preparation |
|---|---|---|---|---|
| E1 | G1 | A2 | 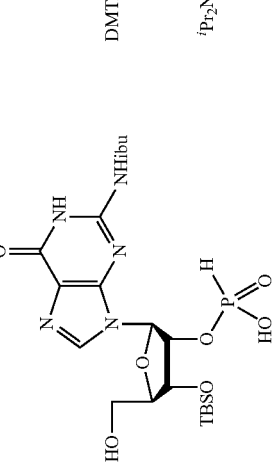 | Example A |
| E2 | G3 | A2 | 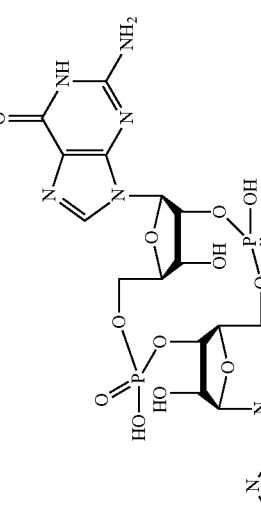 | Example A |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| E3 | G4 | A2 | 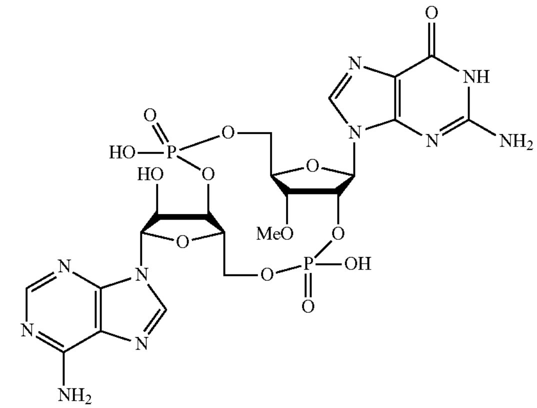 | Example A |
| E4 | G5 | A1 | 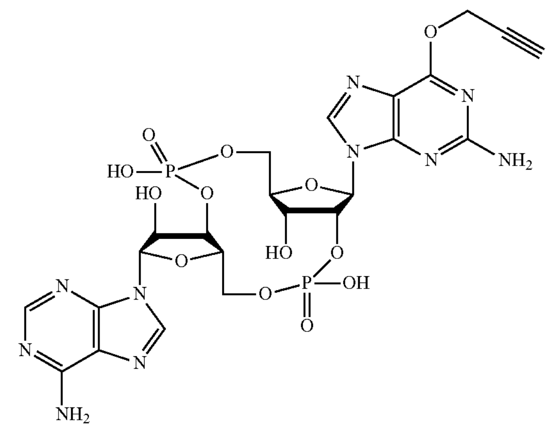 | Example A |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| E5 | G1 | A4 | 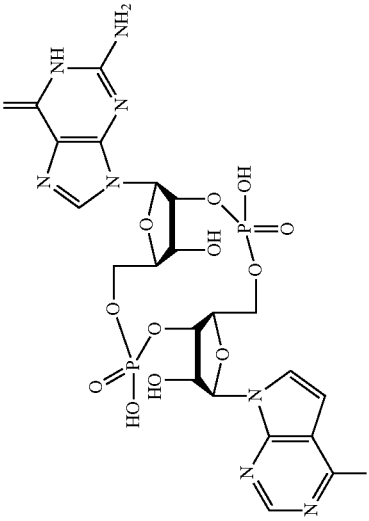 | Example A |
| E6 | C1 | | 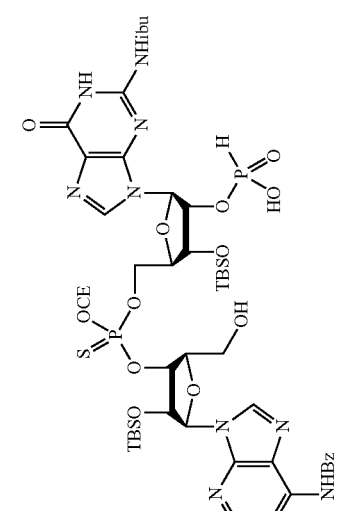 isomer 1 | Example A |
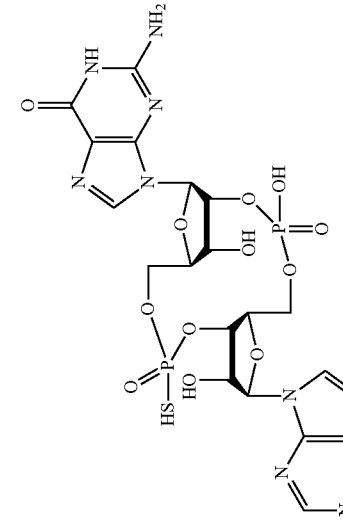
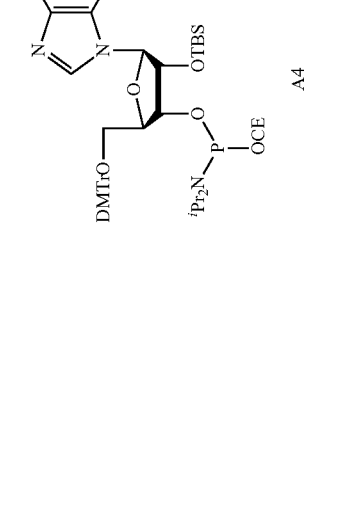

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| E7 | C1 | | 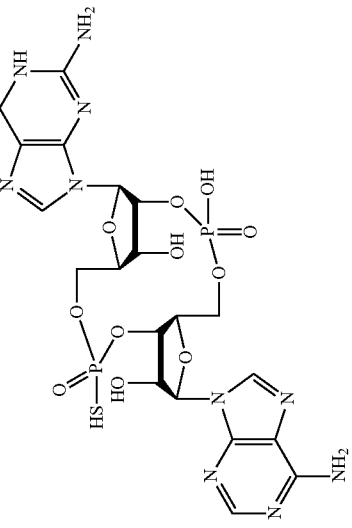 isomer 2 | Example A |
| E8 | 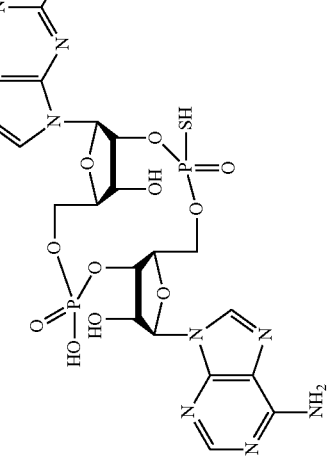 | C2 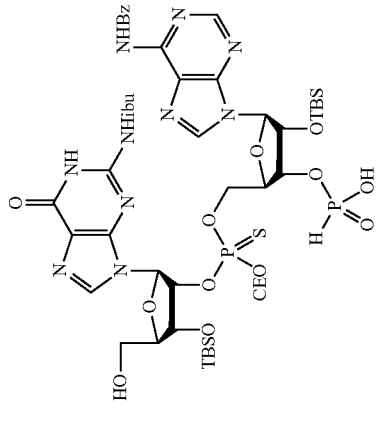 | 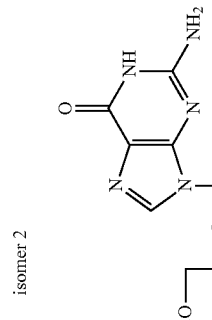 isomer 1 | Example A |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| E9 | | C2 |  isomer 2 | Example A |
| E10 | G6  | A2 | isomer 1 | Example A |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| E11 | G6 | A2 | 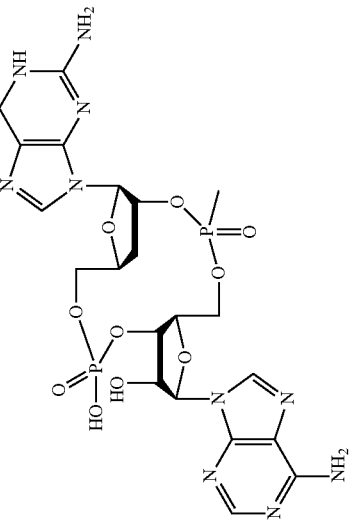 isomer 2 | Example A |
|  |  |  | 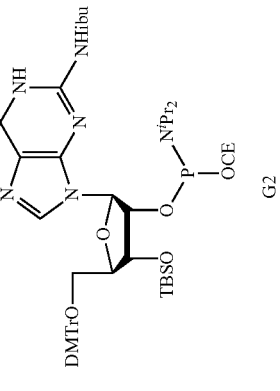 isomer 1 | Example B |
|  |  | A1 |  |  |
| E12 |  |  | 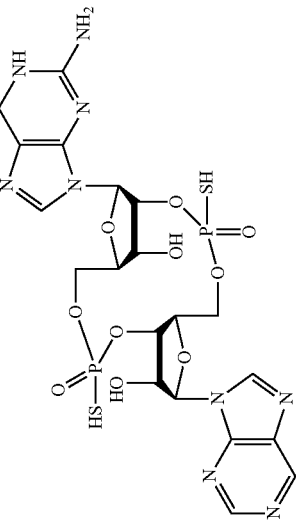 G2 |  |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| E13 | G2 | A1 | isomer 2 | Example B |
| E14 | G2 | A1 | isomer 3 | Example B |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| E15 | G1 | A4 | 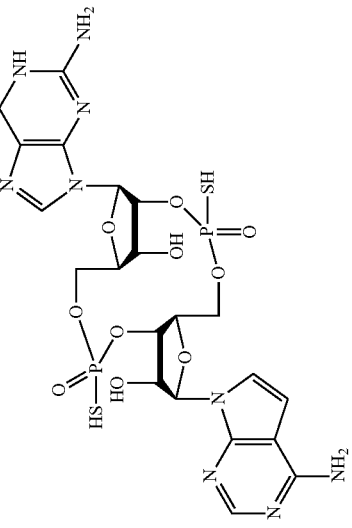 isomer 1 | Example B |
| E16 | G1 | A4 | 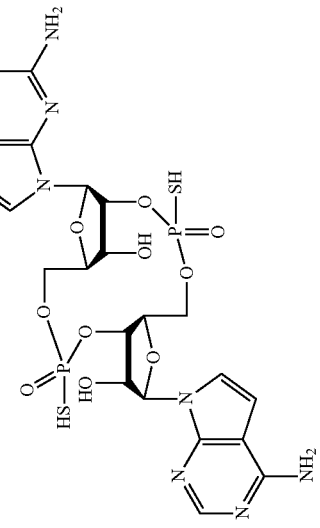 isomer 2 | Example B |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| E17 | G1 | A4 | 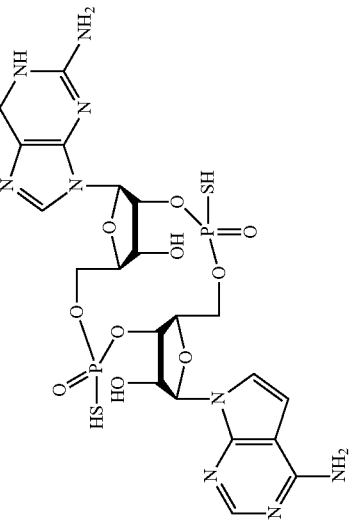 isomer 3 | Example B |
| E18 | G1 | A4 | 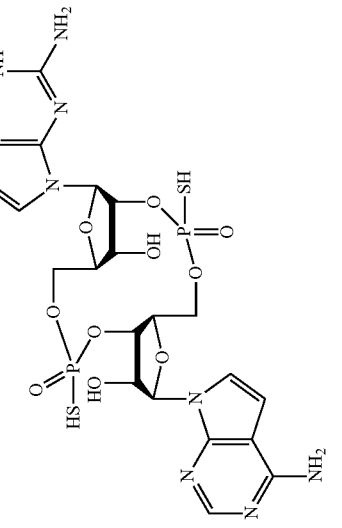 isomer 4 | Example B |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| E19 | G1 | A5 | 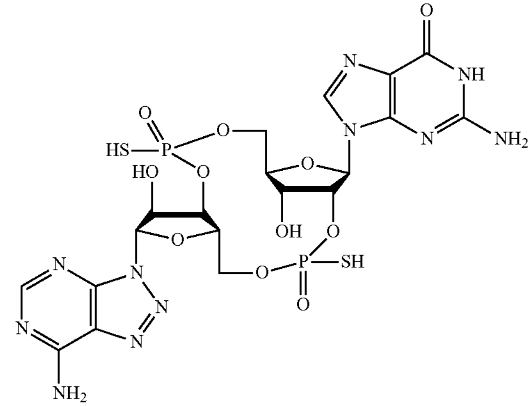 | Example B |
| E20 | G7 | A3 | isomer 1 | Example B |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| E21 | G7 | A3 | isomer 2 | Example B |
| E22 | G7 | A3 | isomer 3 | Example B |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| E23 | G7 | A3 | 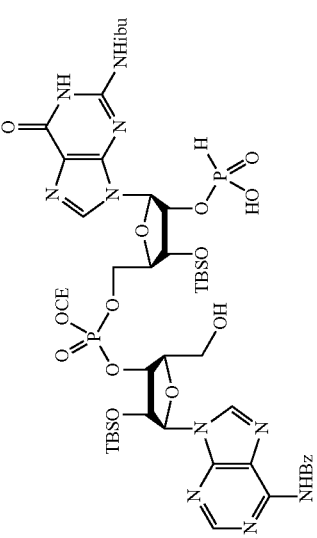 isomer 4 | Example B |
| E24 | | | 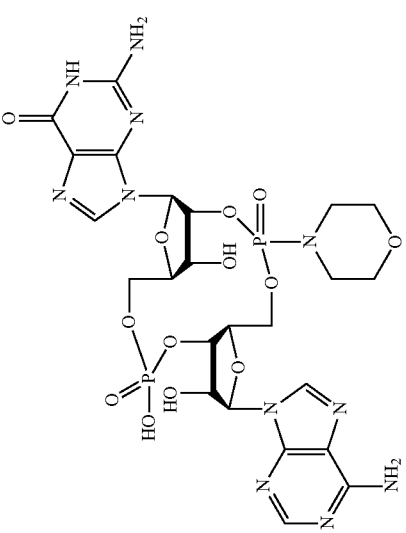 C3 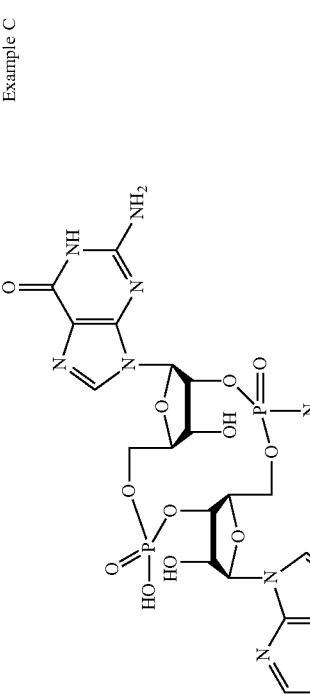 | Example C |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| E25 | G7 | C3 | 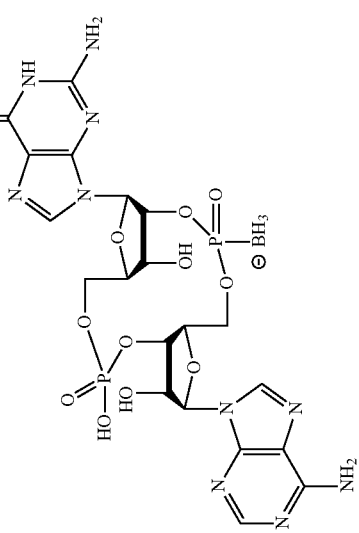 | Example D |
| EA1 | G7 | A3 | 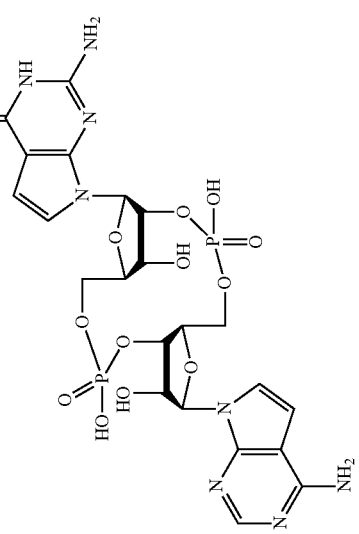 isomer 1 | Example A |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EA2 | | A1 | 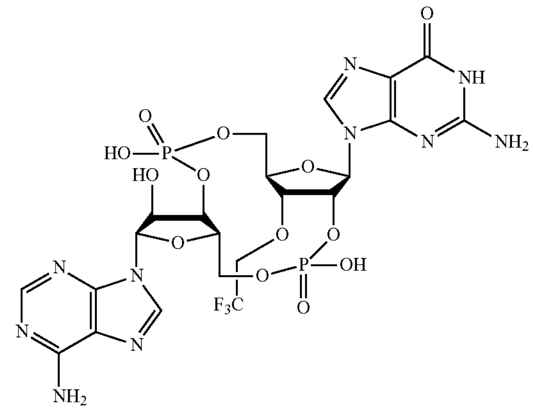 | Example A |
| EA3 | G1 | | 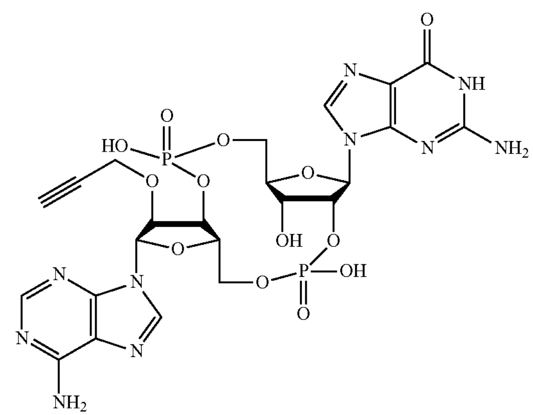 | Example A |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EA4 | G1 | AA2 | isomer 1 | Example B |
| EA5 | G1 | AA2 | isomer 2 | Example B |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| EA6 | G7 | A1 | 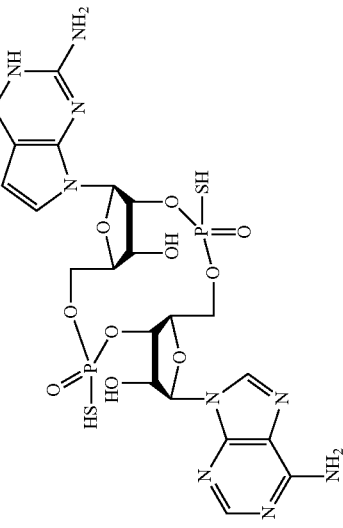 isomer 1 | Example B |
| EA7 | G7 | A1 | 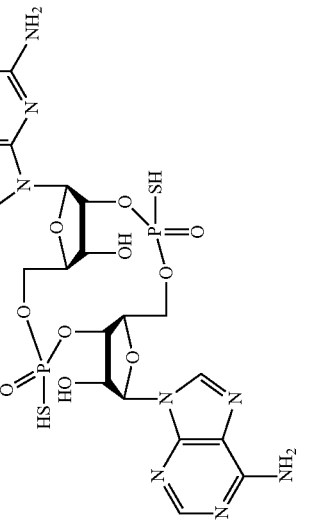 isomer 2 | Example B |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| EA8 | G7 | A1 | 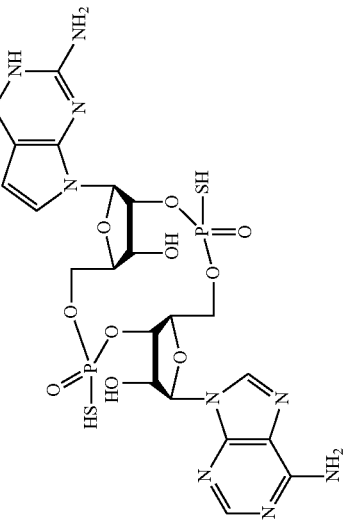 isomer 3 | Example B |
| EA9 | | C3 | 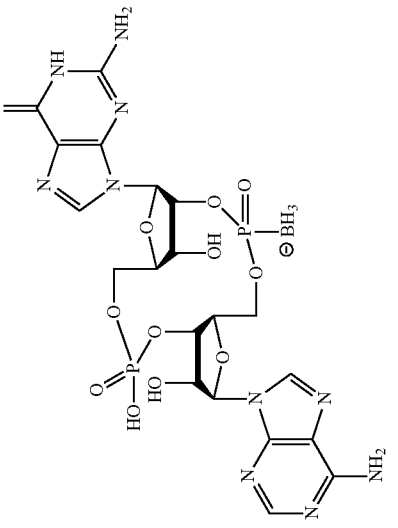 isomer 2 | Example D |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EA10 | | CA1 | (structure shown) | Example A |
| EA11 | | CA1 | (structure shown) | Example D |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| EB1 | 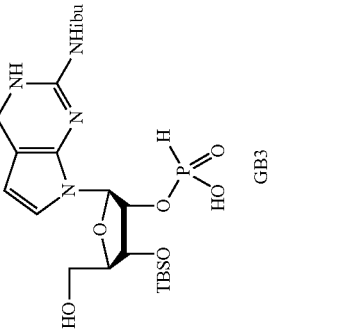GB3 | A4 | 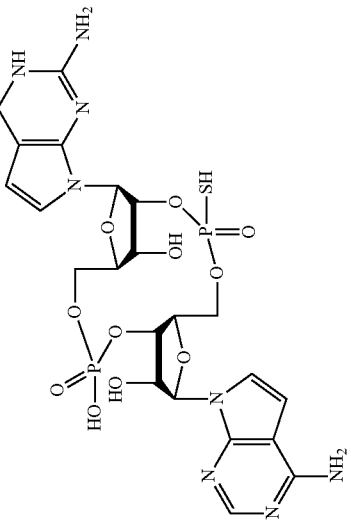isomer 1 | Example E |
| EB2 | GB3 | A4 | 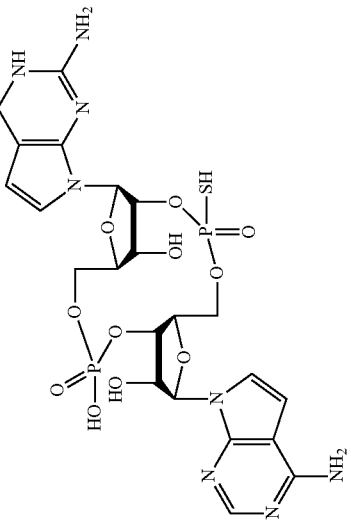isomer 2 | Example E |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| EB3 | GB3 | A2 | 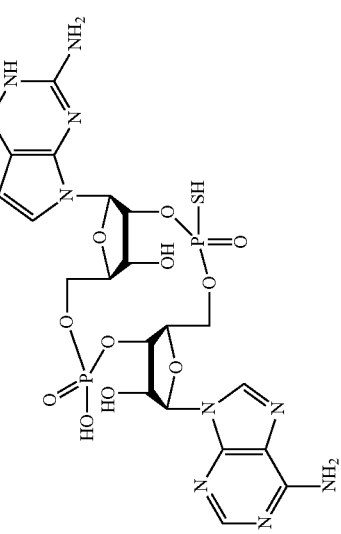 isomer 1 | Example E |
| EB4 | GB3 | A2 | 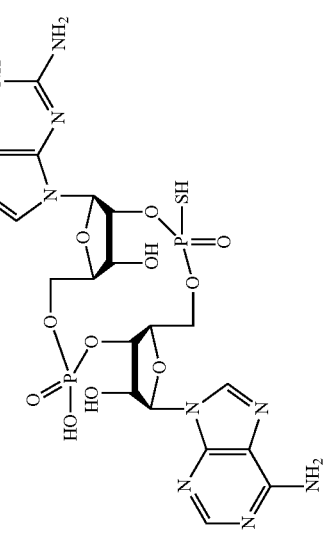 isomer 2 | Example E |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| EB5 | GB3 | AB1 | 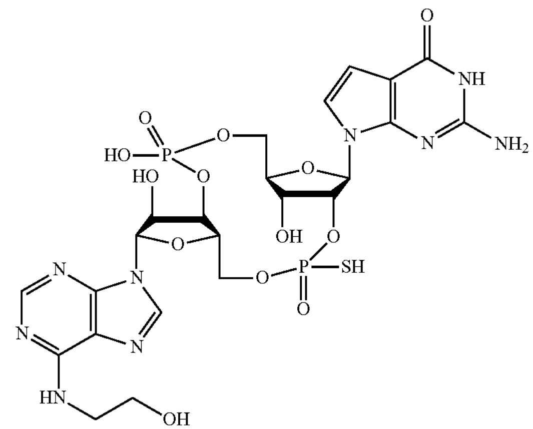 | Example E |
| EB6 |  GB2 | A2 |  isomer 1 | Example E |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| EB7 | GB2 | A2 | 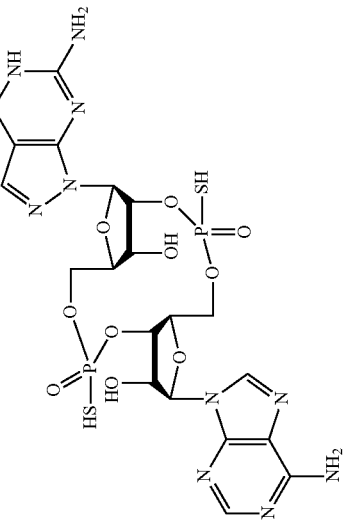 isomer 2 | Example E |
| EC1 | GC3 | A4 | 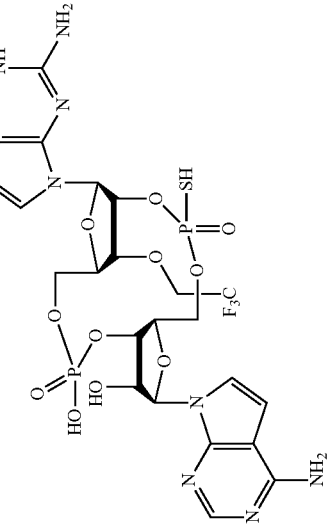 isomer 1 | Example E |
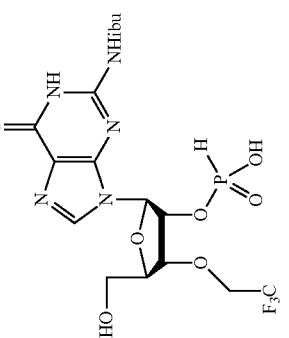

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| EC2 | GC3 | A4 | 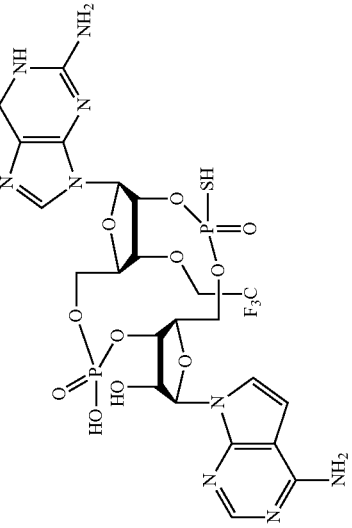 isomer 2 | Example E |
| EC3 | GC3 | A4 | 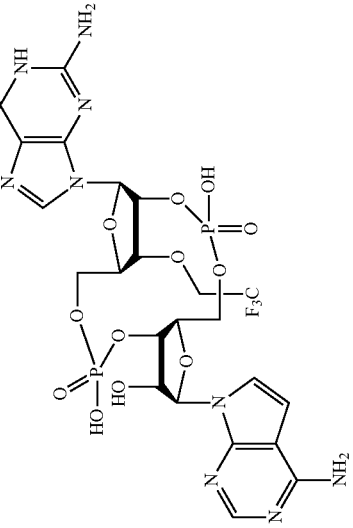 | Example A |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC4 | GB3 | GC4 | isomer 1 | Example E |
| EC5 | GB3 | GC4 | isomer 2 | Example E |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| E6 | 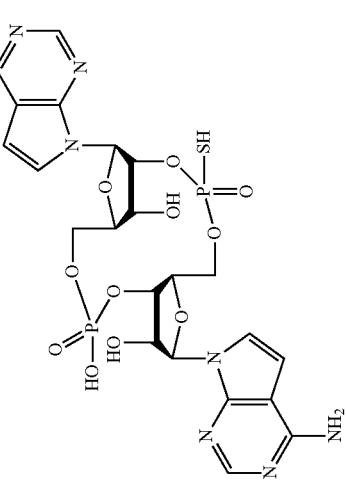 AC3 | A4 | 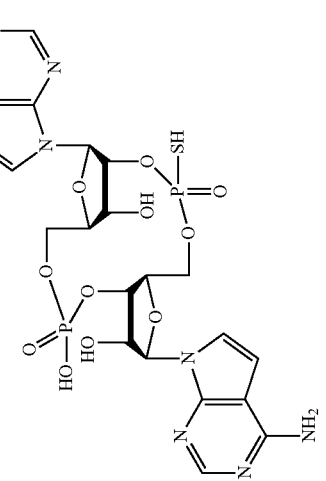 isomer 1 | Example E |
| EC7 | AC3 | A4 | isomer 2 | Example E |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC8 | AC3 | GC4 | isomer 1 | Example E |
| EC9 | AC3 | GC4 | isomer 2 | Example E |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC10 | GC3 | (commercially available) AC8 | 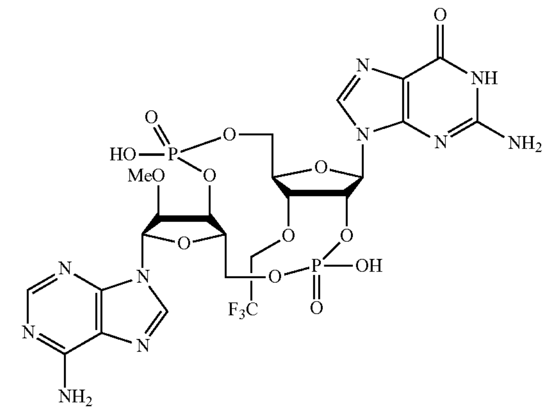 | Example A |
| EC11 | G1 | (commercially available) AC9 | 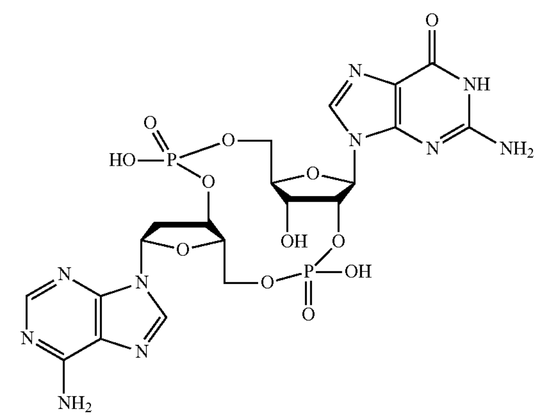 [SMILES: Nc1nc2c(ncn2[C@@H]2O[C@@H]3COP(=O)(O)O[C@@H]4C[C@H](n5cnc6c(N)ncnc65)O[C@@H]4COP(=O)(O)O[C@H]2C3O)c(=O)[nH]1] | Example A |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC12 | GC1 | A2 | 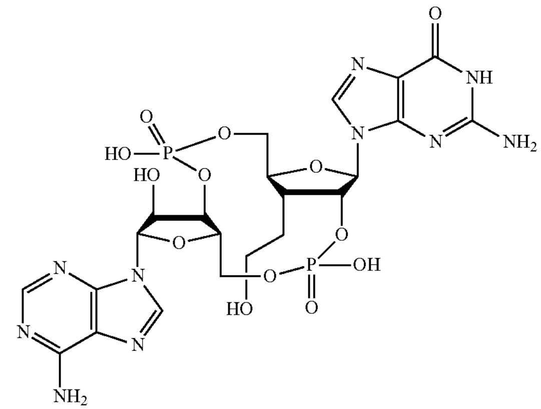 | Example A |
| EC13 | GA1 | AC4 | 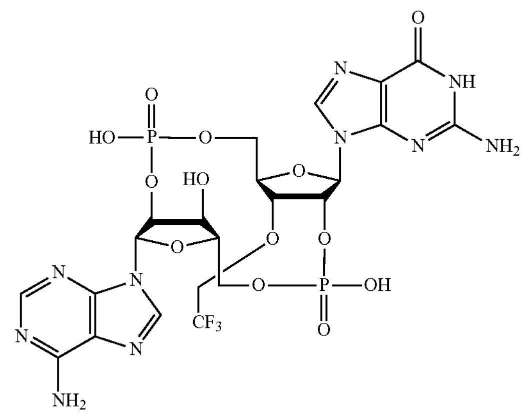 [SMILES: Nc1nc2c(ncn2[C@@H]2O[C@@H]3COP(=O)(O)OC4[C@@H](O)[C@@H](COP(=O)(O)O[C@H]2C3OCC(F)(F)F)O[C@H]4n2cnc3c(N)ncnc32)c(=O)[nH]1] | Example A |

TABLE 3-continued
Examples E1 to E25, EA1 to EA11, EB1 to EB7, and EC1 to EC24
| Example | Intermediate 1 | Intermediate 2 | Structure | Reference of Preparation |
|---|---|---|---|---|
| EC14 | G7 | AC4 | 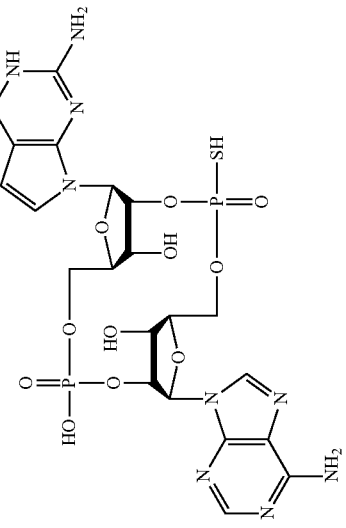 isomer 1 | Example E |
| EC15 | G7 | AC4 | 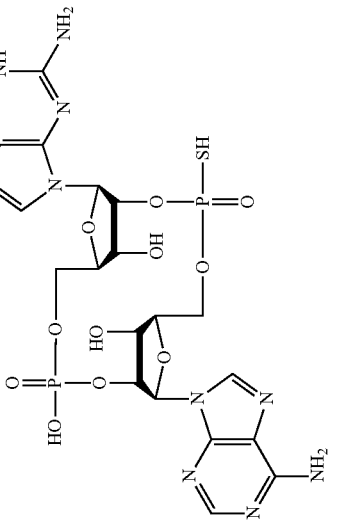 isomer 2 | Example E |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC16 | GA1 | AC2 | 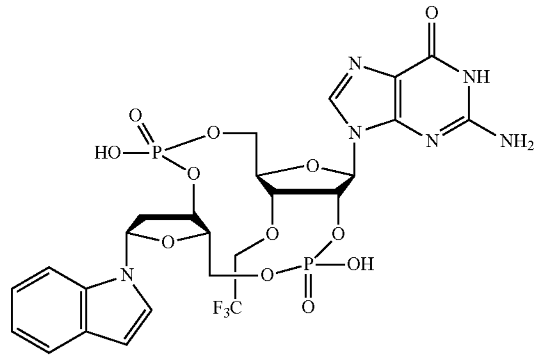 [SMILES: Nc1nc2c(ncn2[C@@H]2O[C@@H]3COP(=O)(O)O[C@@H]4C[C@H](n5ccc6ccccc65)O[C@@H]4COP(=O)(O)O[C@H]2C3OCC(F)(F)F)c(=O)[nH]1] | Example A |
| EC17 | G1 | AC2 | isomer 1 | Example E |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC18 | G1 | AC2 | (structure shown; isomer 2) | Example E |
| EC19 | G1 | AC5 | (structure shown) | Example A |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC20 | G1 | AC6 | isomer 1 | Example E |
| EC21 | GC3 | AC6 | isomer 2 | Example E |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC22 | | CC1 | 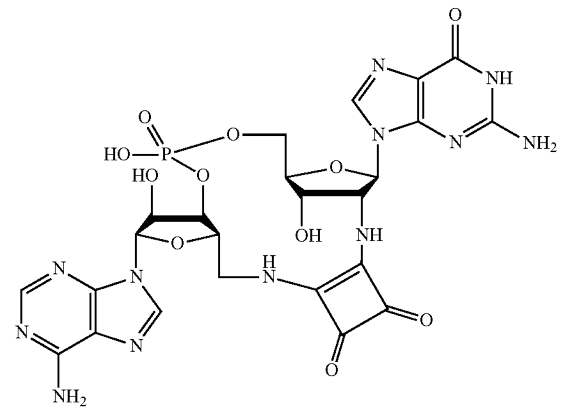 | Example A |
| EC23 | | CC2 | 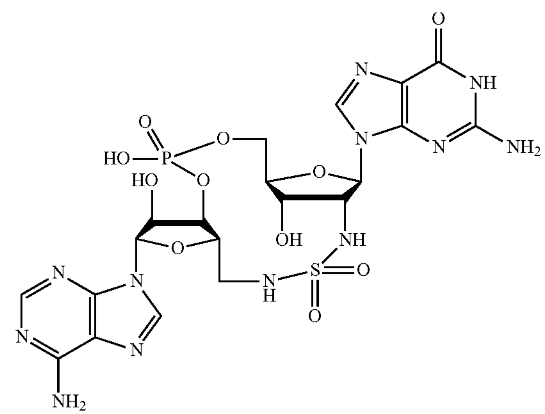 | Example A |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC24 | GC5 | A2 | 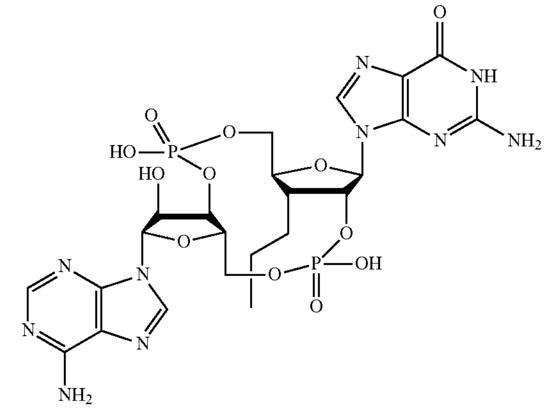 | Example A |
| EC25 | | | E1 | Example F |

TABLE 3-continued

Examples E1 to E25, EA1 to EA11, EB1 to EB7, and EC1 to EC24

| Example | Intermediate 1 | Intermediate 2 | Structure | Reference of Preparation |
|---|---|---|---|---|
| EC26 | | EA2 | 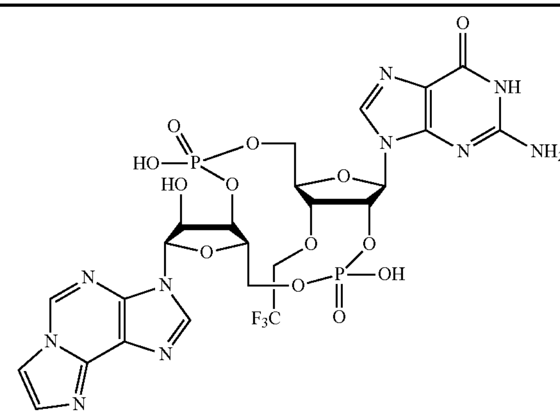 | Example F |

Selected physical data of the example compounds are summarized below.

TABLE 4

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| E1 | 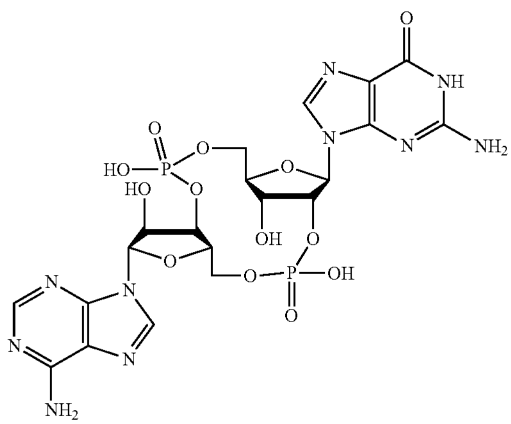 | 8.58 (s, 1H)<br>8.56 (s, 1H)<br>8.16 (s, 1H)<br>6.45 (s, 1H)<br>6.22 (d, J = 8.5 Hz, 1H)<br>5.89 (m, 1H)<br>5.31 (m, 1H)<br>50 °C. | 0.1<br>−0.9<br>50 °C. | [M + H]$^+$<br>675.1 |
| E2 | 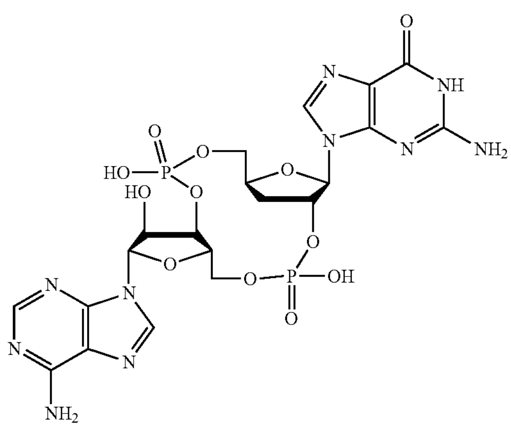 | | | [M + H]$^+$<br>659.0 |
| E3 | 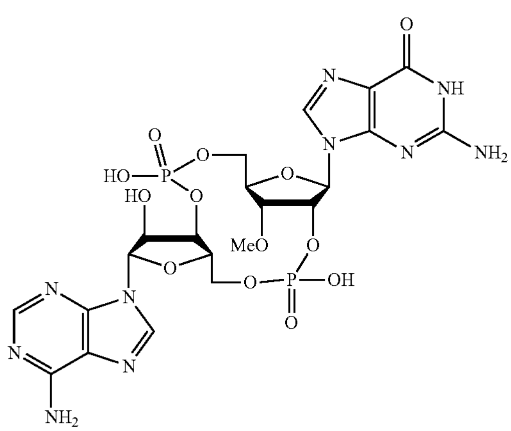 | 8.31 (s, 1H)<br>8.29 (s, 1H)<br>7.88 (s, 1H)<br>6.19 (s, 1H)<br>5.92 (d, J = 8.7 Hz, 1H)<br>5.71 (ddd, J = 8.4, 8.3, 4.3 Hz, 1H)<br>5.09 (ddd, J = 9.8, 6.9, 4.2 Hz, 1H)<br>Na$^+$ salt in D$_2$O | −1.2<br>−2.5<br>Na$^+$ salt in D$_2$O | [M − H]$^−$<br>687.2 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| E4 | 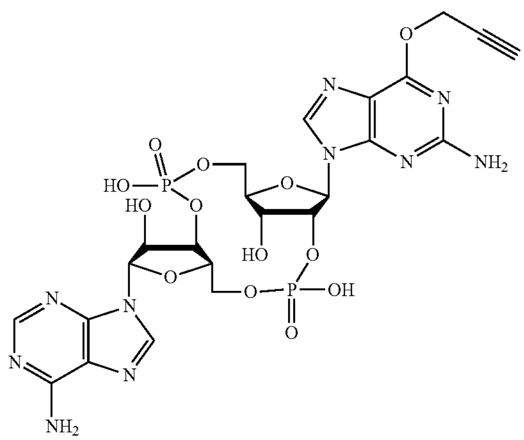 | 8.24 (s, 1H)<br>8.18 (s, 1H)<br>7.97 (s, 1H)<br>6.10 (d, J = 1.4 Hz, 1H)<br>5.97 (d, J = 8.4 Hz, 1H)<br>5.63 (ddd, J = 8.1, 7.9, 4.2 Hz, 1H)<br>5.09 (m, 1H) | −1.5<br>−2.4 | [M + H]$^+$<br>713.2 |
| E5 | 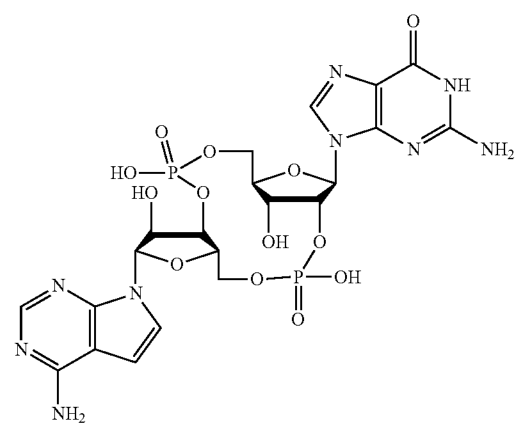 | 8.20 (s, 1H)<br>7.95 (s, 1H)<br>7.47 (d, J = 3.8 Hz, 1H)<br>6.77 (d, J = 3.8 Hz, 1H)<br>6.08 (d, J = 4.7 Hz, 1H)<br>5.80 (d, J = 4.9 Hz, 1H)<br>in D$_2$O—CH$_3$CN | | [M + H]$^+$<br>673.7 |
| E6 | isomer 1 | 8.25 (s, 1H)<br>8.23 (s, 1H)<br>8.02 (s, 1H)<br>6.18 (s, 1H)<br>5.96 (d, J = 8.6 Hz, 1H)<br>5.43 (td, J = 8.1, 3.9 Hz, 1H) | 52.4<br>−2.4 | [M + H]$^+$<br>691.0 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| E7 | isomer 2 | 8.29 (s, 1H)<br>8.26 (s, 1H)<br>7.85 (s, 1H)<br>6.17 (s, 1H)<br>5.92 (d, J = 8.5 Hz, 1H)<br>5.61 (ddd, J = 7.9, 7.9, 4.0 Hz, 1H)<br>5.20 (ddd, J = 8.8, 8.8, 4.1 Hz, 1H) | 55.1<br>−2.5 | [M + H]$^+$<br>691.0 |
| E8 | isomer 1 | 8.59 (s, 1H)<br>8.18 (s, 1H)<br>8.01 (s, 1H)<br>6.18 (s, 1H)<br>5.98 (s, 1H) | 55.1<br>−1.5 | [M + H]$^+$<br>691.0 |
| E9 | isomer 2 | 8.35 (s, 1H)<br>8.13 (s, 1H)<br>7.95 (s, 1H)<br>6.12 (s, 1H)<br>5.92 (s, 1H) | 54.4<br>−1.6 | [M + H]$^+$<br>691.0 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| E10 | isomer 1 | 8.19 (s, 1H)<br>8.10 (s, 1H)<br>7.83 (s, 1H)<br>6.00 (d, J = 3.7 Hz, 1H)<br>5.84 (d, J = 5.0 Hz, 1H) | 33.8<br>−0.4 | [M + H]$^+$<br>657.2 |
| E11 | isomer 2 | 8.08 (s, 1H)<br>8.01 (s, 1H)<br>7.85 (s, 1H)<br>6.00 (1H)<br>5.76 (1H) | 32.1<br>−0.3 | [M + H]$^+$<br>657.2 |
| E12 | isomer 1 | | | [M + H]$^+$<br>707.0 |

TABLE 4-continued
Physical data of cyclic dinucleotide and analogs
| Example | Structure | characteristic $^1$H NMR data δ (ppm)* | $^{31}$P NMR data δ (ppm)* | MS data m/z |
|---|---|---|---|---|
| E13 | 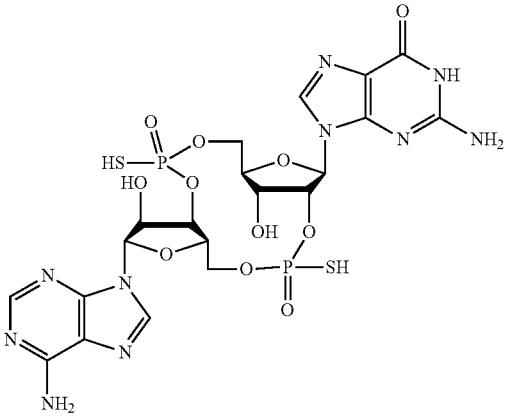<br>isomer 2 | | | [M + H]$^+$<br>707.0 |
| E14 | 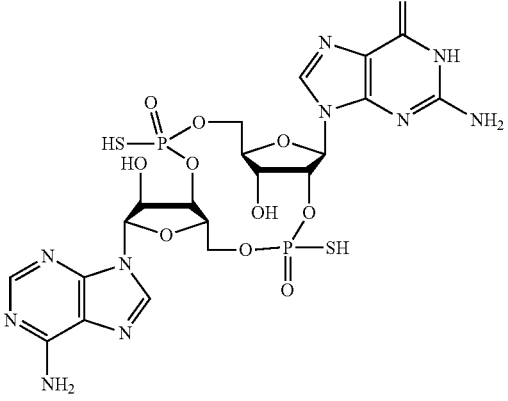<br>isomer 3 | | | [M + H]$^+$<br>707.0 |
| E15 | 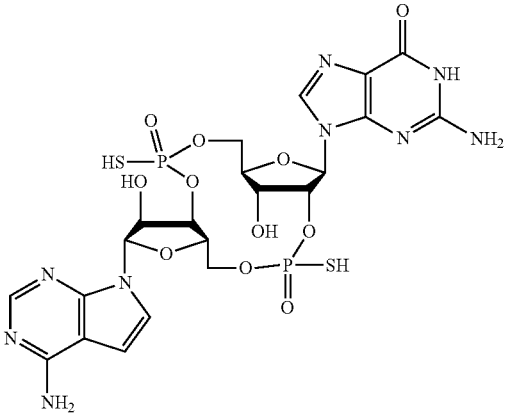<br>isomer 1 | | | $\dfrac{[M + 2H]^{2+}}{2}$<br>354.0 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| E16 | isomer 2 | 8.06 (s, 1H)<br>8.03 (s, 1H)<br>7.23 (d, J = 3.7 Hz, 1H)<br>6.59 (d, J = 3.7 Hz, 1H)<br>6.10 (d, J = 6.4 Hz, 1H)<br>5.87 (d, J = 8.5 Hz, 1H)<br>5.26 (ddd, J = 8.5, 6.8, 4.2 Hz, 1H)<br>5.06 (ddd, J = 8.0, 4.7, 2.8 Hz, 1H)<br>in DMSO-d$_6$ | 57.9<br>51.7<br>in DMSO-d$_6$ | [M + H]$^+$<br>706.1 |
| E17 | isomer 3 | | | [M + H]$^+$<br>706.1 |
| E18 | isomer 4 | 8.23 (s, 1H)<br>8.19 (s, 1H)<br>7.43 (d, J = 3.8 Hz, 1H)<br>6.52 (d, J = 3.8 Hz, 1H)<br>6.19 (s, 1H)<br>5.89 (d, J = 8.5 Hz, 1H)<br>5.23 (m, 1H)<br>4.95 (m, 1H)<br>in CD$_3$CN | 51.3<br>49.1<br>in CD$_3$CN | [M + H]$^+$<br>706.1 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| E19 | | 8.84 (s, 1H)<br>8.58 (s, 1H)<br>6.58 (d, J = 4.6 Hz, 1H)<br>6.24 (d, J = 8.5 Hz, 1H)<br>5.79 (m, 1H)<br>5.60 (m, 1H)<br>in D$_2$O | 59.9<br>56.7<br>in D$_2$O | [M + H]$^+$<br>708.2 |
| E20<br>isomer 1 | | 8.57 (s, 1H)<br>7.83 (d, J = 3.8 Hz, 1H)<br>7.62 (d, J = 3.8 Hz, 1H)<br>7.06 (d, J = 3.8 Hz, 1H)<br>6.84 (d, J = 3.8 Hz, 1H)<br>6.61 (d, J = 6.2 Hz, 1H)<br>6.48 (d, J = 8.4 Hz, 1H)<br>5.69 (ddd, J = 8.0, 4.6, 3.1 Hz, 1H)<br>5.63 (ddd, J = 12.1, 8.4, 4.3 Hz, 1H)<br>in D$_2$O | 59.3<br>57.8<br>in D$_2$O | [M + H]$^+$<br>705.3 |
| E21<br>isomer 2 | | 8.34 (s, 1H)<br>7.62 (d, J = 3.8 Hz, 1H)<br>7.33 (d, J = 3.8 Hz, 1H)<br>6.94 (d, J = 3.8 Hz, 1H)<br>6.28 (d, J = 3.8 Hz, 1H)<br>6.13 (d, J = 5.4 Hz, 1H)<br>6.10 (d, J = 8.4 Hz, 1H)<br>in DMSO-d$_6$ | 54.9<br>50.1<br>in DMSO-d$_6$ | [M + H]$^+$<br>705.1 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| E22 | 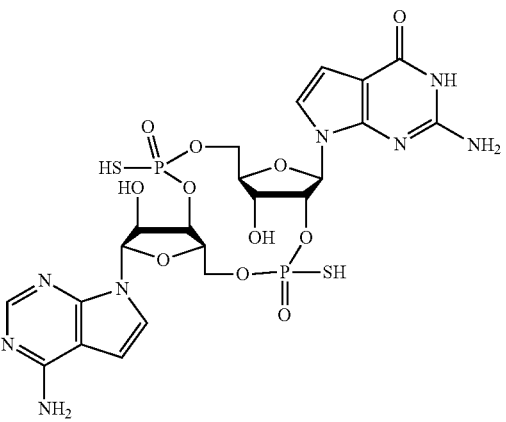<br>isomer 3 | 8.35 (s, 1H)<br>7.65 (d, J = 3.8 Hz, 1H)<br>7.09 (d, J = 3.8 Hz, 1H)<br>6.97 (d, J = 3.7 Hz, 1H)<br>6.28 (d, J = 3.7 Hz, 1H)<br>6.11 (d, J = 7.9 Hz, 1H)<br>6.07 (d, J = 8.5 Hz, 1H)<br>5.28 (dd, J = 8.6, 4.4 Hz, 1H)<br>5.01 (m, 1H)<br>in DMSO-d$_6$ | 59.7<br>58.9<br>in DMSO-d$_6$ | [M + H]$^+$<br>705.1 |
| E23 | 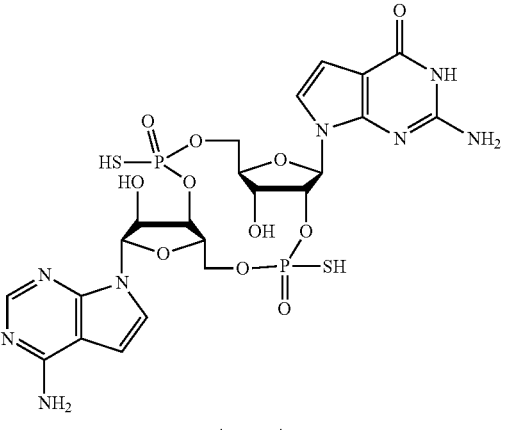<br>isomer 4 | 8.35 (s, 1H)<br>7.69 (d, J = 3.8 Hz, 1H)<br>7.07 (d, J = 3.8 Hz, 1H)<br>6.95 (d, J = 3.7 Hz, 1H)<br>6.31 (d, J = 3.7 Hz, 1H)<br>6.13 (d, J = 7.2 Hz, 1H)<br>6.06 (d, J = 8.5 Hz, 1H)<br>5.05 (m, 1H)<br>4.99 (m, 1H)<br>in DMSO-d$_6$ | 58.5<br>50.9<br>in DMSO-d$_6$ | [M + H]$^+$<br>705.1 |
| E24 | 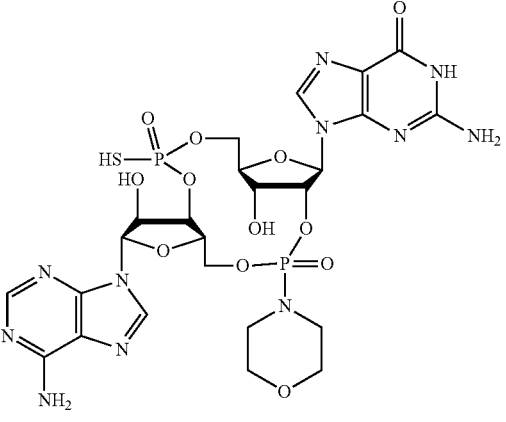 | 8.32 (s, 1H)<br>8.02 (s, 1H)<br>7.98 (s, 1H)<br>6.18 (s, 1H)<br>6.07 (d, J = 8.7 Hz, 1H)<br>5.63 (ddd, J = 9.1, 5.0, 5.0, 1H) | 5.6<br>−1.4 | [M + H]$^+$<br>744.0 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| E25 | isomer 1 | 8.55 (s, 1H)<br>8.45 (s, 1H)<br>8.29 (s, 1H)<br>6.27 (s, 1H)<br>5.96 (d, J = 8.3 Hz, 1H)<br>5.56 (m, 1H)<br>5.03 (ddd, J = 9.4, 6.5, 4.2 Hz, 1H) | −1.3 | [M]$^-$<br>671.2 |
| EA1 | 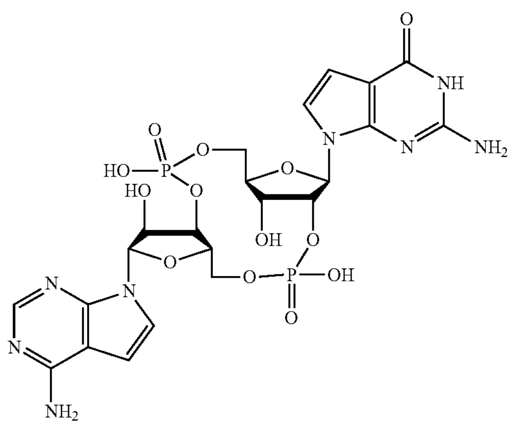 | 8.07 (s, 1H)<br>7.37 (d, J = 3.8 Hz, 1H)<br>7.09 (d, J = 3.8 Hz, 1H)<br>6.65 (d, J = 3.7 Hz, 1H)<br>6.35 (d, J = 3.7 Hz, 1H)<br>6.08 (d, J = 7.4 Hz, 1H)<br>6.04 (d, J = 8.4 Hz, 1H)<br>4.85 (m, 1H)<br>4.81 (m, 1H)<br>in DMSO-d$_6$ | 0.98<br>0.96<br>in DMSO-d$_6$ | [M + H]$^+$<br>673.1 |
| EA2 | 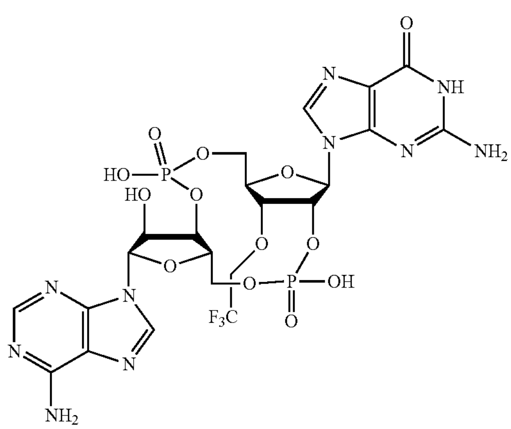 | 8.29 (s, 1H)<br>8.25 (s, 1H)<br>7.89 (s, 1H)<br>6.17 (s, 1H)<br>6.01 (d, J = 8.6 Hz, 1H)<br>5.69 (ddd, J = 8.7, 8.7, 4.0 Hz, 1H)<br>5.09 (m, 1H)<br>Na$^+$ salt in D2O | −1.1<br>−2.3<br>Na$^+$ salt in D$_2$O | [M + H]$^+$<br>757.0<br>[M − H]$^-$<br>755.0 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EA3 | 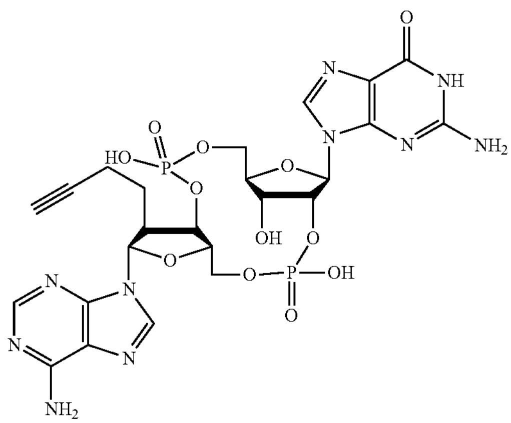 | 8.26 (s, 1H)<br>8.23 (s, 1H)<br>7.85 (s, 1H)<br>6.27 (s, 1H)<br>5.92 (d, J = 8.6 Hz, 1H)<br>5.63 (m, 1H)<br>5.10 (m, 1H) | −1.6<br>−2.3 | [M + H]$^+$<br>713.0<br>[M − H]$^−$<br>711.0 |
| EA4 | isomer 1 | 8.19 (s, 1H)<br>8.18 (s, 1H)<br>8.15 (brs, 1H)<br>6.25 (d, J = 3.3 Hz, 1H)<br>5.92 (d, J = 8.5 Hz, 1H)<br>5.24 (m, 2H)<br>in CD$_3$CN | 55.4<br>53.5<br>in CD$_3$CN | [M + H]$^+$<br>707.1 |
| EA5 | isomer 2 | | 59.6<br>58.1<br>in CD$_3$CN | [M + H]$^+$<br>707.1 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EA6 | isomer 1 | 8.62 (s, 1H)<br>8.55 (s, 1H)<br>7.69 (d, J = 3.7 Hz, 1H)<br>6.59 (d, J = 3.7 Hz, 1H)<br>6.41 (d, J = 8.4 Hz, 1H)<br>6.37 (d, J = 4.6 Hz, 1H)<br>5.59 (m, 1H)<br>5.51 (m, 1H)<br>in D$_2$O | 58.1<br>56.0<br>in D$_2$O | [M + H]$^+$<br>706.0 |
| EA7 | isomer 2 | | 56.7<br>55.6<br>in CD$_3$CN | [M + H]$^+$<br>706.0 |
| EA8 | isomer 3 | | 53.4<br>48.7<br>in CD$_3$CN | [M + H]$^+$<br>705.9 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EA9 | isomer 2 | 8.41 (s, 1H)<br>8.26 (s, 1H)<br>7.85 (s, 1H)<br>6.17 (s, 1H)<br>5.90 (d, J = 8.6 Hz, 1H)<br>5.76 (ddd, J = 8.8, 8.6, 4.1 Hz, 1H)<br>5.08 (m, 1H) | | [M]$^-$<br>671.2 |
| EA10 | 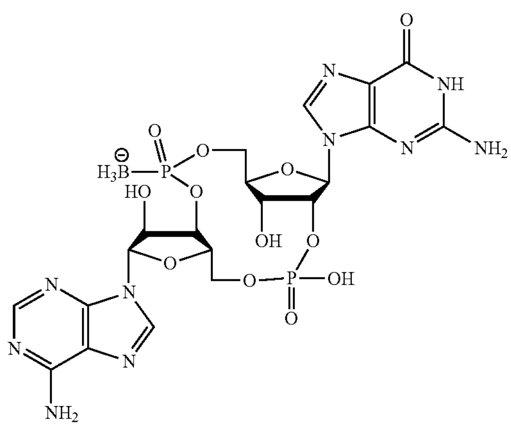 | 8.32 (s, 1H)<br>8.26 (s, 1H)<br>7.86 (s, 1H)<br>6.16 (s, 1H)<br>5.92 (d, J = 8.5 Hz, 1H)<br>5.67 (m, 1H)<br>5.21 (m, 1H) | | [M]$^-$<br>671.2 |
| EA11 | 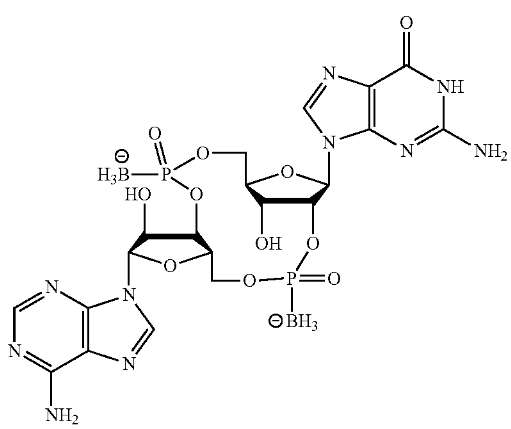 | 8.43 (s, 1H)<br>8.41 (s, 1H)<br>6.19 (s, 1H)<br>6.07 (d, J = 8.2 Hz, 1H) | | [M + H]$^-$<br>669.2 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EB1 | isomer 1 | 8.16 (s, 1H)<br>7.48 (d, J = 3.3 Hz, 1H)<br>7.18 (d, J = 3.3 Hz, 1H)<br>6.50 (d, J = 3.5 Hz, 1H)<br>6.49 (d, J = 3.5 Hz, 1H)<br>6.29 (d, J = 5.1 Hz, 1H)<br>6.09 (d, J = 8.7 Hz, 1H)<br>5.49 (m, 1H)<br>5.17 (m, 1H) | 57.7<br>−0.2 | [M + H]$^+$<br>689.0 |
| EB2 | isomer 2 | 8.16 (s, 1H)<br>7.33 (d, J = 3.8 Hz, 1H)<br>7.07 (d, J = 3.8 Hz, 1H)<br>6.44 (d, J = 3.8 Hz, 1H)<br>6.33 (d, J = 3.8 Hz, 1H)<br>6.27 (d, J = 2.5 Hz, 1H)<br>6.01 (d, J = 8.5 Hz, 1H)<br>5.48 (dd, J = 8.6, 8.5, 4.1 Hz, 1H)<br>5.00 (ddd, J = 7.1, 7.1, 4.7 Hz, 1H) | 52.0<br>−1.1 | [M + H]$^+$<br>689.0 |
| EB3 | isomer 1 | 8.26 (s, 1H)<br>8.25 (s, 1H)<br>6.95 (d, J = 3.8 Hz, 1H)<br>6.29 (d, J = 3.8 Hz, 1H)<br>6.15 (s, 1H)<br>5.93 (d, J = 8.7 Hz, 1H)<br>5.55 (m, 1H)<br>4.99 (m, 1H) | 51.5<br>−1.3 | [M + H]$^+$<br>690.0 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---------|-----------|----------------------------------------|----------------------------|-------------|
| EB4 | isomer 2 | 8.46 (s, 1H)<br>8.26 (s, 1H)<br>7.03 (d, J = 3.7 Hz, 1H)<br>6.38 (d, J = 3.7 Hz, 1H)<br>6.17 (d, J = 2.7 Hz, 1H)<br>5.99 (d, J = 8.4 Hz, 1H)<br>5.63 (m, 1H)<br>5.11 (ddd, J = 6.7, 6.6, 4.5 Hz, 1H) | 56.1<br>−0.7 | [M + H]$^+$<br>690.0 |
| EB5 | 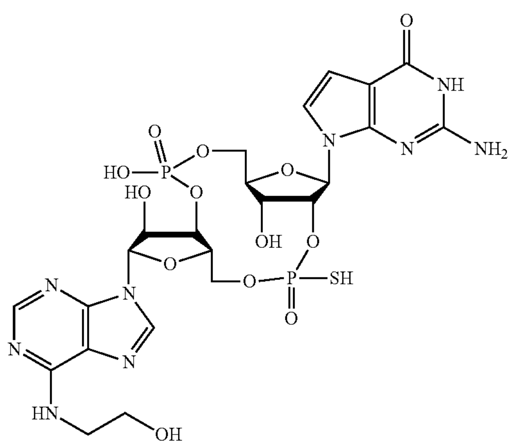 | 8.26 (s, 1H)<br>8.23 (s, 1H)<br>6.94 (d, J = 3.7 Hz, 1H)<br>6.26 (d, J = 3.7 Hz, 1H)<br>6.14 (s, 1H)<br>5.92 (d, J = 8.5 Hz, 1H)<br>5.55 (m, 1H)<br>5.00 (m, 1H) | 51.5<br>−1.3 | [M + H]$^+$<br>734.0<br>[M − H]$^-$<br>732.0 |
| EB6 | isomer 1 | 8.55 (s, 1H)<br>8.26 (s, 1H)<br>7.55 (s, 1H)<br>6.22 (s, 1H)<br>6.08 (d, J = 8.6 Hz, 1H)<br>5.81 (ddd, J = 10.4, 8.6, 4.0 Hz, 1H)<br>5.32 (ddd, J = 8.9, 8.8, 4.3 Hz, 1H) | 54.1<br>52.5 | [M − H]$^-$<br>705.0 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---------|-----------|-----------------------------------------|-----------------------------|-------------|
| EB7 | isomer 2 | 8.59 (s, 1H)<br>8.26 (s, 1H)<br>7.79 (s, 1H)<br>6.21 (s, 1H)<br>6.05 (d, J = 8.6 Hz, 1H)<br>5.88 (ddd, J = 10.5, 8.6, 4.1 Hz, 1H)<br>5.31 (ddd, J = 8.4, 8.4, 4.1 Hz, 1H) | 55.4<br>54.2 | [M − H]$^-$<br>705.0 |
| EC1 | isomer 1 | 8.15 (s, 1H)<br>7.89 (s, 1H)<br>7.35 (d, J = 3.8 Hz, 1H)<br>6.27 (s, 1H)<br>6.26 (d, J = 3.8 Hz, 1H)<br>5.98 (d, J = 8.6 Hz, 1H)<br>5.75 (ddd, J = 9.2, 9.1, 4.1 Hz, 1H)<br>5.07 (m, 1H) | 52.0<br>−1.3 | [M + H]$^+$<br>772.1 |
| EC2 | isomer 2 | 8.15 (s, 1H)<br>7.97 (s, 1H)<br>7.56 (d, J = 3.8 Hz, 1H)<br>6.37 (d, J = 3.8 Hz, 1H)<br>6.30 (d, J = 3.1 Hz, 1H)<br>6.02 (d, J = 8.5 Hz, 1H)<br>5.78 (ddd, J = 12.6, 8.5, 4.1 Hz, 1H)<br>5.16 (m, 1H) | 56.3<br>−0.6 | [M + H]$^+$<br>772.1 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EC3 | 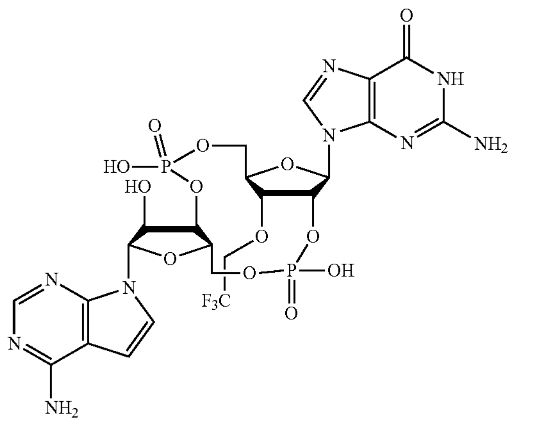 | 8.15 (s, 1H)<br>7.87 (s, 1H)<br>7.33 (d, J = 3.8 Hz, 1H)<br>6.27 (s, 1H)<br>6.24 (d, J = 3.8 Hz, 1H)<br>5.98 (d, J = 8.6 Hz, 1H)<br>5.68 (ddd, J = 8.5, 8.45, 4.0 Hz, 1H)<br>5.08 (ddd, J = 7.7, 7.5, 4.5 Hz, 1H) | −1.4<br>−2.4 | [M + H]$^+$<br>756.2 |
| EC4 | isomer 1 | 7.03 (d, J = 3.7 Hz, 1H)<br>6.88 (m, 1H)<br>6.34 (d, J = 3.7 Hz, 1H)<br>6.31 (d, J = 3.7 Hz, 1H)<br>6.08 (m, 1H)<br>5.93 (m, 1H)<br>5.05 (m, 1H)<br>4.98 (m, 1H)<br>in DMSO-d$_6$ /D$_2$O | 61.1<br>−0.4 | [M + H]$^+$<br>705.0 |
| EC5 | isomer 2 | 7.02 (d, J = 3.7 Hz, 1H)<br>6.92 (d, J = 3.7 Hz, 1H)<br>6.33 (m, 2H)<br>6.09 (d, J = 8.7 Hz, 1H)<br>5.92 (d, J = 7.9 Hz, 1H)<br>4.94 (m, 1H)<br>4.81 (m, 1H)<br>4.60 (m, 1H)<br>4.43 (m, 1H)<br>in DMSO-d$_6$ /D$_2$O | 53.1<br>−0.8 | [M + H]$^+$<br>704.9 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EC6 | isomer 1 | 8.11 (s, 1H)<br>8.11 (s, 1H)<br>7.59 (d, J = 3.8 Hz, 1H)<br>7.20 (d, J = 3.9 Hz, 1H)<br>6.40 (m, 2H)<br>6.22 (m, 2H)<br>5.23 (ddd, J = 9.0, 8.8, 4.2 Hz, 1H)<br>4.94 (m, 1H) | 52.9<br>−1.0 | [M + H]$^+$<br>673.0 |
| EC7 | isomer 2 | 8.103 (s, 1H)<br>8.102 (s, 1H)<br>7.67 (d, J = 3.9 Hz, 1H)<br>7.34 (d, J = 3.9 Hz, 1H)<br>6.58 (d, J = 3.8 Hz, 1H)<br>6.51 (d, J = 3.8 Hz, 1H)<br>6.42 (d, J = 8.4 Hz, 1H)<br>6.23 (d, J = 6.5 Hz, 1H) | 59.1<br>0.1 | [M + H]$^+$<br>673.0 |
| EC8 | isomer 1 | 8.27 (s, 2H)<br>8.05 (s, 1H)<br>7.47 (d, J = 3.8 Hz, 1H)<br>6.92 (d, J = 3.7 Hz, 1H)<br>6.65 (d, J = 3.7 Hz, 1H)<br>6.30 (m, 2H)<br>5.99 (d, J = 8.2 Hz, 1H)<br>5.01 (m, 1H)<br>4.85 (m, 1H)<br>in DMSO-d$_6$ | 49.5<br>0.9<br>in DMSO-d$_6$ | [M + H]$^+$<br>689.2 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EC9 | isomer 2 | 8.29 (s, 2H) 8.04 (s, 1H) 7.50 (d, J = 3.8 Hz, 1H) 6.82 (d, J = 3.7 Hz, 1H) 6.59 (d, J = 3.8 Hz, 1H) 6.35 (d, J = 3.7 Hz, 1H) 6.29 (d, J = 8.5 Hz, 1H) 5.98 (d, J = .5 Hz, 1H) 5.11 (m, 1H) 4.40 (m, 1H) in DMSO-d$_6$ | 57.1 1.4 in DMSO-d$_6$ | [M + H]$^+$ 689.1 |
| EC10 | 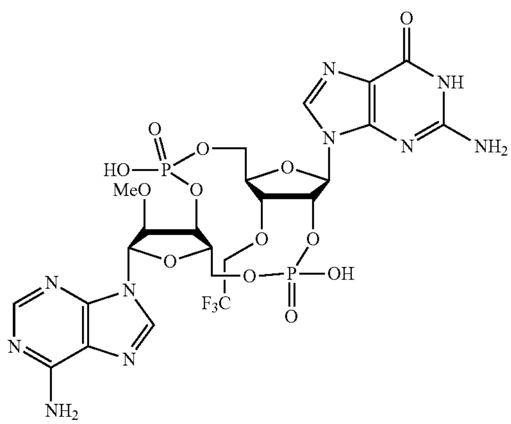 | 8.28 (s, 1H) 8.26 (s, 1H) 7.83 (s, 1H) 6.26 (s, 1H) 5.96 (d, J = 8.6 Hz, 1H) 5.76 (ddd, J = 8.6, 8.6, 4.1 Hz, 1H) 5.09 (m, 1H) | −1.6 −2.7 | [M + H]$^+$ 771.2 |
| EC11 | 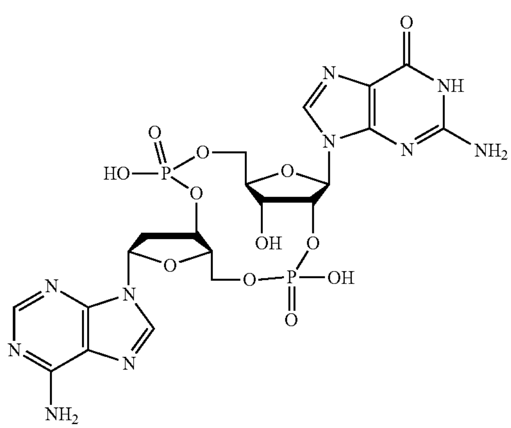 | 8.32 (s, 1H) 8.27 (s, 1H) 7.93 (s, 1H) 6.47 (m, 1H) 5.97 (d, J = 8.3 Hz, 1H) 5.58 (m, 1H) 5.19 (m, 1H) | | [M + H]$^+$ 659.0 [M − H]$^−$ 656.8 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EC12 | 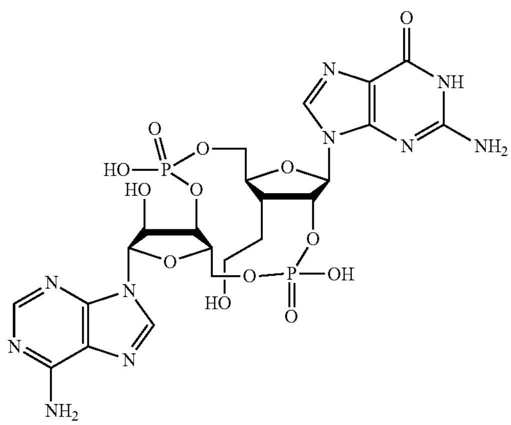 | 8.30 (s, 1H)<br>8.25 (s, 1H)<br>7.84 (s, 1H)<br>6.16 (s, 1H)<br>5.88 (d, J = 8.4 Hz, 1H)<br>5.73 (ddd, J = 8.0, 8.0, 8.0 Hz, 1H)<br>5.08 (m, 1H) | −1.0<br>−2.4 | [M + H]$^+$<br>703.0 |
| EC13 | 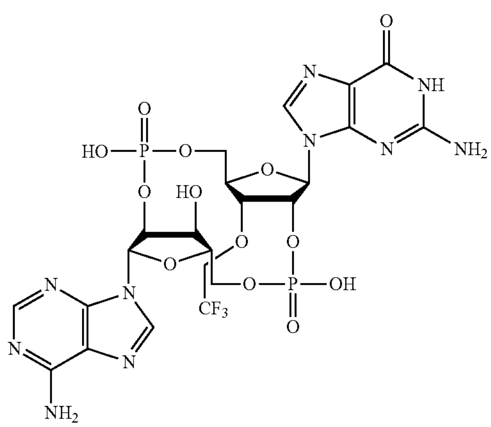 [SMILES: Nc1nc2c(ncn2[C@@H]2O[C@@H]3COP(=O)(O)O[C@H]4C(O)[C@@H](COP(=O)(O)O[C@H]2C3OCC(F)(F)F)O[C@H]4n2cnc3c(N)ncnc32)c(=O)[nH]1] | 8.36 (s, 1H)<br>8.18 (s, 1H)<br>7.84 (s, 1H)<br>6.29 (d, J = 8.1 Hz, 1H)<br>5.99 (d, J = 8.4 Hz, 1H)<br>5.38 (ddd, J = 8.1, 7.9, 4.4 Hz, 1H)<br>5.09 (ddd, J = 8.3, 4.2, 4.2 Hz, 1H) | −1.3<br>−1.8 | [M + H]$^+$<br>757.0 |
| EC14 | | 8.69 (s, 1H)<br>8.13 (s, 1H)<br>6.88 (d, J = 3.8 Hz, 1H)<br>6.34 (d, J = 3.8 Hz, 1H)<br>6.28 (d, J = 8.1 Hz, 1H)<br>6.10 (d, J = 8.1 Hz, 1H)<br>5.17 (m, 2H) | 56.7<br>−1.5 | [M + H]$^+$<br>689.9 | isomer 1

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EC15 | 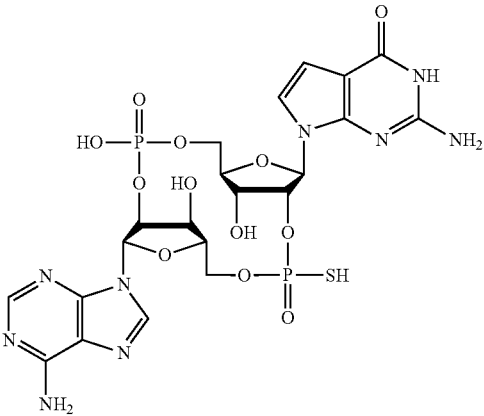<br>isomer 2 | 8.35 (s, 1H)<br>7.93 (s, 1H)<br>6.77 (d, J = 3.8 Hz, 1H)<br>6.25 (d, J = 8.1 Hz, 1H)<br>6.17 (d, J = 3.8 Hz, 1H)<br>6.10 (d, J = 8.1 Hz, 1H)<br>5.19 (ddd, J = 8.6, 4.6, 4.6 Hz, 1H)<br>5.14 (ddd, J = 8.5, 4.4, 4.4 Hz, 1H) | 52.1<br>−1.6 | [M + H]$^+$<br>690.0 |
| EC16 | 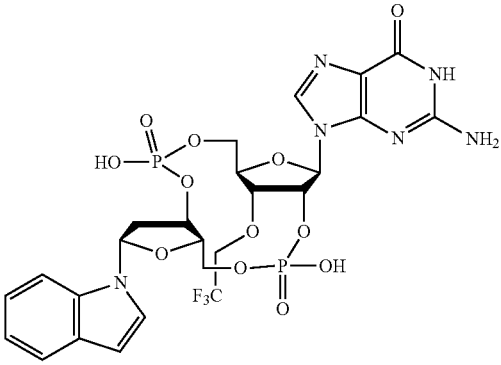 | 8.03 (s, 1H)<br>7.68 (m, 1H)<br>7.58 (d, J = 8.0 Hz, 1H)<br>7.44 (d, J = 3.4 Hz, 1H)<br>7.20 (m, 2H)<br>6.59 (t, J = 6.5 Hz, 1H)<br>6.55 (d, J = 3.4 Hz, 1H)<br>6.05 (d, J = 8.5 Hz, 1H)<br>5.55 (m, 1H)<br>5.20 (m, 1H) | −1.0<br>−1.1 | [M + H]$^+$<br>723.1 |
| EC17 | 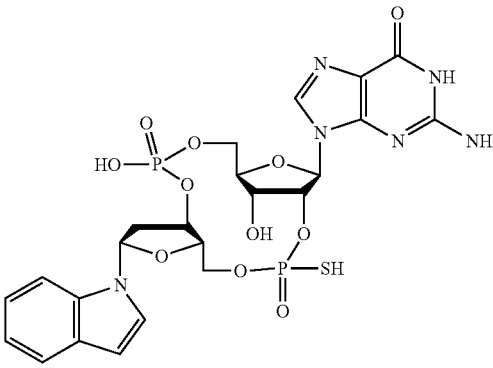<br>isomer 1 | 8.03 (s, 1H)<br>7.67 (m, 1H)<br>7.58 (m, 1H)<br>7.44 (d, J = 3.4 Hz, 1H)<br>7.18 (m, 2H)<br>6.57 (t, J = 6.4 Hz, 1H)<br>6.52 (m, 1H)<br>6.02 (d, J = 8.5 Hz, 1H)<br>5.57 (m, 1H)<br>5.20 (m, 1H) | 53.0<br>−1.0 | [M + H]$^+$<br>657.0<br>[M − H]$^-$<br>655.0 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EC18 | 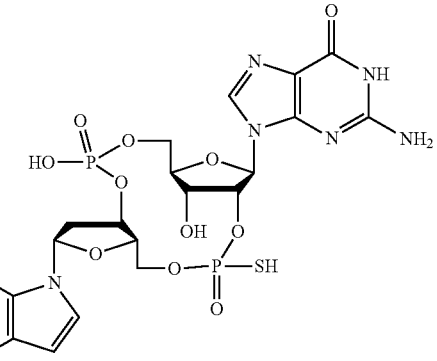<br>isomer 2 | 8.16 (s, 1H)<br>7.68 (d, J = 7.8 Hz, 1H)<br>7.62 (d, J = 8.1 Hz, 1H)<br>7.52 (d, J = 3.5 Hz, 1H)<br>7.26 (m, 1H)<br>7.19 (m, 1H)<br>6.61 (m, 2H)<br>6.05 (d, J = 8.3 Hz, 1H)<br>5.50 (m, 1H)<br>5.31 (m, 1H) | 59.5<br>−1.0 | [M + H]$^+$<br>657.0<br>[M − H]$^−$<br>655.0 |
| EC19 | 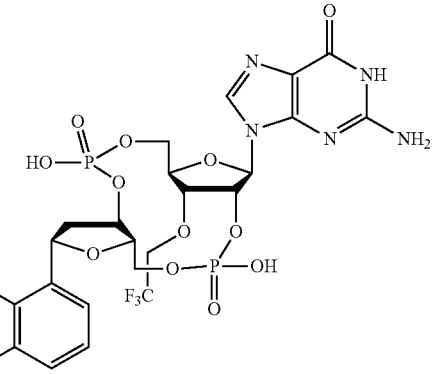 | 8.06 (m, 1H)<br>7.99 (m, 1H)<br>7.97 (s, 1H)<br>7.84 (d, J = 8.3 Hz, 1H)<br>7.69 (d, J = 7.2 Hz, 1H)<br>7.59 (m, 2H)<br>7.32 (t, J = 7.7 Hz, 1H)<br>6.02 (m, 2H)<br>5.52 (ddd, J = 8.7, 8.7, 4.2 Hz, 1H)<br>5.08 (m, 1H) | −1.0<br>−1.2 | [M + H]$^+$<br>734.0 |
| EC20 | 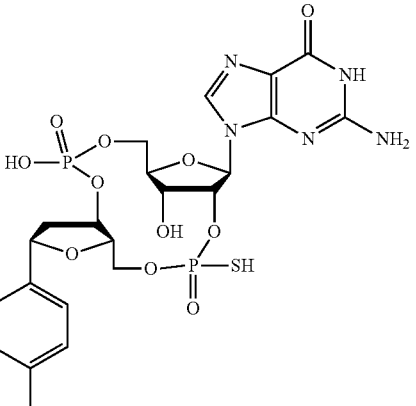<br>isomer 1 | 9.12 (s, 1H)<br>8.29 (d, J = 9.3 Hz, 1H)<br>8.12 (m, 5H)<br>8.00 (s, 2H)<br>7.93 (t, J = 7.6 Hz, 1H)<br>6.18 (m, 2H)<br>5.36 (m, 2H) | 62.8<br>−0.7 | [M + H]$^+$<br>742.1 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EC21 | isomer 2 | 9.09 (s, 1H) 8.28 (d, J = 9.3 Hz, 1H) 8.11 (m, 5H) 7.98 (s, 2H) 7.93 (t, J = 7.6 Hz, 1H) 6.17 (dd, J = 10.5, 5.3 Hz, 1H) 6.13 (d, J = 8.0 Hz, 1H) 5.46 (m, 1H) 5.13 (m, 1H) | 56.5 −0.8 | [M + H]$^+$ 742.0 |
| EC22 | 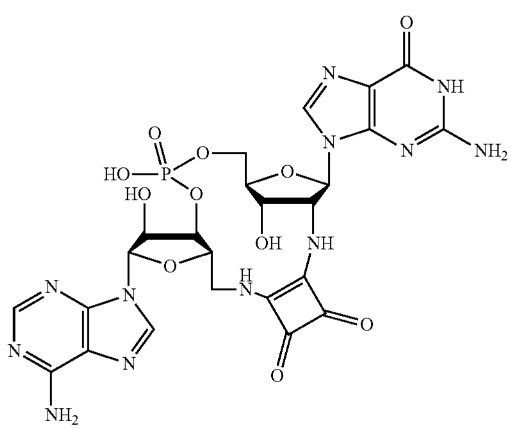 | 8.21 (s, 1H) 8.14 (s, 1H) 7.82 (s, 1H) 6.19 (d, J = 7.7 Hz, 1H) 6.00 (d, J = 3.1 Hz, 1H) | −0.1 | [M + H]$^+$ 689.0 |
| EC23 | 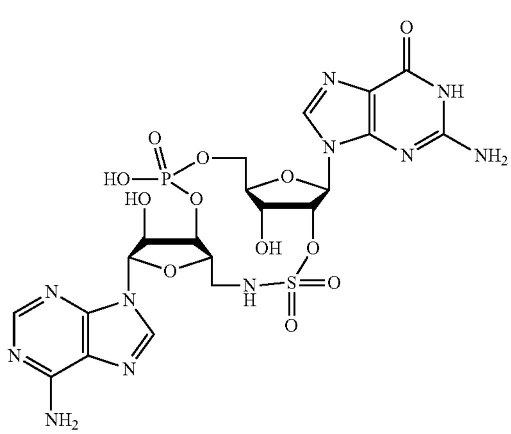 | 8.15 (s, 1H) 7.91 (s, 1H) 7.44 (s, 1H) 6.17 (s, 1H) 5.88 (d, J = 9.0 Hz, 1H) 5.13 (m, 2H) | −1.24 | [M + H]$^+$ 672.9 |

TABLE 4-continued

Physical data of cyclic dinucleotide and analogs

| Example | Structure | characteristic $^1$H NMR data δ (ppm)* | $^{31}$P NMR data δ (ppm)* | MS data m/z |
|---|---|---|---|---|
| EC24 | 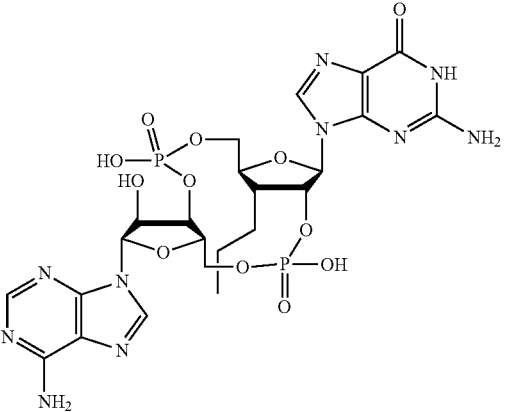 | 8.31 (s, 1H)<br>8.26 (s, 1H)<br>7.84 (s, 1H)<br>6.17 (s, 1H)<br>5.86 (d, J = 8.4 Hz, 1H)<br>5.68 (m, 1H)<br>5.08 (m, 1H) | −1.0<br>−2.2 | [M + H]$^+$<br>701.2<br>[M − H]$^−$<br>699.0 |
| EC25 | 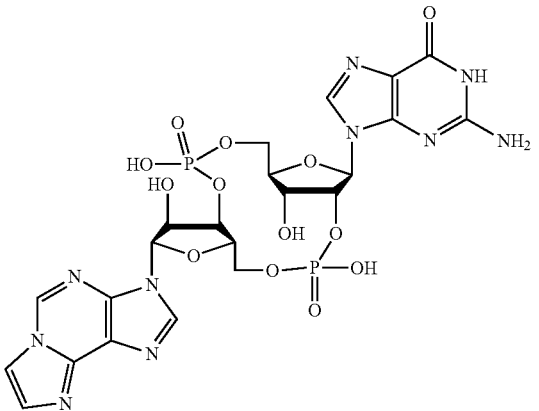 | 9.08 (s, 1H)<br>8.38 (s, 1H)<br>7.96 (s, 1H)<br>7.90 (s, 1H)<br>7.57 (s, 1H)<br>6.28 (s, 1H)<br>5.95 (d, J = 8.5 Hz, 1H)<br>5.64 (ddd, J = 8.3, 8.3, 4.2 Hz, 1H)<br>5.08 (ddd, J = 8.8, 6.5, 4.3 Hz, 1H) | −1.3<br>−2.0 | [M − H]$^−$<br>697.1 |
| EC26 | 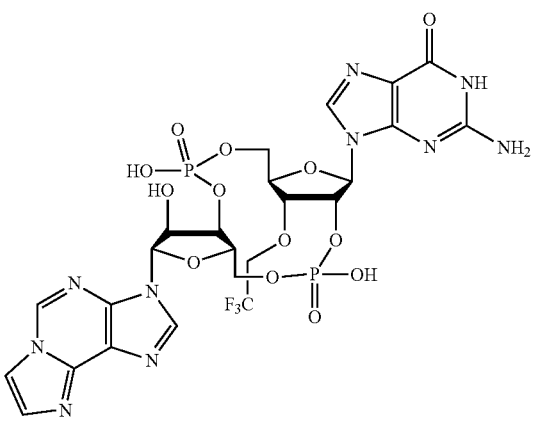 | 9.15 (s, 1H)<br>8.40 (s, 1H)<br>8.02 (s, 1H)<br>7.90 (s, 1H)<br>7.63 (s, 1H)<br>6.32 (s, 1H)<br>5.98 (d, J = 8.6 Hz, 1H)<br>5.72 (ddd, J = 8.7, 8.7, 4.1 Hz, 1H)<br>5.11 (ddd, J = 8.6, 6.8, 4.3 Hz, 1H) | −1.3<br>−2.3 | [M − H]$^−$<br>779.0 |

*In NaH$_2$PO$_4$/Na$_2$HPO$_4$/D$_2$O unless otherwise mentioned.

Stereochemical information of represented compounds is given below.

TABLE 5

P-Configuration of Examples E23 and EB3

E23
[Rp, Rp]

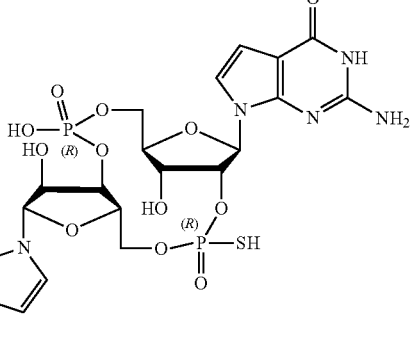

isomer 4

EB3
[Rp]

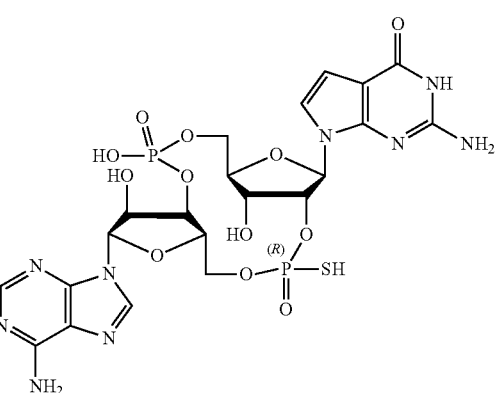

isomer 1

Biological Testing

Serial dilutions of cGAMP analog compounds in phosphate buffer saline (PBS) are mixed with THP1 luciferase reporter cells in a 96-well plate at $0.2\times10^6$/well, in the presence or absence of 1 nM of Perfringolysin O (PFO), which can facilitate compound uptake by forming open channels on the plasma membrane. 16 hours later, 15 µL of the media from each well is transferred to a new plate, and luminescence is measured. Fold increase in luminescence compared to PBS stimulated cells is plotted against logarithm of concentrations of each compound, and $EC_{50}$ is calculated using Graphpad.

TABLE 6

Activity of cyclic dinucleotides and analogs

| Example | THP1-ISG-Luc with PFO, $EC_{50}$, nM | THP-ISG-Luc without PFO, $EC_{50}$, µM |
|---|---|---|
| E1 | A | A |
| E2 | A | A |
| E3 | A | A |
| E4 | A | A |
| E5 | C | C |
| E6 | A | A |
| E7 | A | A |
| E8 | B | C |
| E9 | A | A |
| E10 | C | C |
| E11 | B | C |
| E12 | A | A |
| E13 | B | C |
| E14 | B | C |
| E15 | C | C |
| E16 | A | A |
| E17 | C | C |
| E18 | A | A |
| E19 | C | C |
| E20 | B | A |
| E21 | B | A |
| E22 | B | A |
| E23 | A | A |
| E24 | B | A |
| E25 | A | A |
| EA1 | B | C |
| EA2 | A | A |
| EA3 | C | C |
| EA4 | B | A |
| EA5 | C | C |
| EA6 | C | C |
| EA7 | B | A |
| EA8 | B | A |
| EA9 | A | A |
| EA10 | A | A |
| EA11 | A | A |
| EB1 | C | B |
| EB2 | A | A |
| EB3 | A | A |
| EB4 | C | B |
| EB5 | B | C |
| EB6 | C | C |
| EB7 | C | C |
| EC1 | A | A |
| EC2 | B | B |
| EC3 | B | A |
| EC4 | C | C |
| EC5 | B | B |
| EC6 | C | C |
| EC7 | C | C |
| EC8 | C | C |
| EC9 | C | C |
| EC10 | C | C |
| EC11 | A | C |
| EC12 | A | A |
| EC13 | B | A |
| EC14 | C | C |
| EC15 | B | A |
| EC16 | C | C |
| EC17 | C | C |
| EC18 | C | C |
| EC19 | C | C |
| EC20 | C | C |
| EC21 | C | C |
| EC22 | C | C |
| EC23 | C | C |
| EC24 | A | A |
| EC26 | B | C |

Activity Code

A ≤100 nM    A ≤30 µM
B 100-1000 nm    B 30-100 µM
C >1000 nM    C >100 µM

2'3'-cGAMP can be degraded by the enzyme ecto-nucleotide pyrophosphatase/phosphodiesterase (ENPP1) which is present in fetal bovine serum (FBS) (Li et al., 2015, Nat Chem Biol, 11, 235). To test if cGAMP analogues have improved stability, 5 μL of of synthetic cGAMP analogues (100 μM stock) were incubated with 45 μL of FBS in a final volume of 50 μL at 37° C. for 1, 2 and 4 hours. At the indicated time, 10 μL of the reaction mixture was taken out and mixed with 10 μL phosphate buffered saline (PBS), then heated at 95° C. to denature proteins, which were removed by centrifugation at 13000 g for 5 minutes. The supernatants were delivered to THP1-ISG-luciferase cell line in the presence of PFO to measure the activity of remaining cGAMP analogues, as described above. Category A indicates less than 10% decrease of activity after 4-hour incubation, B indicates 10-75% decrease of activity after 4-hour incubation, and C indicates more than 75% loss of activity after 4-hour incubation.

TABLE 7

Stability of cyclic dinucleotides and analogues in fetal bovine serum

| Example | Reduction of activity after FBS incubation |
|---|---|
| E1 | C |
| E2 | C |
| E3 | A |
| E6 | C |
| E7 | C |
| E8 | A |
| E9 | A |
| E16 | B |
| E18 | B |
| E20 | A |
| E21 | B |
| E22 | A |
| E23 | B |
| E25 | A |
| EA2 | A |
| EA4 | A |
| EA6 | A |
| EA7 | A |
| EA8 | A |
| EA10 | C |
| EA11 | A |
| EB1 | A |
| EB2 | B |
| EB3 | A |
| EB4 | A |
| EB5 | A |
| EC1 | A |
| EC2 | A |
| EC3 | B |
| EC5 | A |
| EC13 | A |
| EC15 | A |
| EC24 | A |
| EC26 | A |

Activity Code
A <10%
B >10%
C >75%

The following series of prophetic examples are also compounds of the present invention:

TABLE 8

Structures of P1 to P15

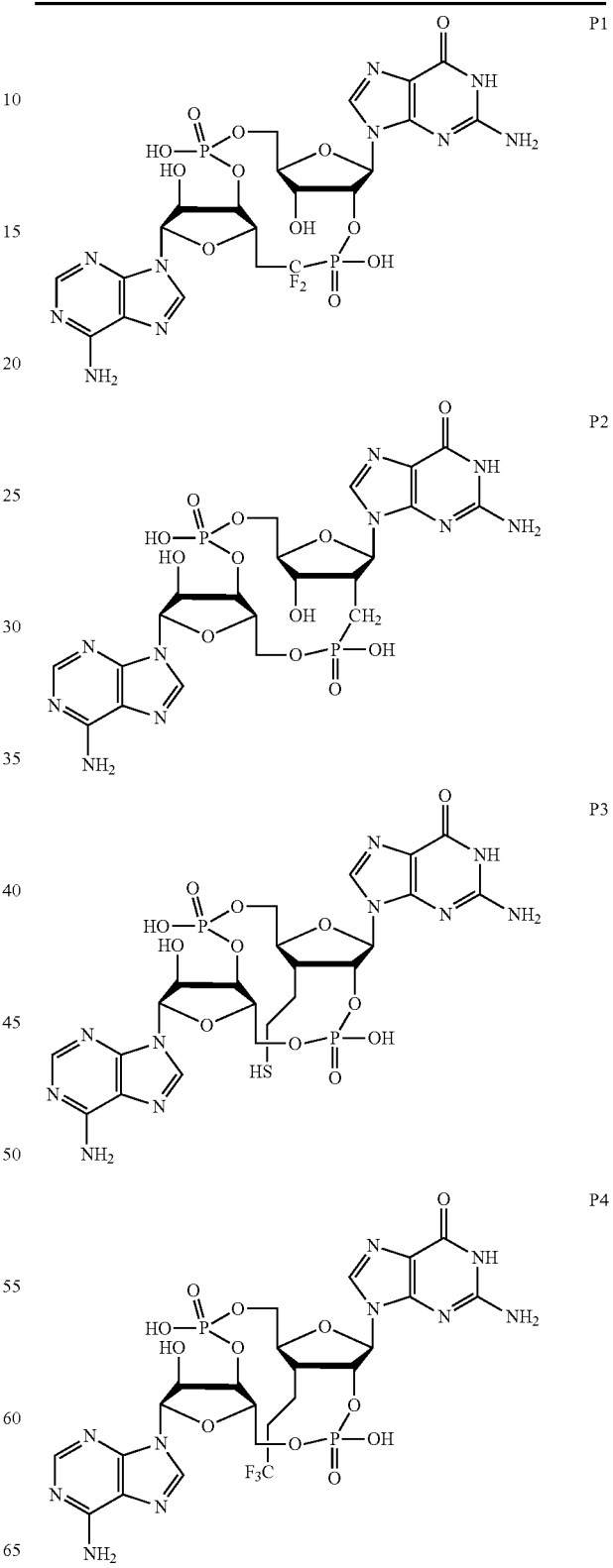

TABLE 8-continued
Structures of P1 to P15
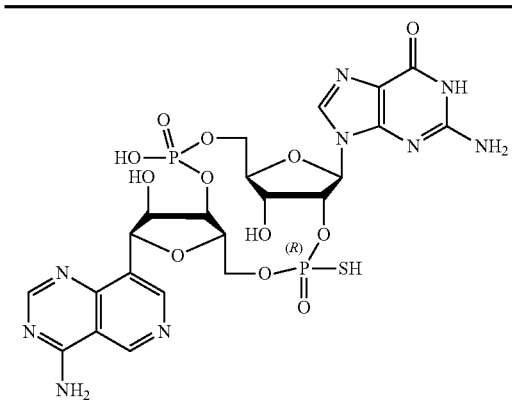
P5
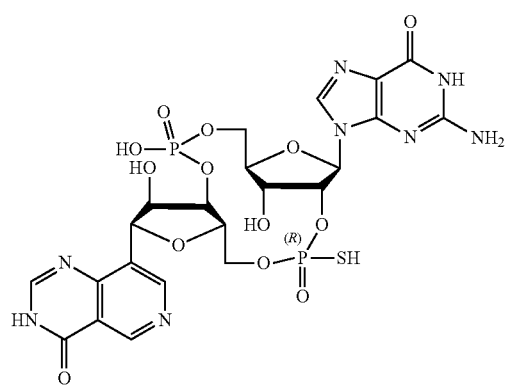
P6
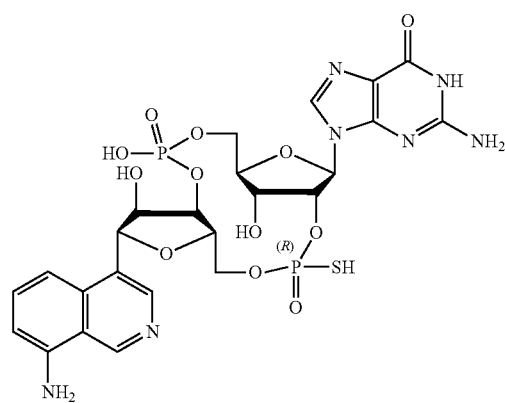
P7
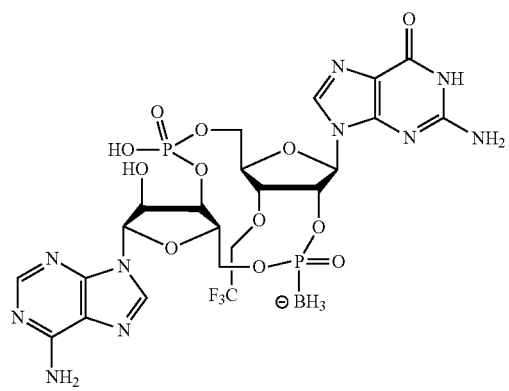
P8
TABLE 8-continued
Structures of P1 to P15
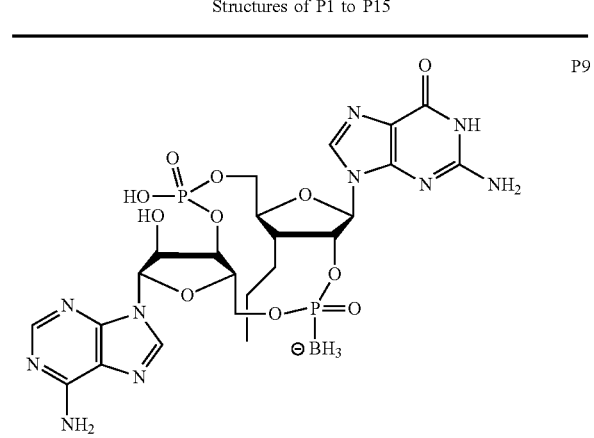
P9
P10
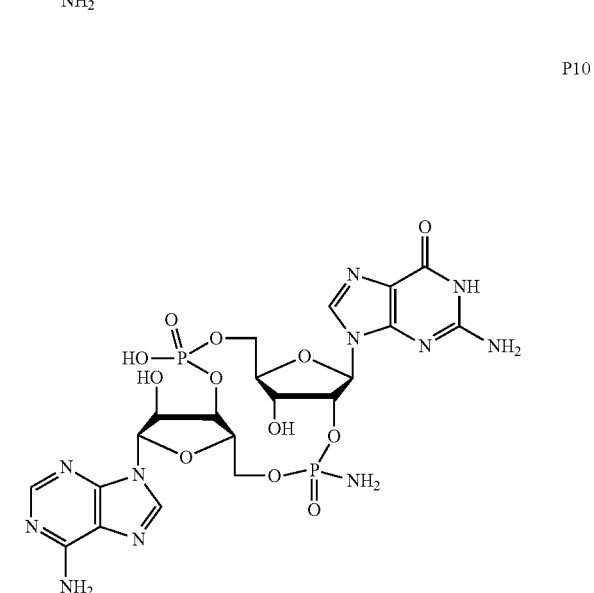
P11
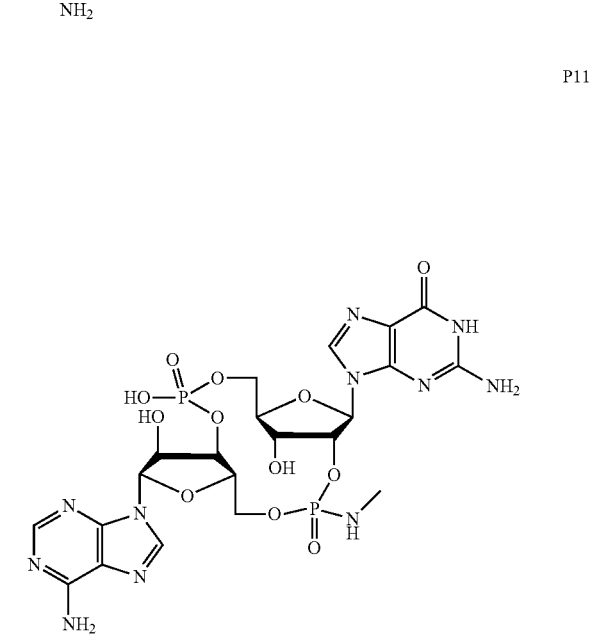

TABLE 8-continued
Structures of P1 to P15
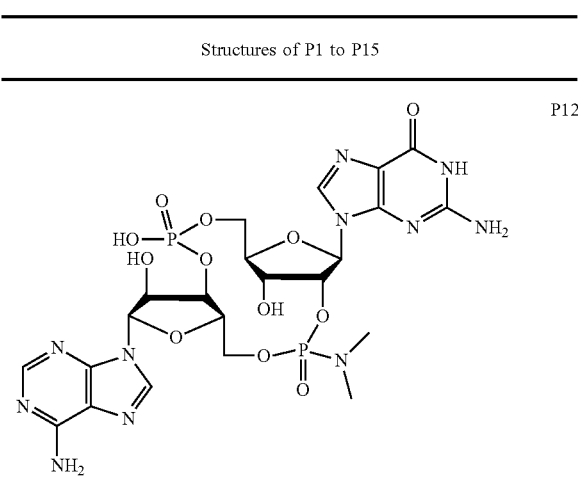
P12
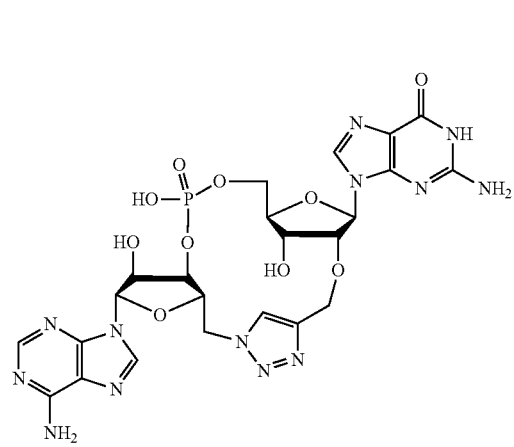
P13
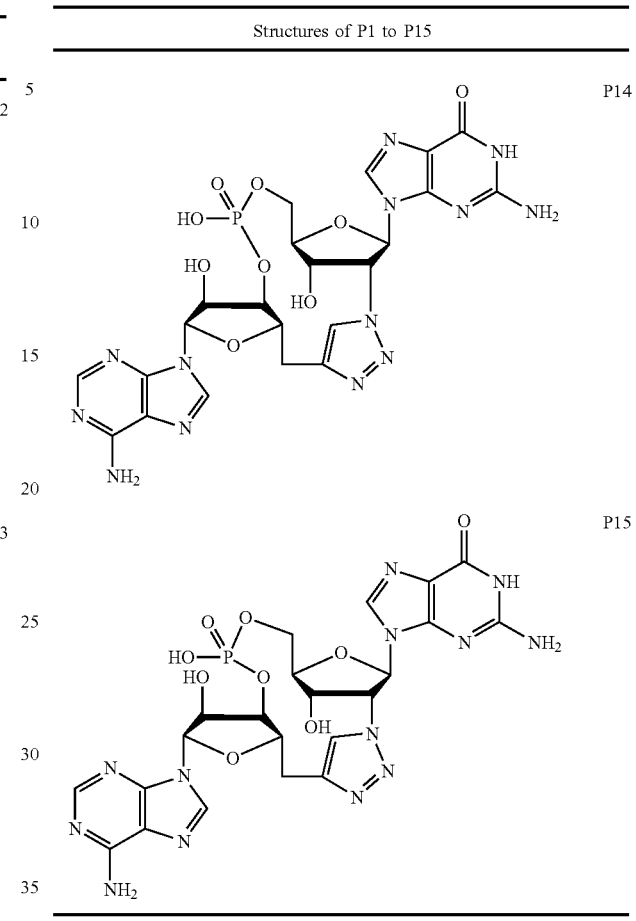
P14
P15
The following Example compounds in Table 9 are also compounds contemplated by the present disclosure.
TABLE 9
| Additional Compounds | |
|---|---|
| Compound | Structure |
| PA1 | 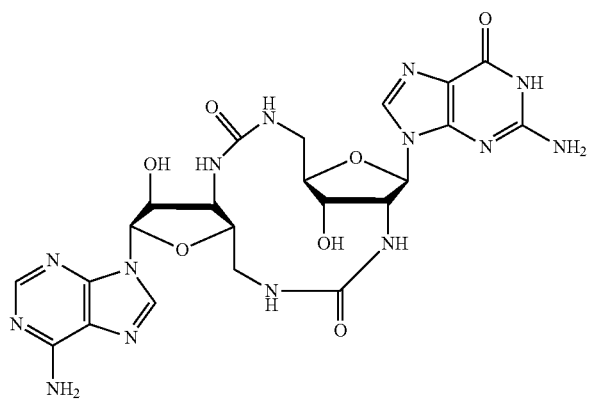 |

TABLE 9-continued
Additional Compounds
| Compound | Structure |
|---|---|
| PA2 | 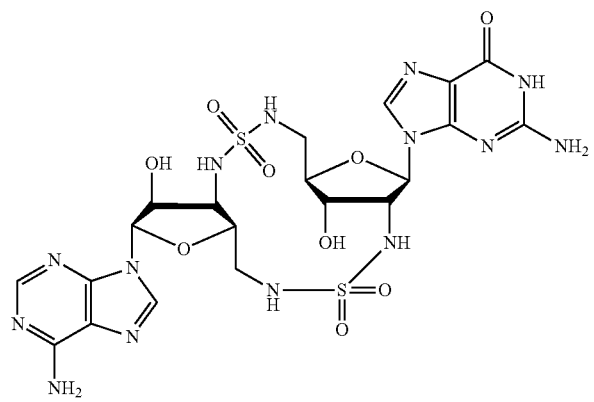 |
| PA3 | 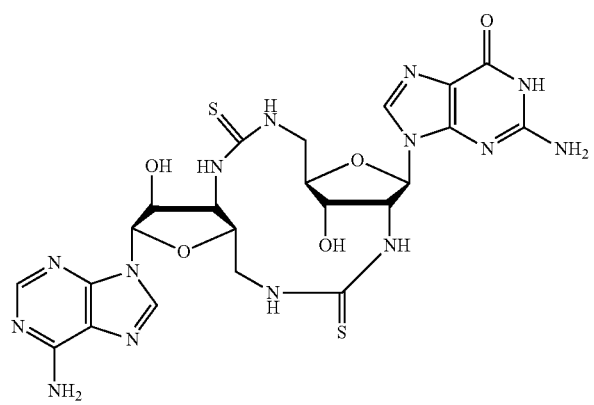 |
| PA4 | 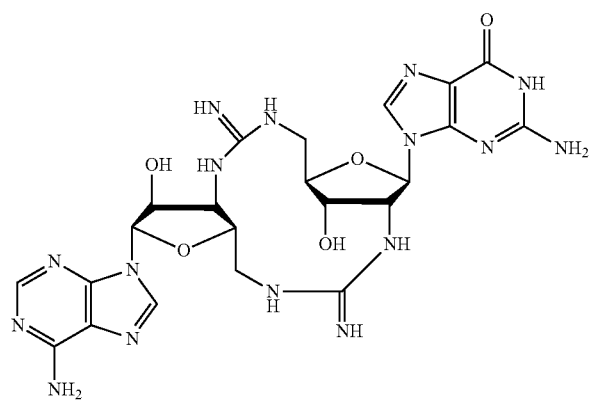 |

TABLE 9-continued

| Additional Compounds | |
|---|---|
| Compound | Structure |
| PA5 | |
| PA6 | |
| PA7 | |

TABLE 9-continued

Additional Compounds

| Compound | Structure |
|---|---|
| PA8 | 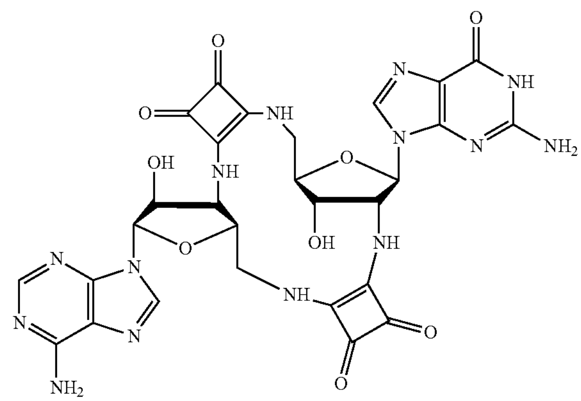 |
| PA9 | 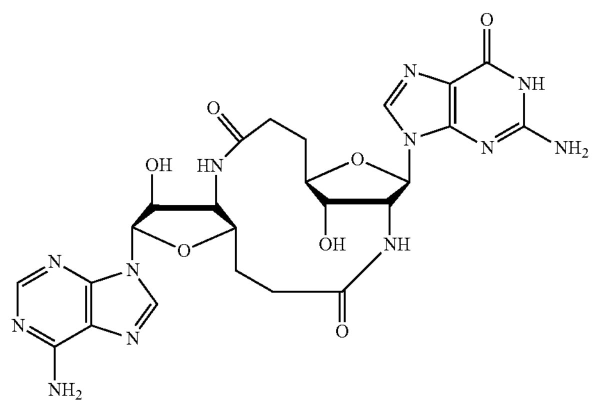 |
| PA10 | 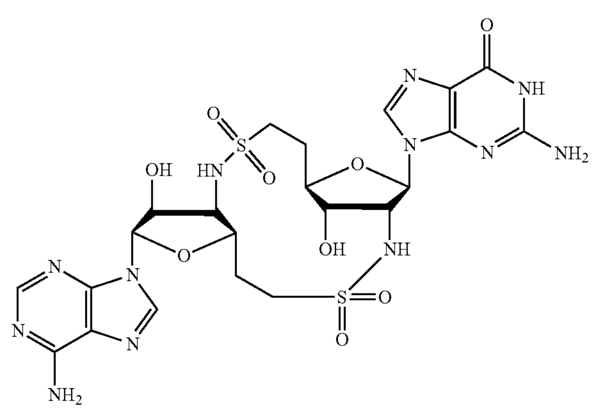 |

281
282
TABLE 9-continued
Additional Compounds
| Compound | Structure |
| --- | --- |
| PA11 | 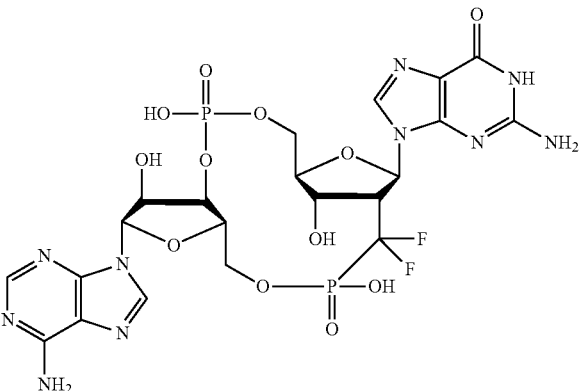 |
| PA12 | 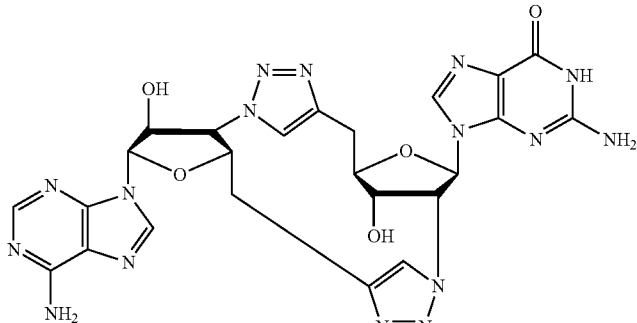 |
| PB1 | 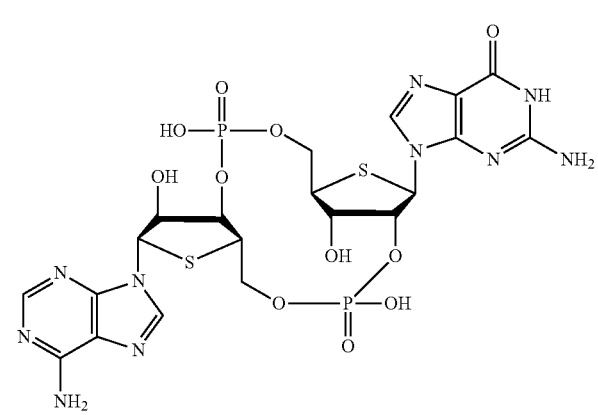 |
| PB2 | 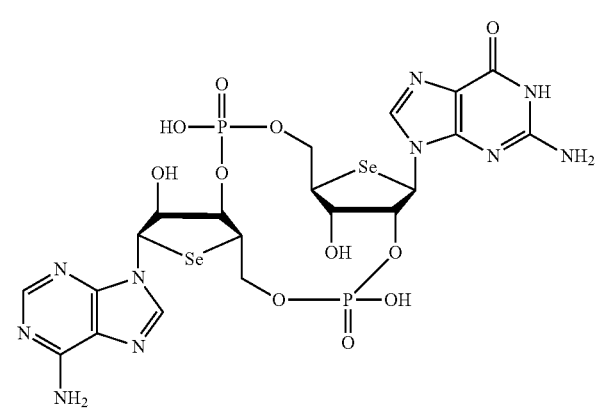 |

TABLE 9-continued

| Additional Compounds | |
|---|---|
| Compound | Structure |

PB3

PB4

PB5

TABLE 9-continued
| Additional Compounds | |
|---|---|
| Compound | Structure |
| PB6 | 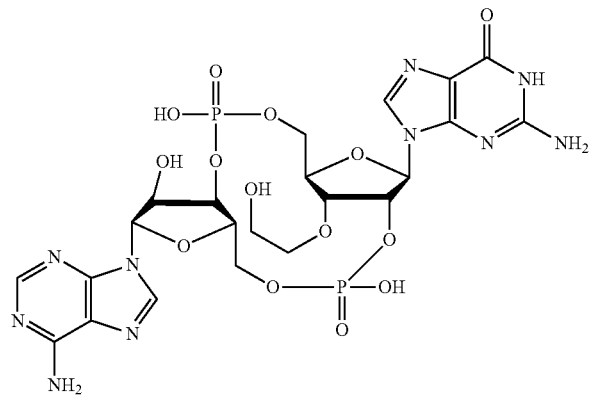 |
| PB7 | 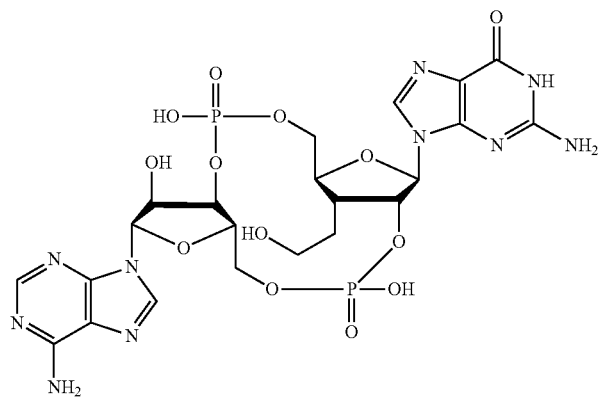 |
| PB8 | 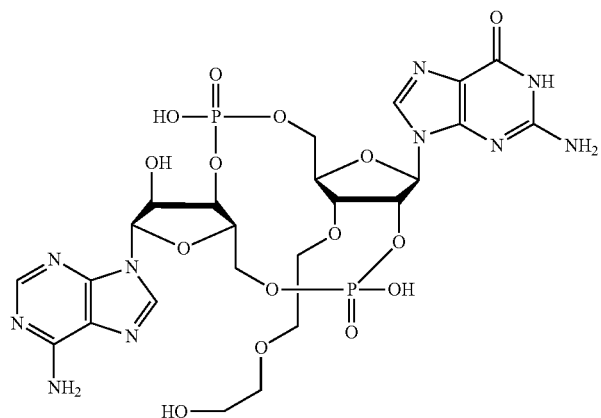 |

TABLE 9-continued

| Additional Compounds | |
|---|---|
| Compound | Structure |

PB9

PB10

PB11

TABLE 9-continued

| Additional Compounds |
|---|
| Compound | Structure |

PB12

PB13

PB14

TABLE 9-continued

| Additional Compounds | |
|---|---|
| Compound | Structure |

PC1

PC2

PC3

TABLE 9-continued

| Additional Compounds | |
|---|---|
| Compound | Structure |

PC4

PC5

PC6

TABLE 9-continued

| Additional Compounds | |
|---|---|
| Compound | Structure |ит

PC7

PC8

PC9

TABLE 9-continued

| Additional Compounds | |
|---|---|
| Compound | Structure |

PC10

PC11

PC12

TABLE 9-continued

Additional Compounds

| Compound | Structure |
|---|---|
| PD1 | 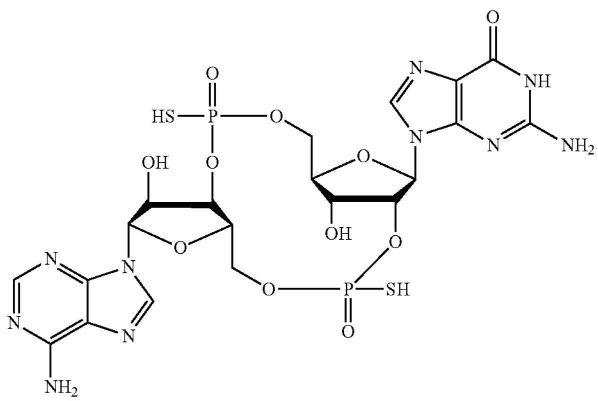 |
| PD2 | 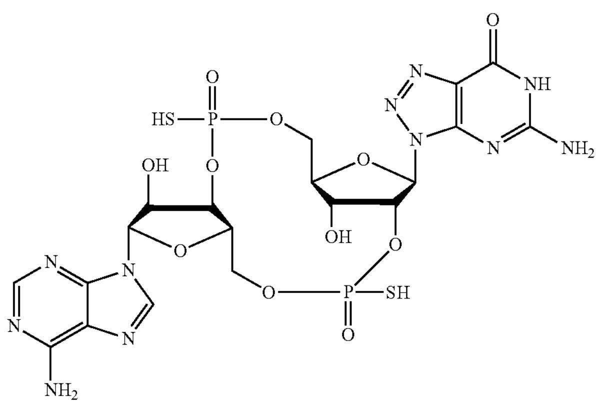 |
| PD3 | 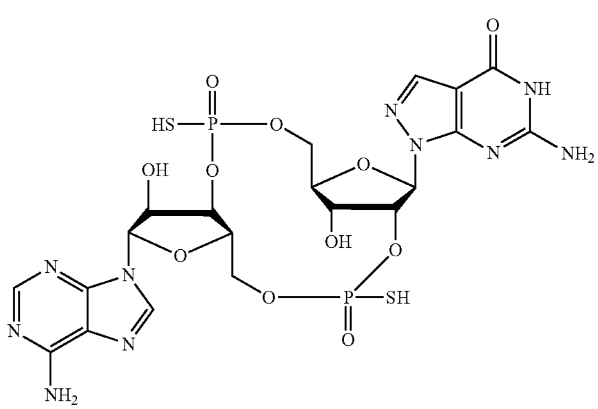 |

TABLE 9-continued
| Additional Compounds | |
|---|---|
| Compound | Structure |
| PD4 | 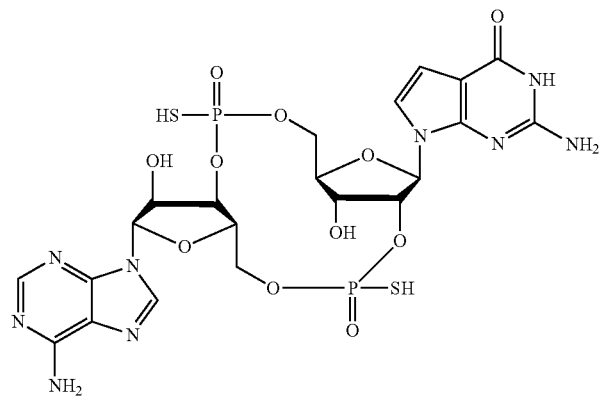 |
| PD5 | 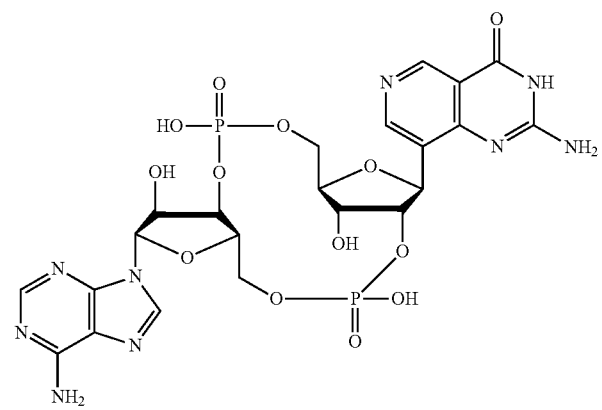 |
| PD6 | 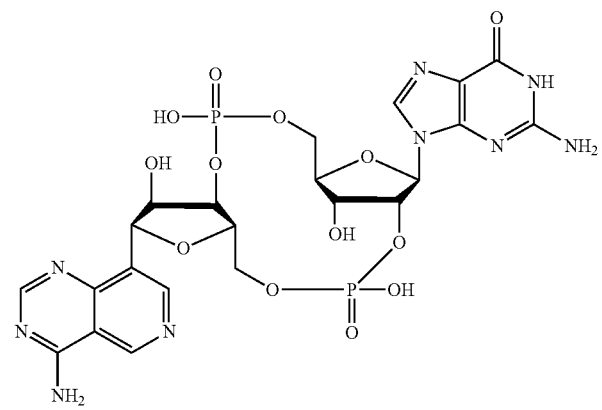 |

The invention claimed is:
1. A compound, wherein the compound is of Formula Ic:

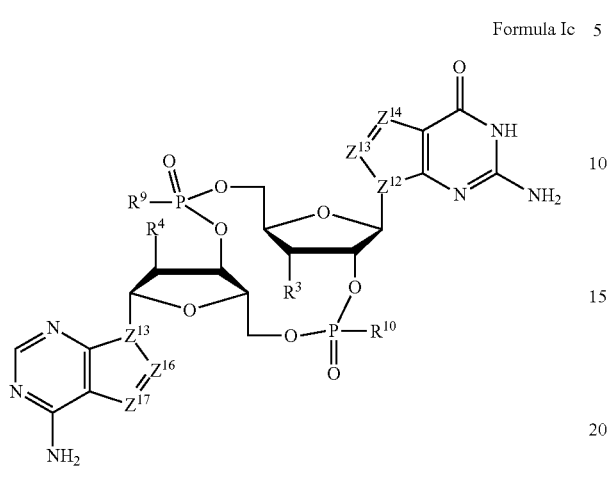

Formula Ic wherein
$Z^{12}$ and $Z^{15}$ are N;
$Z^{13}$, $Z^{14}$, $Z^{16}$ and $Z^{17}$ are independently CH or N;
$R^3$ is $C_2$alkyl functionalized with one or more halogen, thiol, hydroxyl, carboxyl, $C_{1-6}$alkoxy, $C_{1-6}$hydroxyalkoxy, amino, $C_{1-6}$alkylamino, di($C_{1-6}$alkyl)amino, or azido groups;
$R^4$ is hydroxyl;
$R^9$ and $R^{10}$ are independently hydroxyl; thiol; $C_{1-6}$alkyl; $C_{1-6}$alkyl functionalized with one or more halogen, thiol, hydroxyl, carboxyl, $C_{1-6}$alkoxy, $C_{1-6}$hydroxyalkoxy, amino, $C_{1-6}$alkylamino, di($C_{1-6}$alkyl)amino, or azido groups; $C_{1-6}$alkoxy; $C_{1-6}$alkoxy functionalized with one or more halogen, thiol, hydroxyl, carboxyl, $C_{1-6}$hydroxyalkoxy, amino, $C_{1-6}$alkylamino, di($C_{1-6}$alkyl)amino, or azido groups; $C_{3-5}$alkenyl-O—; $C_{3-5}$alkynyl-O—; oligo(ethylene glycol); poly(ethylene glycol); borano (—$BH_3^-$); or —$NR^7R^8$;
$R^7$ and $R^8$ are independently hydrogen; $C_{1-6}$alkyl; $C_{1-6}$alkyl functionalized with one or more halogen, thiol, hydroxyl, carboxyl, $C_{1-6}$alkoxy, $C_{1-6}$hydroxyalkoxy, amino, $C_{1-6}$alkylamino, di($C_{1-6}$alkyl)amino, or azido groups; cyclic —($C_{1-6}$alkyl)-; cyclic —($C_{1-6}$alkyl)-functionalized with one or more halogen, thiol, hydroxyl, carboxyl, $C_{1-6}$alkoxy, $C_{1-6}$hydroxyalkoxy, amino, $C_{1-6}$alkylamino, or di($C_{1-6}$alkyl)amino groups; cyclic —($C_{1-6}$oxaalkyl)-; or cyclic —($C_{1-6}$oxaalkyl)-functionalized with one or more halogen, thiol, hydroxyl, carboxyl, $C_{1-6}$hydroxyalkoxy, amino, $C_{1-6}$alkylamino, or di($C_{1-6}$alkyl)amino groups;
or a pharmaceutically acceptable salt thereof.
2. The compound of claim 1, wherein $Z^{13}$ and $Z^{16}$ are CH.
3. The compound of claim 1, wherein $Z^{14}$ and $Z^{17}$ are N.
4. The compound of claim 1, wherein $Z^{13}$ and $Z^{16}$ are CH, and $Z^{14}$ and $Z^{17}$ are N.
5. The compound of claim 1, wherein $R^9$ and $R^{10}$ are independently hydroxyl or thiol.
6. The compound of claim 1, wherein $R^9$ and $R^{10}$ are hydroxyl.
7. The compound of claim 1, wherein $R^9$ and $R^{10}$ are thiol.
8. The compound of claim 1, wherein $R^3$ is $C_2$alkyl functionalized with one or more thiol, hydroxyl, carboxyl, $C_{1-6}$hydroxyalkoxy, amino, or $C_{1-6}$alkylamino groups.

9. The compound of claim 1, wherein $R^3$ is $C_2$alkyl functionalized with one or more halogen, thiol, or hydroxyl.
10. A compound, wherein the compound is of Formula Ic:

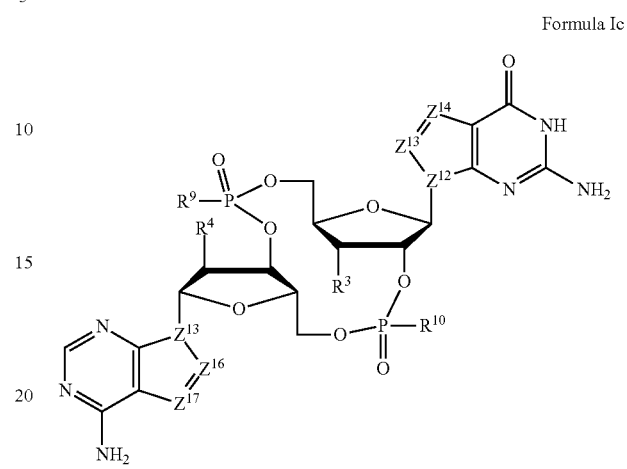

Formula Ic wherein
$Z^{12}$ and $Z^{15}$ are N;
$Z^{13}$ and $Z^{16}$ are CH;
$Z^{14}$ and $Z^{17}$ are independently CH or N;
$R^3$ is $C_2$alkyl functionalized with one or more halogen, thiol, hydroxyl, carboxyl, $C_{1-6}$alkoxy, $C_{1-6}$hydroxyalkoxy, amino, $C_{1-6}$alkylamino, di($C_{1-6}$alkyl)amino, or azido groups;
$R^4$ is hydroxyl;
$R^9$ and $R^{10}$ are independently hydroxyl or thiol;
or a pharmaceutically acceptable salt thereof.
11. The compound of claim 10, wherein $R^3$ is $C_2$alkyl functionalized with one or more thiol, hydroxyl, carboxyl, $C_{1-6}$hydroxyalkoxy, amino, or $C_{1-6}$alkylamino groups.
12. The compound of claim 10, wherein $R^3$ is $C_2$alkyl functionalized with hydroxyl.
13. The compound of claim 10, wherein $R^3$ is $C_2$alkyl functionalized with thiol.
14. The compound of claim 10, wherein $R^3$ is $C_2$alkyl functionalized with halogen.
15. A compound, wherein the compound is of Formula Ic:

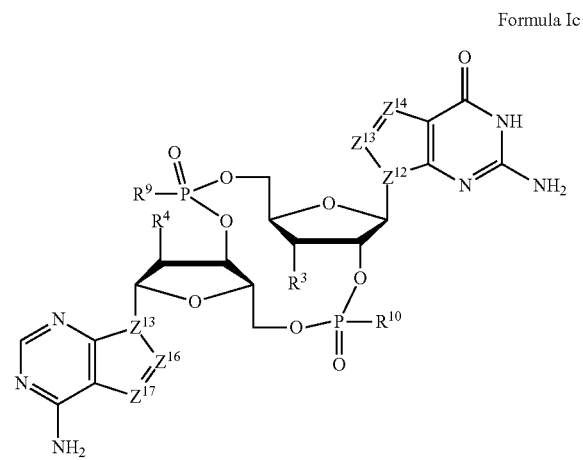

Formula Ic wherein

Z$^{12}$ and Z$^{15}$ are N;

Z$^{13}$, Z$^{14}$, Z$^{16}$ and Z$^{17}$ are independently CH or N;

R$^3$ is C$_{1-6}$alkyl functionalized with one or more halogen, thiol, or hydroxyl;

R$^4$ is hydroxyl;

R$^9$ and R$^{10}$ are independently hydroxyl; thiol; C$_{1-6}$alkyl; C$_{1-6}$alkyl functionalized with one or more halogen, thiol, hydroxyl, carboxyl, C$_{1-6}$alkoxy, C$_{1-6}$hydroxyalkoxy, amino, C$_{1-6}$alkylamino, di(C$_{1-6}$alkyl)amino, or azido groups; C$_{1-6}$alkoxy; C$_{1-6}$alkoxy functionalized with one or more halogen, thiol, hydroxyl, carboxyl, C$_{1-6}$hydroxyalkoxy, amino, C$_{1-6}$alkylamino, di(C$_{1-6}$alkyl)amino, or azido groups; C$_{3-5}$alkenyl-O—; C$_{3-5}$alkynyl-O—; oligo(ethylene glycol); poly(ethylene glycol); borano (—BH$_3^-$); or —NR$^7$R$^8$;

R$^7$ and R$^8$ are independently hydrogen; C$_{1-6}$alkyl; C$_{1-6}$alkyl functionalized with one or more halogen, thiol, hydroxyl, carboxyl, C$_{1-6}$alkoxy, C$_{1-6}$hydroxyalkoxy, amino, C$_{1-6}$alkylamino, di(C$_{1-6}$alkyl)amino, or azido groups; cyclic —(C$_{1-6}$alkyl)-; cyclic —(C$_{1-6}$alkyl)-functionalized with one or more halogen, thiol, hydroxyl, carboxyl, C$_{1-6}$alkoxy, C$_{1-6}$hydroxyalkoxy, amino, C$_{1-6}$alkylamino, or di(C$_{1-6}$alkyl)amino groups; cyclic —(C$_{1-6}$oxaalkyl)-; or cyclic —(C$_{1-6}$oxaalkyl)-functionalized with one or more halogen, thiol, hydroxyl, carboxyl, C$_{1-6}$hydroxyalkoxy, amino, C$_{1-6}$alkylamino, or di(C$_{1-6}$alkyl)amino groups;

or a pharmaceutically acceptable salt thereof.

16. The compound of claim 15 having the structure:

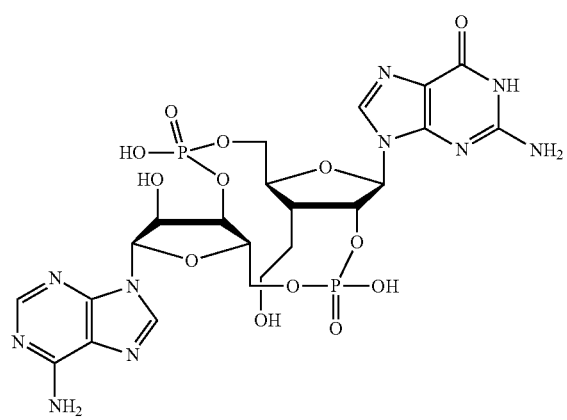

or a pharmaceutically acceptable salt thereof.

17. The compound of claim 15 having the structure:

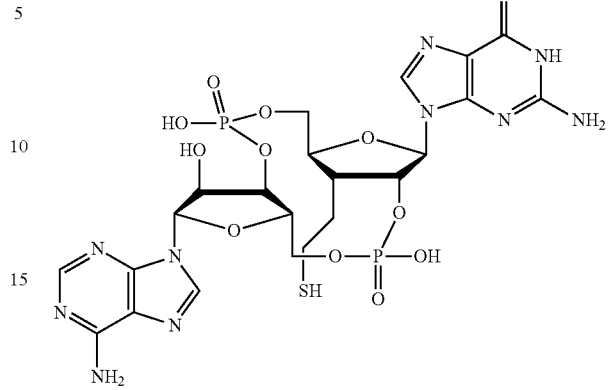

or a pharmaceutically acceptable salt thereof.

18. The compound of claim 15 having the structure:

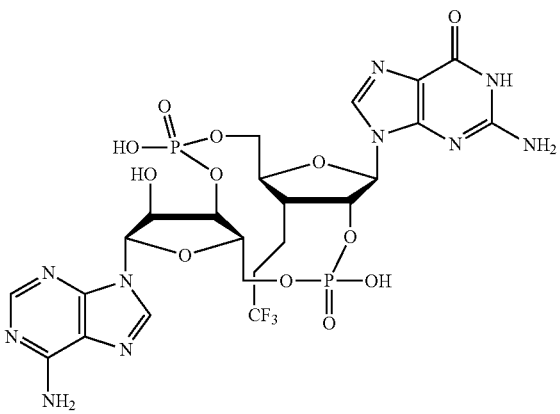

or a pharmaceutically acceptable salt thereof.

19. The compound of claim 15 having the structure:

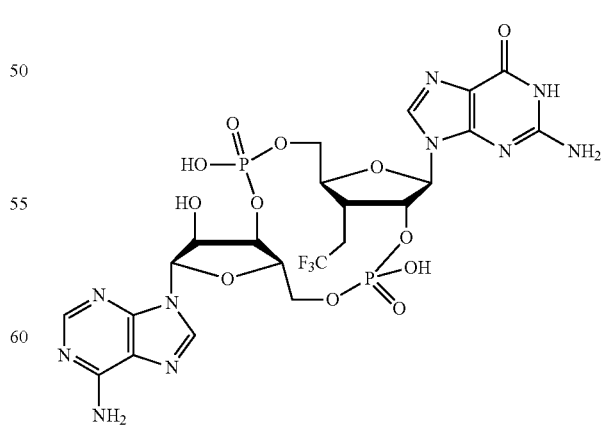

or a pharmaceutically acceptable salt thereof.

20. A compound, wherein the compound is of Formula Ic:

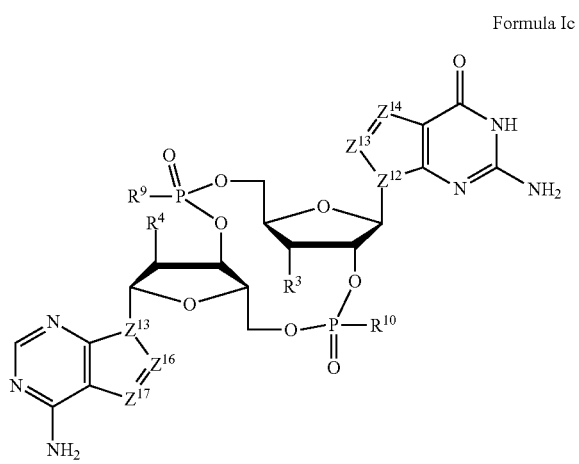

Formula Ic wherein
$Z^{12}$ and $Z^{15}$ are N;
$Z^{13}$ and $Z^{16}$ are CH;
$Z^{14}$ and $Z^{17}$ are independently CH or N;
$R^3$ is $C_{1-6}$alkyl functionalized with one or more halogen, thiol, or hydroxyl;
$R^4$ is hydroxyl;
$R^9$ and $R^{10}$ are independently hydroxyl or thiol;
or a pharmaceutically acceptable salt thereof.

21. The compound of claim 20, wherein $R^3$ is $C_{1-6}$alkyl functionalized with hydroxyl.

22. The compound of claim 20, wherein $R^3$ is $C_{1-6}$alkyl functionalized with thiol.

23. The compound of claim 20, wherein $R^3$ is $C_{1-6}$alkyl functionalized with halogen.

24. A pharmaceutical composition that provides a therapeutically effective amount of a compound of claim 1 and one or more pharmaceutically acceptable excipients.

25. A pharmaceutical composition that provides a therapeutically effective amount of a compound of claim 1 in combination with at least one further therapeutic agent and one or more pharmaceutically acceptable excipients.

26. An immunogenic composition comprising an antigen or antigen composition and a compound of claim 1.

27. A pharmaceutical composition that provides a therapeutically effective amount of a compound of claim 8 and one or more pharmaceutically acceptable excipients.

28. A pharmaceutical composition that provides a therapeutically effective amount of a compound of claim 10 and one or more pharmaceutically acceptable excipients.

29. A pharmaceutical composition that provides a therapeutically effective amount of a compound of claim 11 and one or more pharmaceutically acceptable excipients.

30. A pharmaceutical composition that provides a therapeutically effective amount of a compound of claim 15 and one or more pharmaceutically acceptable excipients.

31. A pharmaceutical composition that provides a therapeutically effective amount of a compound of claim 16 and one or more pharmaceutically acceptable excipients.

32. A pharmaceutical composition that provides a therapeutically effective amount of a compound of claim 17 and one or more pharmaceutically acceptable excipients.

33. A pharmaceutical composition that provides a therapeutically effective amount of a compound of claim 18 and one or more pharmaceutically acceptable excipients.

34. A pharmaceutical composition that provides a therapeutically effective amount of a compound of claim 19 and one or more pharmaceutically acceptable excipients.

* * * * *

UNITED STATES PATENT AND TRADEMARK OFFICE
CERTIFICATE OF CORRECTION

PATENT NO. : 11,299,512 B2
APPLICATION NO. : 16/438153
DATED : April 12, 2022
INVENTOR(S) : Boyu Zhong et al.

It is certified that error appears in the above-identified patent and that said Letters Patent is hereby corrected as shown below:

In the Claims

At Column 303, Claim 1, Formula Ic, Lines 6-21, please replace formula:

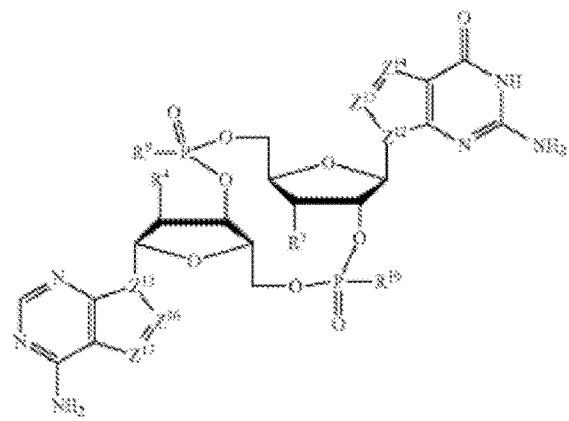

With formula:

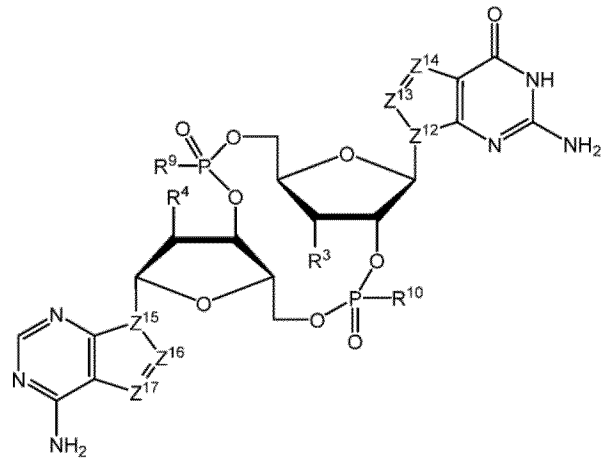

Signed and Sealed this
Ninth Day of August, 2022

Katherine Kelly Vidal
*Director of the United States Patent and Trademark Office*

At Column 304, Claim 10, Formula Ic, Lines 7-22, please replace formula:
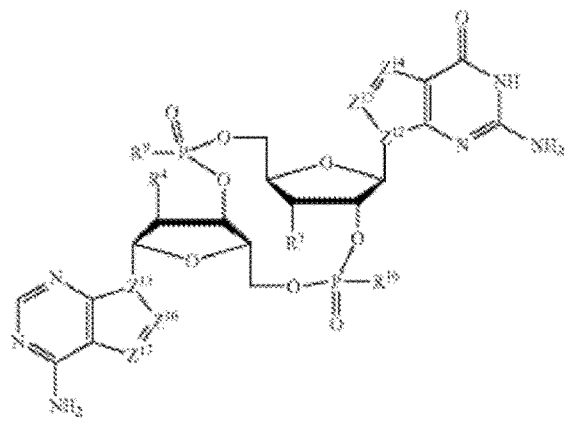
With formula:
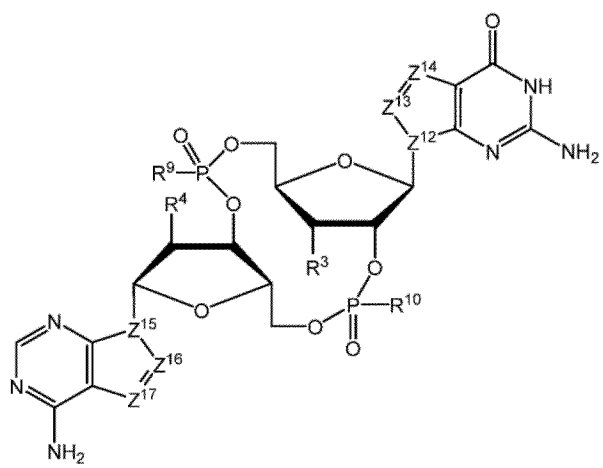
At Column 304, Claim 15, Formula Ic, Lines 50-65, please replace formula:
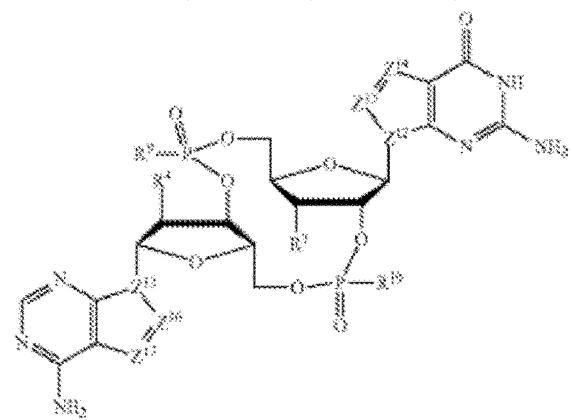

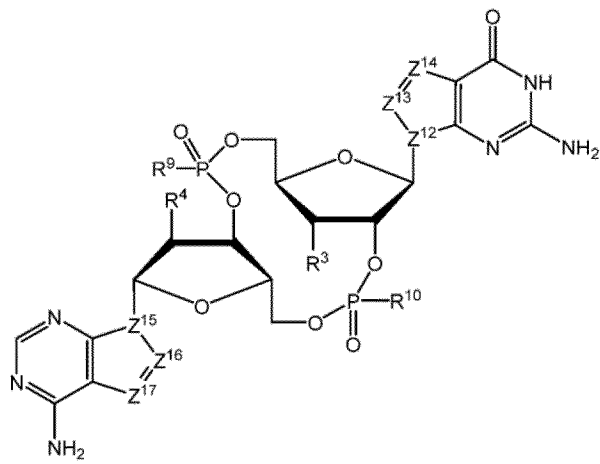

With formula:
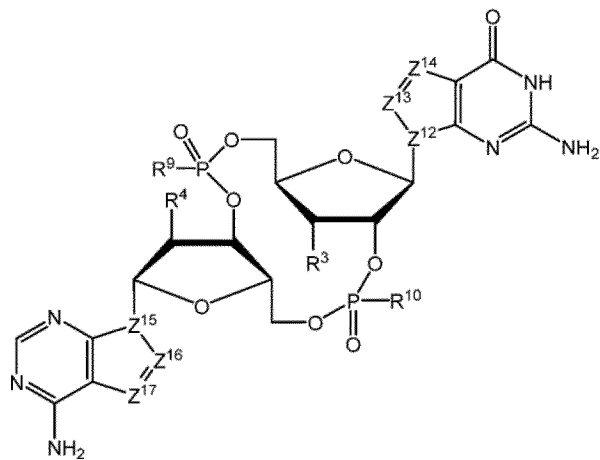
At Column 307, Claim 20, Formula Ic, Lines 5-20, please replace formula:
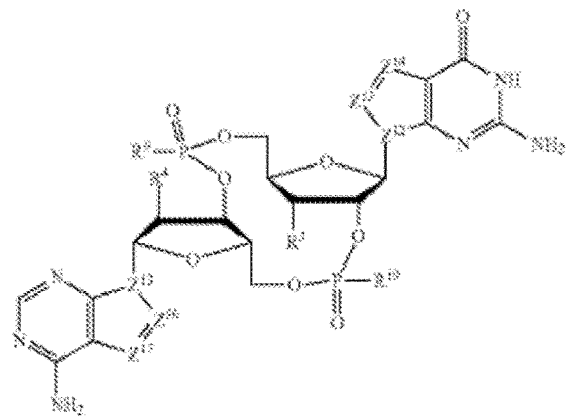
With formula: